(12) United States Patent
Vechorkin et al.

(10) Patent No.: US 9,822,124 B2
(45) Date of Patent: Nov. 21, 2017

(54) BICYCLIC HETEROAROMATIC CARBOXAMIDE COMPOUNDS USEFUL AS PIM KINASE INHIBITORS

(71) Applicant: Incyte Corporation, Wilmington, DE (US)

(72) Inventors: Oleg Vechorkin, Wilmington, DE (US); Yun-Long Li, Chadds Ford, PA (US)

(73) Assignee: Incyte Corporation, Wilmington, DE (US)

(*) Notice: Subject to any disclaimer, the term of this patent is extended or adjusted under 35 U.S.C. 154(b) by 0 days.

(21) Appl. No.: 14/798,137

(22) Filed: Jul. 13, 2015

(65) Prior Publication Data
US 2016/0009726 A1    Jan. 14, 2016

Related U.S. Application Data

(60) Provisional application No. 62/115,842, filed on Feb. 13, 2015, provisional application No. 62/024,366, filed on Jul. 14, 2014.

(51) Int. Cl.
| C07D 495/04 | (2006.01) |
| C07D 491/048 | (2006.01) |
| C07D 513/04 | (2006.01) |
| C07D 487/04 | (2006.01) |
| C07D 471/04 | (2006.01) |

(52) U.S. Cl.
CPC ....... *C07D 491/048* (2013.01); *C07D 471/04* (2013.01); *C07D 487/04* (2013.01); *C07D 495/04* (2013.01); *C07D 513/04* (2013.01)

(58) Field of Classification Search
None
See application file for complete search history.

(56) References Cited

U.S. PATENT DOCUMENTS

| 8,168,794 | B2 | 5/2012 | Burger et al. |
| 8,329,732 | B2 | 12/2012 | Burger et al. |
| 9,200,004 | B2 | 12/2015 | Xue |
| 9,278,950 | B2 | 3/2016 | Li et al. |
| 9,340,546 | B2 * | 5/2016 | Ahmad ............ C07D 487/04 |
| 9,540,347 | B2 | 1/2017 | Vechorkin et al. |
| 9,550,765 | B2 | 1/2017 | Xue et al. |
| 9,556,197 | B2 | 1/2017 | Li et al. |
| 9,580,418 | B2 | 2/2017 | Sun et al. |
| 2011/0059961 | A1 | 3/2011 | Wang et al. |
| 2012/0114663 | A1 | 5/2012 | Gelfand et al. |
| 2012/0225062 | A1 | 9/2012 | Burger et al. |
| 2013/0057956 | A1 | 3/2013 | Iwasa |
| 2014/0086941 | A1 | 3/2014 | Reddy et al. |
| 2014/0088117 | A1 | 3/2014 | Burch et al. |
| 2014/0163000 | A1 | 6/2014 | Ahmad |
| 2014/0200216 | A1 | 7/2014 | Li et al. |
| 2014/0200227 | A1 | 7/2014 | Xue et al. |
| 2015/0057265 | A1 | 2/2015 | Li et al. |
| 2015/0329534 | A1 | 11/2015 | Xue et al. |
| 2016/0009714 | A1 | 1/2016 | Sun et al. |
| 2016/0137626 | A1 | 5/2016 | Li et al. |
| 2016/0347735 | A1 | 12/2016 | Vechorkin et al. |
| 2017/0096411 | A1 | 4/2017 | Vechorkin et al. |
| 2017/0121310 | A1 | 5/2017 | Jia et al. |

FOREIGN PATENT DOCUMENTS

| CN | 101568527 | 10/2009 |
| CN | 102985426 | 3/2013 |
| CN | 103664878 | 3/2014 |
| EP | 2637650 | 9/2013 |
| EP | 2743269 | 6/2014 |
| WO | WO 02/00196 | 1/2002 |
| WO | WO 02/055489 | 7/2002 |
| WO | WO 02/093173 | 11/2002 |
| WO | WO 03/106681 | 12/2003 |
| WO | WO 2004/024895 | 3/2004 |
| WO | WO 2004/090106 | 10/2004 |
| WO | WO 2005/028624 | 3/2005 |
| WO | WO 2005/033310 | 4/2005 |
| WO | WO 2006/006569 | 1/2006 |
| WO | WO 2006/071960 | 7/2006 |
| WO | WO 2006/078228 | 7/2006 |
| WO | WO 2007/002433 | 1/2007 |
| WO | WO 2007/011760 | 1/2007 |
| WO | WO 2007/041712 | 4/2007 |
| WO | WO 2007/044724 | 4/2007 |
| WO | WO 2007/048065 | 4/2007 |
| WO | WO 2007/052843 | 5/2007 |
| WO | WO 2007/084857 | 7/2007 |
| WO | WO 2007/131191 | 11/2007 |
| WO | WO 2008/002676 | 1/2008 |

(Continued)

OTHER PUBLICATIONS

International Search Report and Written Opinion in International Application No. PCT/US2015/040146, dated Oct. 5, 2015, 12 pages.
Search Report, dated Jul. 2, 2014, 6 pages.
Search Report, dated Jul. 8, 2014, 4 pages.
Search Report, dated Jul. 3, 2014, 4 pages.
Blanco-Aparicio, Biochemical Pharmacology, vol. 85, pp. 629-643, 2013.
Chaichian "Targeted Therapies in Systemic Lupus Erythematosus: A State-of-the-Art-Review" J Clin Cell Immunol 2013, S6, 1-8.
Damia "Contemporary pre-clinical development of anticancer agents—What are the optimal preclinical models?" European Journal of Cancer, 2009, 45, 2768-2781.
Georg Pilz, "Modern multiple sclerosis treatment—what is approved, what is on the horizon" Drug Discovery Today Dec. 2008, vol. 13, Nos. 23/24 1013-1025.

(Continued)

*Primary Examiner* — David K O'Dell
(74) *Attorney, Agent, or Firm* — Fish & Richardson P.C.

(57) ABSTRACT

The present disclosure describes bicyclic heteroaromatic carboxamide derivatives, as well as their compositions and methods of use. The compounds inhibit the activity of the Pim kinases, and are useful in the treatment of diseases related to the activity of Pim kinases including, e.g., cancer and other diseases.

43 Claims, No Drawings

(56) References Cited

FOREIGN PATENT DOCUMENTS

| | | |
|---|---|---|
| WO | WO 2008/022164 | 2/2008 |
| WO | WO 2008/045252 | 4/2008 |
| WO | WO 2008/054749 | 5/2008 |
| WO | WO 2008/058126 | 5/2008 |
| WO | WO 2008/082839 | 7/2008 |
| WO | WO 2008/082840 | 7/2008 |
| WO | WO 2008/106692 | 9/2008 |
| WO | WO 2008/121687 | 10/2008 |
| WO | WO 2008/124323 | 10/2008 |
| WO | WO 2008/127728 | 10/2008 |
| WO | WO 2008/133955 | 11/2008 |
| WO | WO 2008/143759 | 11/2008 |
| WO | WO 2009/014637 | 1/2009 |
| WO | WO 2009/017701 | 2/2009 |
| WO | WO 2009/064486 | 5/2009 |
| WO | WO 2009/065080 | 5/2009 |
| WO | WO 2009/108912 | 9/2009 |
| WO | WO 2009/109576 | 9/2009 |
| WO | WO 2009/151845 | 12/2009 |
| WO | WO 2010/000978 | 1/2010 |
| WO | WO 2010/001169 | 1/2010 |
| WO | WO 2010/002933 | 1/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/048314 | 4/2010 |
| WO | WO 2010/057833 | 5/2010 |
| WO | WO 2010/071885 | 6/2010 |
| WO | WO 2010/135401 | 11/2010 |
| WO | WO 2010/135571 | 11/2010 |
| WO | WO 2010/135581 | 11/2010 |
| WO | WO 2010/135650 | 11/2010 |
| WO | WO 2010/148351 | 12/2010 |
| WO | WO 2011/008487 | 1/2011 |
| WO | WO 2011/025859 | 3/2011 |
| WO | WO 2011/028685 | 3/2011 |
| WO | WO 2011/029802 | 3/2011 |
| WO | WO 2011/031979 | 3/2011 |
| WO | WO 2011/035019 | 3/2011 |
| WO | WO 2011/035022 | 3/2011 |
| WO | WO 2011/053861 | 5/2011 |
| WO | WO 2011/057784 | 5/2011 |
| WO | WO 2011/058139 | 5/2011 |
| WO | WO 2011/060295 | 5/2011 |
| WO | WO 2011/063398 | 5/2011 |
| WO | WO 2011/068667 | 6/2011 |
| WO | WO 2011/075613 | 6/2011 |
| WO | WO 2011/075630 | 6/2011 |
| WO | WO 2011/075643 | 6/2011 |
| WO | WO 2011/079274 | 6/2011 |
| WO | WO 2011/101643 | 8/2011 |
| WO | WO 2011/112662 | 9/2011 |
| WO | WO 2011/124580 | 10/2011 |
| WO | WO 2011/130342 | 10/2011 |
| WO | WO 2011/163195 | 12/2011 |
| WO | WO 2012/004217 | 1/2012 |
| WO | WO 2012/007375 | 1/2012 |
| WO | WO 2012/015474 | 2/2012 |
| WO | WO 2012/016217 | 2/2012 |
| WO | WO 2012/064981 | 5/2012 |
| WO | WO 2012/065297 | 5/2012 |
| WO | WO 2012/065546 | 5/2012 |
| WO | WO 2012/068440 | 5/2012 |
| WO | WO 2012/068450 | 5/2012 |
| WO | WO 2012/078777 | 6/2012 |
| WO | WO 2012/080990 | 6/2012 |
| WO | WO 2012/087881 | 6/2012 |
| WO | WO 2012/101029 | 8/2012 |
| WO | WO 2012/101032 | 8/2012 |
| WO | WO 2012/120415 | 9/2012 |
| WO | WO 2012/120428 | 9/2012 |
| WO | WO 2012/125629 | 9/2012 |
| WO | WO 2012/129338 | 9/2012 |
| WO | WO 2012/135009 | 10/2012 |
| WO | WO 2012/137089 | 10/2012 |
| WO | WO 2012/139930 | 10/2012 |
| WO | WO 2012/145617 | 10/2012 |
| WO | WO 2012/146933 | 11/2012 |
| WO | WO 2012/146936 | 11/2012 |
| WO | WO 2012/148775 | 11/2012 |
| WO | WO 2012/154274 | 11/2012 |
| WO | WO 2012/156367 | 11/2012 |
| WO | WO 2012/156756 | 11/2012 |
| WO | WO 2012/163942 | 12/2012 |
| WO | WO 2012/170827 | 12/2012 |
| WO | WO 2012/175591 | 12/2012 |
| WO | WO 2012/177606 | 12/2012 |
| WO | WO 2013/013188 | 1/2013 |
| WO | WO 2013/020369 | 2/2013 |
| WO | WO 2013/020370 | 2/2013 |
| WO | WO 2013/020371 | 2/2013 |
| WO | WO 2013/024002 | 2/2013 |
| WO | WO 2013/026025 | 2/2013 |
| WO | WO 2013/033569 | 3/2013 |
| WO | WO 2013/034570 | 3/2013 |
| WO | WO 2013/036611 | 3/2013 |
| WO | WO 2013/041634 | 3/2013 |
| WO | WO 2013/045461 | 4/2013 |
| WO | WO 2013/050446 | 4/2013 |
| WO | WO 2013/050448 | 4/2013 |
| WO | WO 2013/130660 | 9/2013 |
| WO | WO 2013/134079 | 9/2013 |
| WO | WO 2013/066684 | 10/2013 |
| WO | WO 2013/144189 | 10/2013 |
| WO | WO 2013/149909 | 10/2013 |
| WO | WO 2013/151930 | 10/2013 |
| WO | WO 2013/160873 | 10/2013 |
| WO | WO 2013/163279 | 10/2013 |
| WO | WO 2013/170068 | 11/2013 |
| WO | WO 2013/171639 | 11/2013 |
| WO | WO 2013/173720 | 11/2013 |
| WO | WO 2013/175388 | 11/2013 |
| WO | WO 2013/177219 | 11/2013 |
| WO | WO 2013/186692 | 12/2013 |
| WO | WO 2014/001377 | 1/2014 |
| WO | WO 2014/011974 | 1/2014 |
| WO | WO 2014/022752 | 2/2014 |
| WO | WO 2014/033630 | 3/2014 |
| WO | WO 2014/033631 | 3/2014 |
| WO | WO 2014/041131 | 3/2014 |
| WO | WO 2014/048939 | 4/2014 |
| WO | WO 2014/053568 | 4/2014 |
| WO | WO 2014/060411 | 4/2014 |
| WO | WO 2014/071031 | 5/2014 |
| WO | WO 2014/076162 | 5/2014 |
| WO | WO 2014/079011 | 5/2014 |
| WO | WO 2014/079136 | 5/2014 |
| WO | WO 2014/009447 | 6/2014 |
| WO | WO 2014/097151 | 6/2014 |
| WO | WO 2014/099880 | 6/2014 |
| WO | WO 2014/100158 | 6/2014 |
| WO | WO 2014/100323 | 6/2014 |
| WO | WO 2014/100719 | 6/2014 |
| WO | WO 2014089379 A1 * 6/2014 ........... C07D 487/04 |
| WO | WO 2014/106706 | 7/2014 |
| WO | WO 2014/110574 | 7/2014 |
| WO | WO 2014/134426 | 9/2014 |
| WO | WO 2014/138168 | 9/2014 |
| WO | WO 2014/138906 | 9/2014 |
| WO | WO 2014/138907 | 9/2014 |
| WO | WO 2014/139145 | 9/2014 |
| WO | WO 2014/140597 | 9/2014 |
| WO | WO 2014/140644 | 9/2014 |
| WO | WO 2014/140861 | 9/2014 |
| WO | WO 2014/141171 | 9/2014 |
| WO | WO 2014/142290 | 9/2014 |
| WO | WO 2014/142292 | 9/2014 |
| WO | WO 2014/143601 | 9/2014 |
| WO | WO 2014/143768 | 9/2014 |
| WO | WO 2014/145051 | 9/2014 |
| WO | WO 2014/150258 | 9/2014 |

(56) References Cited

FOREIGN PATENT DOCUMENTS

| WO | WO 2014/150276 | | 9/2014 | | |
|---|---|---|---|---|---|
| WO | WO 2014/151008 | | 9/2014 | | |
| WO | WO 2014/151634 | | 9/2014 | | |
| WO | WO 2015/021153 | | 2/2015 | | |
| WO | WO 2015027124 | A1 * | 2/2015 | ......... | C07D 491/048 |
| WO | WO 2015/131031 | | 9/2015 | | |
| WO | WO 2015/157257 | | 10/2015 | | |
| WO | WO 2015/168246 | | 11/2015 | | |
| WO | WO 2015/184305 | | 12/2015 | | |
| WO | WO 2015/191677 | | 12/2015 | | |

OTHER PUBLICATIONS

Johnson et al., "Relationship between drug activity in NCI preclinical in vitro and in vivo models and early clinical trials" British Journal of Cancer, 2001, 84, 1424-1437.

Konstantinos Markrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.

Ocana, A. "Preclinical development of molecular targeted agents for cancer" Nat. Rev. Clin. Oncol. 2011, 8, 200-209.

Sharma "Cell line-based platforms to evaluate the therapeutic efficacy of candidate anticancer agents" Nature Reviews Cancer Apr. 2010, vol. 10, 241-253.

Simone, Oncology: Introduction, Cecil Textbook of Medicine, 20th Edition, 1996 vol. 1, pp. 1004-1010.

Amson et al., "The human protooncogene product p33pim is expressed during fetal hematopoiesis and in diverse leukemias," Proc. Nat. Acad. Sci., USA, 1989, 86:8857-61.

Arunesh et al., "Small molecule inhibitors of PIM1 kinase: Jul. 2009 to Feb. 2013 patent update," Expert Opin Ther Pat, Jan. 2014, 24(1): 5-17.

Bamborough, "Assessment of Chemical Coverage of Kinome Space and Its Implications for Kinase Drug Discovery," J. Med. Chem., 2008, 51: 7898-7914.

Berge et al., "Pharmaceutical Salts," J. Pharm. Sci., 1977, 66(1):1-19.

Blom et al., "Optimizing Preparative LC-MS Configurations and Methods for Parallel Synthesis Purification," J. Comb. Chem., 2003, 5:670-83.

Blom et al., "Preparative LC-MS Purification: Improved Compound Specific Method Optimization," J. Comb. Chem., 2004, 6:874-883.

Blom, "Two-Pump at Column Dilution Configuration for Preparative Liquid Chromatography—Mass Spectrometry," J. Comb. Chem., 2002, 4:295-301.

Burger et al. "Structure Guided Optimization, in Vitro Activity, and in Vivo Activity of Pan-PIM Kinase Inhibitors," ACS Med Chem Lett., 2013, 4:1193-1197.

Chan et al., "New N- and 0-arylations with phenylboronic acids and cupric acetate," Tetrahedron Letters, May 1998, 39(19): 2933-2936.

Chen et al., "Pim kinase inhibitor, SGI-1776, induces apoptosis in chronic lymphocytic leukemia cells," Blood, 2009, 114:4150-57.

Claudio et al., "A molecular compendium of genes expressed in multiple myeloma," Blood, 2002, 100:2175-86.

Davis et al., "Small Molecule Dual Antagonist of Pim 1 and 3 Kinases Ameliorate Experimental Autoimmune Encephalomyelitis," 26th Congress of the European Committee for Treatment and Research in Multiple Sclerosis, Oct. 13-16, 2010, Gothenburg, Sweden, Poster P436.

Dorwald F. A. Side Reactions in Organic Synthesis, 2005, Wiley: VCH, Weinheim p. IX of Preface p. 1-15.

Freshney, Culture of Animal Cells, A Manual of Basic Technique, Alan R. Liss, Inc., 1983, New York, P4.

Fujii et al., "Aberrant expression of serine-threonine kinase Pim-3 in hepatocellular carcinoma development and its role in the proliferation of human hepatoma cell lines," Int. J. Canc., 2005, 114:209-18.

Gomez-Abad et al., "PIM2 inhibition as a rational therapeutic approach in B-cell lymphoma," Blood, 2011, 118:5517-27.

Gu and Li, "A concise synthesis of (2S,4R)- and (2S,4S)-4-methylglutamic acid," Tetrahedron Lett., 2003, 44:3203-3205.

Hsi et al., "Ki67 and PIM1 expression predict outcome in mantle cell lymphoma treated with high dose therapy, stem cell transplantation and rituximab: a Cancer and Leukemia Group B 59909 correlative science study," Leuk. Lymph., 2008, 49:2081-90.

Hsu et al., "Pim-1 knockdown potentiates paclitaxel-induced apoptosis in human hormone-refractory prostate cancers through inhibition of NHEJ DNA repair," Cancer Lett., 2012, 319:214-222.

Huang et al., "Structure-based design and optimization of 2-aminothiazole-4-carboxamide as a new class of CHK1 inhibitors," Bioorganic Med Chem Lett., Mar. 2013, 23(9):2590-2594.

International Preliminary Report on Patentability in International Application No. PCT/US2014/011486, dated Jul. 21, 2015, 7 pages.

International Preliminary Report on Patentability in International Application No. PCT/US2014/011487, dated Jul. 23, 2015, 6 pages.

International Search Report and Written Opinion in International Application No. PCT/US2014/011486, dated Mar. 17, 2014, 12 pages.

International Search Report and Written Opinion in International Application No. PCT/US2014/011487, dated Apr. 4, 2014, 11 pages.

International Search Report and Written Opinion in International Application No. PCT/US2014/052214, dated Oct. 28, 2014, 13 pages.

Isaac et al., "The oncogenic PIM kinase family regulates drug resistance through multiple mechanisms," Drug Resis. Updates, 2011, 14:203-11.

Ishchenko et al., "Structure-based design of low-nanomolar PIM kinase inhibitors," Bioorg Med Chem Lett., 2015, 25:474-480.

Jiang et al., "3,5-Disubstituted quinolines as novel c-Jun N-terminal kinase inhibitors," Bioorganic & Medicinal Chemistry Letters, 2007, 17: 6378-6382.

Kelly et al., "Targeting PIM kinase activity significantly augments the efficacy of cytarabine," British Journal of Haematology, 2011, 156, 129-152.

Lam et al., "New aryl/heteroaryl C N bond cross-coupling reactions via arylboronic acid/cupric acetate arylation," Tetrahedron Letters, May 1998, 39(19): 2941-2944.

Li et al., "Pim-3, a Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines," Canc. Res., 2006, 66:6741-7.

Liu et al., "Overexpression of Pim-1 is associated with poor prognosis in patients with esophageal squamous cell carcinoma," J. Surg. Oncol., 2010,102:683-88.

Liu et al., "Synthesis and SAR of 1,9-dihydro-9-hydroxypyrazolo[3,4-b]quinolin-4-ones as novel, selective c-Jun N-terminal kinase inhibitors," Bioorganic & Medicinal Chemistry Letters, 2006, 16: 2590-2594.

Merkel et al., "PIM1 kinase as a target for cancer therapy," Exp. Opin. Investig. Drugs, 2012, 21:425-38.

Michelotti et al., "Two classes of p38a MAP kinase inhibitors having a common diphenylether core but exhbiting divergent binding modes," 2005, 15: 5274-5279.

Mikkers et al., "High-throughput retroviral tagging to identify components of specific signaling pathways in cancer," Nature Genet., 2002, 32:153-159.

Mikkers et al., "Mice deficient for all PIM kinases display reduced body size and impaired responses to hematopoietic growth factors," Mol. Cell. Biol., 2004, 24:6104-15.

Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorganic & Medicinal Chemistry Letters, 2007, 17: 250-254.

Mizuki et al., "Suppression of myeloid transcription factors and induction of STAT response genes by AML-specific Flt3 mutations," Blood, 2003, 101:3164-73.

Morwick, "Pim kinase inhibitors: a survey of the patent literature," Exp. Opin. Ther. Patents, 2010, 20(2):193-212.

(56) References Cited

OTHER PUBLICATIONS

Mulvihill et al., "Novel 2-phenylquinolin-7-yl-derived imidazo[1,5-a]pyrazines as potent insulin-like growth factor-I receptor (IFG-IR) inhibitors," Bioorganic & Medicinal Chemistry, 2008, 16: 1359-1375.
Ogawa et al., "Insights from Pim1 structure for anti-cancer drug design," Expert Opin Drug Discov, Dec. 2012, 7(12): 1177-92.
Peltola et al., "Pim-1 kinase expression predicts radiation response in squamocellular carcinoma of head and neck and is under the control of epidermal growth factor receptor," Neoplasia, 2009, 11:629-36.
Peturssion, "Protecting Groups in Carbohydrate Chemistry," J. Chem. Educ., 1997, 74(11):1297-1303.
Ravin, "Preformulation," Remington's Pharmaceutical Sciences, 17$^{th}$ Ed., (Mack Publishing Company, Easton, 1985), p. 1409-1423.
Robinson et al., "A Dual PIM 1/3 Kinase Inhibitor Demonstrates Efficacy in Murine Models of Lupus and Multiple Sclerosis," J. Immunol , 2012, 188:119.9.
Schatz, et al., "Targeting cap-dependent translation blocks converging survival signals by AKT and PIM kinases in lymphoma," J. Exp. Med., 2011, 208:1799-1807.
Shen et al., "Inhibition of Pim-1 kinase ameliorates dextran sodium sulfate-induced colitis in mice," Dig. Dis. Sci., 2012, 57:1822-31.
Shinto et al., "Moloney murine leukemia virus infection accelerates lymphomagenesis in Eμ-bc1-2 transfenic mice," Oncogene, 1995, 11:1729-36.
Swords et al., "The Pim kinases: new targets for drug development," Curr. Drug Targets, 2011, 12(14):2059-66.
U.S. Office Action in U.S. Appl. No. 14/155,134, dated Jul. 27, 2015, 12 pages.
Venkatesh et al., "Role of the Development Scientist in Compound Lead Selection and Optimization," J. Pharm. Sci., 2000, 89:145-54.
Wang et al., "Inhibition of Pim1 kinase prevents peanut allergy by enhancing Runx3 expression and suppressing T(H)2 and T(H)17 T-cell differentiation," J. All. Clin. Immunol., 2012, 130:932-44.
Yang et al., "Proviral integration site 2 is required for interleukin-6 expression induced by interleukin-1, tumour necrosis factor-α and lipopolysaccharide," Immunol., 2010, 131:174-182.
Zippo, et al., "PIM1-dependent phosphorylation of histone H3 at serine 10 is required for MYC-dependent transcriptional activation and oncogenic transformation," Nature Cell Biol., 2007, 9:932-44.
Chilean Office Action, Patent Application No. 1985-2015, dated Jul. 7, 2016, 22 pages (English Translation).
International Preliminary Report on Patentability in International Application No. PCT/US2014/052214, dated Feb. 23, 2016, 7 pages.
International Search Report and Written Opinion in International Application No. PCT/US2016/034520, dated Jul. 12, 2016, 11 pages.
Asano et al., "The serine/threonine kinase Pim-2 is a novel anti-apoptotic mediator in myeloma cells," Leukemia, 2011, 25: 1182-1188.
Baron et al., "PIM1 gene cooperates with human BCL6 gene to promote the development of lymphomas," PNAS, Apr. 2012, 109(15): 5735-5739.
Brault et al., "PIM kinases are progression markers and emerging therapeutic targets in diffuse large B-cell lymphoma," British Journal of Cancer, 2012, 107: 491-500.
Caira, "Crystalline Polymorphism of Organic Compounds," Topics in Current Chemistry, Jan. 1998, 198: 163-208.
Cervantes-Gomez et al., "Biological Effects of the Pim Kinase Inhibitor, SGI-1776, in Multiple Myeloma," Clinical Lymphoma, Myeloma & Leukemia, Sep. 2013, S317-S329.
Chen et al., "Mechanisms of cytotoxicity to Pim kinase inhibitor, SGI-1776, in acute myeloid leukemia," Blood, Jul. 2011, 118(3): 693-702.
Chinese Office Action in Chinese Application No. 201480012783.3. dated Sep. 6, 2016, 16 pages (English Translation).
Colombian Office Action in Colombian Application No. 15-168.544, dated Aug. 10, 2016, 10 pages.
Coperet, "A simple and efficient method for the preparation of pyridine N-Oxides," The Journal of Organic Chemistry, Jan. 1998, 63: 1740-1741.
Database accession No. RN 1795440-67-3, Chemical Abstracts Service, Jul. 6, 2015, 1 page.
Eurasian Office Action in Eurasian Application No. 201690458/28, dated Jan. 25, 2017, 11 pages (with English translation).
Gozgit et al., "Effects of the JAK2 Inhibitor, AZ960, on Pim/BAD/BCL-xL Survival Signaling in the Human JAK2 V617F Cell Line SET-2," Journal of Biological Chemistry, Nov. 2008, 283(47): 32334-32343.
Hammerman et al., "Lymphocyte Transformation by Pim-2 is Dependent on Nuclear Factor-kB Activation," Cancer Research, Nov. 2004, 64: 8341-8348.
International Preliminary Report on Patentability in International Application No. PCT/US2015/040146, dated Jan. 17, 2017, 8 pages.
International Search Report and Written Opinion in International Application No. PCT/US2016/050925, dated Oct. 21, 2016, 13 pages.
International Search Report and Written Opinion in International Application No. PCT/US2016/054779, dated Dec. 9, 2016, 12 pages.
Katano et al., "Synthesis and biological activity of (cyclopentenopyridinium)thiomethylcephalosporins," The Journal of Antibiotics, Jan. 1990, 43(9): 1150-1159.
Lu et al., "Pim2 is required for maintaining multiple myeloma cell growth through modulating TSC2 phosphorylation," Blood, Aug. 2013, 122(9): 1610-1620.
Schwemmers et al., "JAK2V617F-negative ET Patients do not display constitutively active JAK/STAT signaling," Exp. Hematol., Nov. 2007, 35(11): 1695-1703.
www.leukaemia.org' [online]. "Myeloproliferative neoplasms (MPN)," 2016, [retrieved on Dec. 5, 2016]. Retrieved from the Internet: URL<http://www.leukaemia.org.au/blood-cancers/myeloproliferative-neoplasms-mpn>, 3 pages.
Cancer [online], [retrieved on Jul. 6, 2007] Retrieved from the Internet URL: http://www.nlm.nih.gov/medlineplus/cancer.html.
Golub et al., "Molecular Classification of Cancer: Class Discovery and Class Prediction by Gene Expression Monitoring," Science, 1999, 286: 531-537.
Lala et al., "Role of nitric oxide in tumor progression: Lessons from experimental tumors," Cancer and Metastasis Reviews, 1998, 17: 91-106.
Chinese Office Action in Chinese Application No. 201480057613.7, dated Apr. 5, 2017, 15 pages (English Translation).

\* cited by examiner

BICYCLIC HETEROAROMATIC CARBOXAMIDE COMPOUNDS USEFUL AS PIM KINASE INHIBITORS

TECHNICAL FIELD

The present application is concerned with pharmaceutically useful compounds. The disclosure provides new compounds as well as their compositions and methods of use. The compounds inhibit the activity of Pim kinases and are therefore useful in the treatment of diseases related to the activity of Pim kinases including, e.g., cancers and other diseases.

BACKGROUND

Protein kinases regulate diverse biological processes including cell growth, survival, differentiation, organ formation, morphogenesis, neovascularization, tissue repair, and regeneration, among others. Protein kinases also play specialized roles in a host of human diseases including cancer. The three members of the Pim kinase family, one example of a protein kinase family, were initially identified as preferential integration sites of Moloney leukemia virus in mouse models of cancer. Although possessing modest but measurable oncogenic activity alone, they potentiate pro-proliferative and pro-survival oncogenes, e.g., causing a dramatic acceleration of lymphomagenesis in Myc-transgenic or Bcl2-transgenic mice. Mikkers et al., *Nature Genet.*, 2002, 32, 153-159; Shinto et al., *Oncogene*, 1995, 11, 1729-35.

The three non-receptor serine/threonine kinases Pim1, Pim2 and Pim3 regulate cell proliferation and survival by impacting gene transcription and protein translation. Zippo, et al., *Nature Cell Biol.*, 2007, 9, 932-44; Schatz, et al., *J. Exp. Med.*, 2011, 208, 1799-1807. As opposed to numerous other protein kinases which require activation by phosphorylation, the Pim kinases are constitutively activated and family members have overlapping substrate targets and biological functions, with differences between family members dictated, in part, by their varied tissue distribution. Expression of the Pim kinases is induced by cytokines and growth factors. Among the cytokines activating Pim kinase expression are cytokines which signal through the JAK/STAT pathway. Pim kinases act in parallel to the PI3K/AKT pathway, and they share several phosphorylation targets (e.g., pBAD, p4EBP1). Inhibitors of Pim kinases may therefore potentiate regimens including inhibitors of either the JAK pathway or the PI3K/AKT pathway.

Overexpression of Pim kinases is detected in a wide variety of hematologic and solid cancers. Overexpression of various family members have been noted in multiple myeloma, AML, pancreatic and hepatocellular cancers. Claudio et al., *Blood*, 2002, 100, 2175-86; Amson et al., *Proc. Nat. Acad. Sci.*, USA, 1989, 86, 8857-61; Mizuki et al., *Blood*, 2003, 101, 3164-73; Li et al., *Canc. Res.*, 2006, 66, 6741-7; Fujii et al., *Int. J. Canc.*, 2005, 114, 209-18. Pim1 overexpression is associated with poor prognosis in mantle cell lymphoma, esophageal and head and neck cancers. Hsi et al., *Leuk. Lymph.*, 2008, 49, 2081-90; Liu et al., *J. Surg. Oncol.*, 2010, 102, 683-88; Peltola et al., *Neoplasia*, 2009, 11, 629-36 Pim2 overexpression is associated with an aggressive clinical course in a subset of DLBCL patients. Gomez-Abad et al., *Blood*, 2011, 118, 5517-27. Overexpression is often seen where Myc is overexpressed and Pim kinases can convey resistance to traditional chemotherapeutic agents and radiation. Chen et al., *Blood*, 2009, 114, 4150-57; Isaac et al., *Drug Resis. Updates*, 2011, 14, 203-11; Hsu et al., *Cancer Lett.*, 2012, 319, 214; Peltola et al., *Neoplasia*, 2009, 11, 629-36.

As such, these data indicate that inhibition of Pim kinases will be useful to provide therapeutic benefit in cancer patients.

Data from mice deficient for one or multiple Pim kinase family members suggests that pan-Pim inhibitor would have a favorable toxicity profile. Triple knockout mice are viable, but are slightly smaller than their wild type littermates. Mikkers et al., *Mol. Cell. Biol.*, 2004, 24, 6104-15. Since Pim kinases are also involved in a variety of immunologic and inflammatory responses and these indications require drug agents with fewer side effects, Pim kinase inhibitors are expected to be useful in treating patients with colitis (Shen et al., *Dig. Dis. Sci.*, 2012, 57, 1822-31), peanut allergy (Wang et al., *J. All. Clin. Immunol.*, 2012, 130, 932-44), multiple sclerosis and lupus (Davis et al., "Small Molecule Dual Antagonist of Pim 1 and 3 Kinases Ameliorate Experimental Autoimmune Encephalomyelitis", 26th Congress of the European Committee for Treatment and Research in Multiple Sclerosis, 13-16 Oct. 2010, Gothenburg, Sweden, Poster P436; Robinson et al., *J. Immunol.*, 2012, 188, 119.9) and rheumatoid arthritis (Yang et al., *Immunol.* 2010, 131, 174-182) and other immunological and inflammatory disorders.

The Pim kinases have therefore been identified as useful targets for drug development efforts. Swords et al., *Curr. Drug Targets*, 2011, 12(14), 2059-66; Merkel et al., *Exp. Opin. Investig. Drugs*, 2012, 21, 425-38; Morwick et al., *Exp. Opin. Ther. Patents*, 2010, 20(2), 193-212.

Accordingly, there is a need for new compounds that inhibit Pim kinases. The present application describes new inhibitors of Pim kinases that are useful for treating diseases associated with the expression or activity of one or more Pim kinases, e.g., cancer and other diseases.

SUMMARY

The present disclosure provides, inter alia, a compound of Formula (I):

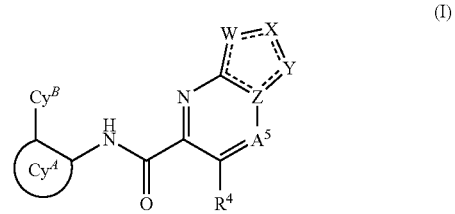

or a pharmaceutically acceptable salt thereof; wherein the variables are as defined below.

The present disclosure also provides a composition comprising a compound of Formula (I), or a pharmaceutically acceptable salt thereof, and at least one pharmaceutically acceptable carrier.

The present disclosure also provides methods of treating cancer and other diseases comprising administering to a patient a therapeutically effective amount of a compound of Formula (I), or a pharmaceutically acceptable salt thereof.

The details of one or more embodiments are set forth in the description below. Other features, objects and advantages will be apparent from the description and from the claims.

DETAILED DESCRIPTION

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

I. Compounds

The present disclosure provides, inter alia, a compound of Formula (I):

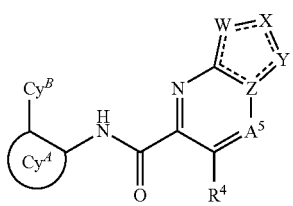

or a pharmaceutically acceptable salt thereof, wherein:

$Cy^A$ is selected from heteroaryl groups of the following Formulae $Cy^A$-1 to $Cy^A$-3:

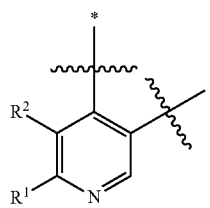

(Cy$^A$-1)

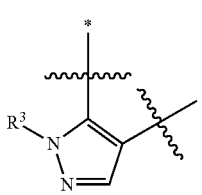

(Cy$^A$-2)

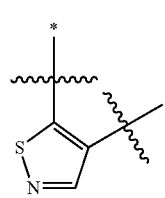

(Cy$^A$-3)

wherein * indicates the bond connecting $Cy^A$ and $Cy^B$;

the moiety represented in Formula (I) by $Cy^C$:

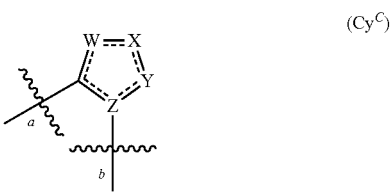

(Cy$^C$)

is a 5-membered heteroaryl or heterocycloalkyl ring wherein:
W is $A^6$ or $A^7$;
X is $A^6$, $A^7$ or C(O);
Y is $A^6$ or $A^7$;
Z is C or N;
each $A^6$ is independently O, S or $NR^6$;
each $A^7$ is independently N or $CR^7$;
a and b indicate bonds by which $Cy^C$ is attached;
wherein W, X, Y and Z are selected such that the 5-membered heteroaryl or heterocycloalkyl ring $Cy^C$ is selected from groups of the following Formulae $Cy^C$-1 to $Cy^C$-5:

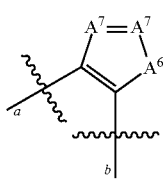

(Cy$^C$-1)

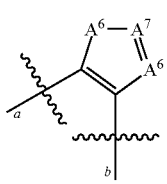

(Cy$^C$-2)

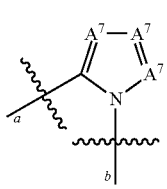

(Cy$^C$-3)

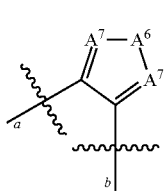

(Cy$^C$-4)

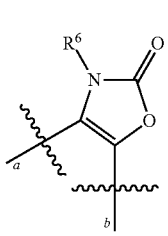

(Cy$^C$-5)

wherein, in each of Formulae $Cy^C$-1, $Cy^C$-2, $Cy^C$-3 and $Cy^C$-4, at least one $A^7$ is $CR^7$;

$Cy^B$ is an unsubstituted or substituted $C_{3-7}$ cycloalkyl or an unsubstituted or substituted 4-10 membered heterocycloalkyl, wherein the ring atoms of the heterocycloalkyl forming $Cy^B$ consist of carbon atoms and 1, 2 or 3 heteroatoms selected from O, N and S, wherein the substituted $C_{3-7}$ cycloalkyl or substituted 4-10 membered heterocycloalkyl forming $Cy^B$ is substituted with 1, 2, 3, 4 or 5 substituents each independently selected from halogen, $R^{CyB}$, $C_{1-6}$ haloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)NR^{c1}R^{d1}$, $S(O)_2R^{b1}$, $NR^{c1}S(O)_2R^{b1}$ and $S(O)_2NR^{c1}R^{d1}$, wherein each $R^{CyB}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-7}$ cycloalkyl and 4-7 membered heterocycloalkyl, each of which is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)NR^{c1}R^{d1}$, $S(O)_2R^{b1}$, $NR^{c1}S(O)_2R^{b1}$ and $S(O)_2NR^{c1}R^{d1}$;

$R^1$ is H; and $R^2$ is H, halogen, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ or $S(O)_2NR^{c2}R^{d2}$;

or $R^1$ and $R^2$ in combination, together with the carbon atoms to which $R^1$ and $R^2$ are attached, form a 5, 6 or 7-membered carbocyclic or heterocyclic ring containing 3 to 7 ring carbon atoms and 0, 1 or 2 ring heteroatoms, each independently selected from N, O and S, wherein the ring formed by the combination of $R^1$ and $R^2$ is unsubstituted or substituted by 1, 2 or 3 substituents independently selected from halogen, $C_{1-6}$ alkyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$ and oxo;

$R^3$ is H, $C_{1-6}$ alkyl, $C_{2-6}$ alkenyl, $C_{2-6}$ alkynyl, $C_{1-6}$ haloalkyl, $C_{3-6}$ cycloalkyl or 4-6 membered heterocycloalkyl;

$R^4$ is H, halogen or $NH_2$;

$A^5$ is N or $CR^5$;

$R^5$ is H or halogen;

each $R^6$ is independently H, $C_{1-6}$ alkyl, $C_{2-6}$ alkenyl, $C_{2-6}$ alkynyl, $C_{1-6}$ haloalkyl, $Cy^6$, or $-L^6-Cy^6$;

each $R^7$ is independently, at each occurrence, H, $C_{1-6}$ alkyl, $C_{2-6}$ alkenyl, $C_{2-6}$ alkynyl, $C_{1-6}$ haloalkyl, $Cy^6$, or $-L^6-Cy^6$, halogen, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ or $S(O)_2NR^{c3}R^{d3}$, wherein said $C_{1-6}$ alkyl, $C_{2-6}$ alkenyl or $C_{2-6}$ alkynyl forming $R^6$ or $R^7$ are each independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$;

$Cy^6$ is unsubstituted or substituted $C_{6-10}$ aryl, unsubstituted or substituted 5-10 membered heteroaryl, unsubstituted or substituted $C_{3-6}$ cycloalkyl, or unsubstituted or substituted 4-12 membered heterocycloalkyl, wherein the substituted $C_{6-10}$ aryl, 5-10 membered heteroaryl, $C_{3-6}$ cycloalkyl or 4-12 membered heterocycloalkyl forming $Cy^6$ is substituted with 1, 2, 3, 4 or 5 substituents each independently selected from halogen, $R^{Cy6}$, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$, wherein each $R^{Cy6}$ is $C_{1-6}$ alkyl, each of which is independently unsubstituted or substituted by 1, 2 or 3 substituents independently selected from halogen, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}NR^{c3}S(O)_2R^{b3}$ and $S(O)_2NR^{c3}R^{d3}$;

alternatively, the substituted $C_{6-10}$ aryl, 5-10 membered heteroaryl, $C_{3-6}$ cycloalkyl or 4-12 membered heterocycloalkyl forming $Cy^6$ is substituted with unsubstituted $C_{6-10}$ aryl or $C_{6-10}$ aryl substituted by 1, 2, 3, 4 or 5 substituents independently selected from halogen, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}NR^{c3}S(O)_2R^{b3}$ and $S(O)_2NR^{c3}R^{d3}$;

$L^6$ is unsubstituted $C_{1-6}$ alkylene or $C_{1-6}$ alkylene substituted with 1, 2 or 3 substituents independently selected from F, Cl, CN, OH, O($C_{1-6}$ alkyl), $NH_2$, $NH(C_{1-6}$ alkyl) and $N(C_{1-6}$ alkyl)$_2$;

or two $R^6$ or $R^7$ groups attached to adjacent ring atoms of $Cy^C$ in combination, together with the ring atoms of $Cy^C$ to which they are attached, form a 5, 6 or 7-membered carbocyclic or heterocyclic ring containing 3 to 7 ring carbon atoms and 0, 1 or 2 ring heteroatoms, each independently selected from N, O and S, wherein the ring formed by the combination of two $R^6$ or $R^7$ groups is unsubstituted or substituted by 1, 2 or 3 substituents independently selected from halogen, $C_{1-6}$ alkyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$ and oxo;

$R^{a1}$, $R^{b1}$, $R^{c1}$ and $R^{d1}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a1}$, $R^{b1}$, $R^{c1}$ and $R^{d1}$ are each optionally substituted with 1, 2, 3, 4 or 5 substituents independently selected from $C_{1-6}$ alkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$ and $S(O)_2NR^{c4}R^{d4}$;

or $R^{c1}$ and $R^{d1}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$ and $S(O)_2NR^{c4}R^{d4}$;

$R^{a2}$, $R^{b2}$, $R^{c2}$ and $R^{d2}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a2}$, $R^{b2}$, $R^{c2}$ and $R^{d2}$ are each optionally substituted with 1, 2, 3, 4 or 5 substituents independently selected from $C_{1-6}$ alkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$ and $S(O)_2NR^{c5}R^{d5}$;

or $R^{c2}$ and $R^{d2}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$ and $S(O)_2NR^{c5}R^{d5}$;

$R^{a3}$, $R^{b3}$, $R^{c3}$ and $R^{d3}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a3}$, $R^{b3}$, $R^{c3}$ and $R^{d3}$ are each optionally substituted with 1, 2, 3, 4 or 5 substituents independently selected from $C_{1-6}$ alkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$ and $S(O)_2NR^{c6}R^{d6}$;

or $R^{c3}$ and $R^{d3}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$ and $S(O)_2NR^{c6}R^{d6}$;

$R^{a4}$, $R^{b4}$, $R^{c4}$ and $R^{d4}$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a4}$, $R^{b4}$, $R^{c4}$ and $R^{d4}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

or $R^{c4}$ and $R^{d4}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

$R^{a5}$, $R^{b5}$, $R^{c5}$ and $R^{d5}$ are each independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl forming $R^{a5}$, $R^{b5}$, $R^{c5}$ and $R^{d5}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

or $R^{c5}$ and $R^{d5}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

$R^{a6}$, $R^{b6}$, $R^{c6}$ and $R^{d6}$ are each independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl forming $R^{a6}$, $R^{b6}$, $R^{c6}$ and $R^{d6}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy;

or $R^{c6}$ and $R^{d6}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy; and $R^{e1}$, $R^{e2}$, $R^{e3}$, $R^{e4}$, $R^{e5}$ and $R^{e6}$ are each, independently, H, CN or NO$_2$.

In some embodiments, each Cy$^6$ is unsubstituted or substituted C$_{6-10}$ aryl, unsubstituted or substituted 5-10 membered heteroaryl, unsubstituted or substituted C$_{3-6}$ cycloalkyl, or unsubstituted or substituted 4-12 membered heterocycloalkyl, wherein the substituted C$_{6-10}$ aryl, 5-10 membered heteroaryl, C$_{3-6}$ cycloalkyl or 4-12 membered heterocycloalkyl forming Cy$^6$ is substituted with 1, 2, 3, 4 or 5 substituents each independently selected from halogen, R$^{Cy6}$, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$ and S(O)$_2$NR$^{c3}$R$^{d3}$.

In some embodiments, Cy$^A$ is a heteroaryl group of Formula Cy$^A$-1:

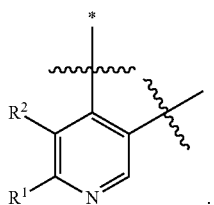

(Cy$^A$-1)

In some embodiments, R$^1$ is H; and R$^2$ is H, halogen, C$_{1-6}$ alkyl, C$_{2-6}$ alkenyl, C$_{2-6}$ alkynyl, C$_{1-6}$ haloalkyl, CN, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{e2}$)NR$^{c2}$R$^{d2}$, NR$^{c2}$C(=NR$^{e2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$ or S(O)$_2$NR$^{c2}$R$^{d2}$.

In some embodiments, R$^1$ is H and R$^2$ is H.

In some embodiments, R$^1$ and R$^2$ in combination, together with the carbon atoms to which R$^1$ and R$^2$ are attached, form a 5, 6 or 7-membered carbocyclic or heterocyclic ring containing 3 to 7 ring carbon atoms and 0, 1 or 2 ring heteroatoms, each independently selected from N, O and S, wherein the ring formed by the combination of R$^1$ and R$^2$ is unsubstituted or substituted by 1, 2 or 3 substituents independently selected from halogen, C$_{1-6}$ alkyl, C$_{1-6}$ haloalkyl, CN, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$ and oxo.

In some embodiments, R$^1$ and R$^2$ in combination form a C$_{3-5}$ alkylene that is unsubstituted or substituted by 1, 2 or 3 substituents independently selected from halogen, C$_{1-6}$ alkyl, CN, OR$^{a2}$, OC(O)R$^{a2}$ and oxo.

In some embodiments, R$^1$ and R$^2$ in combination form a C$_{3-5}$ alkylene that is unsubstituted or substituted by OR$^{a2}$.

In some embodiments, R$^1$ and R$^2$ in combination form a C$_{3-5}$ alkylene that is unsubstituted or substituted by OH.

In some embodiments, Cy$^A$ is a heteroaryl group of Formula Cy$^A$-2:

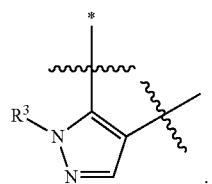

(Cy$^A$-2)

In some embodiments, R$^3$ is H.

In some embodiments, R$^3$ is C$_{1-6}$ alkyl.

In some embodiments, R$^3$ is methyl.

In some embodiments, Cy$^A$ is a heteroaryl group of Formula Cy$^A$-3:

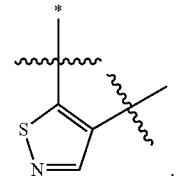

(Cy$^A$-3)

In some embodiments, Cy$^B$ is unsubstituted or substituted C$_{3-7}$ cycloalkyl.

In some embodiments, Cy$^B$ is unsubstituted or substituted cyclohexyl.

In some embodiments, Cy$^B$ is unsubstituted or substituted 4-10 membered heterocycloalkyl.

In some embodiments, Cy$^B$ is unsubstituted or substituted 4-7 membered heterocycloalkyl.

In some embodiments, Cy$^B$ is unsubstituted or substituted heterocycloalkyl, the ring atoms of which consist of carbon atoms and 1 or 2 nitrogen atoms.

In some embodiments, Cy$^B$ is unsubstituted or substituted heterocycloalkyl, the ring atoms of which consist of carbon atoms and 1 or 2 nitrogen atoms, and the heterocycloalkyl forming Cy$^B$, which can be 4-7 membered heterocycloalkyl, is unsubstituted or substituted with 1, 2 or 3 substituents independently selected from F, Cl, methyl, ethyl, cyclopropyl, CF$_3$, CN, OH, methoxy and NH$_2$.

In some embodiments, Cy$^B$ is an unsubstituted or substituted pyrrolidine, piperidine, azepane or diazepane ring.

In some embodiments, Cy$^B$ is selected from piperidin-1-yl, azepan-1-yl, 1,4-diazepan-1-yl and pyrrolidin-1-yl.

In some embodiments, a nitrogen atom of Cy$^B$ forms the bond between Cy$^B$ and Cy$^A$.

In some embodiments, Cy$^B$ is a group of Formula Cy$^B$-1:

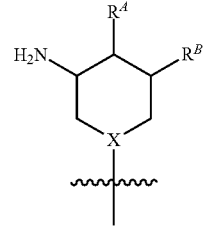

(Cy$^B$-1)

wherein:

X is N or CH;

R$^A$ is H or OH; and

R$^B$ is H, C$_{1-6}$ alkyl, C$_{1-3}$ haloalkyl, or C$_{3-7}$ cycloalkyl.

In some embodiments, Cy$^B$ is a group of Formula Cy$^B$-2:

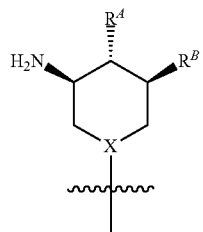
(Cy$^B$-2)

wherein:

X is N or CH;

R$^A$ is H or OH; and

R$^B$ is H, C$_{1-6}$ alkyl, C$_{1-3}$ haloalkyl, or C$_{3-7}$ cycloalkyl.

In some embodiments, X is N.

In some embodiments, X is CH.

In some embodiments, Cy$^B$ is a group of Formula Cy$^B$-3:

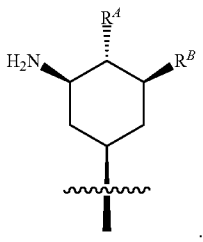
(Cy$^B$-3)

In some embodiments, Cy$^B$ is a group of Formula Cy$^B$-4:

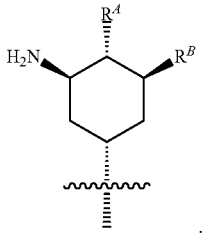
(Cy$^B$-4)

In some embodiments, R$^A$ is H.

In some embodiments, R$^A$ is OH.

In some embodiments, R$^B$ is H.

In some embodiments, R$^B$ is C$_{1-6}$ alkyl.

In some embodiments, R$^B$ is methyl.

In some embodiments, R$^B$ is C$_{1-3}$ haloalkyl.

In some embodiments, R$^B$ is trifluoromethyl.

In some embodiments, R$^B$ is C$_{3-7}$ cycloalkyl.

In some embodiments, R$^B$ is cyclopropyl.

In some embodiments, Cy$^B$ can be a group of any of the following Formulae (B-1) to (B-30):

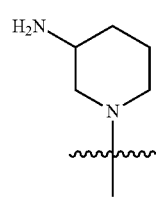
(B-1)

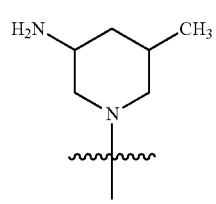
(B-2)

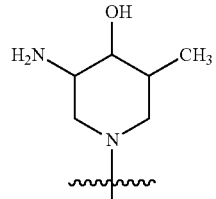
(B-3)

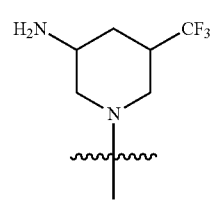
(B-4)

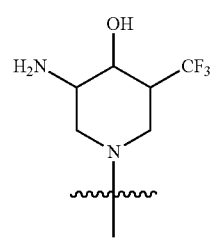
(B-5)

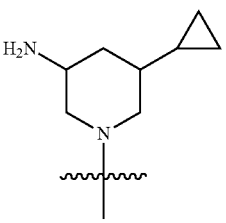
(B-6)

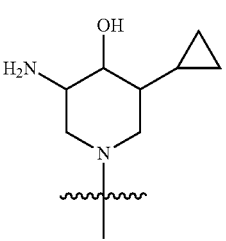
(B-7)

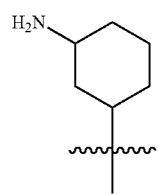
(B-8)
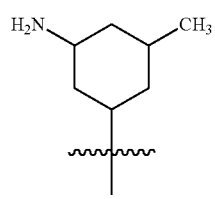
(B-9)
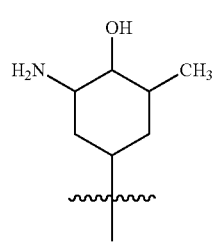
(B-10)
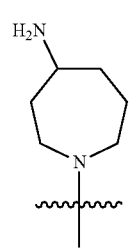
(B-11)
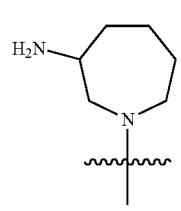
(B-12)
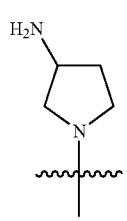
(B-13)
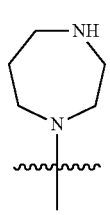
(B-14)
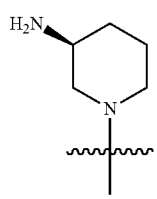
(B-15)
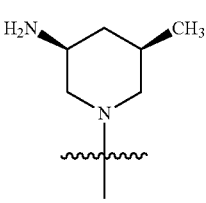
(B-16)
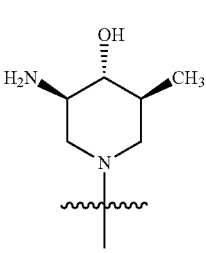
(B-17)
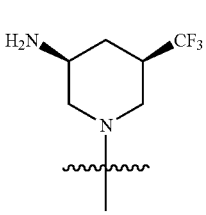
(B-18)
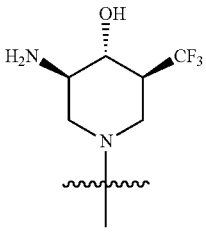
(B-19)
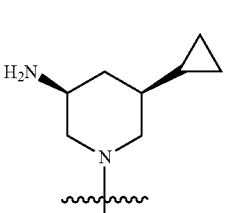
(B-20)
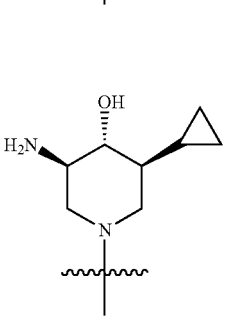
(B-21)

-continued (B-22)
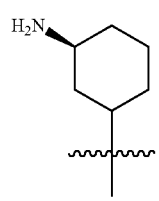

(B-23)
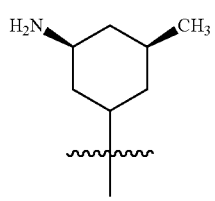

(B-24)
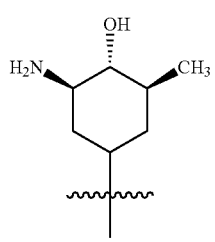

(B-25)
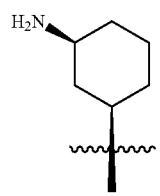

(B-26)
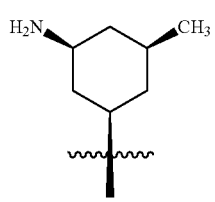

(B-27)
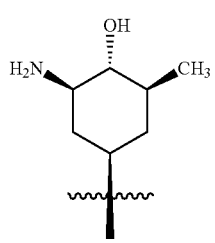

(B-28)
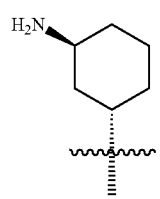

-continued (B-29)
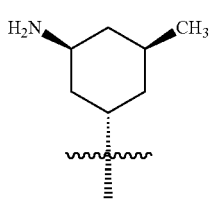

(B-30)
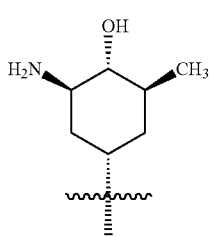

In some embodiments, $R^4$ is H.
In some embodiments, $R^4$ is halogen.
In some embodiments, $R^4$ is $NH_2$.
In some embodiments, $A^5$ is N.
In some embodiments, $A^5$ is $CR^5$.
In some embodiments, $R^5$ is H.
In some embodiments, $R^5$ is halogen.
In some embodiments, $Cy^C$ is of Formula $Cy^C$-1:

(Cy$^C$-1)
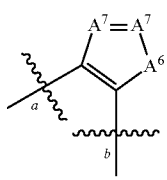

In some embodiments, $Cy^C$ is of Formula $Cy^C$-2:

(Cy$^C$-2)
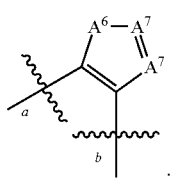

In some embodiments, $Cy^C$ is of Formula $Cy^C$-3:

(Cy$^C$-3)
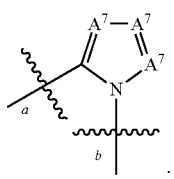

In some embodiments, Cy$^C$ is of Formula Cy$^C$-4:
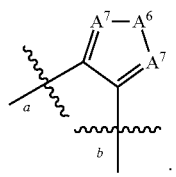
(Cy$^C$-4)
In some embodiments, Cy$^C$ is of Formula Cy$^C$-5:
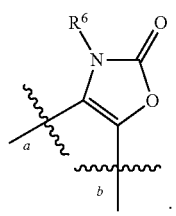
(Cy$^C$-5)
In some embodiments, Cy$^C$ is selected from the group of Formulae C-1 to C-35:
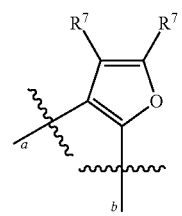
(C-1)
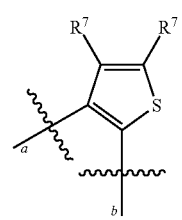
(C-2)
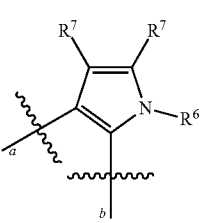
(C-3)
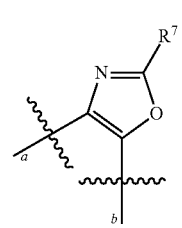
(C-4)
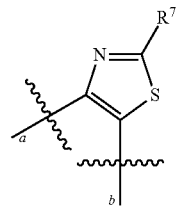
(C-5)
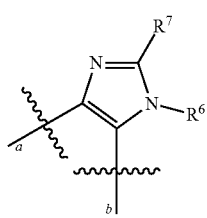
(C-6)
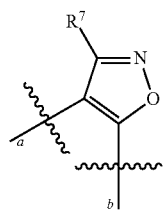
(C-7)
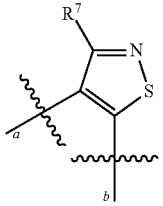
(C-8)
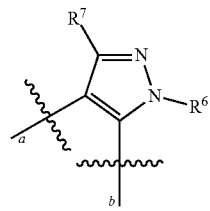
(C-9)
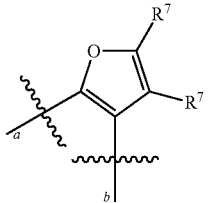
(C-10)
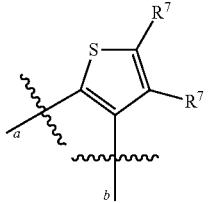
(C-11)

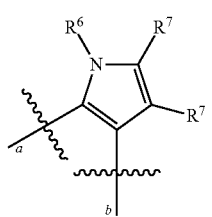
(C-12)
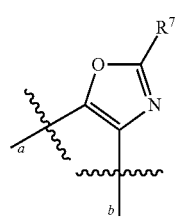
(C-13)
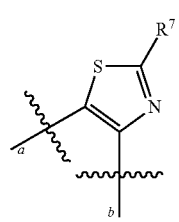
(C-14)
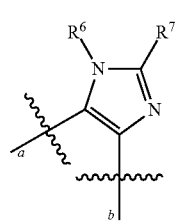
(C-15)
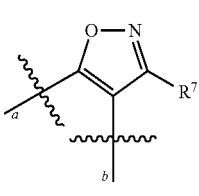
(C-16)
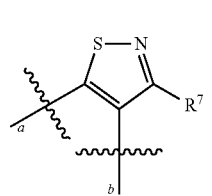
(C-17)
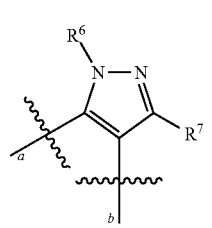
(C-18)
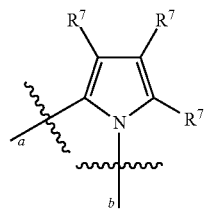
(C-19)
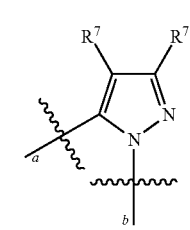
(C-20)
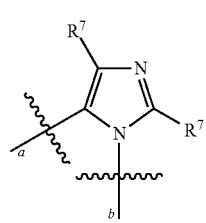
(C-21)
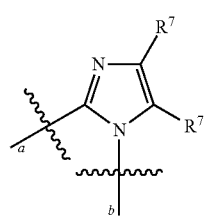
(C-22)
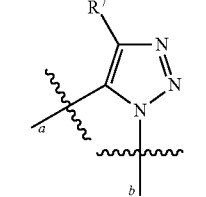
(C-23)
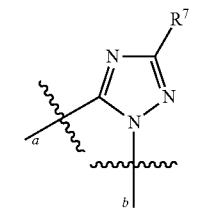
(C-24)
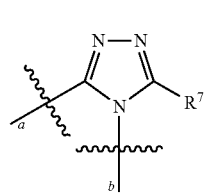
(C-25)

(C-26) 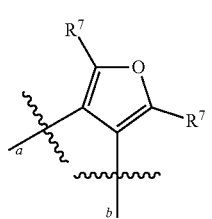
(C-27) 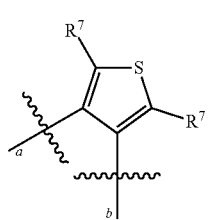
(C-28) 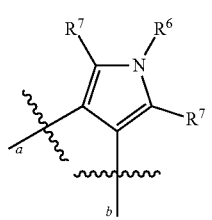
(C-29) 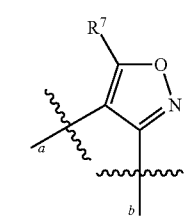
(C-30) 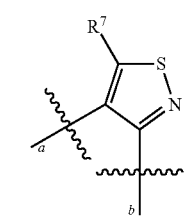
(C-31) 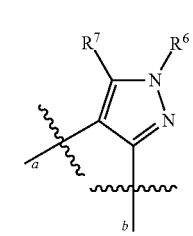
(C-32) 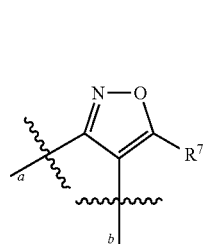
(C-33) 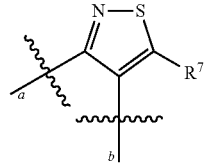
(C-34) 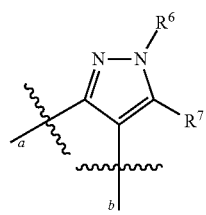
(C-35) 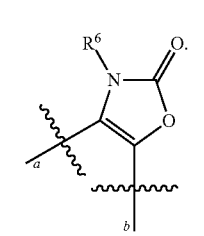
In some embodiments, $Cy^C$ is selected from the group of Formulae C-1, C-2, C-4, C-5, C-10 to C-12, C-15, C-20, and C-35:
(C-1) 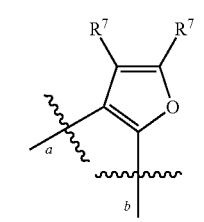
(C-2) 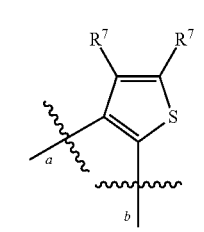
(C-4) 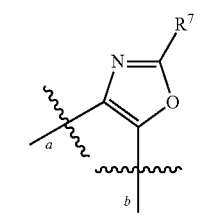

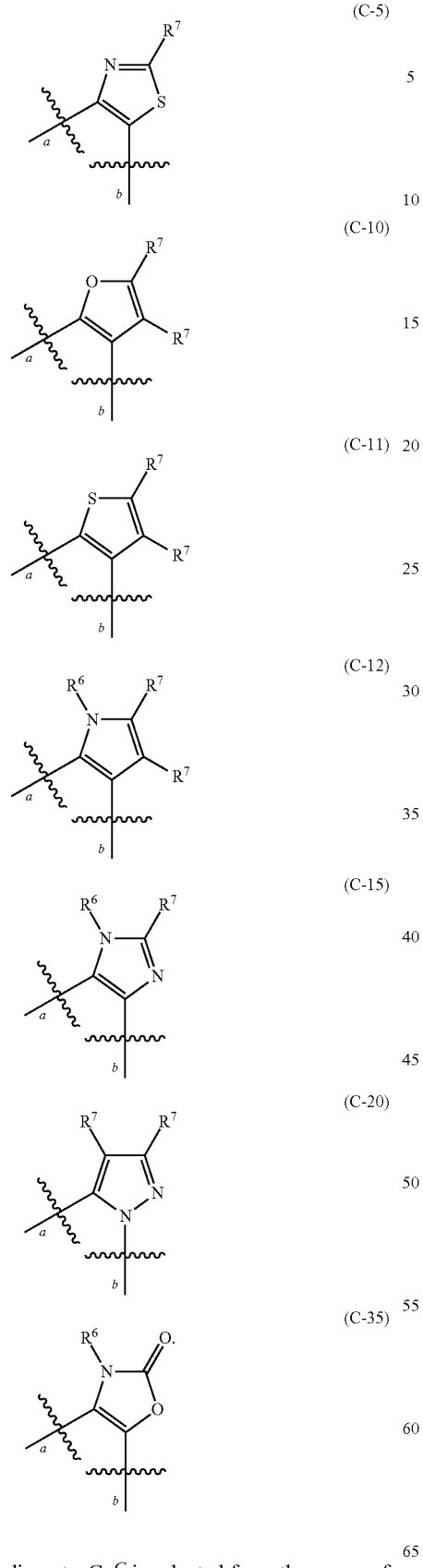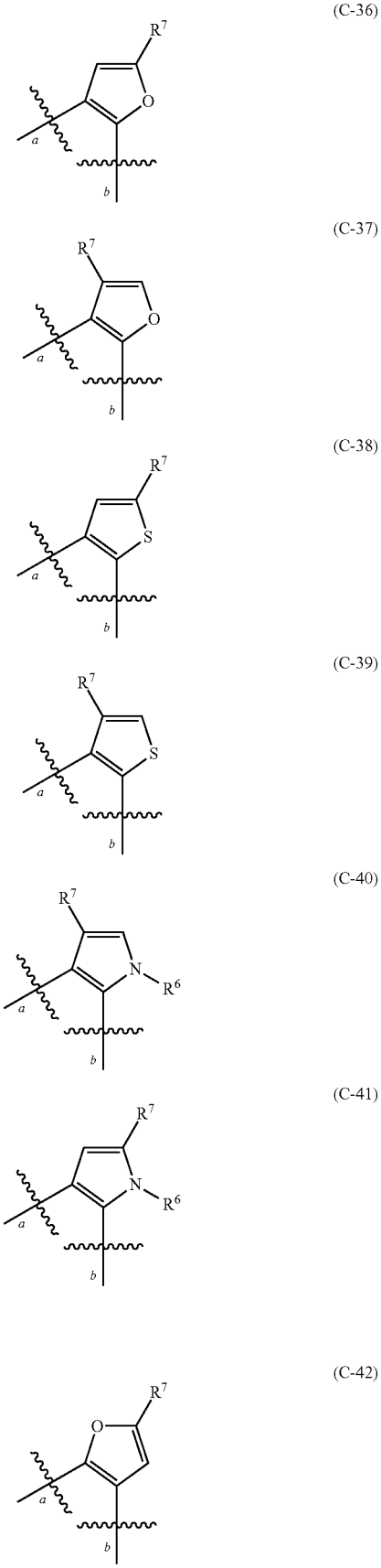
In some embodiments, $Cy^C$ is selected from the group of Formulae C-36 to C-62:

-continued
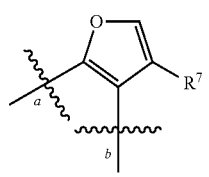 (C-43)
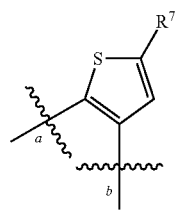 (C-44)
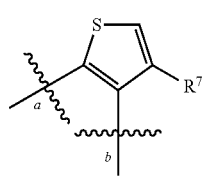 (C-45)
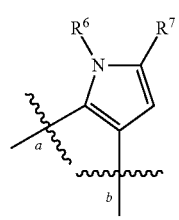 (C-46)
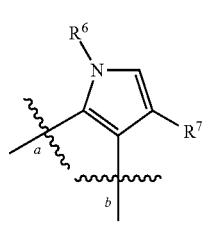 (C-47)
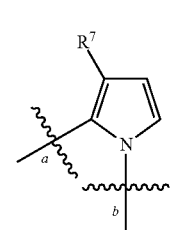 (C-48)
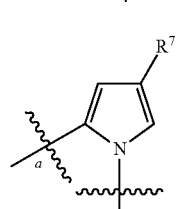 (C-49)
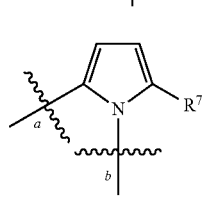 (C-50)
-continued
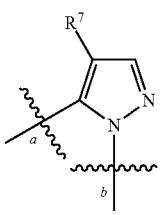 (C-51)
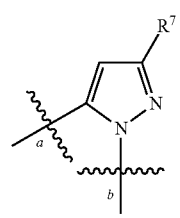 (C-52)
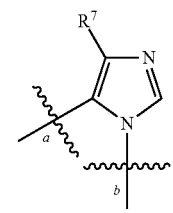 (C-53)
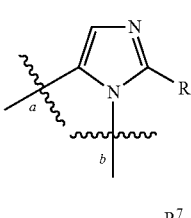 (C-54)
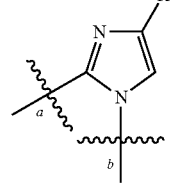 (C-55)
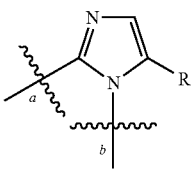 (C-56)
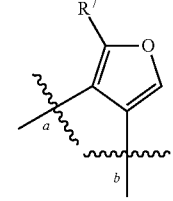 (C-57)
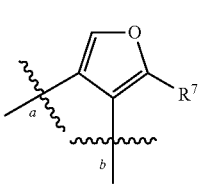 (C-58)

-continued (C-59) 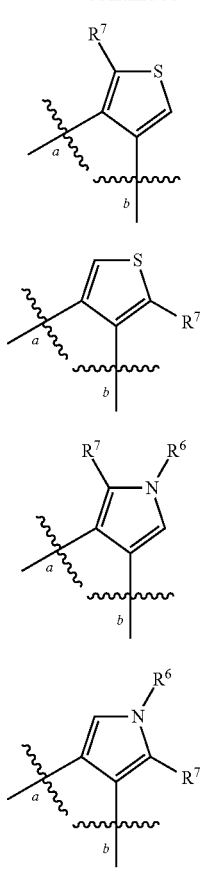

(C-60)

(C-61)

(C-62)

In some embodiments, the compound is of the following Formula (IIa):

(IIa) 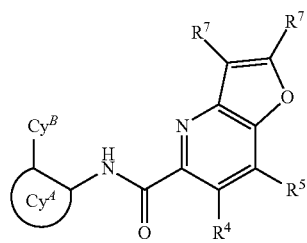

In some embodiments, the compound is of the following Formula (IIb):

(IIb) 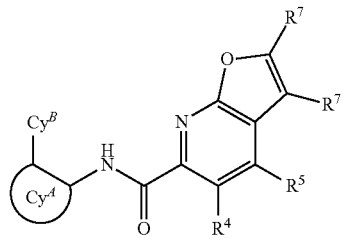

In some embodiments, the compound is of the following Formula (IIIa):

(IIIa) 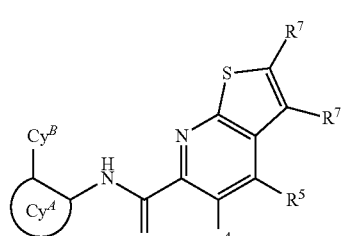

In some embodiments, the compound is of the following Formula (IIIb):

(IIIb) 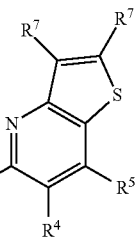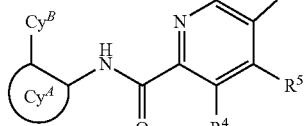

In some embodiments, the compound is of the following Formula (IIIc):

(IIIc) 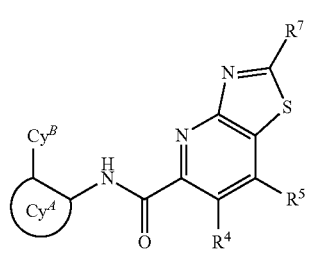

In some embodiments, the compound is of the following Formula (IVa):

(IVa) 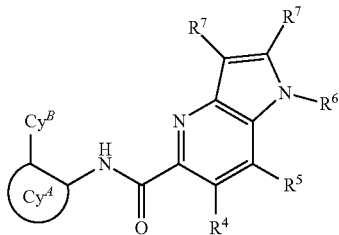

In some embodiments, the compound is of the following Formula (IVb):

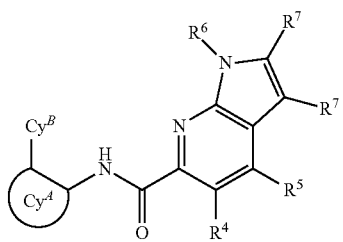

(IVb)

In some embodiments, the compound is of the following Formula (V):

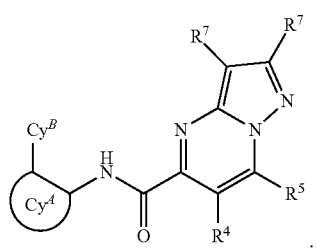

(V)

In some embodiments, each $R^7$ is hydrogen.
In some embodiments, one $R^7$ is hydrogen
In some embodiments, one $R^7$ is hydrogen and one $R^7$ is other than hydrogen.
In some embodiments, none of $R^7$ is hydrogen.
In some embodiments, the compound is of the following Formula (VIa):

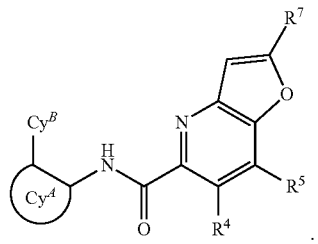

(VIa)

In some embodiments, the compound is of the following Formula (VIb):

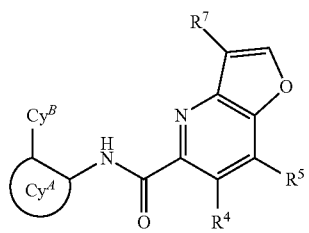

(VIb)

In some embodiments, the compound is of the following Formula (VIIa):

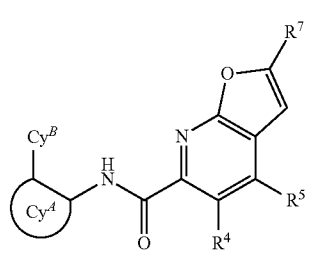

(VIIa)

In some embodiments, the compound is of the following Formula (VIIb):

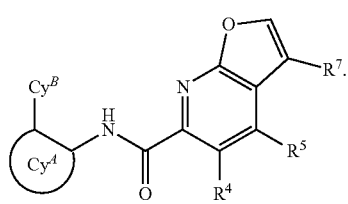

(VIIb)

In some embodiments, the compound is of the following Formula (VIIIa):

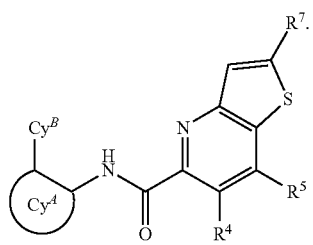

(VIIIa)

In some embodiments, the compound is of the following Formula (VIIIb):

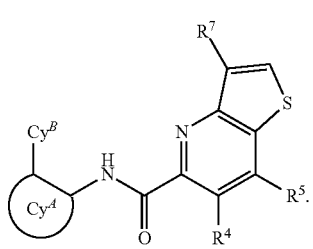

(VIIIb)

In some embodiments, the compound is of the following Formula (IXa):

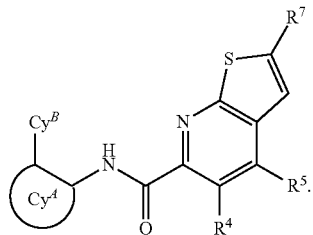
(IXa)
In some embodiments, the compound is of the following Formula (IXb):
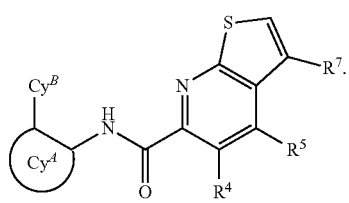
(IXb)
In some embodiments, the compound can be of any of the following Formulae (X) to (XIII) or (XVII) to (XXXV):
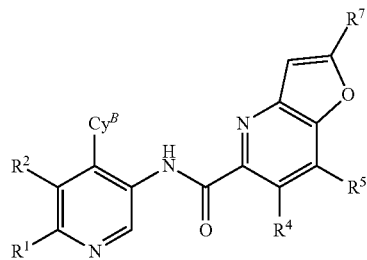
(X)
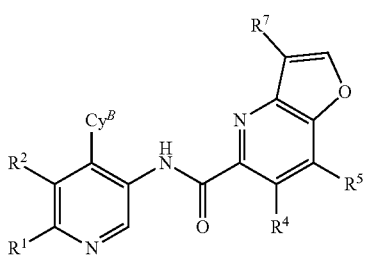
(XI)
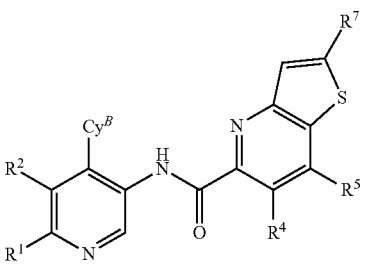
(XII)
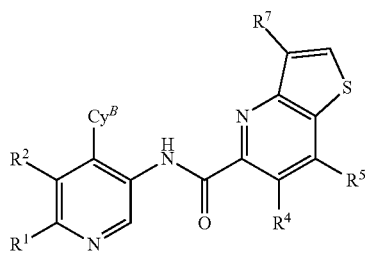
(XIII)
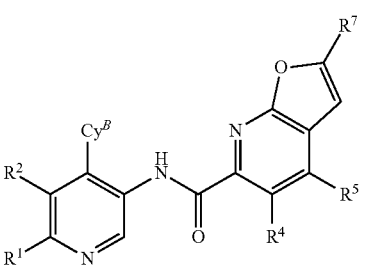
(XXVII)
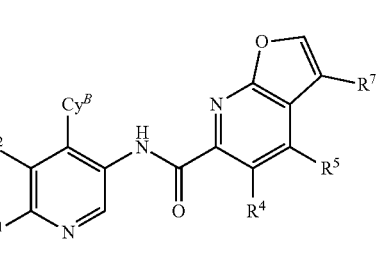
(XXVIII)
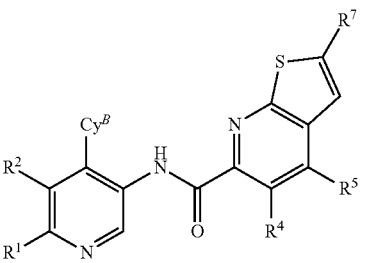
(XXIX)
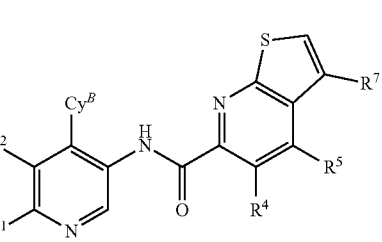
(XXX)
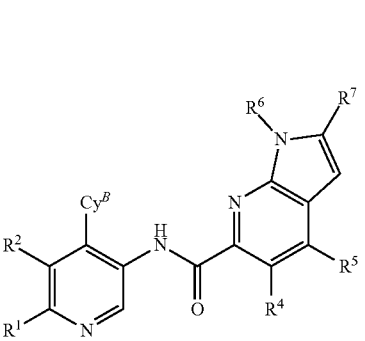
(XXXI)

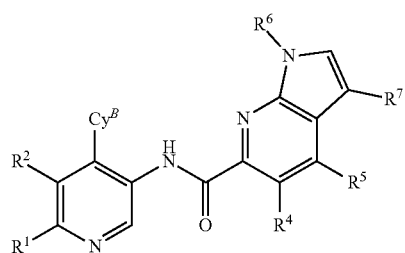
(XXXII)
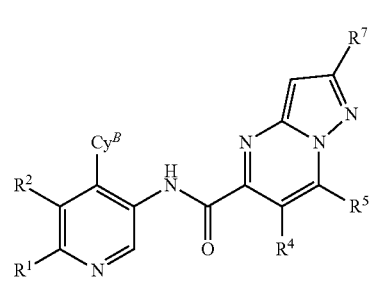
(XXXIII)
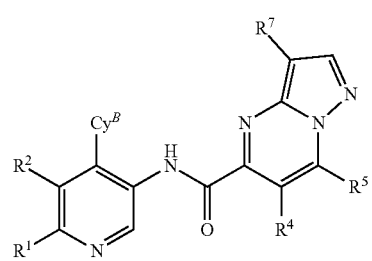
(XXXIV)
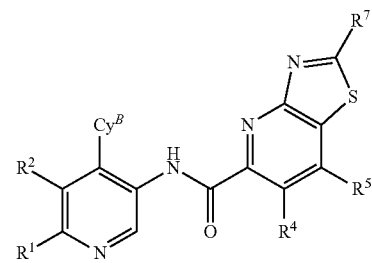
(XXXV)
In some embodiments, the compound can be of any of the following Formulae (XIV) to (XXV) or (XXXVI) to (LXI):
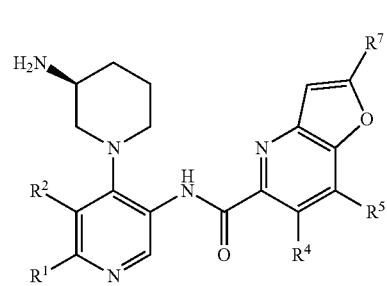
(XIV)
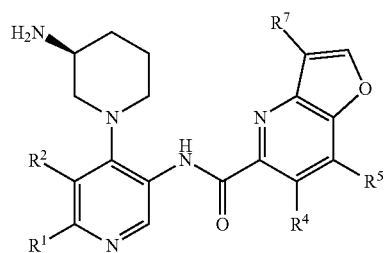
(XV)
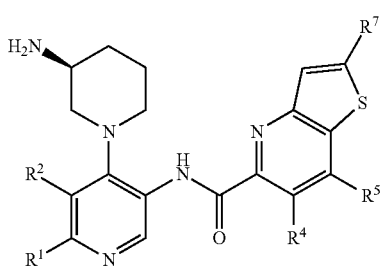
(XVI)
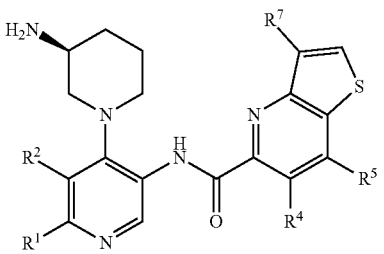
(XVII)
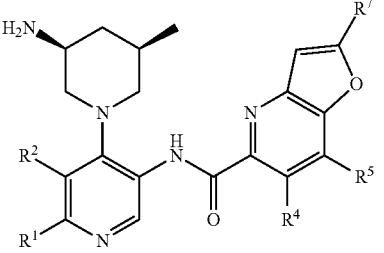
(XVIII)
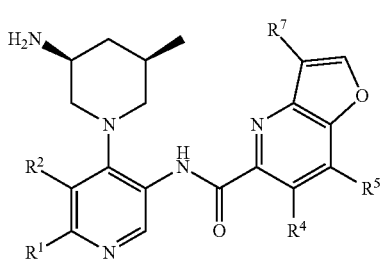
(XIX)
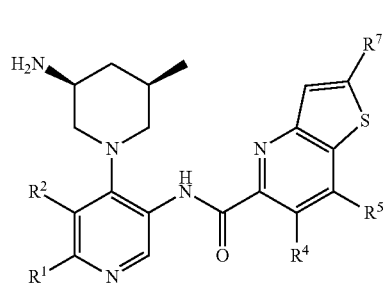
(XX)

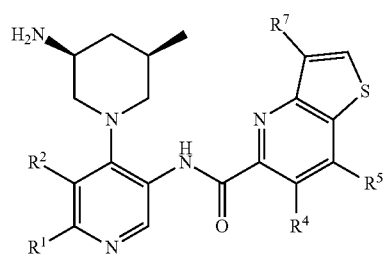 (XXI)
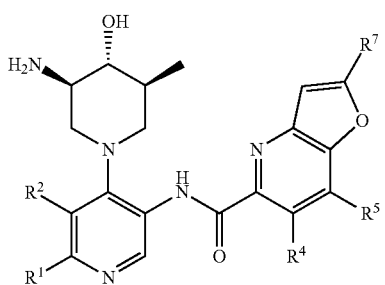 (XXII)
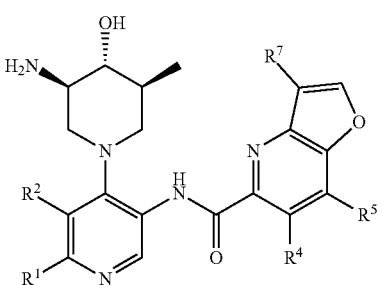 (XXIII)
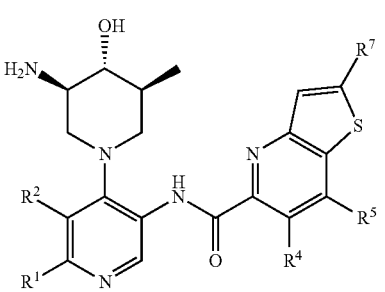 (XXIV)
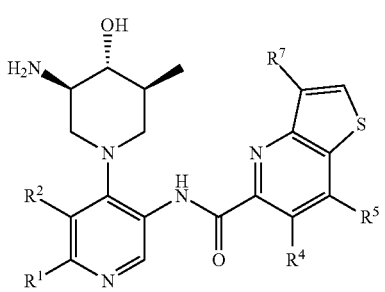 (XXV)
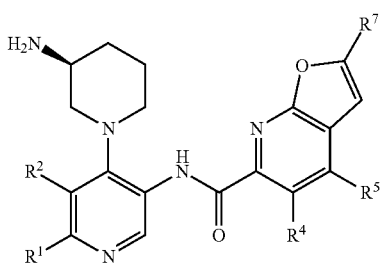 (XXXVI)
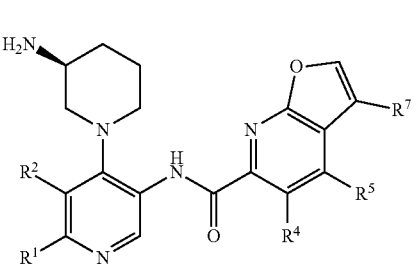 (XXXVII)
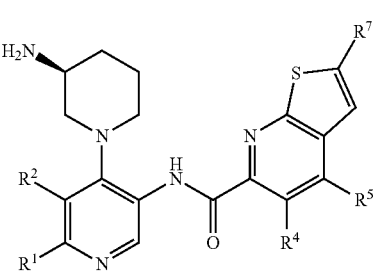 (XXXVIII)
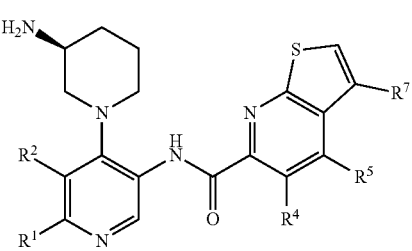 (XXXIX)
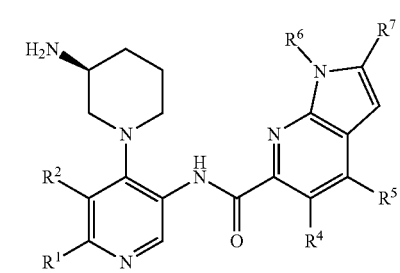 (XL)
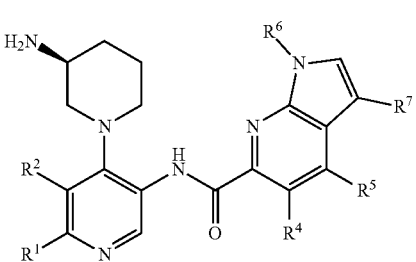 (XLI)

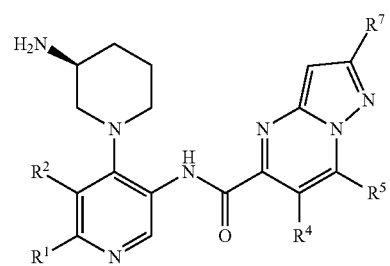
(XLII)
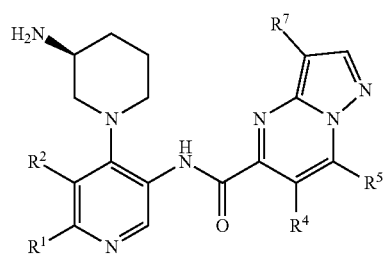
(XLIII)
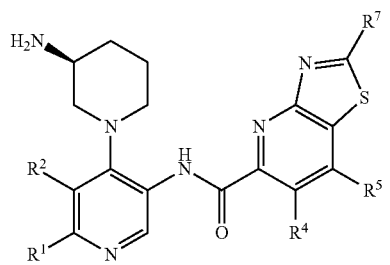
(XLIV)
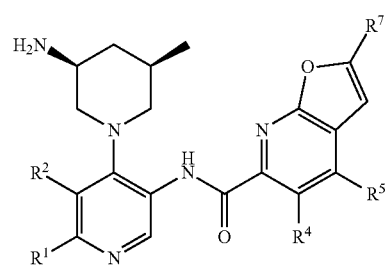
(XLV)
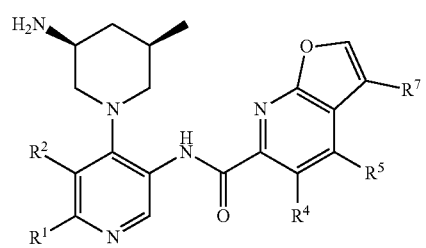
(XLVI)
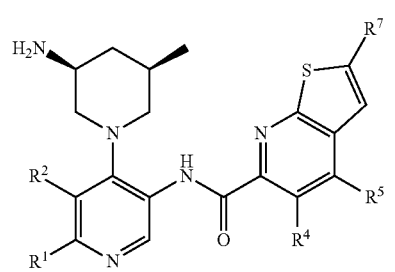
(XLVII)
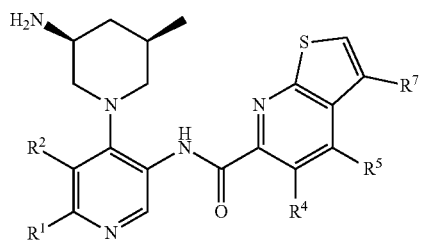
(XLVIII)
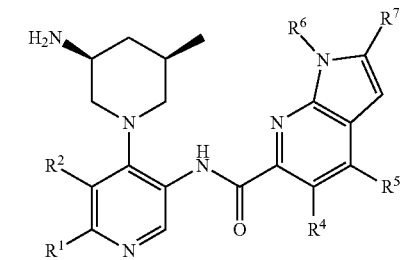
(XLVIII)
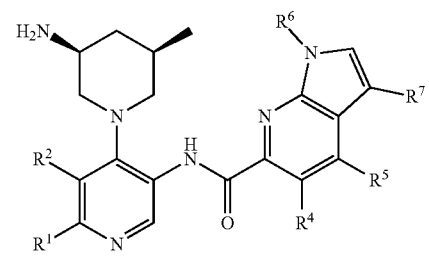
(XLIX)
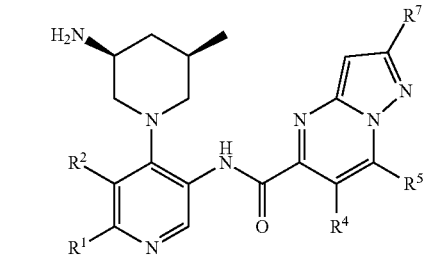
(L)
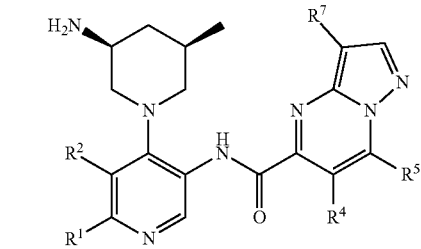
(LI)
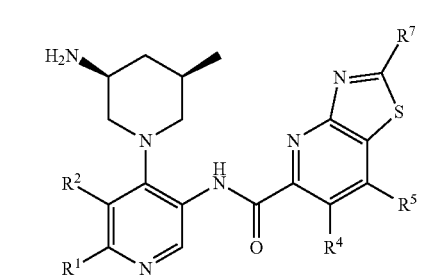
(LII)

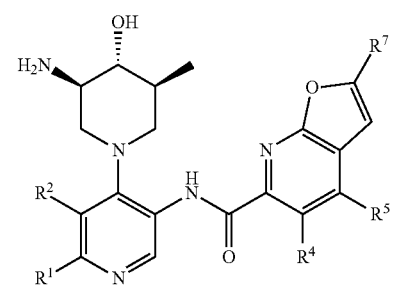
(LIII)
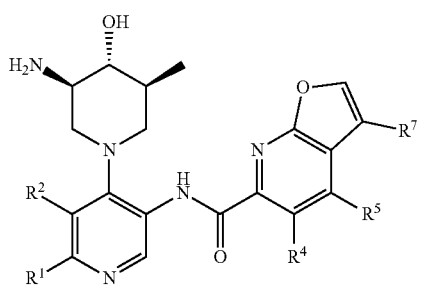
(LIV)
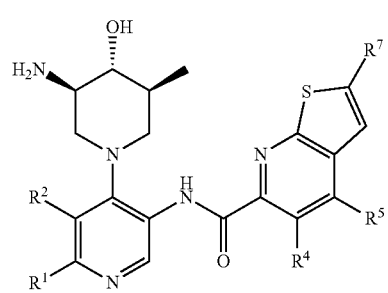
(LV)
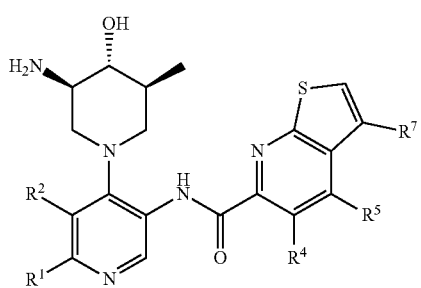
(LVI)
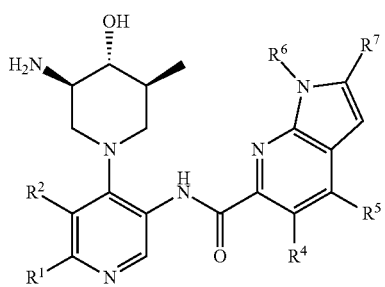
(LVII)
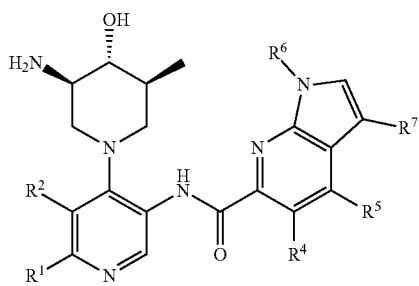
(LVIII)
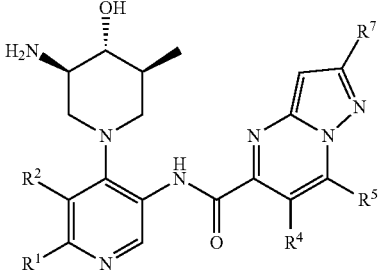
(LIX)
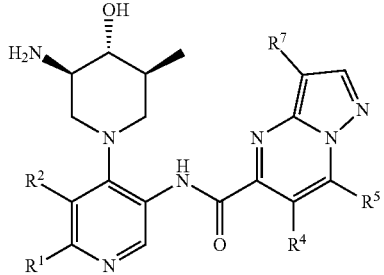
(LX)
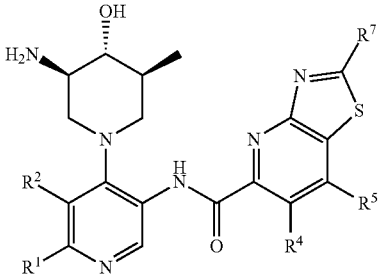
(LXI)
In some embodiments, $R^1$, $R^2$, $R^4$ and $R^5$ are each H.
In some embodiments, the compound is a compound of the following Formula (XXVI):
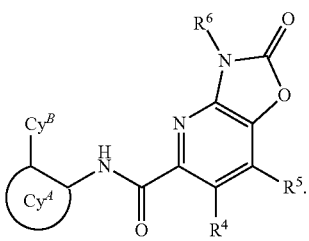
(XXVI)
In some embodiments, each $R^6$ is H is $C_{1-6}$ alkyl, $Cy^6$, or L-$Cy^6$;

wherein the $C_{1-6}$ alkyl forming $R^6$ is unsubstituted or substituted with 1, 2 or 3 substituents independently selected from halogen, $C_{1-6}$ alkyl, $C_{1-6}$ haloalkyl, CN, and $OR^{a1}$.

In some embodiments, each $R^6$ is $C_{1-6}$ alkyl.

In some embodiments, each $R^6$ is Me.

In some embodiments, each $R^6$ is H.

In some embodiments:

each $R^7$ is independently, H, $C_{1-6}$ alkyl, halogen, $Cy^6$, or $L\text{-}Cy^6$;

$Cy^6$ is unsubstituted or substituted $C_{6-10}$ aryl, unsubstituted or substituted 5-10 membered heteroaryl, unsubstituted or substituted $C_{3-6}$ cycloalkyl, or unsubstituted or substituted 4-12 membered heterocycloalkyl, wherein the substituted $C_{6-10}$ aryl, 5-10 membered heteroaryl, $C_{3-6}$ cycloalkyl or 4-12 membered heterocycloalkyl forming $Cy^6$ is substituted with 1, 2 or 3 substituents each independently selected from halogen, $R^{Cy6}$, CN, $OR^{a3}$, and $NR^{c3}R^{d3}$, alternatively, the substituted $C_{6-10}$ aryl, 5-10 membered heteroaryl, $C_{3-6}$ cycloalkyl or 4-12 membered heterocycloalkyl forming $Cy^6$ is substituted with unsubstituted $C_{6-10}$ aryl;

wherein each $R^{Cy6}$ is $C_{1-6}$ alkyl, each of which is independently unsubstituted or substituted by 1, 2 or 3 substituents independently selected from halogen, CN, and $OR^{a3}$; and wherein $R^{c3}$ and $R^{d3}$ attached to the same N atom, together with the N atom to which they are both attached, form a 6-membered heterocycloalkyl group or 5-membered heteroaryl group, each optionally substituted with 1 or 2 substituents independently selected from $C_{1-6}$ alkyl, halo, CN, and $OR^{a6}$.

In some embodiments:

each $R^7$ is independently, H, $C_{1-6}$ alkyl, halogen, $Cy^6$, or $L\text{-}Cy^6$;

$Cy^6$ is unsubstituted or substituted $C_{6-10}$ aryl, unsubstituted or substituted 5-10 membered heteroaryl, unsubstituted or substituted $C_{3-6}$ cycloalkyl or unsubstituted or substituted 4-12 membered heterocycloalkyl, wherein the substituted $C_{6-10}$ aryl, 5-10 membered heteroaryl, $C_{3-6}$ cycloalkyl or 4-12 membered heterocycloalkyl forming $Cy^6$ is substituted with 1, 2 or 3 substituents each independently selected from halogen, $R^{Cy6}$, CN, $OR^{a3}$, and $NR^{c3}R^{d3}$, alternatively, the substituted $C_{6-10}$ aryl, 5-10 membered heteroaryl, $C_{3-6}$ cycloalkyl or 4-12 membered heterocycloalkyl forming $Cy^6$ is substituted with unsubstituted $C_{6-10}$ aryl;

wherein each $R^{Cy6}$ is $C_{1-6}$ alkyl, each of which is independently unsubstituted or substituted by 1, 2 or 3 substituents independently selected from halogen, CN, and $OR^{a3}$; and wherein $R^{c3}$ and $R^{d3}$ attached to the same N atom, together with the N atom to which they are both attached, form a 6-membered heterocycloalkyl group optionally substituted with 1 or 2 substituents independently selected from $C_{1-6}$ alkyl, halo, CN, and $OR^{a6}$.

In some embodiments, each $R^7$ is H.

In some embodiments, at least one $R^7$ is other than H.

In some embodiments, no more than one $R^7$ is other than H.

In some embodiments, each $R^7$ is other than H.

In some embodiments, no more than one $R^7$ is other than H, $C_{1-6}$ alkyl, halogen, $Cy^6$, and $\text{-}L\text{-}Cy^6$.

In some embodiments, one $R^7$ is hydrogen.

In some embodiments, each $R^7$ that is other than H is $C_{1-6}$ alkyl.

In some embodiments, each $R^7$ that is other than H is methyl, ethyl, propyl, or isopropyl.

In some embodiments, no more than one $R^7$ is other than H.

In some embodiments, each $R^7$ is H.

In some embodiments, each $R^7$ is $C_{1-6}$ alkyl.

In some embodiments, each $R^7$ is methyl, ethyl, propyl, or isopropyl.

In some embodiments, one and only one of $R^7$ is $Cy^6$ or $L\text{-}Cy^6$ and the other $R^7$ groups are H.

In some embodiments, one and only one of $R^7$ is $Cy^6$ and the other $R^7$ groups are H.

In some embodiments, one and only one of $R^7$ is $L\text{-}Cy^6$ and the other $R^7$ groups are H.

In some embodiments, each $Cy^6$ unsubstituted or substituted $C_{6-10}$ aryl.

In some embodiments, each $Cy^6$ is unsubstituted or substituted phenyl.

In some embodiments, each $Cy^6$ is phenyl substituted with 1, 2 or 3 substituents.

In some embodiments, each $Cy^6$ is phenyl substituted with 1, 2 or 3 substituents each independently selected from halogen and $OR^{a3}$.

In some embodiments, each $Cy^6$ is 2-fluorophenyl, 2,6-difluorophenyl, 2,6-difluoro-3-methoxyphenyl, or 2,6-difluoro-4-methoxyphenyl.

In some embodiments, each $Cy^6$ is unsubstituted or substituted 5-10 membered heteroaryl.

In some embodiments, each $Cy^6$ is unsubstituted or substituted 5-10 membered heteroaryl, the ring atoms of which consist of carbon atoms and 1 or 2 heteroatoms independently selected from O and N.

In some embodiments, each $Cy^6$ is unsubstituted or substituted 5-10 membered heteroaryl, the ring atoms of which consist of carbon atoms and 1 or 2 nitrogen atoms.

In some embodiments, each $Cy^6$ is unsubstituted or substituted 5-10 membered heteroaryl, the ring atoms of which consist of carbon atoms, 1 oxygen atom and 1 nitrogen atom.

In some embodiments, each $Cy^6$ is unsubstituted or substituted pyridinyl, isoxazolyl, pyrazolyl or pyrimidinyl.

In some embodiments, each $Cy^6$ is unsubstituted or substituted pyridin-3-yl, pyridin-4-yl, isoxazol-4-yl, 1H-pyrazol-4-yl, or pyrimidin-5-yl.

In some embodiments, each $Cy^6$ is pyridin-3-yl, pyridin-4-yl, isoxazol-4-yl, 1H-pyrazol-4-yl, or pyrimidin-5-yl, each of which is unsubstituted or substituted with one or two substituents selected from halogen, $C_{1-6}$ alkyl, CN, $OR^{a3}$, and $NR^{c3}R^{d3}$.

In some embodiments, each $Cy^6$ is 6-morpholinopyridin-3-yl, 6-methoxypyridin-3-yl, 5-methoxypyridin-3-yl, 5-cyanopyridin-3-yl, 2,6-difluoropyridin-4-yl, isoxazol-4-yl, 1-methyl-1H-pyrazol-4-yl, or pyrimidin-5-yl.

In some embodiments, each $Cy^6$ is unsubstituted or substituted $C_{3-6}$ cycloalkyl.

In some embodiments, each $Cy^6$ is cyclopropyl, e.g., unsubstituted cyclopropyl.

In some embodiments, each $Cy^6$ is cyclopropyl, which is either unsubstituted or substituted with $C_{1-6}$ alkyl, e.g., methyl, or $C_{6-10}$ aryl, e.g., phenyl.

In some embodiments, each $Cy^6$ is unsubstituted or substituted 4-12 membered heterocycloalkyl.

In some embodiments, each $Cy^6$ is 4-12 membered heterocycloalkyl which is unsubstituted or substituted with one or two $C_{1-6}$ alkyl groups.

In some embodiments, each $Cy^6$ is 4-tetrahydropyranyl, 3-tetrahydrofuryl, 3,4-dihydro-2H-pyran-5-yl, or 1-methylpiperidin-4-yl.

In some embodiments, each $L^6$ is unsubstituted $C_{1-6}$ alkylene or $C_{1-6}$ alkylene substituted with 1, 2, or 3 substituents independently selected from F, Cl, CN, OH, and $O(C_{1-6}$ alkyl).

In some embodiments, each $L^6$ is unsubstituted $C_{1-6}$ alkylene.

In some embodiments, each $L^6$ is $CH_2$.

In some embodiments, each $R^7$ is H, methyl, ethyl, propyl, isopropyl, cyclopropyl, phenyl, 2-fluorophenyl, 2,6-difluorophenyl, 2,6-difluoro-3-methoxyphenyl, 2,6-difluoro-4-methoxyphenyl, benzyl, 2-fluorobenzyl, 2,6-difluorobenzyl, 2,6-difluoro-3-methoxybenzyl, 2,6-difluoro-4-methoxybenzyl, pyridin-3-yl, pyridin-4-yl, isoxazol-4-yl, 1H-pyrazol-4-yl, pyrimidin-5-yl, 6-morpholinopyridin-3-yl, 6-methoxypyridin-3-yl, 5-methoxypyridin-3-yl, 5-cyanopyridin-3-yl, 2,6-difluoropyridin-4-yl, isoxazol-4-yl, 1-methyl-1H-pyrazol-4-yl, pyrimidin-5-yl, 4-tetrahydropyranyl, 3-tetrahydrofuryl, 3,4-dihydro-2H-pyran-5-yl, or 1-methylpiperidin-4-yl.

In some embodiments, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$ and $R^{d6}$ are each independently selected from H and $C_{1-6}$ alkyl.

In some embodiments, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$ and $R^{d6}$ are each independently selected from H and methyl.

In some embodiments, $R^{e1}$, $R^{e2}$, $R^{e3}$, $R^{e4}$, $R^{e5}$ and $R^{e6}$ are each independently selected from H and $C_{1-6}$ alkyl.

In some embodiments, $R^{e1}$, $R^{e2}$, $R^{e3}$, $R^{e4}$, $R^{e5}$ and $R^{e6}$ are each independently selected from H and methyl.

In some embodiments, $R^{e1}$, $R^{e2}$, $R^{e3}$, $R^{e4}$, $R^{e5}$ and $R^{e6}$ are each H.

Examples of the compounds of Formula (I) include the following compounds and or pharmaceutically acceptable salts thereof:

N-(4-(3-amino-5-methylpiperidin-1-yl)pyridin-3-yl)-2-propylfuro[3,2-b]pyridine-5-carboxamide;

N-{4-[3-amino-5-methylpiperidin-1-yl]pyridin-3-yl}-2-isopropylfuro[3,2-b]pyridine-5-carboxamide;

N-(4-(3-amino-5-methylpiperidin-1-yl)pyridin-3-yl)-2-(6-methoxypyridin-3-yl)furo[3,2-b]pyridine-5-carboxamide;

N-(4-(3-amino-5-methylpiperidin-1-yl)pyridin-3-yl)-2-(2,6-difluorophenyl)furo[3,2-b]pyridine-5-carboxamide;

N-(4-(3-amino-5-methylpiperidin-1-yl)pyridin-3-yl)-2-(6-morpholinopyridin-3-yl)furo[3,2-b]pyridine-5-carboxamide;

N-{4-[3-amino-4-hydroxy-5-methylpiperidin-1-yl]pyridin-3-yl}-2-isopropylfuro[3,2-b]pyridine-5-carboxamide;

N-(4-(3-amino-4-hydroxy-5-methylpiperidin-1-yl)pyridin-3-yl)-2-(6-methoxypyridin-3-yl)furo[3,2-b]pyridine-5-carboxamide;

N-(4-(3-amino-4-hydroxy-5-methylpiperidin-1-yl)pyridin-3-yl)-2-(2,6-difluorophenyl)furo[3,2-b]pyridine-5-carboxamide;

N-(4-(3-amino-4-hydroxy-5-methylpiperidin-1-yl)pyridin-3-yl)-2-(6-morpholinopyridin-3-yl)furo[3,2-b]pyridine-5-carboxamide;

N-(4-(3-amino-4-hydroxy-5-methylpiperidin-1-yl)pyridin-3-yl)-3-isopropylfuro[3,2-b]pyridine-5-carboxamide;

N-(4-(3-amino-4-hydroxy-5-methylpiperidin-1-yl)pyridin-3-yl)-3-(2,6-difluorophenyl)furo[3,2-b]pyridine-5-carboxamide;

N-(4-(3-amino-4-hydroxy-5-methylpiperidin-1-yl)pyridin-3-yl)-3-(2-fluorophenyl)furo[3,2-b]pyridine-5-carboxamide;

N-(4-(3-amino-4-hydroxy-5-methylpiperidin-1-yl)pyridin-3-yl)-3-(2,6-difluoro-3-methoxyphenyl)furo[3,2-b]pyridine-5-carboxamide;

N-(4-(3-amino-4-hydroxy-5-methylpiperidin-1-yl)pyridin-3-yl)-3-(6-methoxypyridin-3-yl)furo[3,2-b]pyridine-5-carboxamide;

N-(4-(3-amino-4-hydroxy-5-methylpiperidin-1-yl)pyridin-3-yl)-3-ethylfuro[3,2-b]pyridine-5-carboxamide;

N-(4-(3-amino-4-hydroxy-5-methylpiperidin-1-yl)pyridin-3-yl)-3-(1-methylpiperidin-4-yl)furo[3,2-b]pyridine-5-carboxamide;

N-(4-(3-amino-4-hydroxy-5-methylpiperidin-1-yl)pyridin-3-yl)-3-(tetrahydro-2H-pyran-4-yl)furo[3,2-b]pyridine-5-carboxamide;

N-(4-(3-amino-5-methylpiperidin-1-yl)pyridin-3-yl)-3-isopropylfuro[3,2-b]pyridine-5-carboxamide;

N-(4-(3-amino-5-methylpiperidin-1-yl)pyridin-3-yl)-3-(2,6-difluorophenyl)furo[3,2-b]pyridine-5-carboxamide;

N-(4-(3-amino-5-methylpiperidin-1-yl)pyridin-3-yl)-3-ethylfuro[3,2-b]pyridine-5-carboxamide;

N-(4-(3-amino-5-methylpiperidin-1-yl)pyridin-3-yl)-3-(2-fluorophenyl)furo[3,2-b]pyridine-5-carboxamide;

N-(4-(3-amino-5-methylpiperidin-1-yl)pyridin-3-yl)-3-(2,6-difluoro-3-methoxyphenyl)furo[3,2-b]pyridine-5-carboxamide;

N-(4-(3-amino-5-methylpiperidin-1-yl)pyridin-3-yl)-3-(6-methoxypyridin-3-yl)furo[3,2-b]pyridine-5-carboxamide;

N-(4-(3-amino-5-methylpiperidin-1-yl)pyridin-3-yl)-3-(1-methylpiperidin-4-yl)furo[3,2-b]pyridine-5-carboxamide;

N-(4-(3-amino-5-methylpiperidin-1-yl)pyridin-3-yl)-3-(tetrahydro-2H-pyran-4-yl)furo[3,2-b]pyridine-5-carboxamide;

N-(4-(3-amino-5-methylpiperidin-1-yl)pyridin-3-yl)-3-(5-cyanopyridin-3-yl)furo[3,2-b]pyridine-5-carboxamide;

N-(4-(3-amino-5-methylpiperidin-1-yl)pyridin-3-yl)-3-(2,6-difluoropyridin-4-yl)furo[3,2-b]pyridine-5-carboxamide;

N-(4-(3-amino-5-methylpiperidin-1-yl)pyridin-3-yl)-3-(isoxazol-4-yl)furo[3,2-b]pyridine-5-carboxamide;

N-(4-(3-amino-5-methylpiperidin-1-yl)pyridin-3-yl)-3-(1-methyl-1H-pyrazol-4-yl)furo[3,2-b]pyridine-5-carboxamide;

N-(4-(3-amino-5-methylpiperidin-1-yl)pyridin-3-yl)-3-(pyrimidin-5-yl)furo[3,2-b]pyridine-5-carboxamide;

N-(4-(3-amino-5-methylpiperidin-1-yl)pyridin-3-yl)-3-(tetrahydrofuran-3-yl)furo[3,2-b]pyridine-5-carboxamide (diastereomeric mixture);

N-(4-(3-amino-5-methylpiperidin-1-yl)pyridin-3-yl)-3-(5-methoxypyridin-3-yl)furo[3,2-b]pyridine-5-carboxamide;

N-(4-(3-amino-5-methylpiperidin-1-yl)pyridin-3-yl)-3-(3,4-dihydro-2H-pyran-5-yl)furo[3,2-b]pyridine-5-carboxamide;

N-(4-(3-amino-4-hydroxy-5-methylpiperidin-1-yl)pyridin-3-yl)-3-cyclopropylfuro[3,2-b]pyridine-5-carboxamide;

N-(4-(3-amino-5-methylpiperidin-1-yl)pyridin-3-yl)-3-cyclopropylfuro[3,2-b]pyridine-5-carboxamide;

N-(4-(3-aminopiperidin-1-yl)pyridin-3-yl)-3-isopropylfuro[3,2-b]pyridine-5-carboxamide;

N-(4-(3-aminopiperidin-1-yl)pyridin-3-yl)-3-(2,6-difluorophenyl)furo[3,2-b]pyridine-5-carboxamide;

N-(4-(3-amino-4-hydroxy-5-methylpiperidin-1-yl)pyridin-3-yl)-2-propylthieno[3,2-b]pyridine-5-carboxamide;

N-(4-(3-amino-4-hydroxy-5-methylpiperidin-1-yl)pyridin-3-yl)-2-isopropylthieno[3,2-b]pyridine-5-carboxamide;

N-(4-(3-amino-4-hydroxy-5-methylpiperidin-1-yl)pyridin-3-yl)-2-(2,6-difluorophenyl)thieno[3,2-b]pyridine-5-carboxamide;

N-(4-(3-amino-4-hydroxy-5-methylpiperidin-1-yl)pyridin-3-yl)-2-(2-fluorophenyl)thieno[3,2-b]pyridine-5-carboxamide;

N-(4-(3-amino-4-hydroxy-5-methylpiperidin-1-yl)pyridin-3-yl)-2-benzylthieno[3,2-b]pyridine-5-carboxamide;

N-(4-(3-amino-4-hydroxy-5-methylpiperidin-1-yl)pyridin-3-yl)-2-(6-methoxypyridin-3-yl)thieno[3,2-b]pyridine-5-carboxamide;

N-(4-(3-amino-4-hydroxy-5-methylpiperidin-1-yl)pyridin-3-yl)-2-(6-morpholinopyridin-3-yl)thieno[3,2-b]pyridine-5-carboxamide;

N-(4-(3-amino-4-hydroxy-5-methylpiperidin-1-yl)pyridin-3-yl)-2-(2,6-difluoro-4-methoxyphenyl)thieno[3,2-b]pyridine-5-carboxamide;

N-(4-(3-amino-4-hydroxy-5-methylpiperidin-1-yl)pyridin-3-yl)-2-phenylthieno[3,2-b]pyridine-5-carboxamide;

N-(4-(3-amino-4-hydroxy-5-methylpiperidin-1-yl)pyridin-3-yl)-2-cyclopropylthieno[3,2-b]pyridine-5-carboxamide;

N-(4-(3-amino-4-hydroxy-5-methylpiperidin-1-yl)pyridin-3-yl)-2-(1-methyl-1H-pyrazol-4-yl)thieno[3,2-b]pyridine-5-carboxamide;

N-(4-(3-amino-4-hydroxy-5-methylpiperidin-1-yl)pyridin-3-yl)-2-methylthieno[3,2-b]pyridine-5-carboxamide;

N-(4-(3-amino-5-methylpiperidin-1-yl)pyridin-3-yl)-2-propylthieno[3,2-b]pyridine-5-carboxamide;

N-(4-(3-amino-5-methylpiperidin-1-yl)pyridin-3-yl)-2-isopropylthieno[3,2-b]pyridine-5-carboxamide;

N-(4-(3-amino-5-methylpiperidin-1-yl)pyridin-3-yl)-2-(2,6-difluorophenyl)thieno[3,2-b]pyridine-5-carboxamide;

N-(4-(3-amino-5-methylpiperidin-1-yl)pyridin-3-yl)-2-(2-fluorophenyl)thieno[3,2-b]pyridine-5-carboxamide;

N-(4-(3-amino-5-methylpiperidin-1-yl)pyridin-3-yl)-2-benzylthieno[3,2-b]pyridine-5-carboxamide;

N-(4-(3-amino-5-methylpiperidin-1-yl)pyridin-3-yl)-2-(6-methoxypyridin-3-yl)thieno[3,2-b]pyridine-5-carboxamide;

N-(4-(3-amino-5-methylpiperidin-1-yl)pyridin-3-yl)-2-(6-morpholinopyridin-3-yl)thieno[3,2-b]pyridine-5-carboxamide;

N-(4-(3-amino-5-methylpiperidin-1-yl)pyridin-3-yl)-2-(2,6-difluoro-4-methoxyphenyl)thieno[3,2-b]pyridine-5-carboxamide;

N-(4-(3-amino-5-methylpiperidin-1-yl)pyridin-3-yl)-2-phenylthieno[3,2-b]pyridine-5-carboxamide;

N-(4-(3-amino-5-methylpiperidin-1-yl)pyridin-3-yl)-2-cyclopropylthieno[3,2-b]pyridine-5-carboxamide;

N-(4-(3-amino-5-methylpiperidin-1-yl)pyridin-3-yl)-2-(1-methyl-1H-pyrazol-4-yl)thieno[3,2-b]pyridine-5-carboxamide;

N-(4-(3-amino-5-methylpiperidin-1-yl)pyridin-3-yl)-2-methylthieno[3,2-b]pyridine-5-carboxamide;

N-(4-(3-amino-5-methylpiperidin-1-yl)pyridin-3-yl)-3-isopropylthieno[3,2-b]pyridine-5-carboxamide;

N-(4-(3-amino-5-methylpiperidin-1-yl)pyridin-3-yl)-3-(1-methyl-1H-pyrazol-4-yl)thieno[3,2-b]pyridine-5-carboxamide;

N-(4-(3-amino-5-methylpiperidin-1-yl)pyridin-3-yl)-3-(2,6-difluoro-3-methoxyphenyl)thieno[3,2-b]pyridine-5-carboxamide;

N-(4-(3-amino-5-methylpiperidin-1-yl)pyridin-3-yl)-3-cyclopropylthieno[3,2-b]pyridine-5-carboxamide;

N-{4-[3-aminopiperidin-1-yl]pyridin-3-yl}-3-ethylthieno[3,2-b]pyridine-5-carboxamide;

N-(4-(3-aminopiperidin-1-yl)pyridin-3-yl)-3-cyclopropylthieno[3,2-b]pyridine-5-carboxamide;

N-{4-[3-amino-5-methylcyclohexyl]pyridin-3-yl}-3-isopropylfuro[3,2-b]pyridine-5-carboxamide;

N-(4-(3-amino-5-methylpiperidin-1-yl)pyridin-3-yl)-2-cyclopropylthiazolo[4,5-b]pyridine-5-carboxamide;

N-(4-(3-amino-5-methylpiperidin-1-yl)pyridin-3-yl)-2-cyclopropylfuro[2,3-b]pyridine-6-carboxamide;

N-(4-(3-amino-5-methylpiperidin-1-yl)pyridin-3-yl)-2-(2-methylcyclopropyl)furo[2,3-b]pyridine-6-carboxamide;

N-(4-(3-amino-5-methylpiperidin-1-yl)pyridin-3-yl)-1-cyclobutyl-1H-pyrrolo[2,3-b]pyridine-6-carboxamide;

N-(4-(3-amino-5-methylcyclohexyl)pyridin-3-yl)-3-isopropylpyrazolo[1,5-a]pyrimidine-5-carboxamide;

N-(4-(3-amino-5-methylcyclohexyl)pyridin-3-yl)-3-(2,6-difluorophenyl)pyrazolo[1,5-a]pyrimidine-5-carboxamide;

N-(4-(3-amino-5-methylcyclohexyl)pyridin-3-yl)-3-(2,6-difluoro-4-methoxyphenyl)pyrazolo[1,5-a]pyrimidine-5-carboxamide;

N-(4-(3-amino-5-methylcyclohexyl)pyridin-3-yl)-3-(2,6-difluoro-4-(hydroxymethyl)phenyl)pyrazolo[1,5-a]pyrimidine-5-carboxamide;

N-(4-(3-amino-4-hydroxy-5-methylpiperidin-1-yl)pyridin-3-yl)-2-cyclopropylthiazolo[4,5-b]pyridine-5-carboxamide;

N-(4-(3-amino-4-hydroxy-5-methylpiperidin-1-yl)pyridin-3-yl)-2-cyclopropylfuro[2,3-b]pyridine-6-carboxamide;

N-(4-(3-amino-4-hydroxy-5-methylpiperidin-1-yl)pyridin-3-yl)-2-(2-phenylcyclopropyl)furo[2,3-b]pyridine-6-carboxamide;

N-(4-(3-amino-4-hydroxy-5-methylpiperidin-1-yl)pyridin-3-yl)-2-(2-methylcyclopropyl)furo[2,3-b]pyridine-6-carboxamide; and N-(4-(3-amino-4-hydroxy-5-methylpiperidin-1-yl)pyridin-3-yl)-1-cyclobutyl-1H-pyrrolo[2,3-b]pyridine-6-carboxamide.

Examples of the compounds of Formula (I) also include the following compounds and or pharmaceutically acceptable salts thereof:

N-(4-((3S,5R)-3-amino-5-methylpiperidin-1-yl)pyridin-3-yl)-2-propylfuro[3,2-b]pyridine-5-carboxamide;

N-{4-[(3S,5R)-3-amino-5-methylpiperidin-1-yl]pyridin-3-yl}-2-isopropylfuro[3,2-b]pyridine-5-carboxamide;

N-(4-((3S,5R)-3-amino-5-methylpiperidin-1-yl)pyridin-3-yl)-2-(6-methoxypyridin-3-yl)furo[3,2-b]pyridine-5-carboxamide;

N-(4-((3S,5R)-3-amino-5-methylpiperidin-1-yl)pyridin-3-yl)-2-(2,6-difluorophenyl)furo[3,2-b]pyridine-5-carboxamide;

N-(4-((3S,5R)-3-amino-5-methylpiperidin-1-yl)pyridin-3-yl)-2-(6-morpholinopyridin-3-yl)furo[3,2-b]pyridine-5-carboxamide;

N-{4-[(3R,4R,5S)-3-amino-4-hydroxy-5-methylpiperidin-1-yl]pyridin-3-yl}-2-isopropylfuro[3,2-b]pyridine-5-carboxamide;

N-(4-((3R,4R,5S)-3-amino-4-hydroxy-5-methylpiperidin-1-yl)pyridin-3-yl)-2-(6-methoxypyridin-3-yl)furo[3,2-b]pyridine-5-carboxamide;

N-(4-((3R,4R,5S)-3-amino-4-hydroxy-5-methylpiperidin-1-yl)pyridin-3-yl)-2-(2,6-difluorophenyl)furo[3,2-b]pyridine-5-carboxamide;

N-(4-((3R,4R,5S)-3-amino-4-hydroxy-5-methylpiperidin-1-yl)pyridin-3-yl)-2-(6-morpholinopyridin-3-yl)furo[3,2-b]pyridine-5-carboxamide;

N-(4-((3R,4R,5S)-3-amino-4-hydroxy-5-methylpiperidin-1-yl)pyridin-3-yl)-3-isopropylfuro[3,2-b]pyridine-5-carboxamide;

N-(4-((3R,4R,5S)-3-amino-4-hydroxy-5-methylpiperidin-1-yl)pyridin-3-yl)-3-(2,6-difluorophenyl)furo[3,2-b]pyridine-5-carboxamide;

N-(4-((3R,4R,5S)-3-amino-4-hydroxy-5-methylpiperidin-1-yl)pyridin-3-yl)-3-(2-fluorophenyl)furo[3,2-b]pyridine-5-carboxamide;

N-(4-((3R,4R,5S)-3-amino-4-hydroxy-5-methylpiperidin-1-yl)pyridin-3-yl)-3-(2,6-difluoro-3-methoxyphenyl)furo[3,2-b]pyridine-5-carboxamide;

N-(4-((3R,4R,5S)-3-amino-4-hydroxy-5-methylpiperidin-1-yl)pyridin-3-yl)-3-(6-methoxypyridin-3-yl)furo[3,2-b]pyridine-5-carboxamide;

N-(4-((3R,4R,5S)-3-amino-4-hydroxy-5-methylpiperidin-1-yl)pyridin-3-yl)-3-ethylfuro[3,2-b]pyridine-5-carboxamide;

N-(4-((3R,4R,5S)-3-amino-4-hydroxy-5-methylpiperidin-1-yl)pyridin-3-yl)-3-(1-methylpiperidin-4-yl)furo[3,2-b]pyridine-5-carboxamide;

N-(4-((3R,4R,5S)-3-amino-4-hydroxy-5-methylpiperidin-1-yl)pyridin-3-yl)-3-(tetrahydro-2H-pyran-4-yl)furo[3,2-b]pyridine-5-carboxamide;

N-(4-((3S,5R)-3-amino-5-methylpiperidin-1-yl)pyridin-3-yl)-3-isopropylfuro[3,2-b]pyridine-5-carboxamide;

N-(4-((3S,5R)-3-amino-5-methylpiperidin-1-yl)pyridin-3-yl)-3-(2,6-difluorophenyl)furo[3,2-b]pyridine-5-carboxamide;

N-(4-((3S,5R)-3-amino-5-methylpiperidin-1-yl)pyridin-3-yl)-3-ethylfuro[3,2-b]pyridine-5-carboxamide;

N-(4-((3S,5R)-3-amino-5-methylpiperidin-1-yl)pyridin-3-yl)-3-(2-fluorophenyl)furo[3,2-b]pyridine-5-carboxamide;

N-(4-((3S,5R)-3-amino-5-methylpiperidin-1-yl)pyridin-3-yl)-3-(2,6-difluoro-3-methoxyphenyl)furo[3,2-b]pyridine-5-carboxamide;

N-(4-((3S,5R)-3-amino-5-methylpiperidin-1-yl)pyridin-3-yl)-3-(6-methoxypyridin-3-yl)furo[3,2-b]pyridine-5-carboxamide;

N-(4-((3S,5R)-3-amino-5-methylpiperidin-1-yl)pyridin-3-yl)-3-(1-methylpiperidin-4-yl)furo[3,2-b]pyridine-5-carboxamide;

N-(4-((3S,5R)-3-amino-5-methylpiperidin-1-yl)pyridin-3-yl)-3-(tetrahydro-2H-pyran-4-yl)furo[3,2-b]pyridine-5-carboxamide;

N-(4-((3S,5R)-3-amino-5-methylpiperidin-1-yl)pyridin-3-yl)-3-(5-cyanopyridin-3-yl)furo[3,2-b]pyridine-5-carboxamide;

N-(4-((3S,5R)-3-amino-5-methylpiperidin-1-yl)pyridin-3-yl)-3-(2,6-difluoropyridin-4-yl)furo[3,2-b]pyridine-5-carboxamide;

N-(4-((3S,5R)-3-amino-5-methylpiperidin-1-yl)pyridin-3-yl)-3-(isoxazol-4-yl)furo[3,2-b]pyridine-5-carboxamide;

N-(4-((3S,5R)-3-amino-5-methylpiperidin-1-yl)pyridin-3-yl)-3-(1-methyl-1H-pyrazol-4-yl)furo[3,2-b]pyridine-5-carboxamide;

N-(4-((3S,5R)-3-amino-5-methylpiperidin-1-yl)pyridin-3-yl)-3-(pyrimidin-5-yl)furo[3,2-b]pyridine-5-carboxamide;

N-(4-((3S,5R)-3-amino-5-methylpiperidin-1-yl)pyridin-3-yl)-3-(tetrahydrofuran-3-yl)furo[3,2-b]pyridine-5-carboxamide (diastereomeric mixture);

N-(4-((3S,5R)-3-amino-5-methylpiperidin-1-yl)pyridin-3-yl)-3-(5-methoxypyridin-3-yl)furo[3,2-b]pyridine-5-carboxamide;

N-(4-((3S,5R)-3-amino-5-methylpiperidin-1-yl)pyridin-3-yl)-3-(3,4-dihydro-2H-pyran-5-yl)furo[3,2-b]pyridine-5-carboxamide;

N-(4-((3R,4R,5S)-3-amino-4-hydroxy-5-methylpiperidin-1-yl)pyridin-3-yl)-3-cyclopropylfuro[3,2-b]pyridine-5-carboxamide;

N-(4-((3S,5R)-3-amino-5-methylpiperidin-1-yl)pyridin-3-yl)-3-cyclopropylfuro[3,2-b]pyridine-5-carboxamide;

(S)-N-(4-(3-aminopiperidin-1-yl)pyridin-3-yl)-3-isopropylfuro[3,2-b]pyridine-5-carboxamide;

(S)-N-(4-(3-aminopiperidin-1-yl)pyridin-3-yl)-3-(2,6-difluorophenyl)furo[3,2-b]pyridine-5-carboxamide;

N-(4-((3R,4R,5S)-3-amino-4-hydroxy-5-methylpiperidin-1-yl)pyridin-3-yl)-2-propylthieno[3,2-b]pyridine-5-carboxamide;

N-(4-((3R,4R,5S)-3-amino-4-hydroxy-5-methylpiperidin-1-yl)pyridin-3-yl)-2-isopropylthieno[3,2-b]pyridine-5-carboxamide;

N-(4-((3R,4R,5S)-3-amino-4-hydroxy-5-methylpiperidin-1-yl)pyridin-3-yl)-2-(2,6-difluorophenyl)thieno[3,2-b]pyridine-5-carboxamide;

N-(4-((3R,4R,5S)-3-amino-4-hydroxy-5-methylpiperidin-1-yl)pyridin-3-yl)-2-(2-fluorophenyl)thieno[3,2-b]pyridine-5-carboxamide;

N-(4-((3R,4R,5S)-3-amino-4-hydroxy-5-methylpiperidin-1-yl)pyridin-3-yl)-2-benzylthieno[3,2-b]pyridine-5-carboxamide;

N-(4-((3R,4R,5S)-3-amino-4-hydroxy-5-methylpiperidin-1-yl)pyridin-3-yl)-2-(6-methoxypyridin-3-yl)thieno[3,2-b]pyridine-5-carboxamide;

N-(4-((3R,4R,5S)-3-amino-4-hydroxy-5-methylpiperidin-1-yl)pyridin-3-yl)-2-(6-morpholinopyridin-3-yl)thieno[3,2-b]pyridine-5-carboxamide;

N-(4-((3R,4R,5S)-3-amino-4-hydroxy-5-methylpiperidin-1-yl)pyridin-3-yl)-2-(2,6-difluoro-4-methoxyphenyl)thieno[3,2-b]pyridine-5-carboxamide;

N-(4-((3R,4R,5S)-3-amino-4-hydroxy-5-methylpiperidin-1-yl)pyridin-3-yl)-2-phenylthieno[3,2-b]pyridine-5-carboxamide;

N-(4-((3R,4R,5S)-3-amino-4-hydroxy-5-methylpiperidin-1-yl)pyridin-3-yl)-2-cyclopropylthieno[3,2-b]pyridine-5-carboxamide;

N-(4-((3R,4R,5S)-3-amino-4-hydroxy-5-methylpiperidin-1-yl)pyridin-3-yl)-2-(1-methyl-1H-pyrazol-4-yl)thieno[3,2-b]pyridine-5-carboxamide;

N-(4-((3R,4R,5S)-3-amino-4-hydroxy-5-methylpiperidin-1-yl)pyridin-3-yl)-2-methylthieno[3,2-b]pyridine-5-carboxamide;

N-(4-((3S,5R)-3-amino-5-methylpiperidin-1-yl)pyridin-3-yl)-2-propylthieno[3,2-b]pyridine-5-carboxamide;

N-(4-((3S,5R)-3-amino-5-methylpiperidin-1-yl)pyridin-3-yl)-2-isopropylthieno[3,2-b]pyridine-5-carboxamide;

N-(4-((3S,5R)-3-amino-5-methylpiperidin-1-yl)pyridin-3-yl)-2-(2,6-difluorophenyl)thieno[3,2-b]pyridine-5-carboxamide;

N-(4-((3S,5R)-3-amino-5-methylpiperidin-1-yl)pyridin-3-yl)-2-(2-fluorophenyl)thieno[3,2-b]pyridine-5-carboxamide;

N-(4-((3S,5R)-3-amino-5-methylpiperidin-1-yl)pyridin-3-yl)-2-benzylthieno[3,2-b]pyridine-5-carboxamide;

N-(4-((3S,5R)-3-amino-5-methylpiperidin-1-yl)pyridin-3-yl)-2-(6-methoxypyridin-3-yl)thieno[3,2-b]pyridine-5-carboxamide;

N-(4-((3S,5R)-3-amino-5-methylpiperidin-1-yl)pyridin-3-yl)-2-(6-morpholinopyridin-3-yl)thieno[3,2-b]pyridine-5-carboxamide;

N-(4-((3S,5R)-3-amino-5-methylpiperidin-1-yl)pyridin-3-yl)-2-(2,6-difluoro-4-methoxyphenyl)thieno[3,2-b]pyridine-5-carboxamide;

N-(4-((3S,5R)-3-amino-5-methylpiperidin-1-yl)pyridin-3-yl)-2-phenylthieno[3,2-b]pyridine-5-carboxamide;

N-(4-((3S,5R)-3-amino-5-methylpiperidin-1-yl)pyridin-3-yl)-2-cyclopropylthieno[3,2-b]pyridine-5-carboxamide;

N-(4-((3S,5R)-3-amino-5-methylpiperidin-1-yl)pyridin-3-yl)-2-(1-methyl-1H-pyrazol-4-yl)thieno[3,2-b]pyridine-5-carboxamide;

N-(4-((3S,5R)-3-amino-5-methylpiperidin-1-yl)pyridin-3-yl)-2-methylthieno[3,2-b]pyridine-5-carboxamide;

N-(4-((3S,5R)-3-amino-5-methylpiperidin-1-yl)pyridin-3-yl)-3-isopropylthieno[3,2-b]pyridine-5-carboxamide;

N-(4-((3S,5R)-3-amino-5-methylpiperidin-1-yl)pyridin-3-yl)-3-(1-methyl-1H-pyrazol-4-yl)thieno[3,2-b]pyridine-5-carboxamide;

N-(4-((3S,5R)-3-amino-5-methylpiperidin-1-yl)pyridin-3-yl)-3-(2,6-difluoro-3-methoxyphenyl)thieno[3,2-b]pyridine-5-carboxamide;

N-(4-((3S,5R)-3-amino-5-methylpiperidin-1-yl)pyridin-3-yl)-3-cyclopropylthieno[3,2-b]pyridine-5-carboxamide;

N-{4-[(3S)-3-aminopiperidin-1-yl]pyridin-3-yl}-3-ethylthieno[3,2-b]pyridine-5-carboxamide;

(S)-N-(4-(3-aminopiperidin-1-yl)pyridin-3-yl)-3-cyclopropylthieno[3,2-b]pyridine-5-carboxamide;

N-{4-[(1R,3S,5S)-3-amino-5-methylcyclohexyl]pyridin-3-yl}-3-isopropylfuro[3,2-b]pyridine-5-carboxamide;

N-{4-[(3S,5R)-3-amino-5-methylpiperidin-1-yl]pyridin-3-yl}-2-cyclopropylfuro[2,3-b]pyridine-6-carboxamide;

N-{4-[(3S,5R)-3-amino-5-methylpiperidin-1-yl]pyridin-3-yl}-2-(trans-2-methylcyclopropyl)furo[2,3-b]pyridine-6-carboxamide;

N-{4-[(3S,5R)-3-amino-5-methylpiperidin-1-yl]pyridin-3-yl}-2-(cis-2-methylcyclopropyl)furo[2,3-b]pyridine-6-carboxamide;

N-{4-[(3S,5R)-3-amino-5-methylpiperidin-1-yl]pyridin-3-yl}-1-cyclobutyl-1H-pyrrolo[2,3-b]pyridine-6-carboxamide;

N-{4-[(3R,4R,5S)-3-amino-4-hydroxy-5-methylpiperidin-1-yl]pyridin-3-yl}-2-cyclopropylfuro[2,3-b]pyridine-6-carboxamide;

N-{4-[(3R,4R,5S)-3-amino-4-hydroxy-5-methylpiperidin-1-yl]pyridin-3-yl}-2-cyclopropyl[1,3]thiazolo[4,5-b]pyridine-5-carboxamide;

N-{4-[(3R,4R,5S)-3-amino-4-hydroxy-5-methylpiperidin-1-yl]pyridin-3-yl}-2-(trans-2-methylcyclopropyl)furo[2,3-b]pyridine-6-carboxamide;

N-{4-[(3R,4R,5S)-3-amino-4-hydroxy-5-methylpiperidin-1-yl]pyridin-3-yl}-2-(cis-2-methylcyclopropyl)furo[2,3-b]pyridine-6-carboxamide;

N-{4-[(3R,4R,5S)-3-amino-4-hydroxy-5-methylpiperidin-1-yl]pyridin-3-yl}-1-cyclobutyl-1H-pyrrolo[2,3-b]pyridine-6-carboxamide;

N-{4-[(1R,3S,5S)-3-amino-5-methylcyclohexyl]pyridin-3-yl}-3-isopropylpyrazolo[1,5-a]pyrimidine-5-carboxamide;

N-{4-[(1R,3S,5S)-3-amino-5-methylcyclohexyl]pyridin-3-yl}-3-[2,6-difluoro-4-(hydroxymethyl)phenyl]pyrazolo[1,5-a]pyrimidine-5-carboxamide;

N-{4-[(1R,3S,5S)-3-amino-5-methylcyclohexyl]pyridin-3-yl}-3-(2,6-difluorophenyl)pyrazolo[1,5-a]pyrimidine-5-carboxamide;

N-{4-[(1R,3S,5S)-3-amino-5-methylcyclohexyl]pyridin-3-yl}-3-(2,6-difluoro-4-methoxyphenyl)pyrazolo[1,5-a]pyrimidine-5-carboxamide;

N-(4-((3S,5R)-3-amino-5-methylpiperidin-1-yl)pyridin-3-yl)-2-cyclopropylthiazolo[4,5-b]pyridine-5-carboxamide;

N-(4-((3R,4R,5S)-3-amino-4-hydroxy-5-methylpiperidin-1-yl)pyridin-3-yl)-2-((1S,2S)-2-phenylcyclopropyl)furo[2,3-b]pyridine-6-carboxamide; and N-(4-((3R,4R,5S)-3-amino-4-hydroxy-5-methylpiperidin-1-yl)pyridin-3-yl)-2-((1R,2R)-2-phenylcyclopropyl)furo[2,3-b]pyridine-6-carboxamide.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of Formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "amino" refers to a group of Formula —NH$_2$.

The term "carbamyl" refers to a group of Formula —C(O)NH$_2$.

The term "carbonyl", employed alone or in combination with other terms, refers to a —C(=O)— group, which also may be written as C(O).

The term "cyano" or "nitrile" refers to a group of Formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo is F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of Formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group.

The term "sulfido" refers to a sulfur atom as a divalent substituent, forming a thiocarbonyl group (C=S) when attached to carbon.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl.

The term "arylalkyl," employed alone or in combination with other terms, refers to a group of formula -alkylene-aryl. In some embodiments, arylalkyl is $C_{6-10}$ aryl-$C_{1-3}$ alkyl. In some embodiments, arylalkyl is $C_{6-10}$ aryl-$C_{1-4}$ alkyl. In some embodiments, arylalkyl is benzyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, naphthyridine (including 1,2-, 1,3-, 1,4-, 1,5-, 1,6-, 1,7-, 1,8-, 2,3- and 2,6-naphthyridine), indole, benzothiophene, benzofuran, benzisoxazole, imidazo[1,2-b]thiazole, purine, or the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "heteroarylalkyl," employed alone or in combination with other terms, refers to a group of formula alkylene-heteroaryl. In some embodiments, heteroarylalkyl is $C_{1-9}$ heteroaryl-$C_{1-3}$ alkyl, wherein the heteroaryl portion is monocyclic or bicyclic and has 1, 2, 3, or 4 heteroatom ring members independently selected from nitrogen, sulfur and oxygen. In some embodiments, heteroarylalkyl is $C_{1-9}$ heteroaryl-$C_{1-4}$ alkyl, wherein the heteroaryl portion is monocyclic or bicyclic and has 1, 2, 3, or 4 heteroatom ring members independently selected from nitrogen, sulfur and oxygen.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "cycloalkylalkyl," employed alone or in combination with other terms, refers to a group of formula -alkylene-cycloalkyl. In some embodiments, cycloalkylalkyl is $C_{3-7}$ cycloalkyl-$C_{1-3}$ alkyl, wherein the cycloalkyl portion is monocyclic or bicyclic. In some embodiments, cycloalkylalkyl is $C_{3-7}$ cycloalkyl-$C_{1-4}$ alkyl, wherein the cycloalkyl portion is monocyclic or bicyclic.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-12 ring members, 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfide group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidine, azepane, dihydrobenzofuran, dihydrofuran, dihydropyran, morpholine, 3-oxa-9-azaspiro[5.5]undecane, 1-oxa-8-azaspiro[4.5]decane, piperidine, piperazine, pyran, pyrrolidine, quinuclidine, tetrahydrofuran, tetrahydropyran, 1,2,3,4-tetrahydroquinoline, tropane, and thiomorpholine.

As used herein, the term "heterocycloalkylalkyl," employed alone or in combination with other terms, refers to a group of formula -alkylene-heterocycloalkyl. In some embodiments, heterocycloalkylalkyl is $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen. In some embodiments, heterocycloalkylalkyl is $C_{2-9}$ heterocycloalkyl-$C_{1-4}$ alkyl, wherein the heterocycloalkyl portion is monocyclic or bicyclic and has 1, 2, 3, or 4 heteroatom ring members independently selected from nitrogen, sulfur and oxygen.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical Formula and total charge. Example prototropic tautomers include ketone enol pairs, amide-imidic acid pairs, lactam lactim pairs, enamine imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); aq. (aqueous); atm. (atmosphere(s)); Boc (t-butoxycarbonyl); BOP ((benzotriazol-1-yloxy)tris(dimethylamino)phosphonium hexafluorophosphate); Br$_2$ (bromine); Cbz (carboxybenzyl); calc. (calculated); CeCl$_3$.7H$_2$O (cerium (III) chloride heptahydrate); CuI (copper (I) iodide); d (doublet); dd (doublet of doublets); DCM (dichloromethane); DIAD (N,N'-diisopropyl azidodicarboxylate); DIC (N,N'-diisopropylcarbodiimide); DIPEA (N,N-diisopropylethylamine); DMAP (4-dimethylaminopyridine); DMF (N,N-dimethylformamide); Et (ethyl); Et$_2$O (diethyl ether); EtOAc (ethyl acetate); EtOH (ethanol); Fmoc (9-fluorenylmethylmethoxycarbonyl); g (gram(s)); h (hour(s)); H$_2$ (hydrogen gas); HATU (N,N,N',N'-tetramethyl-O-(7-azabenzotriazol-1-yl)uronium hexafluorophosphate); HCl (hydrochloric acid/hydrogen chloride); HPLC (high performance liquid chromatography); H$_2$SO$_4$ (sulfuric acid); Hz (hertz); I$_2$ (iodine); IPA (isopropyl alcohol); J (coupling constant); KOH (potassium hydroxide); $K_3PO_4$ (potassium phosphate); $K_3PO_4 \cdot H_2O$ (tripotassium phosphate hydrate); LiHMDS (lithium hexamethyldisilazide); LCMS (liquid chromatography-mass spectrometry); $LiAlH_4$ (lithium tetrahydroaluminate); $LiBH_4$ (lithium tetrahydroborate); LiOH (lithium hydroxide); m (multiplet); M (molar); MeI (methyl iodide); MS (Mass spectrometry); Me (methyl); MeCN (acetonitrile); MeOH (methanol); mg (milligram(s)); min. (minutes(s)); mL (milliliter(s)); mmol (millimole(s)); $MnO_2$ (manganese (IV) oxide); $MoSO_4$ (molybdenum sulfate); N (normal); $NaBH_4$ (sodium tetrahydroborate); $Na_2Co_3$ (sodium carbonate); $NH_3$ (ammonia); $NaHCO_3$ (sodium bicarbonate); NaOH (sodium hydroxide); $Na_2S$ (sodium sulfide); $Na_2SO_4$ (sodium sulfate); $Na_2S_2O_3$ (sodium thiosulfate); $NH_4OH$ (ammonium hydroxide); nM (nanomolar); NMR (nuclear magnetic resonance spectroscopy); Pd (palladium); $Pd(OAc)_2$ (palladium acetate); pM (picomolar); $PPh_3$ (triphenylphosphine); RP-HPLC (reverse phase high performance liquid chromatography); t (triplet or tertiary); t-Bu (tert-butyl); TEA (triethylamine); TFA (trifluoroacetic acid); THF (tetrahydrofuran); $TiCl_4$ (titanium tetrachloride); TLC (thin layer chromatography); μg (microgram(s)); μL (microliter(s)); μM (micromolar); wt % (weight percent).

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in Scheme 1. In the process depicted in Scheme 1, a suitable aromatic amine of Formula 1-1 is reacted with an acid of Formula 1-2 under conditions suitable for forming an amide bond to provide the compound of Formula (I). Suitable combinations for forming the amide bond include, e.g., the methods used to form amide bonds in peptides as described, e.g., in Jones, *Amino Acid and Peptide Synthesis*, 2nd Ed., Oxford University Press, 2002; and Jones, *The Chemical Synthesis of Peptides* (*International Series of Monographs on Chemistry*) (Oxford University Press, 1994). An example of a suitable coupling agent is HATU/DIPEA.

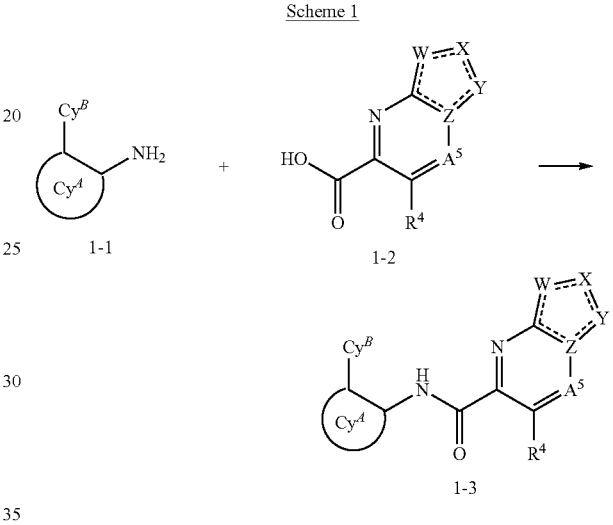

Amine compounds 1-1 of Scheme 1 can be prepared as shown in Scheme 2. A suitably substituted 4-chloro-3-nitropyridine 2-1 can react with $Cy^B$ in the presence of a suitable base to give compounds 2-2. Reduction of the nitro group, e.g., in the presence of iron in acetic acid, provides amine 2-3.

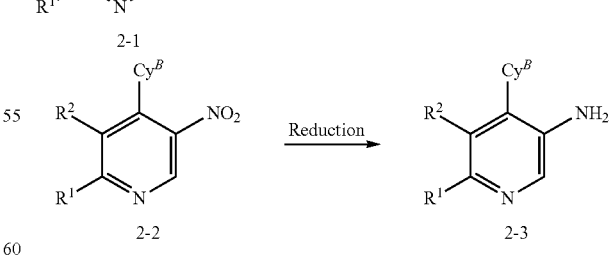

Amine compounds of Scheme 1 can also be prepared as shown in Scheme 3. Pyrazole analogues can be prepared by reacting suitably substituted 5-chloro-4-nitro-1H-pyrazoles 3-1 with $Cy^B$ in the presence of a base affords the coupled compound 3-2. Reduction of the nitro group, e.g., in the presence of iron in acetic acid, provides amine 3-3.

Scheme 3

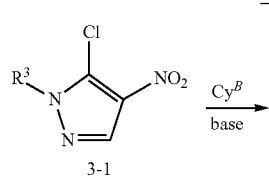

4-2. Treatment with Lawesson's reagent (2,4-bis(4-methoxyphenyl)-1,3,2,4-dithiadiphosphetane-2,4-disulfide) results in thioamide formation 4-3, which is reacted with a base, e.g., sodium hydride, to form the thiazole 4-4. The ester group is hydrolyzed using standard saponification conditions, e.g., reaction with lithium hydroxide, and subsequent acidification forms carboxylic acid 4-5. HATU coupling with an appropriate substituted amine provides the compounds of Formula 4-7.

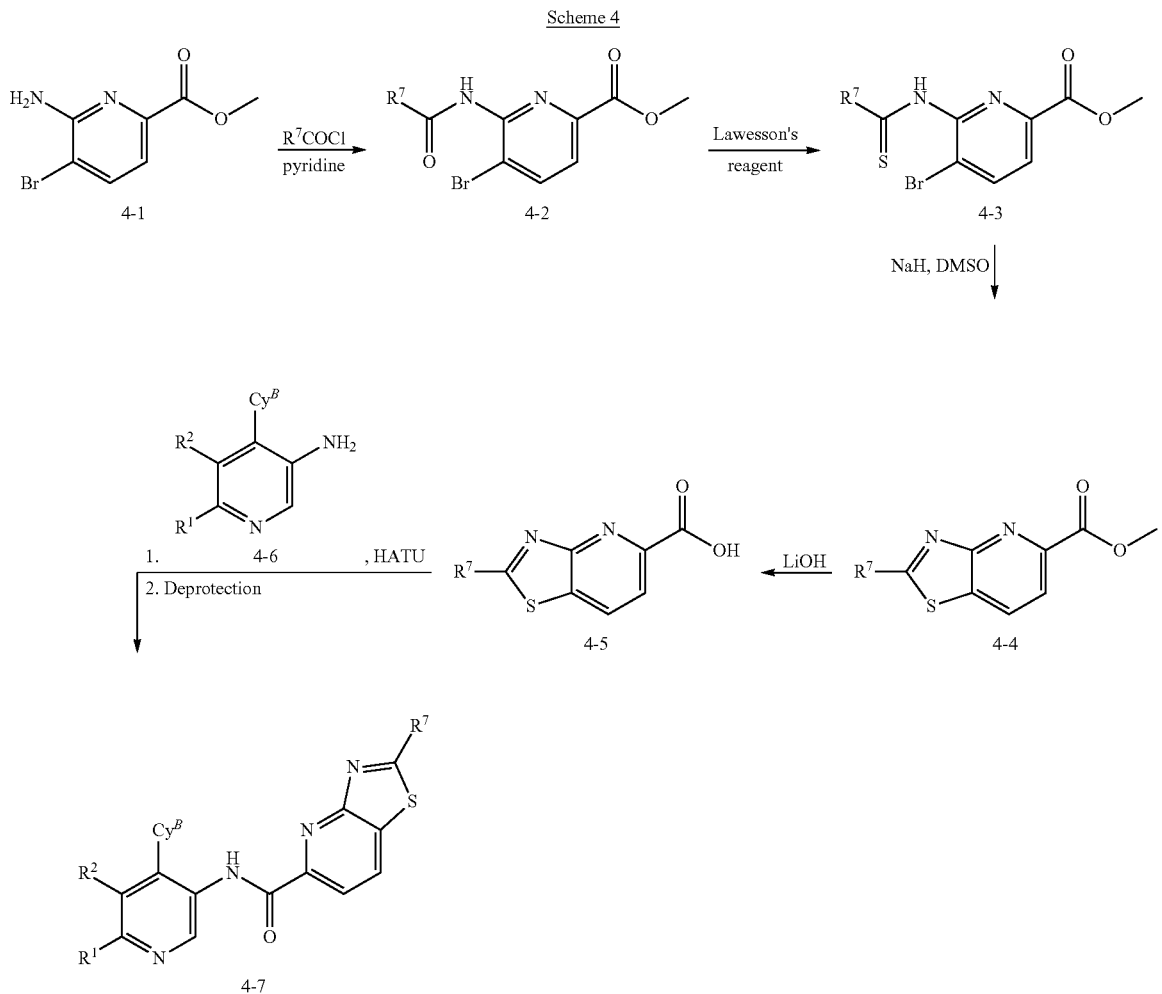

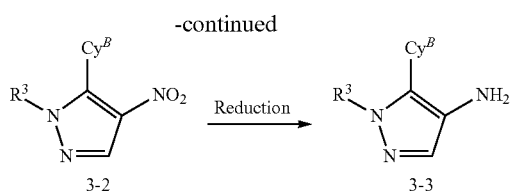

The synthetic method illustrated by Scheme 1 can be applied to the synthesis of compounds where $Cy^C$ is a thiazole ring is represented in Scheme 4. Commercially available methyl 6-amino-5-bromopicolinate 4-1 is reacted with appropriate substituted acid chlorides to form amide The synthetic method illustrated by Scheme 1 can be applied to the synthesis of compounds where $Cy^C$ is a furan ring, when $R^7$ is H, as represented in Scheme 5. Reaction of 5-hydroxypicolinic acid 5-1 with concentrated sulfuric acid afford ester 5-2. Iodination of the ester, e.g., reaction with iodine in the presence of sodium carbonate, forms compound 5-3. Subsequent Sonogashira coupling affords the fused furanyl compound 5-4, substituted by $R^7$. The ester group of 5-4 can be hydrolyzed by treatment using standard saponification conditions, e.g., reaction with LiOH and subsequent acidification, to give carboxylic acid 5-5. Finally, HATU coupling with amine 5-6 followed by deprotection of any protecting groups results in the formation of amide 5-7.

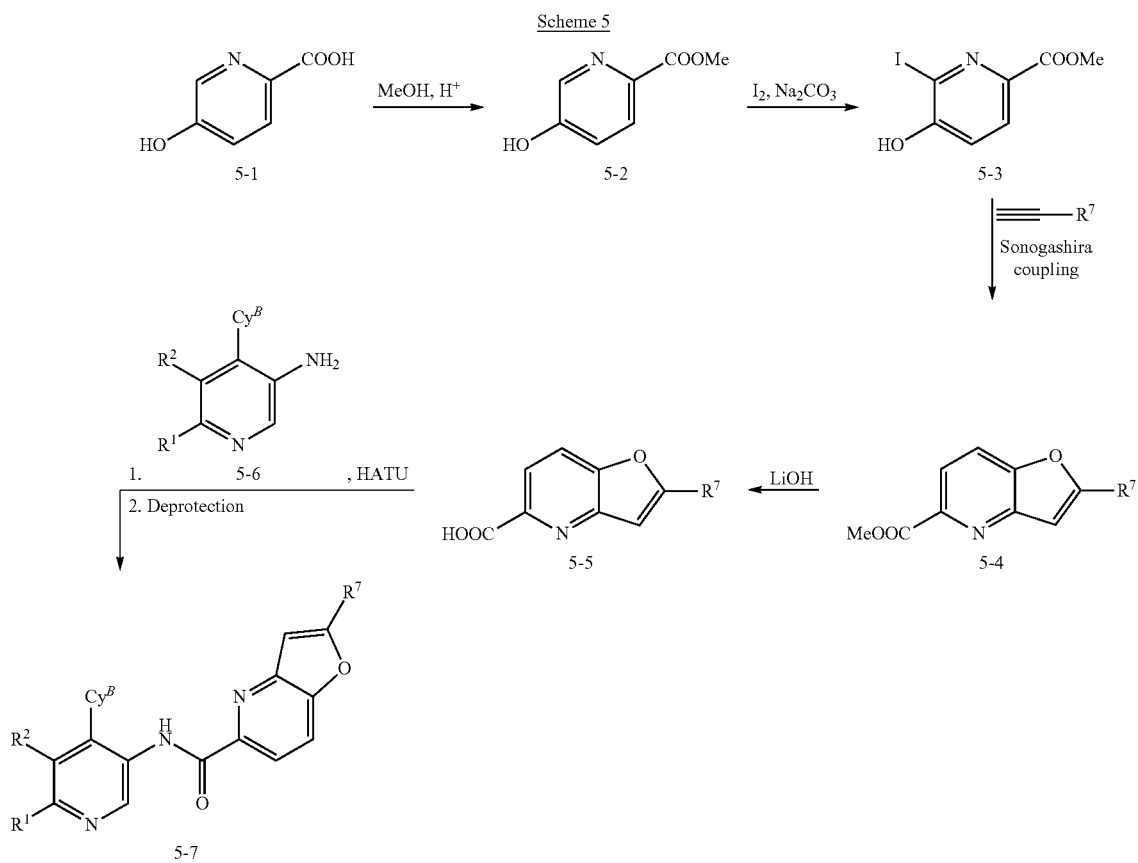

The synthetic method illustrated by Scheme 1 can be applied to the synthesis of compounds where $Cy^C$ is a furan ring, when $R^6$ is H, as represented in Scheme 6. Sonogashira coupling of TMS-acetylene with iodopyridine 6-1 affords the fused furanyl compound 6-2. Base catalyzed deprotection of TMS group results in the formation of ester 6-3, which is then brominated to form the dibromo compound 6-4. Hydrolysis of the ester group, e.g., reaction with potassium hydroxide in ethanol, and elimination of HBr forms carboxylic acid 6-5. HATU coupling with the amine 6-6 forms amide 6-7, which can be used in, e.g., subsequent Suzuki coupling reactions or other suitable organometallic cross-coupling reactions. When alkenyl boronic esters are used as Suzuki coupling substrates to form 6-7, the double bond of the alkenyl group is reduced using standard hydrogenation conditions, e.g., hydrogen gas in the presence of catalytic amounts of palladium on carbon. Deprotection of any protecting groups results in the fused furanyl compound of Formula 6-8.

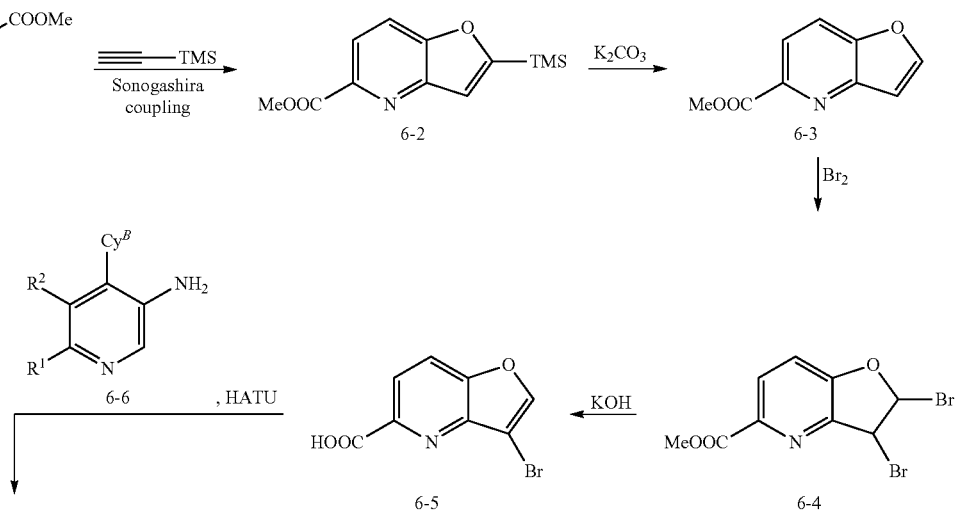

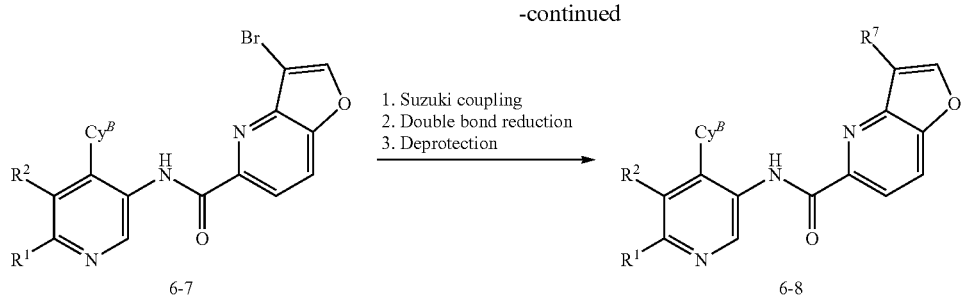

The synthetic method illustrated by Scheme 1 can be applied to the synthesis of compounds where $Cy^C$ is a disubstituted furan ring, when both $R^{7A}$ and $R^{7B}$ are other than H, as represented in Scheme 7. Sonogashira coupling of an appropriately substituted acetylene with iodopyridine 7-1 affords the fused furanyl compound 7-2. Treatment of 7-2 with NBS forms brominated compound 7-3. Ester hydrolysis, e.g. with lithium hydroxide, results in carboxylic acid 7-4. HATU coupling with 7-5 forms the amide 7-6, which can be used in subsequent Suzuki coupling reactions or other suitable organometallic cross-coupling reactions. When alkenyl boronic esters are used as Suzuki coupling substrates to form compound 7-7, the double bond of the alkenyl group is reduced using standard hydrogenation conditions, e.g., hydrogen gas in the presence of catalytic amounts of palladium on carbon. Deprotection of any protecting groups results in the fused furanyl compound of Formula 7-8.

Scheme 7

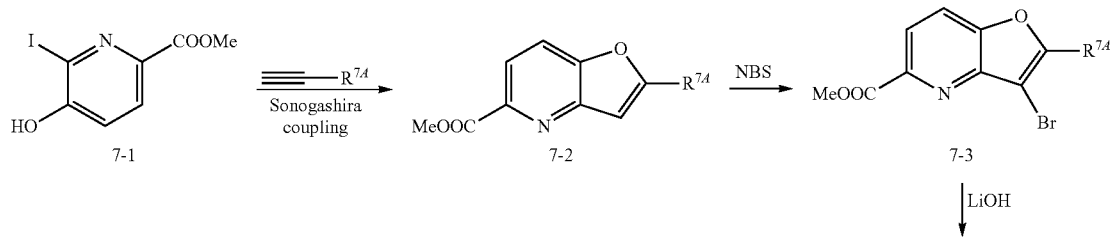

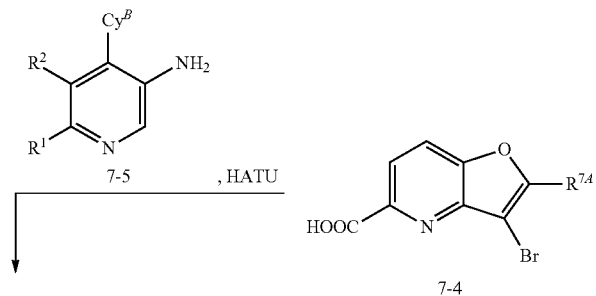

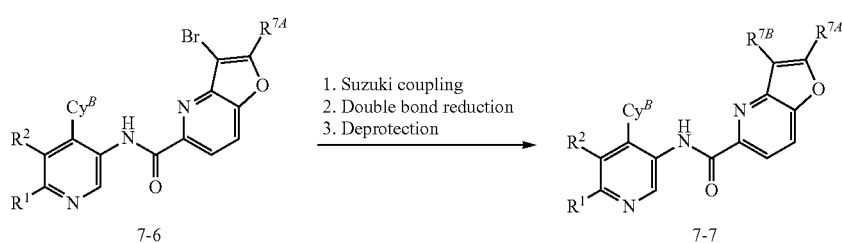

The synthetic method illustrated by Scheme 1 can be applied to the synthesis of compounds where $Cy^C$ is a thiophene ring and $R^7$ is H, as represented in Scheme 8. Sonogashira coupling of an appropriately substituted acetylene with methyl 6-bromo-5-fluoropicolinate (8-1) results in the acetylated compound 8-2. Treatment of 8-2 with sodium sulfide and in-situ deprotection of the ester group forms thiophene 8-3. HATU coupling of 8-3 with amine 8-4, followed by deprotection of any protecting groups results in the formation of amide 8-5.

Scheme 8

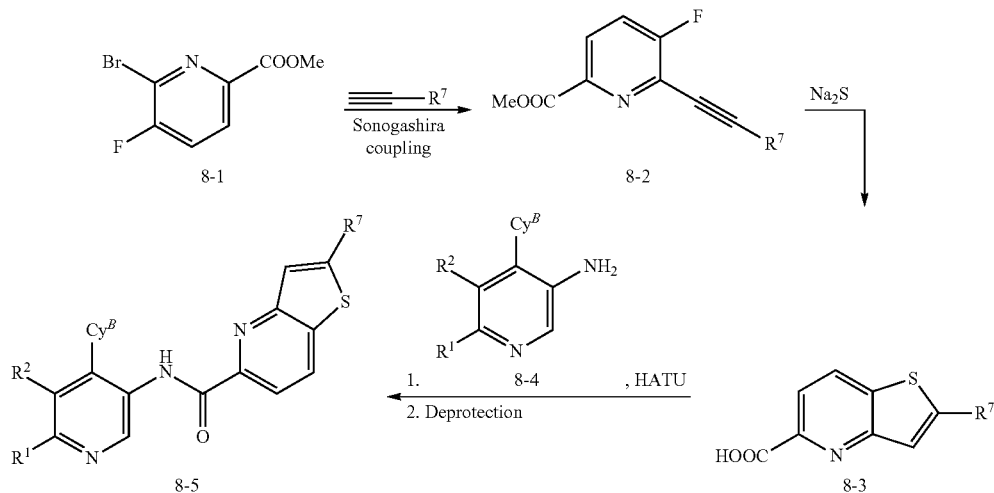

The synthetic method illustrated by Scheme 1 can be applied to the synthesis of compounds where $Cy^C$ is a thiophene ring and $R^7$ is H, as represented in Scheme 9. Reduction of ethyl 3-aminothiophene-2-carboxylate (9-1), e.g., in the presence of lithium tetrahydroaluminate (LAH) forms alcohol 9-2, which is then oxidized, e.g., in the presence of $Mn_2O$, to form aldehyde 9-3. Reaction of 9-3 with methyl 2-oxopropanoate in the presence of a suitable base and subsequent acidification form carboxylic acid 9-4, which is then esterified, e.g., heating in methanol in the presence of acid, to give ester 9-5. Treatment with NBS and hydrolysis of the ester group, e.g., reaction with LiOH, and subsequent acidification forms carboxylic acid 9-6. HATU coupling with amine 9-7 forms amide 9-8, which can be used in subsequent Suzuki coupling reactions or other suitable organometallic cross-coupling reactions. When alkenyl boronic esters are used as Suzuki coupling substrates to form compound 9-9, the double bond of the alkenyl group is reduced using standard hydrogenation conditions, e.g., hydrogen gas in the presence of catalytic amounts of palladium on carbon. Deprotection of any protecting groups results in the fused thiophene compound of Formula 9-9.

Scheme 9

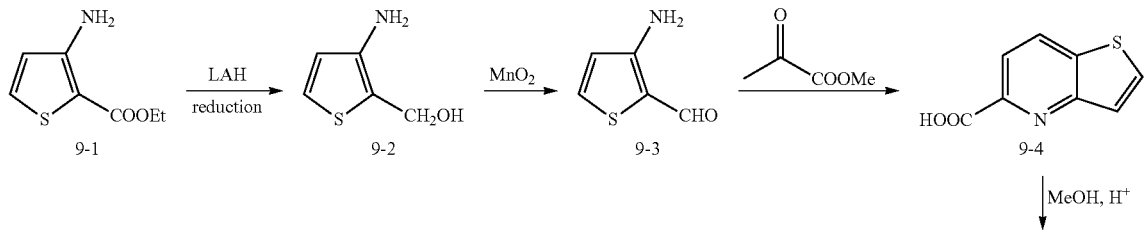

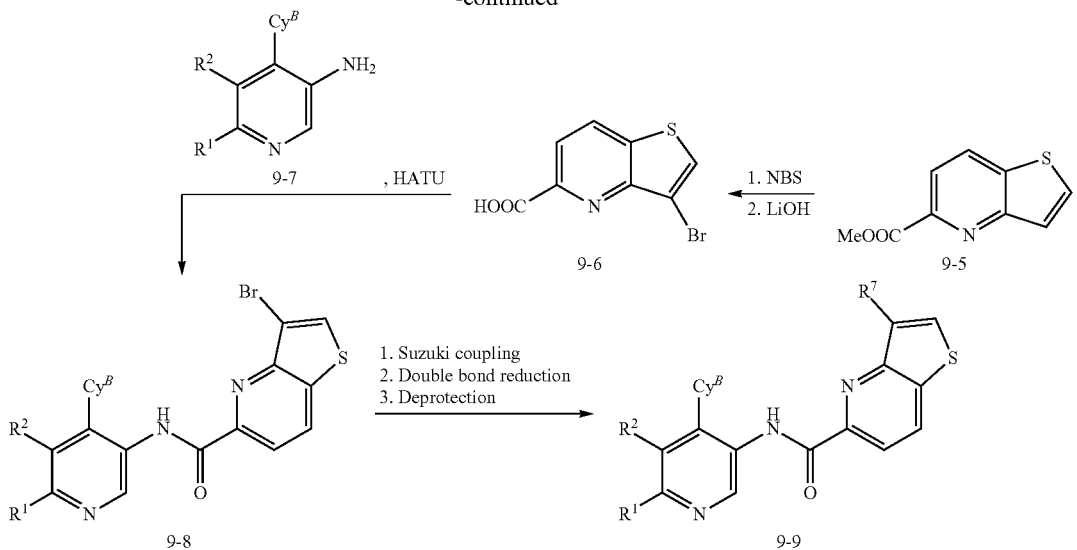

The synthetic method illustrated by Scheme 1 can be applied to the synthesis of compounds where $Cy^C$ is a disubstituted thiophene ring, when both $R^{7A}$ and $R^{7B}$ are other than H, as represented in Scheme 10. Esterification of compound 10-1, e.g., heating in methanol in the presence of a suitable acid, affords ester 10-2. Treatment with NBS forms the brominated compound 10-3, and hydrolysis of the ester group, e.g., reaction with LiOH, and subsequent acidification forms carboxylic acid 10-4. HATU coupling with amine 10-5 forms amide 10-6, which can be used in subsequent Suzuki coupling reactions or other suitable organometallic cross-coupling reactions. When alkenyl boronic esters are used as Suzuki coupling substrates to form compound 10-7, the double bond of the alkenyl group is reduced using standard hydrogenation conditions, e.g., hydrogen gas in the presence of catalytic amounts of palladium on carbon. Deprotection of any protecting groups results in the fused thiophene compound of Formula 10-7.

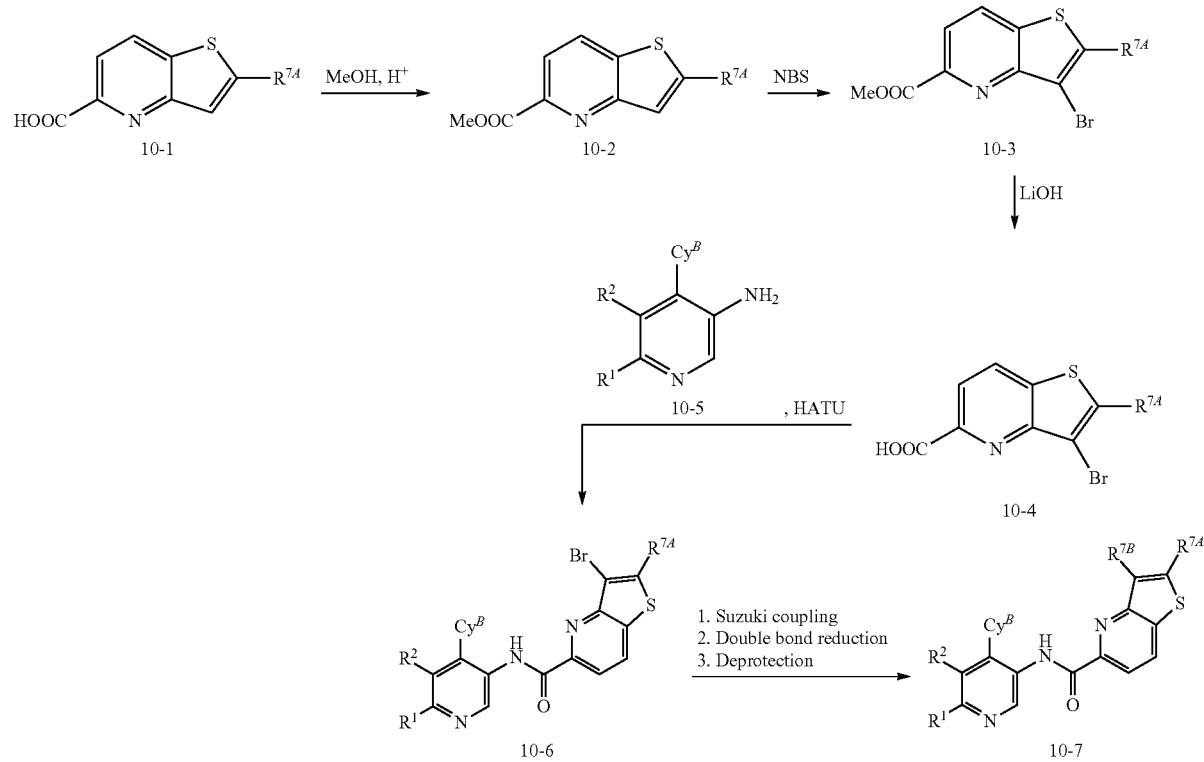

The synthetic method illustrated by Scheme 1 can be applied to the synthesis of compounds where containing a furo[2,3-b]pyridine ring and $R^7$ is H, as represented in Scheme 11. Esterification of 6-oxo-1,6-dihydropyridine-2-carboxylic acid (11-1), e.g., heating in methanol in the presence of a suitable acid, affords ester 11-2. Treatment with NBS forms the brominated compound 11-3. Sonogashira coupling of an appropriately substituted acetylene with 11-3 forms the fused furanyl compound 11-4, substituted with $R^6$. Hydrolysis of the ester group, e.g., reaction with LiOH, and subsequent acidification forms carboxylic acid 11-5. Finally, HATU coupling with amine 11-6 followed by deprotection of any protecting groups results in the formation of amide 11-7.

with NBS forms the brominated compound 12-2. Sonogashira coupling of 12-2 with TMS-acetylene forms 12-3. Base catalyzed deprotection of the TMS group results in the formation of ester 12-4, which is then brominated to form the dibromo compound 12-5. Hydrolysis of the ester group, e.g., reaction with potassium hydroxide in ethanol, and elimination of HBr forms carboxylic acid 12-6. HATU coupling with the amine 12-7 forms amide 12-8, which can be used, e.g., in subsequent Suzuki coupling reactions or other suitable organometallic cross-coupling reactions. When alkenyl boronic esters are used as Suzuki coupling substrates to form 12-9, the double bond of the alkenyl group is reduced using standard hydrogenation conditions,

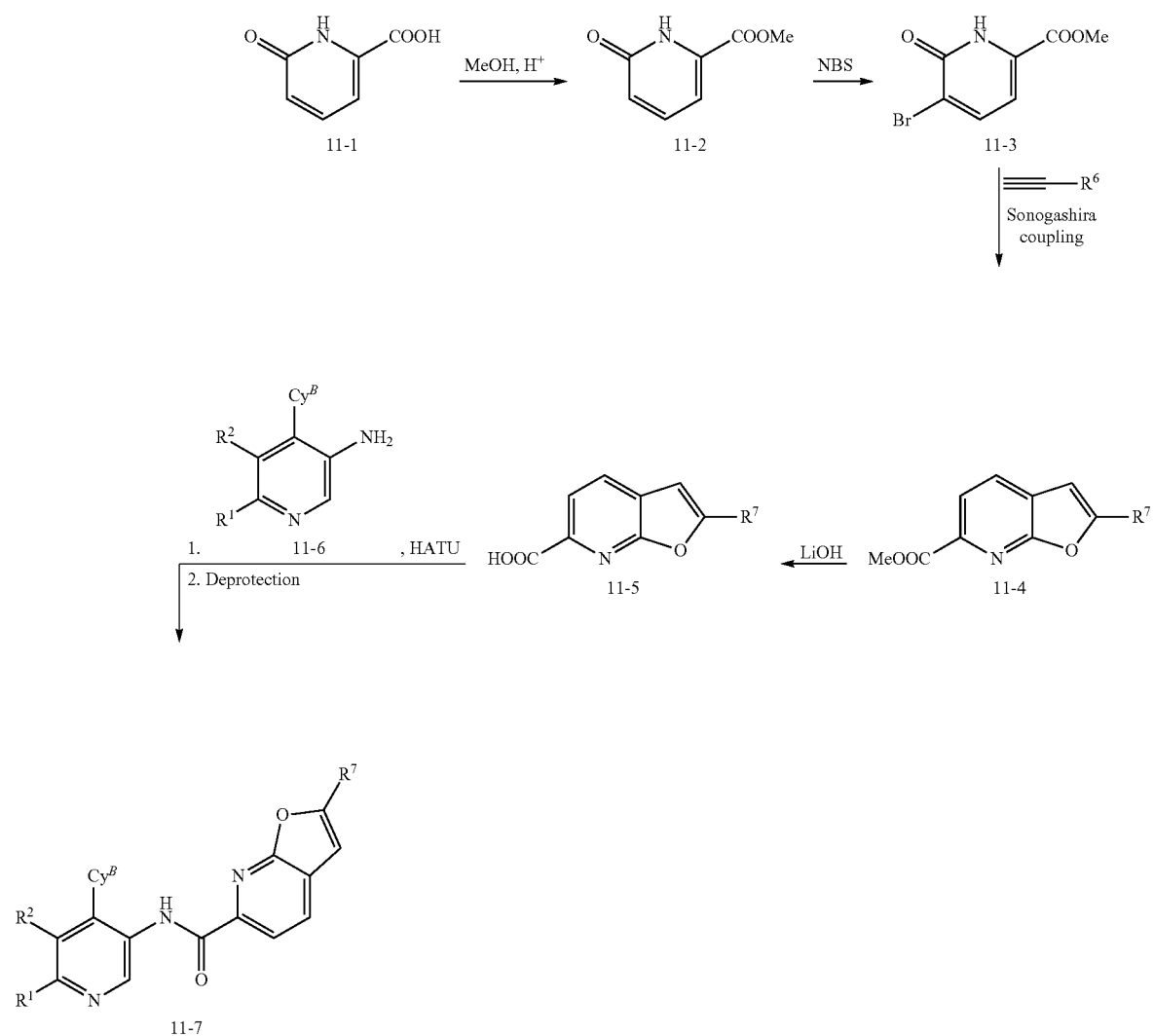

The synthetic method illustrated by Scheme 1 can be applied to the synthesis of furo[2,3-b]pyrazine compounds wherein $R^7$ is H, as represented in Scheme 12. Treatment methyl 5-oxo-4,5-dihydropyrazine-2-carboxylate (12-1)

e.g., hydrogen gas in the presence of catalytic amounts of palladium on carbon. Deprotection of any protecting groups results in the furo[2,3-b]pyrazine compound of Formula 12-9.

Scheme 12

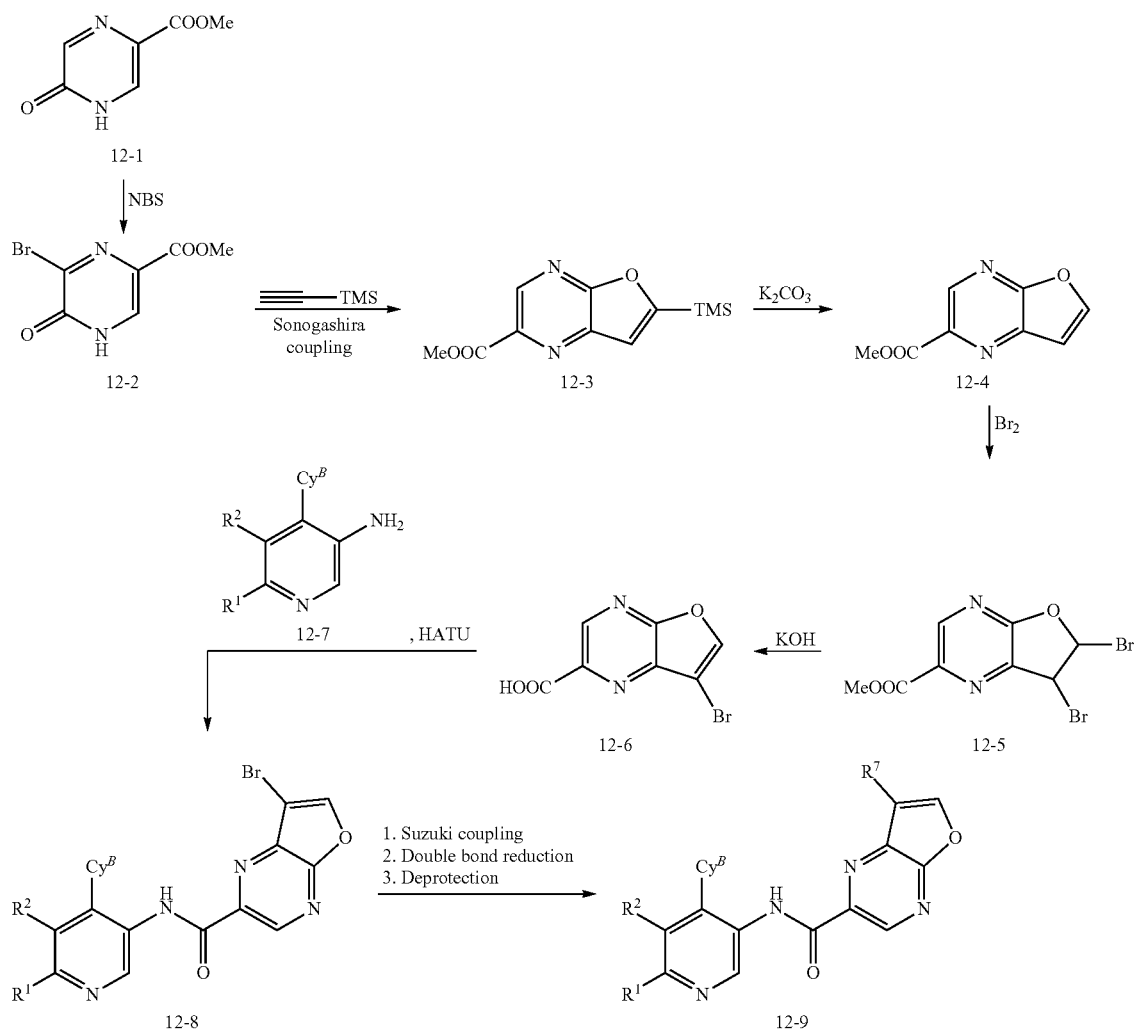

The synthetic method illustrated by Scheme 1 can be applied to the synthesis of compounds where $Cy^C$ is an isoxazole ring is represented in Scheme 13. Suzuki coupling of methyl 6-bromo-5-fluoropicolinate (13-1) forms alkene 13-2, which is then oxidized to form aldehyde 13-3. Addition of hydroxylamine, e.g., hydroxylamine hydrochloride forms 13-4, and chlorination of the hydroxyimino group, e.g., reaction with NCS, affords compound 13-5. Cyclization upon treatment with a suitable base, e.g., sodium hydride, affords isoxazole 13-6. Hydrolysis of the ester group, e.g., reaction with LiOH, and subsequent acidification forms carboxylic acid 13-7. HATU coupling with the amine 13-8 forms amide 13-9, which can be used, e.g., in subsequent Suzuki coupling reactions or other suitable organometallic cross-coupling reactions. When alkenyl boronic esters are used as Suzuki coupling substrates to form 13-10, the double bond of the alkenyl group is reduced using standard hydrogenation conditions, e.g., hydrogen gas in the presence of catalytic amounts of palladium on carbon. Deprotection of any protecting groups results in the isoxazole compound of Formula 13-10.

Scheme 13

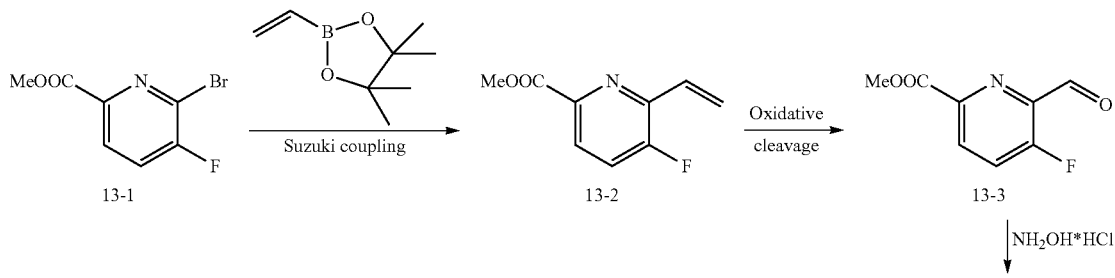

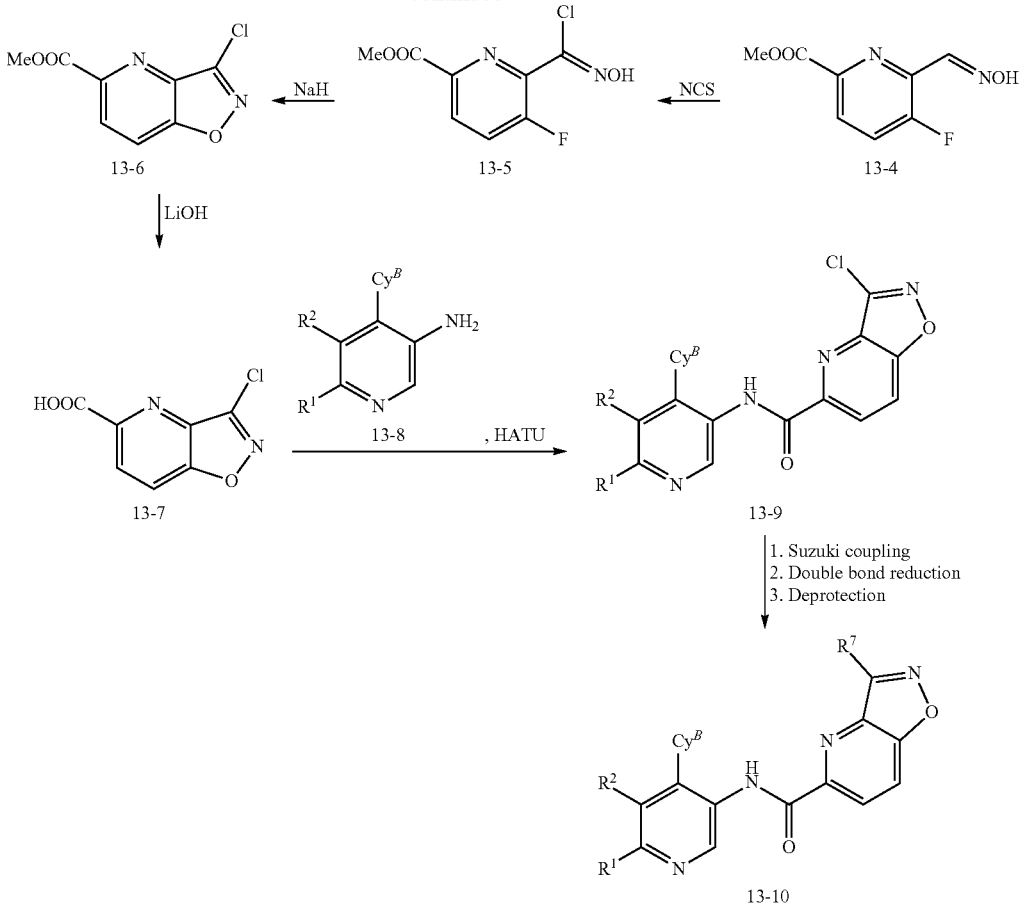

Pyrazolo[1,5-a]pyrimidine compounds of Formula (I) can be prepared, e.g., using a process as illustrated in Scheme 14. 1H-Pyrazol-3-amine 14-1 is reacted with diethyl 2-oxosuccinate in acetic acid under reflux to give ethyl 7-hydroxy-pyrazolo[1,5-a]pyrimidine-5-carboxylate 14-2, which can be converted to the corresponding chloride 14-3 by treatment with POCl$_3$ under thermal conditions. Removal of the chlorine group under reducing conditions, e.g., palladium on carbon under H$_2$ atmosphere, affords ethyl pyrazolo[1,5-a]pyrimidine-5-carboxylate 14-4. Bromination of 14-4, e.g., by reaction with NBS, affords bromide 14-5. Hydrolysis of the ester group, e.g., reaction with LiOH, and subsequent acidification forms carboxylic acid 14-6. The amide 14-8 can be prepared by coupling carboxylic acid 14-6 with amine 14-7 in the presence of an amide coupling reagent, e.g., BOP, PyBop, HATU, HBTU, EDC, or CDI. Subsequent Suzuki coupling of amide 14-8 with an appropriately substituted boronic ester or boronic acid, followed by deprotection of any protecting groups affords the compound of Formula 14-9. Other cross-coupling reactions or other functional group interconversion reactions can be employed to provide further compounds of Formula 14-9.

Scheme 14

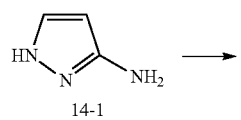

-continued

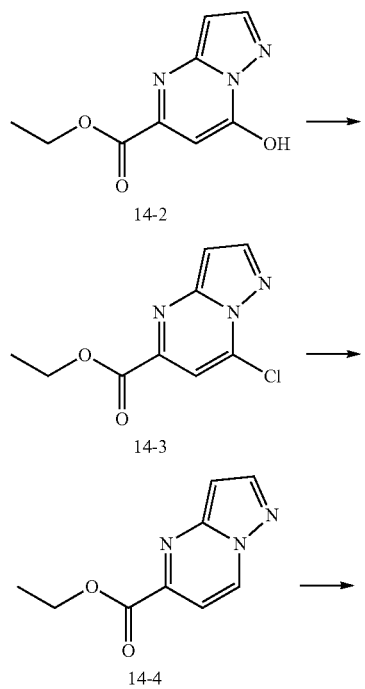

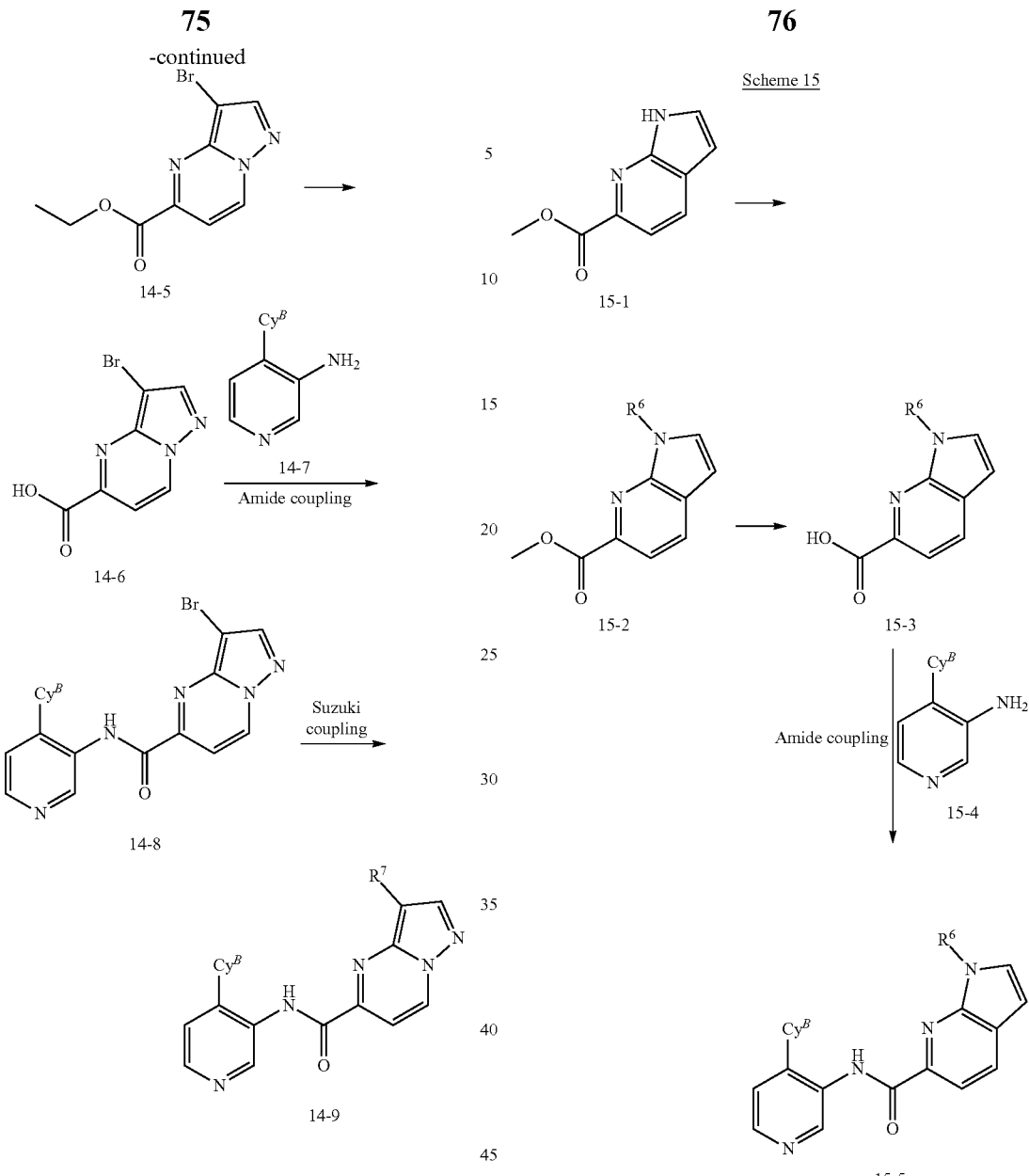

Pyrrolo[2,3-b]pyridine compounds of Formula (I) can be prepared, e.g., using a process as illustrated in Scheme 15. Commercially available methyl 1H-pyrrolo[2,3-b]pyridine-6-carboxylate 15-1 (Combi-Blocks, Inc) is converted to the corresponding $R^7$-substituted compound 15-2. For example, if $R^6$ is alkyl, compound 15-1 is reacted with an appropriate alkyl halide under basic conditions to afford 15-2; if $R^6$ is an aromatic ring, compound 15-1 is reacted with an appropriate boronic acid under copper-mediated C—N bond formation conditions to afford compound 15-2 (see: D. M. T. Chan, K. L. Monaco, R.-P. Wang, M, P. Winters, Tetrahedron Lett. 1998, 39, 2933-2936; P. Y. S. Lam, C. G. Clark, S. Saubern, J. Adams, M. P. Winters, D. M. T. Chan, A. Combs, Tetrahedron Lett. 1998, 39, 2941-2944). Hydrolysis of the ester group, e.g., reaction with LiOH, and subsequent acidification forms carboxylic acid 15-3. Coupling of carboxylic acid 15-3 with amine 15-4 in the presence of an amide coupling reagent, e.g., BOP, PyBop, HATU, HBTU, EDC, or CDI, affords amide 15-5.

Imidazo[4,5-b]pyridine, compounds of Formula (I) can be prepared, e.g., using a process as illustrated in Scheme 16. Commercially available ethyl 3H-imidazo[4,5-b]pyridine-5-carboxylate 16-1 (Anichem Inc.) is converted to the corresponding $R^7$-substituted compound 16-2. For example, if $R^7$ is alkyl, compound 16-1 is reacted with an appropriate alkyl halide under basic conditions to afford 15-2; if $R^7$ is an aromatic ring, compound 16-1 is reacted with an appropriate boronic acid under copper-mediated C—N bond formation conditions to afford compound 16-2 (see: D. M. T. Chan, K, L, Monaco, R.-P. Wang, M. P. Winters, Tetrahedron Lett. 1998, 39, 2933-2936; P. Y. S. Lam, C. G. Clark, S. Saubern, J. Adams, M. P. Winters, D, M. T. Chan, A. Combs, Tetrahedron Lett. 1998, 39, 2941-2944), Hydrolysis of the ester group, e.g., reaction with LiOH, and subsequent acidification forms carboxylic acid 16-3. Coupling of carboxylic acid 16-3 with amine 16-4 in the presence of an amide coupling reagent, e.g., BOP, PyBop, HATU, HBTU, EDC, or CDI, affords amide 16-5.

Scheme 16

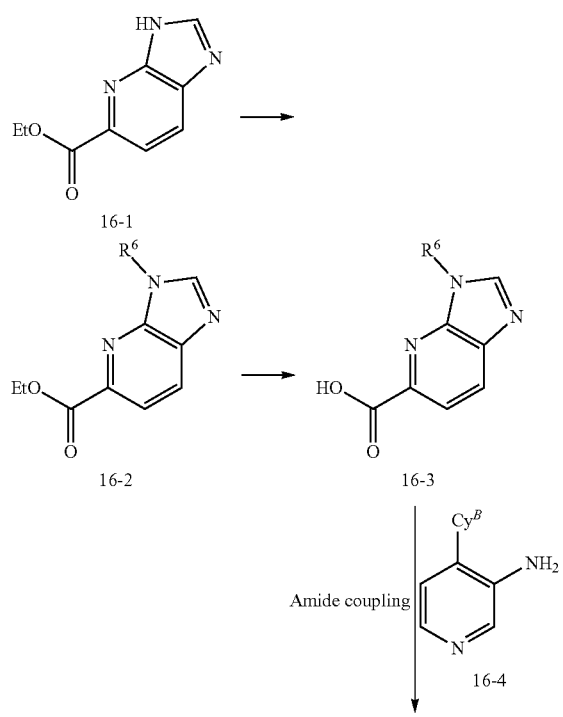

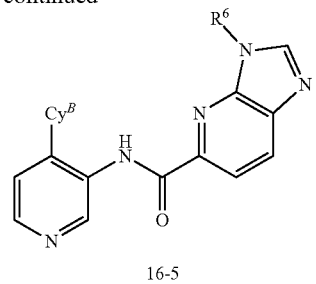

2-Oxo-2,3-dihydromazolo[4,5-b]pyridine compounds of Formula (I) can be prepared, e.g., using a process as illustrated in Scheme 17. Commercially available methyl 6-bromo-5-methoxypicolinate 17-2 (Ark Pharm, Inc.) is converted to the corresponding $R^7$-substituted amine 17-2 under palladium-mediated C—N bond formation conditions, e.g., reaction in the presence of Pd(OAc)$_2$, Binap, Na$^t$OBu; Pd(OAc)$_2$, Xantphos, Cs$_2$CO$_3$. Cleavage of the methyl ether group, e.g., in the presence of HBr or BBr$_3$, affords the hydroxyl compound 17-3, and subsequent treatment of 17-3 with CDI or phosgene can gives the 2-oxo-2,3-dihydrooxazolo[4,5-b]pyridine 17-4. Hydrolysis of the ester group, e.g., reaction with LiOH, and subsequent acidification forms carboxylic acid 17-5. Coupling of carboxylic acid 17-5 with amine 17-6 in the presence of an amide coupling reagent, e.g., BOP, PyBop, HATU, HBTU, EDC, or CDI, affords amide 17-7.

Scheme 17

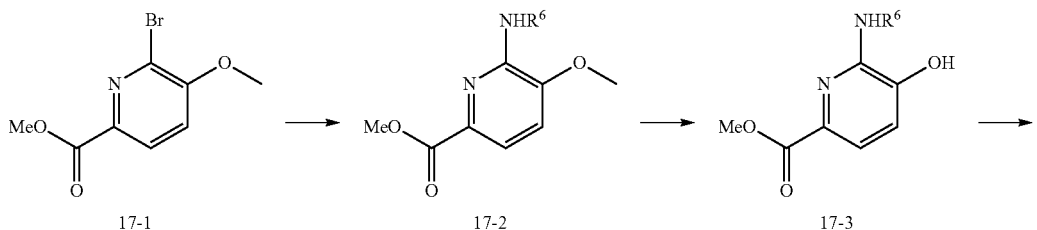

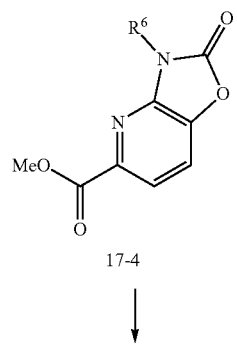

-continued

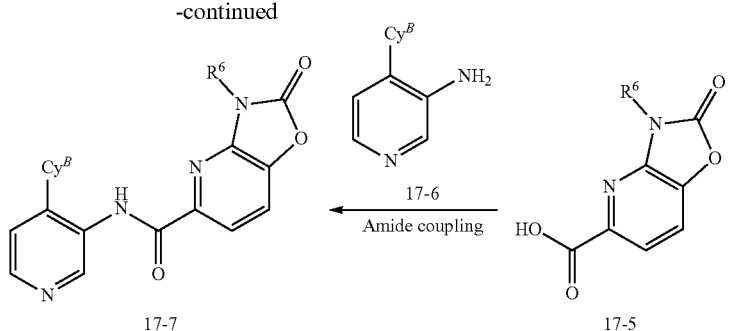

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

III. Uses of the Compounds

Compounds of the invention can inhibit the activity of one or more members of the Pim kinase family and, thus, are useful in treating diseases and disorders associated with activity of Pim kinases. For the uses described herein, any of the compounds of the invention, including any of the embodiments thereof, may be used.

The compounds of the invention can inhibit one or more of Pim1, Pim2 and Pim3. In some embodiments the compounds are selective for one Pim kinase over another. "Selective" means that the compound binds to or inhibits a Pim kinase with greater affinity or potency, respectively, compared to a reference enzyme, such as another Pim kinase. For example, the compounds can be selective for Pim1 over Pim2 and Pim3, selective for Pim2 over Pim1 and Pim3, or selective for Pim3 over Pim1 and Pim2 In some embodiments, the compounds inhibit all of the Pim family members (e.g., Pim1, Pim2 and Pim3). In some embodiments, the compounds can be selective for Pim over other kinases such as receptor and non-receptor Ser/Thr kinases such as Akt1, Akt2, Akt3, TGF-βR, PKA, PKG, PKC, CaM-kinase, phosphorylase kinase, MEKK, ERK, MAPK and mTOR; receptor Tyr kinases such as EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2; and non-receptor Tyr kinases such as Src, Fyn, Lck, Fgr, Btk, Fak, SYK, FRK, JAK or ABL. In general, selectivity can be at least about 5-fold, at least about 10-fold, at least about 20-fold, at least about 50-fold, at least about 100-fold, at least about 200-fold, at least about 500-fold or at least about 1000-fold. The method of inhibiting a Pim1, Pim2 or Pim3 kinase includes contacting the appropriate enzyme with the compound of the invention, or any of the embodiments thereof, or a pharmaceutically acceptable salt thereof.

Thus, the present disclosure provides methods of treating a Pim kinase-associated disease or disorder in an individual (e.g., patient) by administering to the individual in need of such treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a Pim kinase-associated disease or disorder. Also provided is the use of a compound of the invention, or any of the embodiments thereof, or a pharmaceutical composition thereof, in the manufacture of a medicament for treating a Pim kinase-associated disease or disorder.

A Pim kinase-associated disease can include any disease, disorder or condition that is directly or indirectly linked to expression or activity of the Pim kinase, including overexpression and/or abnormal activity levels. Abnormal activity levels can be determined by comparing activity level in normal, healthy tissue or cells with activity level in diseased cells. A Pim kinase-associated disease can also include any disease, disorder or condition that can be prevented, ameliorated, inhibited or cured by modulating Pim kinase activity. In some embodiments, the disease is characterized by the abnormal activity or expression (e.g., overexpression) of one or more Pim1, Pim2 and Pim3. In some embodiments, the disease is characterized by mutant Pim1, Pim2 or Pim3. A Pim kinase associated disease can also refer to any disease, disorder or condition wherein modulating the expression or activity of one or more Pim kinases is beneficial.

Pim kinase associated diseases that can be treated using the compounds of the invention include cancer, including, in particular, cancers in which Pim kinases are upregulated or an oncogene, e.g., Myc or Bcl2, is activated. Pim kinase associated diseases include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Pim kinase associated diseases also include hematological cancers, e.g., lymphoma, leukemia such as acute lymphoblastic leukemia (ALL), acute myelogenous leukemia (AML), chronic lymphocytic leukemia (CLL), chronic myelogenous leukemia (CML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

Pim kinase associated diseases that can be treated using the compounds of the invention also include myeloproliferative disorders such as polycythemia vera (PV), essential thrombocythemia (ET), chronic myelogenous leukemia (CML) and the like. The myeloproliferative disorder can be myelofibrosis such as primary myelofibrosis (PMF), myelofibrosis with myeloid metaplasia (MMM), post-polycythemia vera/essential thrombocythemia myelofibrosis (Post-PV/ET MF), post-essential thrombocythemia myelofibrosis (Post-ET MF) or post-polycythemia vera myelofibrosis (Post-PV MF).

Pim kinase associated diseases that can be treated using the compounds of the invention also include myelodysplastic syndrome, including refractory anemia (RA), refractory cytopenia with unilineage dysplasia (refractory anemia, Refractory neutropenia, and Refractory thrombocytopenia), refactory anemia with ringed sideroblasts (RARS), refractory anemia with ring sideroblasts-thrombocytosis (RARS-t), Refractory cytopenia with multilineage dysplasia (RCMD), refactory anemia with excess blasts (RAEB) (including refactory anemia with excess blasts-I (RAEB-I) and refactory anemia with excess blasts-II (RAEB-II), refactory anemia with excess blasts in transformation (RAEB-t), 5q-syndrome, myelodysplasia unclassifiable refractory cytopenia of childhood and chronic myelomonocytic leukemia (CMML).

Pim kinase associated diseases that can be treated using the compounds of the invention also include myelodysplastic/myeloproliferative diseases. Myelodysplastic/myeloproliferative diseases include myeloid disorders that have both dysplastic and proliferative features, such as chronic myelomonocytic leukemia (CMML), atypical chronic myeloid leukemia, juvenile myelomonocytic leukemia, and unclassifiable myelodysplastic/myeloproliferative disease.

Pim kinase-associated diseases that can be treated with compounds according to the invention also include immune disorders such as autoimmune diseases. The immune disorders include multiple sclerosis, rheumatoid arthritis, allergy, food allergy, asthma, lupus, inflammatory bowel disease and ulcerative colitis.

Pim kinase-associated diseases that can be treated with compounds according to the invention also include atherosclerosis.

The compounds of the invention can also be used to inhibit disease processes in which Pim-kinases are involved, including angiogenesis and tumor metastasis.

Due to the fact that Pim kinases are regulated by the JAK/STAT pathway, the compounds of the invention are useful to treat diseases in which modulating JAK/STAT signaling is beneficial. Thus, other diseases that can be treated using the compounds of the invention include Crohn's disease, irritable bowel syndrome, pancreatitis, diverticulosis, Grave's disease, juvenile rheumatoid arthritis, osteoarthritis, psoriatic arthritis, ankylosing spondylitis, myasthenia gravis, vasculitis, autoimmune thyroiditis, dermatitis, psoriasis, scleroderma, systemic sclerosis, vitiligo, graft versus host disease, Sjogren's syndrome, glomerulonephritis and diabetes mellitus (type I).

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Accordingly, the Pim inhibitors of the present invention can be used in combination with one or more other kinase inhibitors for the treatment of diseases, such as cancer, that are impacted by multiple signaling pathways. For example, the compounds of the invention can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the Pim inhibitors of the invention can be combined with inhibitors of kinases associated with the PI3K/Akt/mTOR signaling pathway, such as PI3K, including PI3Kγ, PI3Kδ, Akt (including Akt1, Akt2 and Akt3) and mTOR kinases.

The Pim inhibitors of the present invention can be used in combination with one or more other BET bromodomain inhibitors such a BRD2, BRD3, BRD4 and BRDT that are useful for the treatment of diseases, such as cancer.

The Pim inhibitors of the present invention can further be used in combination with other methods of treating cancers, for example by chemotherapy, irradiation or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

The Pim inhibitors of the present invention can further be used in combination with one or more anti-inflammatory agents, steroids, immunosuppressants or therapeutic antibodies.

When more than one pharmaceutical agent is administered to a patient, they can be administered simultaneously, sequentially, or in combination (e.g., for more than two agents).

IV. Formulation, Dosage Forms and Administration

When employed as pharmaceuticals, the compounds of the invention can be administered in the form of pharmaceutical compositions. Thus the present disclosure provides a composition comprising a compound Formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a Formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the Formulation, e.g., about 40 mesh.

The compounds of the invention may be milled using known milling procedures such as wet milling to obtain a particle size appropriate for tablet formation and for other Formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The Formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be Formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™) In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be Formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to Formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or Formulated under Good Manufacturing Practice standards as defined in the applicable regulations of the U.S. Food and Drug Administration. For example, suitable Formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, Formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preFormulation composition containing a homogeneous mixture of a compound of the present invention. When referring to these preFormulation compositions as homogeneous, the active ingredient is typically dispersed evenly throughout the composition so that the composition can be readily subdivided into equally effective unit dosage forms such as tablets, pills and capsules. This solid preFormulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the Formulation in an appropriate manner.

Topical Formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be Formulated using isopropyl alcohol and water, suitably in combination with other components such as, e.g., glycerol, hydroxyethyl cellulose, and the like. In some embodiments, topical Formulations contain at least about 0.1, at least about 0.25, at least about 0.5, at least about 1, at least about 2 or at least about 5 wt % of the compound of the invention. The topical Formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, Formulation of the excipient, and its route of administration. Effective doses can be extrapolated from dose-response curves derived from in vitro or animal model test systems.

V. Labeled Compounds and Assay Methods

The compounds of the invention can further be useful in investigations of biological processes, including kinase signaling, in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating Pim kinases in tissue samples, including human, and for identifying Pim kinase ligands by inhibition binding of a labeled compound. Accordingly, the present invention includes Pim kinase assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro Pim kinase labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$. In some embodiments, the compound incorporates 1, 2 or 3 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a Pim-kinase by monitoring its concentration variation when contacting with the Pim kinase, through tracking of the labeling. For example, a test compound (labeled) can be evaluated for its ability to reduce binding of another compound which is known to bind to a Pim kinase (i.e., standard compound). Accordingly, the ability of a test compound to compete with the standard compound for binding to the Pim kinase directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of Pim kinase-associated diseases or disorders, such as cancer, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner Those of skill in the art will readily recognize a variety of non-critical parameters which can be changed or modified to yield essentially the same results.

The compounds of the Examples have been found to be Pim-kinase inhibitors according to at least one assay described herein.

EXAMPLES

Experimental procedures for compounds of the invention are provided below. Open Access Prep LC-MS Purification of some of the compounds prepared was performed on Waters mass directed fractionation systems. The basic equipment setup, protocols and control software for the operation of these systems have been described in detail in literature. See, e.g., Blom, "Two-Pump At Column Dilution Configuration for Preparative LC-MS", K. Blom, *J. Combi. Chem.*, 2002, 4, 295-301; Blom et al., "Optimizing Preparative LC-MS Configurations and Methods for Parallel Synthesis Purification", *J. Combi. Chem.*, 2003, 5, 670-83; and Blom et al., "Preparative LC-MS Purification: Improved Compound Specific Method Optimization", *J. Combi. Chem.*, 2004, 6, 874-883.

Intermediate 1 tert-Butyl [(3S, 5R)-1-(3-aminopyridin-4-yl)-5-methyl-piperidin-3-yl]carbamate

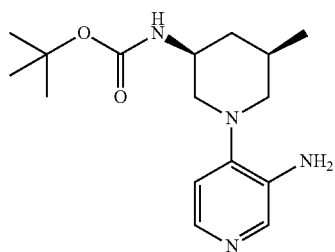 [SMILES: C[C@@H]1C[C@H](NC(=O)OC(C)(C)C)CN(c2ccncc2N)C1]

Step 1. 1-tert-butyl 2-methyl (2S, 4R)-4-methyl-5-oxopyrrolidine-1,2-dicarboxylate

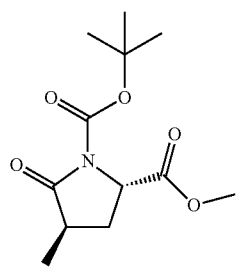 [SMILES: COC(=O)[C@@H]1C[C@@H](C)C(=O)N1C(=O)OC(C)(C)C]

A solution of 1-tert-butyl 2-methyl (2S)-5-oxopyrrolidine-1,2-dicarboxylate (16.1 g, 66.2 mmol) in THF (100 mL) was cooled to −78° C. LiHMDS in THF (1.0 M, 68.2 mL, 68.2 mmol) was added dropwise over 5 min. The resulting mixture was stirred at −78° C. for 35 min., then MeI (10.0 mL, 160 mmol) was added. The reaction mixture was allowed to warm to room temperature slowly overnight. The reaction was quenched with AcOH (7.5 mL, 130 mmol) and water (5 mL) and then concentrated under reduced pressure. The concentrated residue was further diluted with water and extracted with EtOAc (3 times). The combined extracts were washed with water and brine, dried over Na$_2$SO$_4$, filtered, and concentrated under reduced pressure. The residue was purified by silica gel column and eluted with 0-50% EtOAc/Hexanes over 45 min. Fractions were checked by TLC (MoSO$_4$ stain) and LCMS. 6.1 g (35% yield) of the sub-title compound was obtained. LCMS calc. for C$_2$H$_{12}$NO$_3$ (M+H-Boc+H)$^+$: m/z=158.1; found: 158.1.

Step 2. tert-butyl [(1S,3R)-4-hydroxy-1-(hydroxymethyl)-3-methylbutyl]carbamate

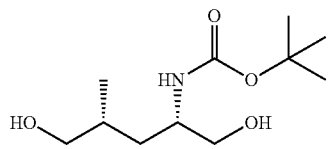 [SMILES: C[C@@H](CO)C[C@@H](CO)NC(=O)OC(C)(C)C]

A solution of 1-tert-butyl 2-methyl (2S,4R)-4-methyl-5-oxopyrrolidine-1,2-dicarboxylate (11.0 g, 42.8 mmol) in THF (100 mL) was cooled to 0° C. then LiBH$_4$ (2.8 g, 130 mmol) and then EtOH (22 mL) were added. The mixture was slowly warmed to room temperature and stirred for 4 h. The reaction was quenched with water then extracted with EtOAc (3 times). The combined extracts were dried over Na$_2$SO$_4$, filtered, and concentrated under reduced pressure to give 4.5 g (45% yield) of the crude sub-title compound. The crude product was used without further purification.

Step 3. tert-butyl [(3S,5R)-1-benzyl-5-methylpiperidin-3-yl]carbamate

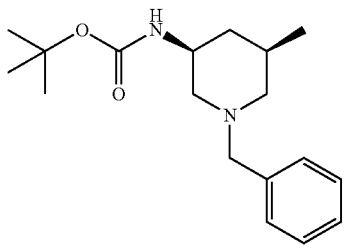 [SMILES: C[C@@H]1C[C@H](NC(=O)OC(C)(C)C)CN(Cc2ccccc2)C1]

A solution of tert-butyl [(1S,3R)-4-hydroxy-1-(hydroxymethyl)-3-methylbutyl]carbamate (9.50 g, 40.7 mmol) in DCM (200 mL) was cooled to 0° C. TEA (23 mL, 160 mmol) was added followed by dropwise addition of methanesulfonyl chloride (9.4 mL, 120 mmol). The clear solution became cloudy and yellow and the mixture was stirred at 0° C. for 1 h. The mixture was diluted with DCM and washed with saturated aq. NaHCO$_3$ and water. The organic layer was dried over Na$_2$SO$_4$, filtered, and concentrated under reduced pressure to give an intermediate mesylate as a yellow oil that was used immediately for the next step.

The intermediate mesylate and benzylamine (90 mL, 800 mmol) were combined in microwave vial, sealed and heated at 70° C. overnight. After 18 h, the mixture was quenched with 10% aq. NaOH. The mixture was then extracted with hexanes (3 times). The combined extracts were washed with brine, dried over MgSO$_4$, filtered, and concentrated under reduced pressure. The residue was purified on a silica gel column and eluted with 0-40% EtOAc/hexane over 34 min.

Step 4. tert-butyl [(3S,5R)-5-methylpiperidin-3-yl]carbamate

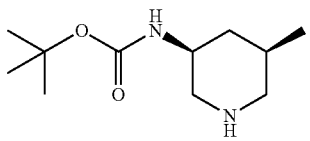

A mixture of tert-butyl [(3S,5R)-1-benzyl-5-methylpiperidin-3-yl]carbamate (4.5 g, 15 mmol), AcOH (2.0 mL, 35 mmol) and 10% Pd on carbon (1.6 g, 1.5 mmol) in EtOH (100 mL) was stirred in a Par-shaker under H$_2$ (50 psi) overnight. The mixture was filtered through a pad of diatomaceous earth and concentrated under reduced pressure. The residue was diluted with DCM (500 mL) and washed with saturated aq. NaHCO$_3$ solution. The aqueous layer was extracted twice with DCM. The combined DCM extract was dried over Na$_2$SO$_4$, and concentrated under reduced pressure to give 2.2 g (67% yield) of the sub-title compound as a white solid. LCMS calc. for C$_{11}$H$_{23}$N$_2$O$_2$ (M+H)$^+$: m/z=: 215.2; found: 215.1.

Step 5. tert-butyl [(3S,5R)-5-methyl-1-(3-nitropyridin-4-yl)piperidin-3-yl]carbamate

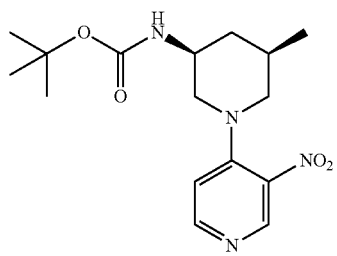 [SMILES: C[C@@H]1C[C@H](NC(=O)OC(C)(C)C)CN(c2ccncc2[N+](=O)[O-])C1]

A mixture of 4-chloro-3-nitropyridine (740 mg, 4.7 mmol), tert-butyl [(3S,5R)-5-methylpiperidin-3-yl]carbamate (1000.0 mg, 4.67 mmol) and DIPEA (2.4 mL, 14 mmol) was irradiated in a microwave oven for 1 h at 130° C. The reaction mixture was concentrated under reduced pressure and the residue was purified by column chromatography on silica gel using a CombiFlash® apparatus eluting with EtOAc/hexane (10-60%). The purification gave 1.21 g (80% yield) of the sub-title compound as a colorless oil. LCMS calc. for C$_{16}$H$_{25}$N$_4$O$_4$ (M+H)$^+$: m/z=337.2; found: 337.1.

Step 6. tert-butyl [(3S,5R)-1-(3-aminopyridin-4-yl)-5-methylpiperidin-3-yl]carbamate A mixture of tert-butyl [(3S,5R)-5-methyl-1-(3-nitropyridin-4-yl)piperidin-3-yl]carbamate (100 mg, 0.3 mmol), iron powder (0.072 g, 1.3 mmol), AcOH (2.0 mL, 35 mmol) and water (0.2 mL, 10 mmol) was stirred at room temperature for 60 min. When the reaction was complete, the reaction mixture was concentrated under reduced pressure, diluted with EtOAc, filtered through a pad of diatomaceous earth, washed with aqueous NaHCO$_3$ solution, washed with water and brine, dried over Na$_2$SO$_4$, and concentrated under reduced pressure to give 60 mg (60% yield) of the title compound as a brown solid. LCMS calc. for C$_{16}$H$_{22}$N$_4$O$_2$ (M+H)+: m/z=307.1; found: 307.1.

Intermediate 2 tert-Butyl ((3R,4R,5S)-1-(3-aminopyridin-4-yl)-4-{[tert-butyl(dimethyl)silyl]oxy}-5-methylpiperidin-3-yl)carbamate

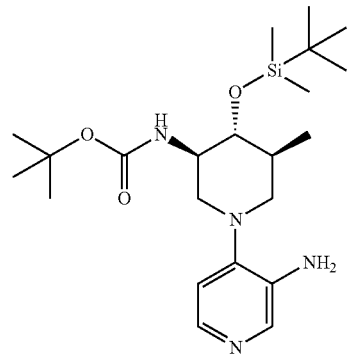

Step 1. tert-butyl (4R)-4-{(1R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate

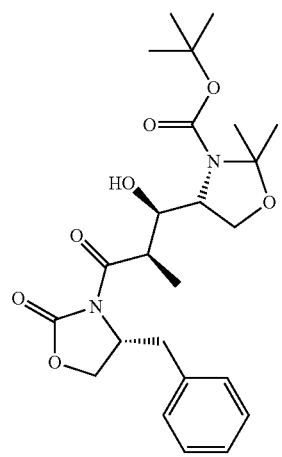

To a solution of (R)-3-(1-oxopropyl)-4-benzyl-2-oxazolidinone (12 g, 51 mmol) in DCM (300 mL) (0.13 M), 1.0 M TiCl$_4$ in DCM (51 mL, 51 mmol) was added at −40° C. The mixture was stirred at −40° C. for 10 min., then DIPEA (22 mL, 130 mmol) was added, forming a dark red solution. The mixture was stirred at 0° C. for 20 min. tert-Butyl (4R)-4-formyl-2,2-dimethyl-1,3-oxazolidine-3-carboxylate (12 g, 51 mmol) in DCM (100 mL) (0.5 M) was then added dropwise and the resulting mixture was stirred for 1.5 h at 0° C. LCMS showed 2 peaks with a mass corresponding to the sub-title compound, one major peak and one minor peak (5:2). The reaction mixture was quenched by the addition of aq. NH$_4$Cl solution and the mixture was extracted with DCM. The organic phase was separated, washed with brine, dried over MgSO$_4$, concentrated under reduced pressure, and purified by chromatography on silica gel (0-40% EtOAc/hexane) to give 8 g (30% yield) of the sub-title compound as a colorless oil. LCMS calc. for C$_{24}$H$_{35}$N$_2$O$_7$ (M+H)$^+$: m/z=463.2; found: 463.1.

Step 2. tert-butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate

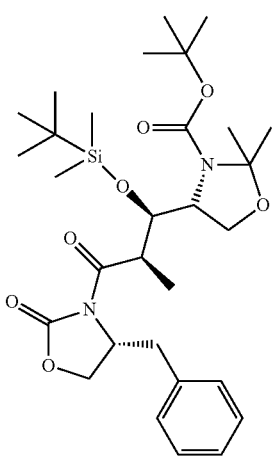

To a solution of tert-butyl (4R)-4-{(1R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate (12.1 g, 26.2 mmol) and 2,6-lutidine (5.4 mL, 47 mmol) in DCM (260 mL) (0.1 M) was added tert-butyldimethylsilyl trifluoromethanesulfonate (8.41 mL, 36.6 mmol) at −40° C. The mixture was stirred at −40° C. for 2 h. The reaction mixture was diluted with DCM, washed with saturated aq. NaHCO$_3$ solution, dried over Na$_2$SO$_4$, concentrated under reduced pressure, and purified by chromatography on silica gel (0-20% EtOAc/hexane) to give 14 g (92.8% yield) of the sub-title compound as a colorless gel. LCMS calc. for C$_{25}$H$_{41}$N$_2$O$_5$Si (M+H-Boc+H)$^+$: m/z=477.3; found: 477.1.

Step 3. tert-butyl (4R)-4-((1R,2S)-1-{[tert-butyl(dimethyl)silyl]oxy}-3-hydroxy-2-methylpropyl)-2,2-dimethyl-1,3-oxazolidine-3-carboxylate

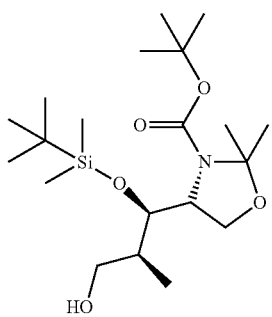

To a solution of tert-butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate (14.0 g, 24.3 mmol) and EtOH (4.2 mL, 73 mmol) in THF (300 mL) (0.09 M) was added LiBH$_4$ (1.6 g, 73 mmol) at −30° C. The mixture allowed to warm to 0° C. and stirred overnight. The reaction mixture was diluted with Et$_2$O and 1 M NaOH was added. The resulting mixture was extracted with EtOAc and the organic extract was washed with brine, dried over Na$_2$SO$_4$, concentrated under reduced pressure, and purified by chromatography on silica gel (0-20% EtOAc/hexane) to give 4.1 g (42% yield) of the sub-title compound as a colorless oil. LCMS calc. for C$_{15}$H$_{34}$NO$_3$Si (M+H-Boc+H)$^+$: m/z=304.2; found: 304.1.

Step 4. tert-butyl (4R)-4-((1R,2S)-3-azido-1-{[tert-butyl(dimethyl)silyl]oxy}-2-methylpropyl)-2,2-dimethyl-1,3-oxazolidine-3-carboxylate

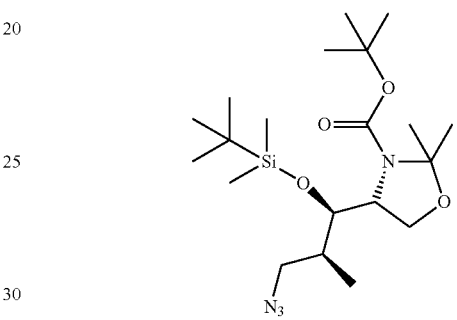

To a mixture of tert-butyl (4R)-4-((1R,2S)-1-{[tert-butyl(dimethyl)silyl]oxy}-3-hydroxy-2-methylpropyl)-2,2-dimethyl-1,3-oxazolidine-3-carboxylate (8.20 g, 20.3 mmol), diisopropyl azodicarboxylate (8.0 mL, 41 mmol) and PPh$_3$ (11 g, 41 mmol) in THF (100 mL) (0.18 M), diphenylphosphonic azide (8.8 mL, 41 mmol) was added. The mixture was stirred at room temperature overnight. The mixture was concentrated under reduced pressure, and the residue was purified by chromatography on silica gel (0-15% EtOAc/hexane) to give 5.2 g (60% yield) of the sub-title compound as a yellowish oil. LCMS calc. for C$_{20}$H$_{41}$N$_4$O$_4$Si (M+H)$^+$: m/z=429.3; found: 429.1.

Step 5. tert-butyl [(1R,2R,3S)-4-azido-2-{[tert-butyl(dimethyl)silyl]oxy}-1-(hydroxymethyl)-3-methylbutyl]carbamate

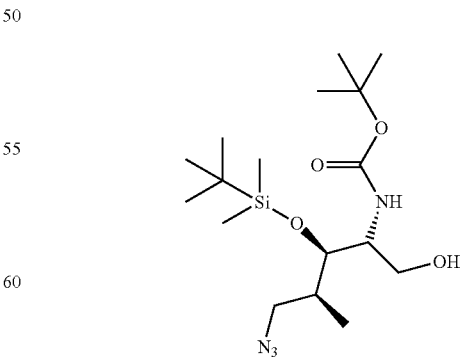

A solution of tert-butyl (4R)-4-((1R,2S)-3-azido-1-{[tert-butyl(dimethyl)silyl]oxy}-2-methylpropyl)-2,2-dimethyl-1,3-oxazolidine-3-carboxylate (10.5 g, 24.5 mmol) in EtOH (70 mL) was added pyridinium p-toluenesulfonate (12.3 g, 49.0 mmol) and the mixture was heated under reflux for 2 days.

The volatiles were removed under reduced pressure and the residue was dissolved in DCM (200 mL) (0.1 M). To the resulting solution were added DIPEA (8.53 mL, 49.0 mmol) and di-tert-butyldicarbonate (6.42 g, 29.4 mmol). The reaction mixture was stirred at room temperature for 5 h. The mixture was concentrated under reduced pressure and purified by chromatography on silica gel (0-25% EtOAc/Hexane) to give 5.8 g (61% yield) of the sub-title compound as a colorless oil. LCMS calc. for $C_{12}H_{29}N_4O_2Si$ (M+H-Boc+H)$^+$: m/z=289.2; found: 289.1.

Step 6. (2R,3R,4S)-5-azido-2-[(tert-butoxycarbonyl)amino]-3-{[tert-butyl(dimethyl)silyl]oxy}-4-methylpentyl methanesulfonate

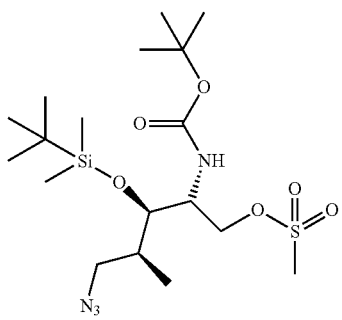

To a solution of tert-butyl [(1R,2R,3S)-4-azido-2-{[tert-butyl(dimethyl)silyl]oxy}-1-(hydroxymethyl)-3-methylbutyl]carbamate (5.80 g, 14.9 mmol) in pyridine (75 mL) at 0° C. was added methanesulfonyl chloride (1.50 mL, 19.4 mmol) and DMAP (0.36 g, 3.0 mmol). The mixture was stirred at 0° C. for 1 h. The solution was diluted with EtOAc, washed with saturated aq. NaHCO$_3$ solution, concentrated under reduced pressure, and purified by chromatography on silica gel (0-25% EtOAc/Hexane) to give 4.8 g (69% yield) of the sub-title compound as a colorless oil. LCMS calc. for $C_{13}H_{31}N_4O_4SSi$ (M+H-Boc)$^+$: m/z=367.2; found: 367.2.

Step 7. tert-butyl ((3R,4R,5S)-4-{[tert-butyl(dimethyl)silyl]oxy}-5-methylpiperidin-3-yl)carbamate

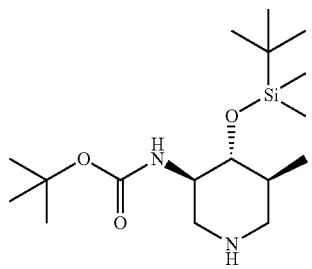 [SMILES: C[C@H]1CNC[C@@H](NC(=O)OC(C)(C)C)[C@@H]1O[Si](C)(C)C(C)(C)C]

A solution of (2R,3R,4S)-5-azido-2-[(tert-butoxycarbonyl)amino]-3-{[tert-butyl(dimethyl)silyl]oxy}-4-methylpentyl methanesulfonate (4.25 g, 9.11 mmol) in MeOH (100 mL) (0.09M) was deoxygenated with a stream of N$_2$ for 20 min. DIPEA (4.0 mL, 23 mmol) was added, followed by mixture of 10% Pd on carbon (0.97 g, 0.91 mmol). The reaction mixture was stirred under a balloon containing H$_2$ for 2 h. The solution was filtered through a pad of diatomaceous earth and rinsed with MeOH. The filtrate was concentrated under reduced pressure to give 2.10 g (66% yield) of the sub-title compound as a white solid. LCMS calc. for $C_{12}H_{37}N_2O_3Si$ (M+H)$^+$: m/z=345.3; found: 345.1.

Step 8. tert-butyl [(3R,4R,5S)-4-{[tert-butyl(dimethyl)silyl]oxy}-5-methyl-1-(3-nitropyridin-4-yl)piperidin-3-yl]carbamate

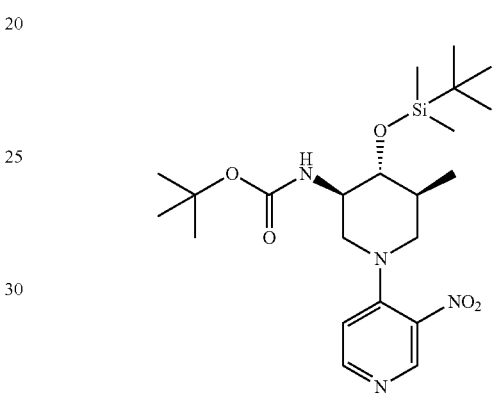

A mixture of 4-chloro-3-nitropyridine (150.0 mg, 0.9461 mmol) and tert-butyl ((3R,4R,5S)-4-{[tert-butyl(dimethyl)silyl]oxy}-5-methylpiperidin-3-yl)carbamate (300.0 mg, 0.8707 mmol) and TEA (0.3763 mL, 2.700 mmol) in IPA (10.0 mL) was stirred at 60° C. for 2 h. The reaction mixture was concentrated under reduced pressure and the residue was purified by column chromatography on silica gel using CombiFlash® apparatus (eluting with 0 to 30% EtOAc in hexane) to give 100 mg (24% yield) of the sub-title compound. LCMS calc. for $C_{22}H_{39}N_4O_5Si$ (M+H)$^+$: m/z=467.3; found: 467.1.

Step 9. tert-butyl ((3R,4R,5S)-1-(3-aminopyridin-4-yl)-4-{[tert-butyl(dimethyl)silyl]oxy}-5-methylpiperidin-3-yl)carbamate A mixture of tert-butyl [(3R,4R,5S)-4-{[tert-butyl(dimethyl)silyl]oxy}-5-methyl-1-(3-nitropyridin-4-yl)piperidin-3-yl]carbamate (100.00 mg, 0.27858 mmol), AcOH (10.00 mL) and iron powder (558.4 mg, 9.999 mmol) was stirred at ambient temperature for 2 h. The mixture was diluted with 30 mL of EtOAc and filtered through a pad of diatomaceous earth. The combined organic filtrate was concentrated under reduced pressure. The residue was diluted with EtOAc and washed with aq. Na$_2$CO$_3$ solution and 0.2 M NaOH. The organic phase was concentrated under reduced pressure to give 50 mg (47% yield) of the title compound. LCMS calc. for $C_{22}H_{41}N_4O_3Si$ (M+H)$^+$: m/z=437.3; found: 437.1.

97

Intermediate 3

4-tert-Butyl [(1S,3R,5S)-3-(3-aminopyridin-4-yl)-5-methylcyclohexyl]carbamate and 4-tert-butyl [(1R,3S,5R)-3-(3-aminopyridin-4-yl)-5-methylcyclohexyl]carbamate

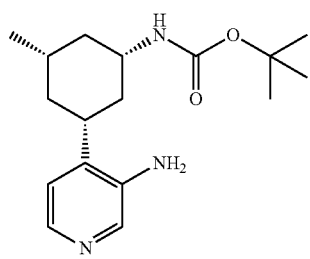

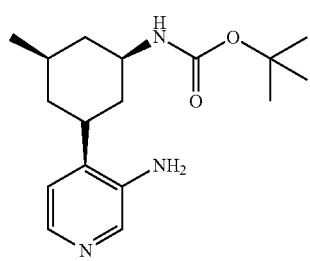

Step 1. 5-Methyl-3-oxocyclohex-1-en-1-yl trifluoromethanesulfonate

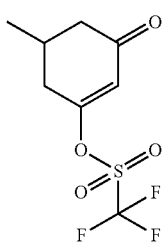 [SMILES: CC1CC(=O)C=C(OS(=O)(=O)C(F)(F)F)C1]

To a solution of 5-methylcyclohexane-1,3-dione (50.1 g, 397 mmol) in DCM (700 mL) was added $Na_2CO_3$ (46.3 g, 437 mmol) and the resulting mixture was cooled to 0° C. A solution of trifluoromethanesulfonic anhydride (66.8 mL, 397 mmol) in DCM (600 mL) was added dropwise over 1 h at 0° C. The reaction mixture was stirred at room temperature for 2 h. The solution was filtered and the filtrate was quenched by careful addition of saturated aq. $NaHCO_3$ to pH=7. The organic layer was washed with water, brine, dried over $Na_2SO_4$ and concentrated under reduced pressure to give the sub-title product as light yellow oil, which was used for next step without further purification. LCMS calc. for $C_8H_{10}F_3O_4S$ (M+H)$^+$: m/z=259.0. Found: 259.1.

98

Step 2. 5-Methyl-3-(4,4,5,5-tetramethyl-1,3,2-dioxaborolan-2-yl)cyclohex-2-en-1-one

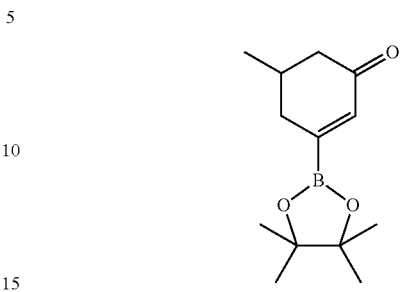

To a mixture of 4,4,5,5,4',4',5',5'-octamethyl-[2,2']bi[[1,3,2]dioxaborolanyl] (77.6 g, 306 mmol), potassium acetate (77.1 g, 785 mmol) and [1,1'-bis(diphenylphosphino)ferrocene]dichloropalladium(II), complex with DCM (1:1) (8.6 g, 10.0 mmol) under $N_2$ was added a solution of 5-methyl-3-oxocyclohex-1-en-1-yl trifluoromethanesulfonate (67.6 g, 262 mmol) in 1,4-dioxane (420 mL). The reaction mixture was degassed with $N_2$ and the mixture was stirred at 80° C. overnight. After cooling to room temperature, the mixture was filtered through a pad of diatomaceous earth (eluted with EtOAc). The filtrate was concentrated under reduced pressure, and the crude product was used in next step without further purification.

Step 3. 5-Methyl-3-(3-nitropyridin-4-yl)cyclohex-2-en-1-one

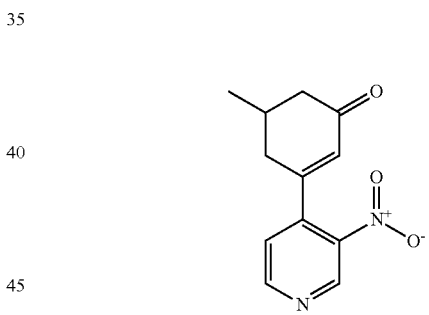

A solution of 5-methyl-3-(4,4,5,5-tetramethyl-1,3,2-dioxaborolan-2-yl)cyclohex-2-en-1-one (20.0 g, 84.7 mmol) in 1,4-dioxane (120 mL), 4-chloro-3-nitropyridine (10.0 g, 63.1 mmol), 2.0 M $Na_2Co_3$ in water (63.1 mL, 126 mmol) and [1,1'-bis(diphenylphosphino)ferrocene]dichloropalladium(II), complex with DCM (1:1) (2.58 g, 3.15 mmol) was refluxed under a $N_2$ atmosphere for 1 h. The reaction mixture was diluted with EtOAc and water, then filtered through a pad of diatomaceous earth, and washed with EtOAc. The two layers were separated, and the aqueous layer was extracted with EtOAc (2×). The combined organic phases were washed with water and brine, and dried over $Na_2SO_4$. The crude residue was purified by flash chromatography (eluting with a gradient 0-60% EtOAc in hexanes) to give the sub-title product as an orange oil (6.6 g, 45%). LCMS calc. for $C_{12}H_{13}N_2O_3$ (M+H)$^+$: m/z=233.1. Found: 233.1.

Step 4. cis-(+/−)-5-Methyl-3-(3-nitropyridin-4-yl)cyclohex-2-en-1-ol

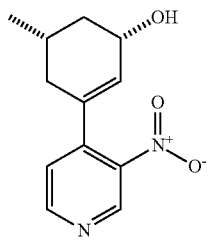 [SMILES: C[C@H]1CC(c2ccncc2[N+](=O)[O-])=C[C@@H](O)C1]

To a solution of 5-methyl-3-(3-nitropyridin-4-yl)cyclohex-2-en-1-one (6.6 g, 28 mmol) in EtOH (93 mL) was added CeCl$_3$.7H$_2$O (12.7 g, 34.1 mmol), The resulting mixture was cooled to 0° C. and NaBH$_4$ (1.29 g, 34.1 mmol) was added portion-wise. After stirring at 0° C. for 1 h, the reaction was quenched with water and concentrated under reduced pressure to remove the EtOH. The residue was then extracted with EtOAc. The organic layer was washed with brine, dried over Na$_2$SO$_4$, filtered, and concentrated. The crude product was purified by flash chromatography (eluting with a gradient of 20-90% EtOAc in hexanes) to give the sub-title product as a racemic mixture (6.4 g, 96%). LCMS calc. for C$_{12}$H$_{15}$N$_2$O$_3$ (M+H)$^+$: m/z=235.1. Found: 235.1.

Step 5. 4-(3-(tert-Butyldimethylsilyloxy)-5-methylcyclohex-1-enyl)3-nitropyridine

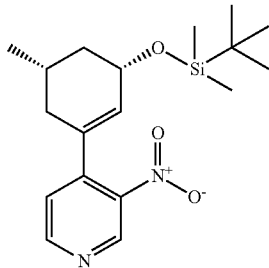 [SMILES: C[C@H]1CC(c2ccncc2[N+](=O)[O-])=C[C@@H](O[Si](C)(C)C(C)(C)C)C1]

A solution of cis(+/−)-5-methyl-3-(3-nitropyridin-4-yl)cyclohex-2-en-1-ol (6.4 g, 27 mmol) in DMF (51 mL) was added 1H-imidazole (3.7 g, 55 mmol) and tert-butyldimethylsilyl chloride (5.8 g, 38 mmol). The resulting mixture was stirred at room temperature overnight. The reaction solution was diluted with water and EtOAc. The organic layer was washed with water (2×), brine, dried over Na$_2$SO$_4$ and concentrated under reduced pressure to give product as an orange oil. LCMS calc. for C$_{18}$H$_{29}$N$_2$O$_3$Si (M+H)$^+$: m/z=349.2. Found: 349.2.

Step 6. 4-(3-(tert-Butyldimethylsilyloxy)-5-methylcyclohex-1-enyl)pyridin-3-amine

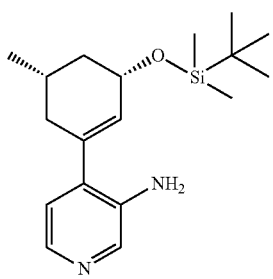 [SMILES: C[C@H]1CC(c2ccncc2N)=C[C@@H](O[Si](C)(C)C(C)(C)C)C1]

A mixture of 4-(3-(tert-butyldimethylsilyloxy)-5-methylcyclohex-1-enyl)3-nitropyridine (9.3 g, 27 mmol), iron (8.9 g, 160 mmol) and AcOH (67 mL) was stirred at room temperature for 2 h. The reaction mixture was filtered through a pad of diatomaceous earth, washed with MeOH. The filtrate was concentrated under reduced pressure to remove the volatiles, the residue was dissolved in EtOAc, washed with saturated aq. Na$_2$CO$_3$, washed with brine, dried over Na$_2$SO$_4$, filtered, and concentrated under reduced pressure to give the sub-title product as a yellow oil (7.7 g, 90%). LCMS calc. for C$_{18}$H$_{31}$N$_2$OSi (M+H)$^+$: m/z=319.2. Found: 319.2.

Step 7. 4-(3-(tert-Butyldimethylsilyloxy)-5-methylcyclohexyl)pyridin-3-amine

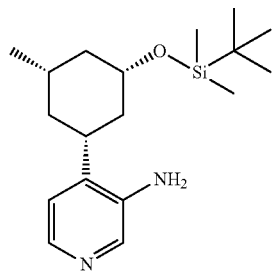 [SMILES: C[C@@H]1C[C@H](O[Si](C)(C)C(C)(C)C)C[C@H](c2ccncc2N)C1]

To a suspension of 4-(3-(tert-butyldimethylsilyloxy)-5-methylcyclohex-1-enyl)pyridin-3-amine (7.7 g, 24 mmol) in MeOH (203 mL) under N$_2$ was added 10% Pd on carbon (2.64 g). The mixture was purged with H$_2$ and stirred under a H$_2$ balloon for 3 h. The mixture was filtered through a pad of diatomaceous earth and eluted with MeOH. The filtrate was concentrated under reduced pressure to give the crude product as an off-white foamy solid (7.3 g, 93%). The crude product was used directly in the next step without further purification. LCMS calc. for C$_{18}$H$_{33}$N$_2$OSi (M+H)$^+$: m/z=321.2. Found: 321.3.

Step 8. cis (+/−) Benzyl 4-3-(tert-butyldimethylsilyloxy)-5-methylcyclohexylpyridin-3-ylcarbamate

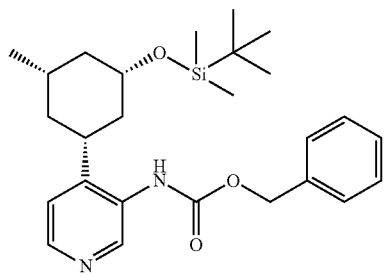 [SMILES: C[C@@H]1C[C@H](O[Si](C)(C)C(C)(C)C)C[C@H](c2ccncc2NC(=O)OCc2ccccc2)C1]

To a solution of 4-(3-(tert-butyldimethylsilyloxy)-5-methylcyclohexyl)pyridin-3-amine (7.3 g, 23 mmol) in DCM (50 mL) was added N-(benzyloxycarbonyloxy)succinimide (6.5 g, 26 mmol) and DMAP (0.14 g, 1.2 mmol). After stirring for 16 h, another portion of N-(benzyloxycarbonyloxy)succinimide (3.1 g, 12 mmol) was added, followed by DMAP. The reaction mixture was stirred overnight. The reaction solution was partitioned between EtOAc and saturated aq. Na$_2$CO$_3$ solution. The organic layer was washed with saturated aq. Na$_2$CO$_3$ solution and brine, dried over Na$_2$SO$_4$, filtered and concentrated. The residue was purified by flash chromatography (eluting with a gradient of 0-40% EtOAc in hexanes) to give the sub-title product as a brown oil. LCMS calc. for C$_{26}$H$_{39}$N$_2$O$_3$Si (M+H)$^+$: m/z=455.3. Found: 455.2.

Step 9. cis-(+/−)Benzyl 4-(-3-hydroxy-5-methylcyclohexyl)pyridin-3-ylcarbamate

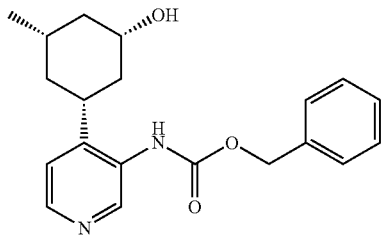 [SMILES: C[C@@H]1C[C@H](O)C[C@H](c2ccncc2NC(=O)OCc2ccccc2)C1]

To a solution of cis (+/−) benzyl 4-3-(tert-butyldimethylsilyloxy)-5-methylcyclohexylpyridin-3-ylcarbamate (7.0 g, 15 mmol) in MeOH (100.0 mL) was added 6.0 M HCl in water (50.0 mL, 300 mmol). The resulting mixture was stirred at room temperature for 6 h. The pH was then adjusted to pH=7 by addition of 6 N NaOH and the volatiles were removed under reduced pressure. The aqueous layer was extracted with EtOAc and the organic was washed with brine, dried over MgSO$_4$, filtered and concentrated under reduced pressure to give the crude product which was used in next step without purification (4.8 g, 92%). LCMS calc. for C$_{20}$H$_{25}$N$_2$O$_3$ (M+H)$^+$: m/z=341.2. Found: 341.1.

Step 10. cis-(+/−)-Benzyl 4-(3-methyl-5-oxocyclohexyl)pyridin-3-ylcarbamate

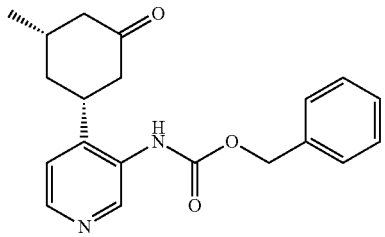 [SMILES: C[C@@H]1CC(=O)C[C@H](c2ccncc2NC(=O)OCc2ccccc2)C1]

To a solution of cis-(+/−)benzyl 4-(-3-hydroxy-5-methylcyclohexyl)pyridin-3-ylcarbamate (4.8 g, 14 mmol) in DCM (90 mL) was added Dess-Martin periodinane (8.97 g, 21.2 mmol). The reaction mixture was stirred at room temperature for 2 h. The reaction mixture was diluted with Et$_2$O and saturated aq. NaHCO$_3$ solution and stirred for 30 min. The organic layer was separated and washed with brine, dried over Na$_2$SO$_4$, filtered and concentrated. The crude product was purified by flash chromatography (eluting with a gradient of 0-50% EtOAc in hexanes) to give the sub-title product (2.5 g, 52%). LCMS calc. for C$_{20}$H$_{23}$N$_2$O$_3$ (M+H)$^+$: m/z=339.2. Found: 339.1.

Step 11. cis-(+/−)-Benzyl 4-(3-(benzylamino)-5-methylcyclohexyl)pyridin-3-ylcarbamate

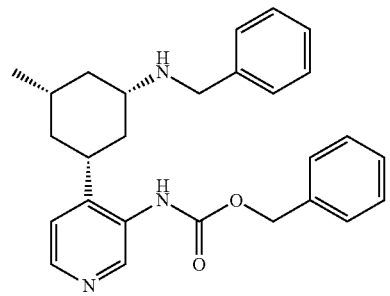 [SMILES: C[C@@H]1C[C@H](NCc2ccccc2)C[C@H](c2ccncc2NC(=O)OCc2ccccc2)C1]

To a solution of cis-(+/−)-benzyl 4-(3-methyl-5-oxocyclohexyl)pyridin-3-ylcarbamate (2.50 g, 7.39 mmol) in MeOH (30 mL) was added benzylamine (2.42 mL, 22.2 mmol). The resulting mixture was stirred at room temperature for 2 h. After cooling to −78° C., 2.0 M LiBH$_4$ in THF (4.1 mL, 8.1 mmol) was added. The reaction mixture was warmed to room temperature and stirred overnight. The solution was partitioned between EtOAc and saturated aq. NaHCO$_3$, then the resulting layers were separated. The organic layer was washed with additional saturated aq. NaHCO$_3$ and brine, dried over MgSO$_4$, filtered, and concentrated. The crude product was used in the next step without purification (3.1 g, 98%). LCMS calc. for C$_{22}$H$_{32}$N$_3$O$_2$ (M+H)$^+$: m/z=430.2. Found: 430.2.

Step 12. 4-tert-Butyl [(1S,3R,5S)-3-(3-aminopyridin-4-yl)-5-methylcyclohexyl]carbamate and 4 tert-Butyl [(1R,3S,5R)-3-(3-aminopyridin-4-yl)-5-methylcyclohexyl]carbamate To a solution of cis-(+/−)-benzyl 4-(3-(benzylamino)-5-methylcyclohexyl)pyridin-3-ylcarbamate (3.10 g, 7.22 mmol) in MeOH (100 mL) was added 20% palladium hydroxide on carbon (1.0 g, 1.4 mmol). The resulting heterogeneous solution was put under an atmosphere of H$_2$ and was stirred for 14 h, at which time the reaction mixture was purged with N$_2$, di-tert-butyldicarbonate (1.6 g, 7.2 mmol) was added and the solution was stirred for 7 h. Additional di-tert-butyldicarbonate (1.6 g, 7.2 mmol) was added and the solution was stirred overnight. The solvent was removed under reduced pressure and the residue was purified by flash chromatography (eluting with a gradient of 20-100% EtOAc in hexanes) to give the racemic product. The racemic mixture was separated by chiral column (CHIRALPAK® IA column eluting with 15% EtOH/85% Hexanes, 12 mL/min) to give two peaks.

Peak 1 retention time 14.3 min., LCMS calc. for C$_{17}$H$_{28}$N$_3$O$_2$ (M+H)$^+$: m/z=306.2. Found: 306.2.

Peak 2 retention time 18.6 min., LCMS calc. for C$_{17}$H$_{28}$N$_3$O$_2$ (M+H)$^+$: m/z=306.2. Found: 306.2.

Peak 1 is tentatively identified as 4-tert-butyl [(1R,3S,5R)-3-(3-aminopyridin-4-yl)-5-methylcyclohexyl]carbamate.

Peak 2 is tentatively identified as 4-tert-butyl [(1S,3R,5S)-3-(3-aminopyridin-4-yl)-5-methylcyclohexyl]carbamate.

Example 1

N-(4-((3S,5R)-3-Amino-5-methylpiperidin-1-yl)pyridin-3-yl)-2-propylfuro[3,2-b]pyridine-5-carboxamide

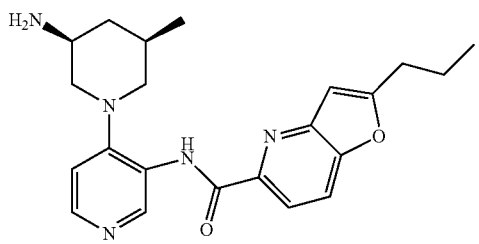

Step 1. Methyl 5-hydroxypyridine-2-carboxylate

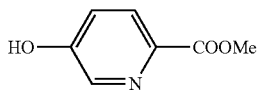 [SMILES: COC(=O)c1ccc(O)cn1]

MeOH (70 mL) was added to 5-hydroxypyridine-2-carboxylic acid (Combi-blocks, 5.01 g, 36.0 mmol). Then H$_2$SO$_4$ (5.8 mL, 110 mmol) was added and the reaction mixture was stirred at 75° C. overnight. The solvent was then evaporated and the product was dissolved in EtOAc and a saturated solution of NaHCO$_3$ was added to a pH=3. The solids were collected and dried under reduced pressure. The remaining solution was extracted 3 times with EtOAc. The organic phase was washed with brine, dried over Na$_2$SO$_4$, and solvent was evaporated under reduced pressure. The obtained solid product (5.3 g, 96%) was used in the next step without further purification. LCMS calc. for C$_7$H$_8$NO$_3$ (M+H)$^+$ m/z=154.1; found: 154.1.

Step 2. Methyl 5-hydroxy-6-iodopyridine-2-carboxylate

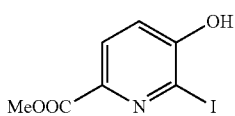

I$_2$ (3.331 g, 13.12 mmol) was added to the mixture of Na$_2$CO$_3$ (3.034 g, 28.63 mmol) and methyl 5-hydroxypyridine-2-carboxylate (2.0 g, 13 mmol) in water (60 mL). The mixture was stirred at room temperature overnight. The reaction mixture was acidified with 1 M solution of HCl to pH 5 and the product was extracted 3 times with EtOAc. The organic phase was washed with brine, dried over Na$_2$SO$_4$, and the solvent was evaporated under reduced pressure to give a white solid (3.4 g, 93%). The obtained product was used in the next step without further purification. LCMS calc. for C$_7$H$_7$INO$_3$ (M+H)$^+$ m/z=280.0; found: 279.9.

Step 3. Methyl 2-propylfuro[3,2-b]pyridine-5-carboxylate

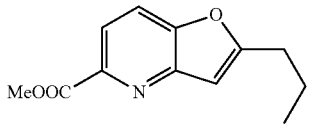 [SMILES: CCCc1cc2nc(C(=O)OC)ccc2o1]

Methyl 5-hydroxy-6-iodopyridine-2-carboxylate (320 mg, 1.1 mmol), CuI (32.3 mg, 0.170 mmol) and dichloro[bis(triphenylphosphonio)]palladate (79 mg, 0.11 mmol) were placed in a vial, which was then evacuated and backfilled with N$_2$ three times. After this, DMF (1.50 mL) and TEA (390 µL, 2.8 mmol) were added and the reaction mixture was stirred for 5 min. Then 1-pentyne (127 µL, 1.29 mmol) was added and the reaction mixture was stirred at 60° C. for 3 h. After this time the reaction mixture was quenched with water and the product extracted with EtOAc. The organic fraction was then washed with brine, dried over Na$_2$SO$_4$, and the solvent was evaporated under reduced pressure. The crude product was purified by chromatography on silica gel using Biotage Isolera™ apparatus to give the sub-title product as a brown oil (127 mg, 51%). LCMS calc. for C$_{12}$H$_{14}$NO$_3$ (M+H)$^+$ m/z=220.1; found: 219.8.

Step 4. 2-Propylfuro[3,2-b]pyridine-5-carboxylic acid

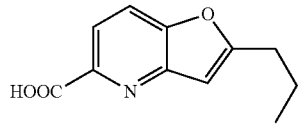

Methyl 2-propylfuro[3,2-b]pyridine-5-carboxylate (127 mg, 0.579 mmol) was dissolved in THF (6 mL), then water (2 mL) and MeOH (4 mL) were added. After addition of LiOH (100 mg, 4 mmol), the reaction mixture was stirred at 60° C. for 4 h. The mixture was cooled to room temperature and the pH was adjusted to 5 by addition of 1 M HCl. The product was then extracted with EtOAc, washed with brine, dried over Na$_2$SO$_4$, and the solvent was evaporated. The obtained solid product was used in the next step without further purification (118 mg, 99%). LCMS calc. for C$_{11}$H$_{12}$NO$_3$ (M+H)$^+$ m/z=206.1; found: 206.2.

Step 5. tert-Butyl [(3S,5R)-5-methyl-1-(3-{[(2-propylfuro[3,2-b]pyridin-5-yl)carbonyl]amino}pyridin-4-yl)piperidin-3-yl]carbamate

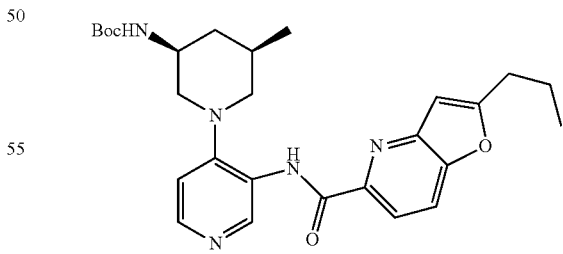

tert-Butyl [(3S,5R)-1-(3-aminopyridin-4-yl)-5-methylpiperidin-3-yl]carbamate (25 mg, 0.081 mmol) and 2-propylfuro[3,2-b]pyridine-5-carboxylic acid (20.0 mg, 0.0975 mmol) were dissolved in DMF (1.4 mL). Then DIPEA (42 µL, 0.24 mmol) and HATU (77 mg, 0.20 mmol) were added and reaction mixture was stirred at room temperature for 2 h. After full conversion was achieved, the reaction mixture was quenched with saturated aq. NaHCO$_3$ and the product was extracted with EtOAc. The organic phase was washed with brine and dried over Na$_2$SO$_4$. After the solvent was evaporated, the product was purified by chromatography on silica gel using Biotage Isolera™ apparatus to give the sub-title compound (34 mg, 85%). LCMS calc. for C$_{27}$H$_{36}$N$_5$O$_4$ (M+H)$^+$ m/z=494.3; found: 494.3.

Step 6. N-(4-((3S,5R)-3-amino-5-methylpiperidin-1-yl)pyridin-3-yl)-2-propylfuro[3,2-b]pyridine-5-carboxamide tert-Butyl [(3S,5R)-5-methyl-1-(3-{[(2-propylfuro[3,2-b]pyridin-5-yl)carbonyl]amino}pyridin-4-yl)piperidin-3-yl]carbamate (22 mg, 0.046 mmol) was dissolved in DCM (1.0 mL) and TFA (1.1 mL, 14 mmol) was added. The reaction mixture was then stirred at 40° C. for 1 h. The mixture was neutralized by addition of NH$_3$ solution and purified by RP-HPLC (water XBridge™ C18 column, 30 mm×100 mm, 5 μm particle size, eluting with a gradient of MeCN/water containing 0.1% NH$_4$OH, at flow rate of 60 mL/min) LCMS calc. for C$_{22}$H$_{28}$N$_5$O$_2$ (M+H)$^+$ m/z=394.2; found: 394.1.

Example 2

N-{4-[(3S,5R)-3-Amino-5-methylpiperidin-1-yl]pyridin-3-yl}-2-isopropylfuro[3,2-b]pyridine-5-carboxamide

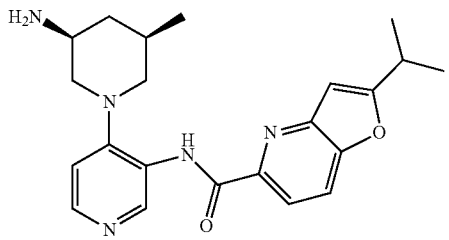 [SMILES: CC(C)c1cc2nc(C(=O)Nc3cnccc3N3C[C@H](C)C[C@H](N)C3)ccc2o1]

The title compound was synthesized by a procedure analogous to Example 1, using 3-methylbut-1-yne. LCMS calc. for C$_{22}$H$_{28}$N$_5$O$_2$ (M+H)$^+$ m/z=394.2; found: 394.2.

Example 3

N-(4-((3S,5R)-3-Amino-5-methylpiperidin-1-yl)pyridin-3-yl)-2-(6-methoxypyridin-3-yl)furo[3,2-b]pyridine-5-carboxamide

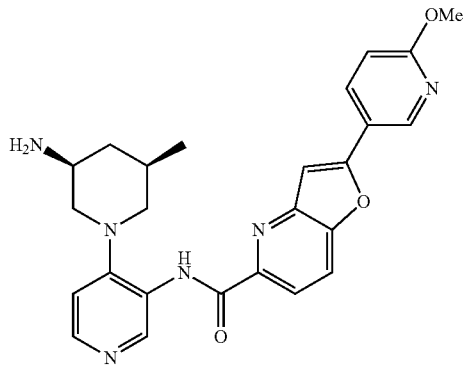 [SMILES: COc1ccc(-c2cc3nc(C(=O)Nc4cnccc4N4C[C@H](C)C[C@H](N)C4)ccc3o2)cn1]

The title compound was synthesized by a procedure analogous to that of Example 1, using 5-ethynyl-2-methoxypyridine. LCMS calc. for C$_{25}$H$_{27}$N$_6$O$_3$ (M+H)$^+$ m/z=459.2. found: 459.2.

Example 4

N-(4-((3S,5R)-3-Amino-5-methylpiperidin-1-yl)pyridin-3-yl)-2-(2,6-difluorophenyl)furo[3,2-b]pyridine-5-carboxamide

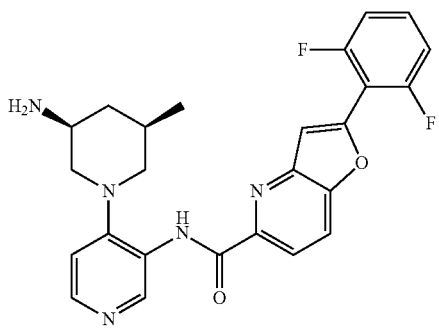 [SMILES: C[C@@H]1C[C@H](N)CN(c2ccncc2NC(=O)c2ccc3oc(-c4c(F)cccc4F)cc3n2)C1]

The title compound was synthesized by a procedure analogous to that of Example 1, using 1-ethynyl-3,5-difluorobenzene. LCMS calc. for C$_{25}$H$_{24}$F$_2$N$_5$O$_2$ (M+H)$^+$ m/z=464.2. found: 464.2.

Example 5

N-(4-((3S,5R)-3-Amino-5-methylpiperidin-1-yl)pyridin-3-yl)-2-(6-morpholinopyridin-3-yl)furo[3,2-b]pyridine-5-carboxamide

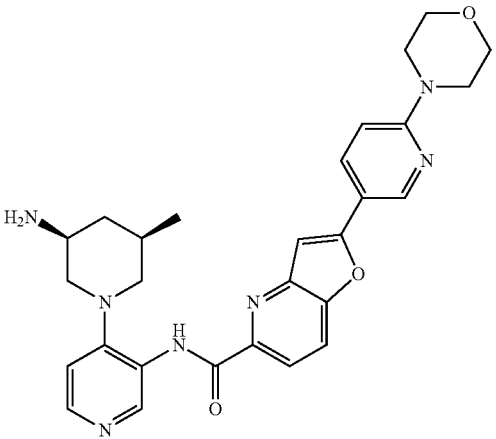 [SMILES: C[C@@H]1C[C@H](N)CN(c2ccncc2NC(=O)c2ccc3oc(-c4ccc(N5CCOCC5)nc4)cc3n2)C1]

The title compound was synthesized by a procedure analogous to that of Example 1, using 4-(5-ethynylpyridin-2-yl)morpholine. LCMS calc. for C$_{28}$H$_{32}$N$_7$O$_3$ (M+H)$^+$ m/z=514.3. found: 514.3.

Example 6

N-{4-[(3R,4R,5S)-3-Amino-4-hydroxy-5-methylpiperidin-1-yl]pyridin-3-yl}-2-isopropylfuro[3,2-b]pyridine-5-carboxamide

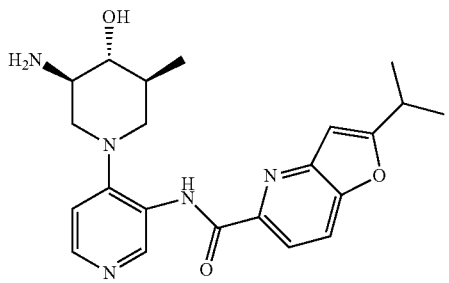

Step 1. tert-Butyl [(3R,4R,5S)-4-{[tert-butyl(dimethyl)silyl]oxy}-1-(3-{[(2-isopropylfuro[3,2-b]pyridin-5-yl)carbonyl]amino}pyridin-4-yl)-5-methylpiperidin-3-yl]carbamate

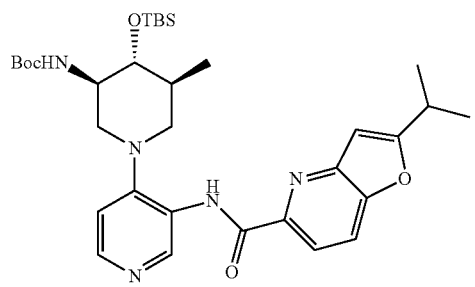 [SMILES: CC(C)c1cc2nc(C(=O)Nc3cnccc3N3C[C@H](C)[C@@H](O[Si](C)(C)C(C)(C)C)[C@H](NC(=O)OC(C)(C)C)C3)ccc2o1]

tert-Butyl ((3R,4R,5S)-1-(3-aminopyridin-4-yl)-4-{[tert-butyl(dimethyl)silyl]oxy}-5-methylpiperidin-3-yl)carbamate (35 mg, 0.081 mmol) and 2-propylfuro[3,2-b]pyridine-5-carboxylic acid (20.0 mg, 0.0975 mmol) were dissolved in DMF (1.4 mL). Then DIPEA (42 µL, 0.24 mmol) and HATU (77 mg, 0.20 mmol) were added and reaction mixture was stirred at room temperature for 2 h. After full conversion was achieved, reaction mixture was quenched with a saturated solution of NaHCO$_3$ and the product extracted with EtOAc. The organic phase was washed with brine and dried over Na$_2$SO$_4$. After the solvent was evaporated, the product was purified by chromatography on silica gel using Biotage Isolera™ apparatus to give the sub-title compound (41 mg, 80%). LCMS calc. for C$_{33}$H$_{50}$N$_5$O$_5$Si (M+H)$^+$ m/z=624.4. found: 624.3.

Step 2. N-{4-[(3R,4R,5S)-3-Amino-4-hydroxy-5-methylpiperidin-1-yl]pyridin-3-yl}-2-isopropylfuro[3,2-b]pyridine-5-carboxamide tert-Butyl [(3R,4R,5S)-4-{[tert-butyl(dimethyl)silyl]oxy}-1-(3-{[(2-isopropylfuro[3,2-b]pyridin-5-yl)carbonyl]amino}pyridin-4-yl)-5-methylpiperidin-3-yl]carbamate (28 mg, 0.046 mmol) was dissolved in DCM (1.0 mL) and TFA (1.1 mL, 14 mmol) was added. The reaction mixture was then stirred at 40° C. for 1 h. Then it was neutralized by addition of NH$_3$ solution and purified by RP-HPLC (water XBridge™ C18 column, 30 mm×100 mm, 5 µm particle size, eluting with a gradient of MeCN/water containing 0.1% NH$_4$OH, at flow rate of 60 mL/min) LCMS calc. for C$_{22}$H$_{28}$N$_5$O$_3$ (M+H)$^+$ m/z=410.2. found: 410.2.

Example 7

N-(4-((3R,4R,5S)-3-Amino-4-hydroxy-5-methylpiperidin-1-yl)pyridin-3-yl)-2-(6-methoxypyridin-3-yl)furo[3,2-b]pyridine-5-carboxamide

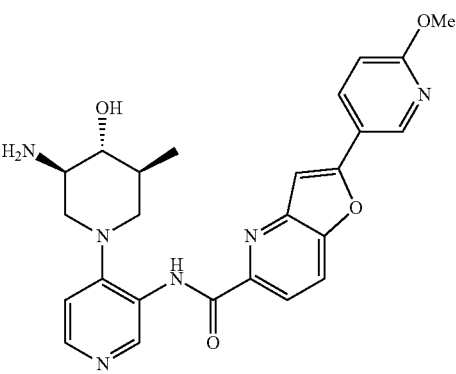 [SMILES: COc1ccc(-c2cc3nc(C(=O)Nc4cnccc4N4C[C@@H](N)[C@H](O)[C@@H](C)C4)ccc3o2)cn1]

The title compound was synthesized by the same way as by analogous to that Example 6, using 5-ethynyl-2-methoxypyridine. LCMS calc. for C$_{25}$H$_{27}$N$_6$O$_4$ (M+H)$^+$ m/z=475.2. found: 475.2.

Example 8

N-(4-((3R,4R,5S)-3-Amino-4-hydroxy-5-methylpiperidin-1-yl)pyridin-3-yl)-2-(2,6-difluorophenyl)furo[3,2-b]pyridine-5-carboxamide

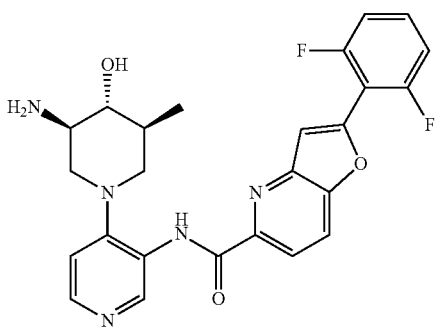 [SMILES: C[C@H]1CN(c2ccncc2NC(=O)c2ccc3oc(-c4c(F)cccc4F)cc3n2)C[C@@H](N)[C@@H]1O]

The title compound was synthesized by a procedure analogous to Example 6, using 1-ethynyl-3,5-difluorobenzene. LCMS calc. for C$_{25}$H$_{24}$F$_2$N$_5$O$_3$ (M+H)$^+$ m/z=480.2. found: 480.2.

Example 9

N-(4-((3R,4R,5S)-3-Amino-4-hydroxy-5-methylpiperidin-1-yl)pyridin-3-yl)-2-(6-morpholinopyridin-3-yl)furo[3,2-b]pyridine-5-carboxamide

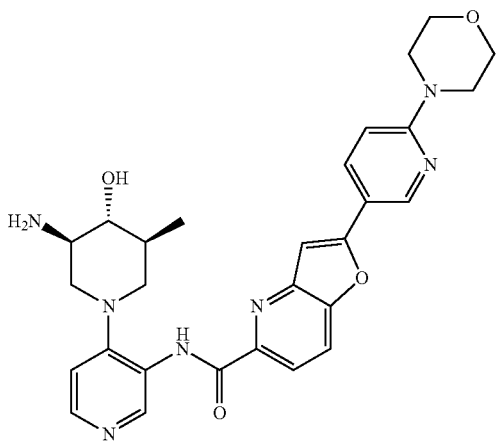 [SMILES: C[C@H]1CN(c2ccncc2NC(=O)c2ccc3oc(-c4ccc(N5CCOCC5)nc4)cc3n2)C[C@@H](N)[C@@H]1O]

The title compound was synthesized by a procedure analogous to Example 6, using 4-(5-ethynylpyridin-2-yl)morpholine. LCMS calc. for $C_{28}H_{32}N_7O_4$ $(M+H)^+$ m/z=530.3. found: 530.2.

Example 10

N-(4-((3R,4R,5S)-3-Amino-4-hydroxy-5-methylpiperidin-1-yl)pyridin-3-yl)-3-isopropylfuro[3,2-b]pyridine-5-carboxamide

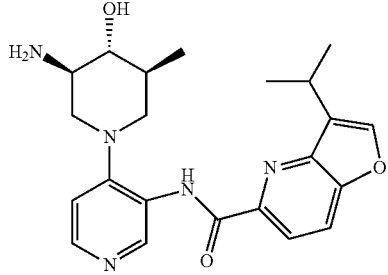 [SMILES: CC(C)c1coc2ccc(C(=O)Nc3cnccc3N3C[C@@H](N)[C@H](O)[C@@H](C)C3)nc12]

Step 1. Methyl 2-(trimethylsilyl)furo[3,2-b]pyridine-5-carboxylate

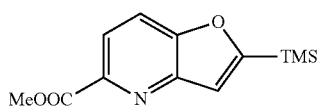 [SMILES: COC(=O)c1ccc2oc([Si](C)(C)C)cc2n1]

Methyl 5-hydroxy-6-iodopyridine-2-carboxylate (Step 2, Example 1, 7.6 g, 27 mmol), CuI (360 mg, 1.9 mmol) and dichloro[bis(triphenylphosphonio)]palladate (1.1 g, 1.6 mmol) were placed in a vial. The vial was then evacuated and backfilled with nitrogen three times. After this, 1,4-dioxane (120 mL) and TEA (5.69 mL, 40.8 mmol) were added and the reaction mixture was stirred for 5 min. Then (trimethylsilyl)acetylene (4.62 mL, 32.7 mmol) was added and the reaction mixture was stirred at 60° C. for 3 h. The reaction was then quenched with water and product extracted with EtOAc. The organic fraction was then washed with brine, dried over $Na_2SO_4$, and the solvent was evaporated under reduced pressure. The crude product was purified by chromatography on silica gel using Biotage Isolera™ apparatus to give the sub-title product as a brown oil (4.2 g, 62%). LCMS calc. for $C_{12}H_{16}NO_3Si$ $(M+H)^+$ m/z=250.1. found: 250.0.

Step 2. Methyl furo[3,2-b]pyridine-5-carboxylate

Methyl 2-(trimethylsilyl)furo[3,2-b]pyridine-5-carboxylate (4.2 g, 17 mmol) was dissolved in MeOH (50 mL, 1000 mmol) and $K_2CO_3$ (7.0 g, 50 mmol) was added. The reaction mixture was stirred at room temperature for 2 h. Water was then added and the product was extracted with EtOAc. The organic phase was washed with brine, dried over $Na_2SO_4$, and the solvent evaporated. The obtained product was used in the next step without further purification (2.1 g, 72%). LCMS calc. for $C_9H_8NO_3$ $(M+H)^+$ m/z=178.1. found: 178.1.

Step 3. Methyl 2,3-dibromo-2,3-dihydrofuro[3,2-b]pyridine-5-carboxylate

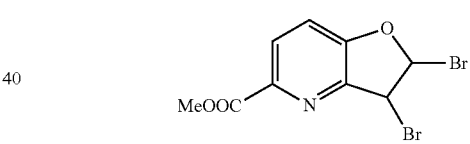

$Br_2$ (3.1 mL, 60 mmol) was slowly added to a solution of methyl furo[3,2-b]pyridine-5-carboxylate (2.138 g, 12.07 mmol) in DCM (50 mL) and reaction mixture was stirred at room temperature for 3 h. Excess $Br_2$ was carefully quenched with saturated solution of $Na_2S_2O_3$ and the product was extracted with DCM. The combined organic phases were washed with brine, dried over $Na_2SO_4$, and solvent was evaporated. The obtained crude product was purified by chromatography on silica gel using Biotage Isolera™ apparatus to give the sub-title compound (1.65 g, 41%). LCMS calc. for $C_9H_8Br_2NO_3$ $(M+H)^+$ m/z=337.9. found: 337.9.

Step 4. 3-Bromofuro[3,2-b]pyridine-5-carboxylic acid

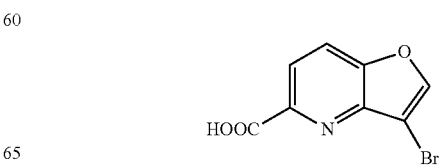

Methyl 2,3-dibromo-2,3-dihydrofuro[3,2-b]pyridine-5-carboxylate (1.65 g, 4.90 mmol) was dissolved in THF (15 mL) and 1.0 M KOH in EtOH (15 mL, 15 mmol) was added. The reaction mixture was then stirred at room temperature for 20 min. After this time, the mixture was diluted with EtOAc, and water was added. The reaction mixture was neutralized with a solution of 1 M HCl and product was extracted with EtOAc. The organic phase was washed with brine and the solvent evaporated to give pure compound (0.94 g, 79%) which was used in the next step without further purification. LCMS calc. for $C_8H_5BrNO_3$ (M+H)$^+$ m/z=242.0 and 244.0. found: 241.9 and 244.0.

Step 5. tert-Butyl (3R,4R,5S)-1-(3-(3-bromofuro[3,2-b]pyridine-5-carboxamido)pyridin-4-yl)-4-(tert-butyldimethylsilyloxy)-5-methylpiperidin-3-ylcarbamate

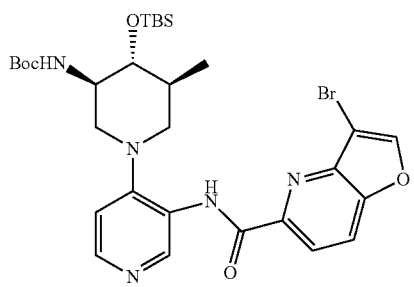 [SMILES: C[C@H]1CN(c2ccncc2NC(=O)c2ccc3occ(Br)c3n2)C[C@@H](NC(=O)OC(C)(C)C)[C@@H]1O[Si](C)(C)C(C)(C)C]

((3R,4R,5S)-1-(3-Aminopyridin-4-yl)-4-{[tert-butyl(dimethyl)silyl]oxy}-5-methylpiperidin-3-yl)carbamate (200 mg, 0.45 mmol) and 3-bromofuro[3,2-b]pyridine-5-carboxylic acid (132 mg, 0.545 mmol) were dissolved in DMF (7.8 mL), then DIPEA (240 μL, 1.4 mmol) and HATU (430 mg, 1.1 mmol) were added and reaction mixture was stirred at room temperature for 2 h. After full conversion was achieved, reaction mixture was quenched with a saturated solution of $NaHCO_3$ and the product extracted with EtOAc. The organic phase was washed with brine and dried over $Na_2SO_4$. After the solvent was evaporated, the product was purified by chromatography on silica gel using Biotage Isolera™ apparatus to give the sub-title compound (231 mg, 77%). LCMS calc. for $C_{30}H_{43}BrN_5O_5Si$ (M+H)$^+$ m/z=660.2 and 662.2. found: 660.2 and 662.2.

Step 6. tert-Butyl [(3R,4R,5S)-4-{[tert-butyl(dimethyl)silyl]oxy}-1-(3-{[(3-isopropenylfuro[3,2-b]pyridin-5-yl)carbonyl]amino}pyridin-4-yl)-5-methylpiperidin-3-yl]carbamate

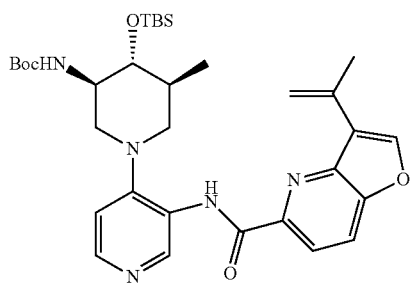 [SMILES: C=C(C)c1coc2ccc(C(=O)Nc3cnccc3N3C[C@H](C)[C@@H](O[Si](C)(C)C(C)(C)C)[C@H](NC(=O)OC(C)(C)C)C3)nc12]

tert-Butyl ((3R,4R,5S)-1-(3-{[(3-bromofuro[3,2-b]pyridin-5-yl)carbonyl]amino}pyridin-4-yl)-4-{[tert-butyl(dimethyl)silyl]oxy}-5-methylpiperidin-3-yl)carbamate (100 mg, 0.151 mmol), dicyclohexyl(2',4',6'-triisopropylbiphenyl-2-yl)phosphine-(2'-aminobiphenyl-2-yl)(chloro)palladium (1:1) (12 mg, 0.015 mmol), $K_3PO_4$ (100 mg, 0.4 mmol) and a magnetic stirring bar were placed in a vial with septum. The vial was then evacuated and backfilled with $N_2$ three times. 1,4-Dioxane (1.1 mL) and degassed water (0.4 mL) were added. Finally, 2-isopropenyl-4,4,5,5-tetramethyl-1,3,2-dioxaborolane (51 mg, 0.30 mmol) was added and reaction mixture was stirred at 55° C. for 1 h. The reaction mixture was then diluted with EtOAc. The obtained solution was washed with brine, dried over $Na_2SO_4$, and the solvent evaporated. The crude product was purified by chromatography on silica gel using Biotage Isolera™ apparatus to give the sub-title compound (85 mg, 90%). LCMS calc. for $C_{33}H_{48}N_5O_5Si$ (M+H)$^+$ m/z=622.3. found: 622.3.

Step 7. tert-Butyl [(3R,4R,5S)-4-{[tert-butyl(dimethyl)silyl]oxy}-1-(3-{[(3-isopropylfuro[3,2-b]pyridin-5-yl)carbonyl]amino}pyridin-4-yl)-5-methylpiperidin-3-yl]carbamate

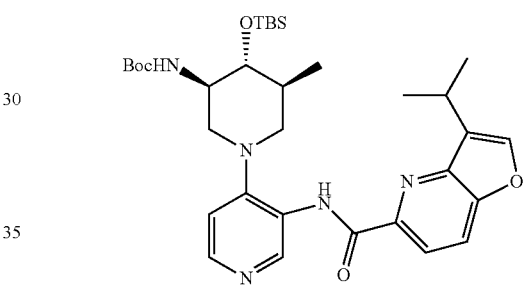

tert-Butyl [(3R,4R,5S)-4-{[tert-butyl(dimethyl)silyl]oxy}-1-(3-{[(3-isopropenylfuro[3,2-b]pyridin-5-yl)carbonyl]amino}pyridin-4-yl)-5-methylpiperidin-3-yl]carbamate (85 mg, 0.2 mmol) was dissolved in MeOH (2.0 mL) and 5 wt % of Pd on carbon (13 mg) was added. The vial was closed with a septum and was connected to a balloon with $H_2$ and stirred at room temperature overnight. The reaction mixture was filtered through diatomaceous earth and the solvent was evaporated to give pure product which was used in the next step without further purification (85 mg, 99%). LCMS calc. for $C_{33}H_{50}N_5O_5Si$ (M+H)$^+$ m/z=624.4. found: 624.3.

Step 8. N-(4-((3R,4R,5S)-3-Amino-4-hydroxy-5-methylpiperidin-1-yl)pyridin-3-yl)-3-isopropylfuro[3,2-b]pyridine-5-carboxamide tert-Butyl [(3R,4R,5S)-4-{[tert-butyl(dimethyl)silyl]oxy}-1-(3-{[(3-isopropylfuro[3,2-b]pyridin-5-yl)carbonyl]amino}pyridin-4-yl)-5-methylpiperidin-3-yl]carbamate (29 mg, 0.046 mmol) was dissolved in DCM (2.0 mL) and TFA (2 mL, 14 mmol), followed by addition of 4.0 M HCl in dioxane (1 mL, 4 mmol). The reaction mixture was stirred at 50° C. for 3 h. The mixture was then neutralized by addition of $NH_3$ solution and purified by RP-HPLC (water XBridge™ C18 column, 30 mm×100 mm, 5 μm particle size, eluting with a gradient of MeCN/water containing 0.1% $NH_4OH$, at flow rate of 60 mL/min) LCMS calc. for $C_{22}H_{28}N_5O_3$ (M+H)$^+$ m/z=410.2. found: 410.2. $^1$H NMR (500 MHz, DMSO-d$_6$) δ 10.37 (s, 1H), 9.46 (s, 1H), 8.28-8.19 (m, 4H), 7.18 (d, J=5.3 Hz, 1H), 4.91 (d, J=4.1 Hz, 1H), 3.38-3.31 (m, 1H), 3.22-3.15 (m, 1H), 3.15-3.08 (m, 1H), 2.93 (td, J=10.4, 4.6 Hz, 1H), 2.77 (td, J=9.4, 4.0 Hz, 1H), 2.02-1.85 (m, 1H), 1.62 (br, 2H), 1.41 (dd, J=6.8, 2.5 Hz, 6H), 0.89 (d, J=6.6 Hz, 3H) ppm.

Example 11

N-(4-((3R,4R,5S)-3-Amino-4-hydroxy-5-methylpiperidin-1-yl)pyridin-3-yl)-3-(2,6-difluorophenyl)furo[3,2-b]pyridine-5-carboxamide

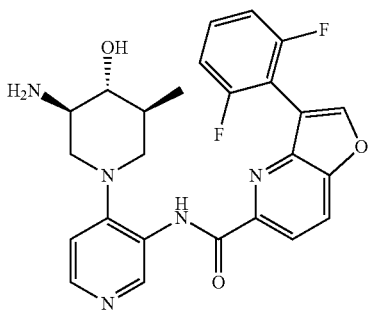 [SMILES: C[C@H]1CN(c2ccncc2NC(=O)c2ccc3occ(-c4c(F)cccc4F)c3n2)C[C@@H](N)[C@@H]1O]

The title compound was synthesized by a procedure analogous to Example 10, using 2,6-difluorophenylboronic acid. LCMS calc. for C$_{25}$H$_{24}$F$_2$N$_5$O$_3$ (M+H)$^+$ m/z=480.2. found: 480.2. $^1$H NMR (500 MHz, DMSO-d$_6$) δ 9.99 (s, 1H), 9.28 (s, 1H), 8.81 (s, 1H), 8.43 (d, J=8.6 Hz, 1H), 8.31 (d, J=8.6 Hz, 1H), 8.22 (d, J=5.4 Hz, 1H), 7.59 (ddd, J=15.0, 8.4, 6.6 Hz, 1H), 7.35 (t, J=8.0 Hz, 2H), 7.11 (d, J=5.4 Hz, 1H), 4.73 (d, J=4.2 Hz, 1H), 3.13 (d, J=10.4 Hz, 1H), 3.06 (d, J=11.5 Hz, 1H), 2.64 (td, J=9.3, 4.3 Hz, 1H), 2.55-2.50 (m, 1H), 2.37 (dt, J=18.4, 11.6 Hz, 2H), 1.62-1.33 (m, 2H), 0.78 (d, J=6.5 Hz, 3H) ppm.

Example 12

N-(4-((3R,4R,5S)-3-Amino-4-hydroxy-5-methylpiperidin-1-yl)pyridin-3-yl)-3-(2-fluorophenyl)furo[3,2-b]pyridine-5-carboxamide

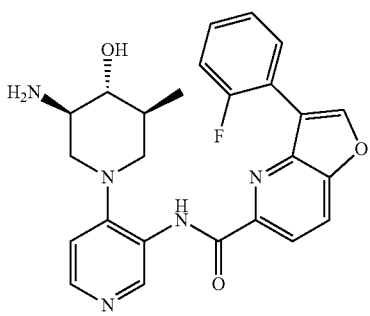 [SMILES: C[C@H]1CN(c2ccncc2NC(=O)c2ccc3occ(-c4ccccc4F)c3n2)C[C@@H](N)[C@@H]1O]

The title compound was synthesized by a procedure analogous to that of Example 10, using 2-fluorophenylboronic acid. LCMS calc. for C$_{25}$H$_{25}$FN$_5$O$_3$ (M+H)$^+$ m/z=462.2. found: 462.2.

Example 13

N-(4-((3R,4R,5S)-3-Amino-4-hydroxy-5-methylpiperidin-1-yl)pyridin-3-yl)-3-(2,6-difluoro-3-methoxyphenyl)furo[3,2-b]pyridine-5-carboxamide

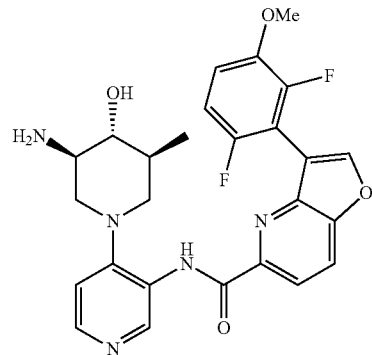 [SMILES: COc1ccc(F)c(-c2coc3ccc(C(=O)Nc4cnccc4N4C[C@@H](N)[C@H](O)[C@@H](C)C4)nc23)c1F]

The title compound was synthesized by a procedure analogous to that of Example 10, using 2,6-difluoro-3-methoxyphenylboronic acid. LCMS calc. for C$_{26}$H$_{26}$F$_2$N$_5$O$_4$ (M+H)$^+$ m/z=510.2. found: 510.2.

Example 14

N-(4-((3R,4R,5S)-3-Amino-4-hydroxy-5-methylpiperidin-1-yl)pyridin-3-yl)-3-(6-methoxypyridin-3-yl)furo[3,2-b]pyridine-5-carboxamide

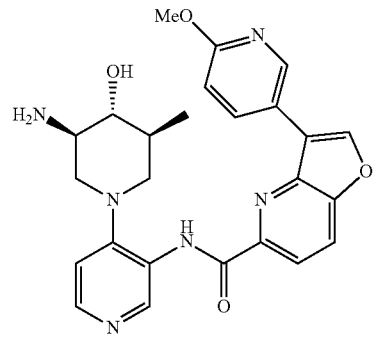 [SMILES: COc1ccc(-c2coc3ccc(C(=O)Nc4cnccc4N4C[C@@H](N)[C@H](O)[C@@H](C)C4)nc23)cn1]

The title compound was synthesized by a procedure analogous to that of Example 10, using 2-methoxy-5-(4,4,5,5-tetramethyl-1,3,2-dioxaborolan-2-yl)pyridine. LCMS calc. for C$_{25}$H$_{27}$N$_6$O$_4$ (M+H)$^+$ m/z=475.2. found: 475.2.

Example 15

N-(4-((3R,4R,5S)-3-Amino-4-hydroxy-5-methylpiperidin-1-yl)pyridin-3-yl)-3-ethylfuro[3,2-b]pyridine-5-carboxamide

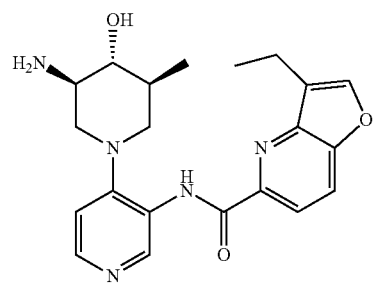 [SMILES: CCc1coc2ccc(C(=O)Nc3cnccc3N3C[C@@H](N)[C@H](O)[C@@H](C)C3)nc12]

The title compound was synthesized by a procedure analogous to that of Example 10, using 4,4,5,5-tetramethyl-2-vinyl-1,3,2-dioxaborolane. LCMS calc. for $C_{21}H_{26}N_5O_3$ $(M+H)^+$ m/z=396.2. found: 396.2.

$^1$H NMR (500 MHz, DMSO-d$_6$) δ 10.45 (s, 1H), 9.47 (s, 1H), 8.29 (t, J=1.2 Hz, 1H), 8.26 (d, J=5.3 Hz, 1H), 8.25-8.18 (m, 2H), 7.17 (d, J=5.3 Hz, 1H), 4.98 (s, 1H), 3.19 (d, J=10.2 Hz, 1H), 3.14-3.07 (m, 1H), 2.96 (td, J=10.1, 9.7, 4.2 Hz, 1H), 2.87-2.74 (m, 3H), 2.52 (dd, J=12.0, 4.6 Hz, 1H), 2.01-1.89 (m, 1H), 1.35 (t, J=7.5 Hz, 3H), 0.89 (d, J=6.6 Hz, 3H) ppm.

Example 16

N-(4-((3R,4R,5S)-3-Amino-4-hydroxy-5-methylpiperidin-1-yl)pyridin-3-yl)-3-(1-methylpiperidin-4-yl)furo[3,2-b]pyridine-5-carboxamide

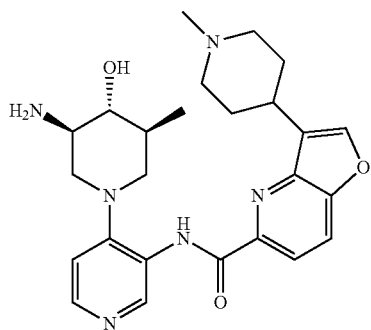 [SMILES: C[C@H]1CN(c2ccncc2NC(=O)c2ccc3occ(C4CCN(C)CC4)c3n2)C[C@@H](N)[C@@H]1O]

The title compound was synthesized by a procedure analogous to that of Example 10, using 1-methyl-4-(4,4,5,5-tetramethyl-1,3,2-dioxaborolan-2-yl)-1,2,3,6-tetrahydropyridine hydrochloride. LCMS calc. for $C_{25}H_{33}N_6O_3$ $(M+H)^+$ m/z=465.3. found: 465.2.

Example 17

N-(4-((3R,4R,5S)-3-Amino-4-hydroxy-5-methylpiperidin-1-yl)pyridin-3-yl)-3-(tetrahydro-2H-pyran-4-yl)furo[3,2-b]pyridine-5-carboxamide

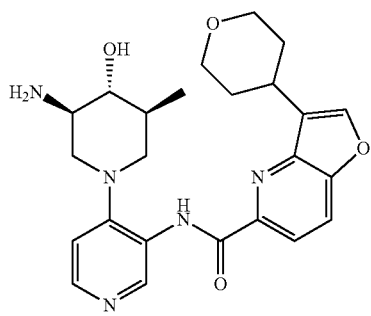 [SMILES: C[C@H]1CN(c2ccncc2NC(=O)c2ccc3occ(C4CCOCC4)c3n2)C[C@@H](N)[C@@H]1O]

The title compound was synthesized by a procedure analogous to that of Example 10, using 2-(3,6-dihydro-2H-pyran-4-yl)-4,4,5,5-tetramethyl-1,3,2-dioxaborolane. LCMS calc. for $C_{24}H_{30}N_5O_4$ $(M+H)^+$ m/z=452.2. found: 452.2.

Example 18

N-(4-((3S,5R)-3-Amino-5-methylpiperidin-1-yl)pyridin-3-yl)-3-isopropylfuro[3,2-b]pyridine-5-carboxamide

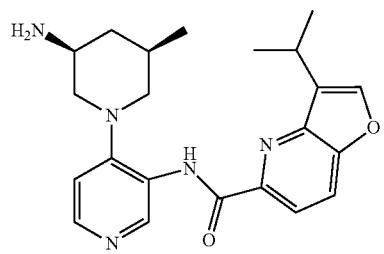 [SMILES: CC(C)c1coc2ccc(C(=O)Nc3cnccc3N3C[C@H](C)C[C@H](N)C3)nc12]

Step 1. tert-Butyl (3S,5R)-1-(3-(3-bromofuro[3,2-b]pyridine-5-carboxamido)pyridin-4-yl)-5-methylpiperidin-3-ylcarbamate

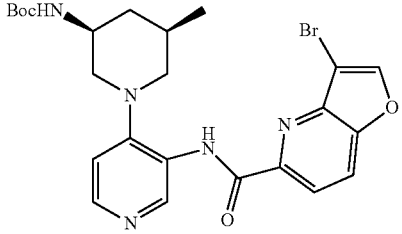 [SMILES: C[C@@H]1C[C@H](NC(=O)OC(C)(C)C)CN(c2ccncc2NC(=O)c2ccc3occ(Br)c3n2)C1]

tert-Butyl (3S,5R)-1-(3-aminopyridin-4-yl)-5-methylpiperidin-3-ylcarbamate (138 mg, 0.45 mmol) and 3-bromofuro[3,2-b]pyridine-5-carboxylic acid (132 mg, 0.545 mmol) were dissolved in DMF (7.8 mL). Then DIPEA (240 µL, 1.4 mmol) and HATU (430 mg, 1.1 mmol) were added and the reaction mixture was stirred at room temperature for 2 h. After full conversion was achieved, reaction mixture was quenched with a saturated solution of NaHCO$_3$ and the product extracted with EtOAc. The organic phase was washed with brine and dried over Na$_2$SO$_4$. After the solvent was evaporated, the product was purified by chromatography on silica gel using Biotage Isolera™ apparatus to give the sub-title compound (177 mg, 74%). LCMS calc. for $C_{24}H_{29}BrN_5O_4$ $(M+H)^+$ m/z=530.1 and 532.1. found: 530.0 and 532.0.

Step 2. tert-Butyl (3S,5R)-5-methyl-1-(3-(3-(prop-1-en-2-yl)furo[3,2-b]pyridine-5-carboxamido)pyridin-4-yl)piperidin-3-ylcarbamate

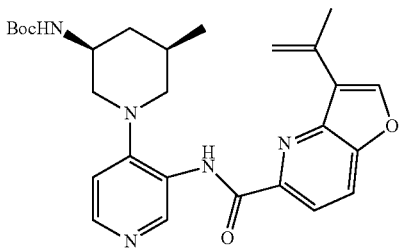

tert-Butyl (3S,5R)-1-(3-(3-bromofuro[3,2-b]pyridine-5-carboxamido)pyridin-4-yl)-5-methylpiperidin-3-ylcarbamate (80 mg, 0.151 mmol), dicyclohexyl(2',4',6'-triisopropylbiphenyl-2-yl)phosphine-(2'-aminobiphenyl-2-yl)(chloro) palladium (1:1) (12 mg, 0.015 mmol), $K_3PO_4$ (100 mg, 0.4 mmol), and a magnetic stirring bar were placed in a vial with a septum. The vial was then evacuated and backfilled with $N_2$ three times, followed by addition of 1,4-dioxane (1.1 mL) and degassed water (0.4 mL). Finally, 2-isopropenyl-4,4,5,5-tetramethyl-1,3,2-dioxaborolane (51 mg, 0.30 mmol) was added and reaction mixture was stirred at 55° C. for 1 h, then diluted with EtOAc. The obtained solution was washed with brine, dried over $Na_2SO_4$, and the solvent evaporated. The crude product was purified by chromatography on silica gel using Biotage Isolera™ apparatus to give the sub-title compound (64 mg, 86%). LCMS calc. for $C_{27}H_{33}N_5O_4$ $(M+H)^+$ m/z=491.3. found: 491.3.

Step 3. tert-Butyl (3S,5R)-1-(3-(3-isopropylfuro[3,2-b]pyridine-5-carboxamido)pyridin-4-yl)-5-methylpiperidin-3-ylcarbamate

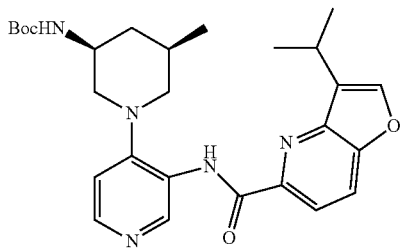 [SMILES: CC(C)c1coc2ccc(C(=O)Nc3cnccc3N3C[C@H](C)C[C@H](NC(=O)OC(C)(C)C)C3)nc12]

tert-Butyl (3S,5R)-5-methyl-1-(3-(3-(prop-1-en-2-yl)furo[3,2-b]pyridine-5-carboxamido)pyridin-4-yl)piperidin-3-ylcarbamate (64 mg, 0.13 mmol) was dissolved in MeOH (2.0 mL) and 5 wt % of Pd on carbon (13 mg) was added. The vial was closed with a septum and was connected to a balloon with $H_2$, and the mixture was stirred at room temperature overnight. The reaction mixture was filtered through diatomaceous earth and the solvent was evaporated to give pure product which was used in the next step without further purification (63 mg, 99%). LCMS calc. for $C_{27}H_{36}N_5O_4$ $(M+H)^+$ m/z=494.3. found: 494.2.

Step 4. N-(4-((3S,5R)-3-Amino-5-methylpiperidin-1-yl)pyridin-3-yl)-3-isopropylfuro[3,2-b]pyridine-5-carboxamide tert-Butyl (3S,5R)-1-(3-(3-isopropylfuro[3,2-b]pyridine-5-carboxamido)pyridin-4-yl)-5-methylpiperidin-3-ylcarbamate (23 mg, 0.046 mmol) was dissolved in DCM (2.0 mL) and TFA (2 mL, 14 mmol), and the reaction mixture was stirred at 40° C. for 1 h. The mixture was then neutralized by addition of $NH_3$ solution and purified by RP-HPLC (water XBridge™ C18 column, 30 mm×100 mm, 5 μm particle size, eluting with a gradient of MeCN/water containing 0.1% $NH_4OH$, at flow rate of 60 mL/min) LCMS calc. for $C_{22}H_{28}N_5O_2$ $(M+H)^+$ m/z=394.2. found: 394.2. $^1H$ NMR (500 MHz, DMSO-$d_6$) δ 10.38 (s, 1H), 9.48 (s, 1H), 8.28 (d, J=1.0 Hz, 1H), 8.27 (d, J=5.2 Hz, 1H), 8.25-8.19 (m, 2H), 7.17 (d, J=5.3 Hz, 1H), 3.27-3.20 (m, 1H), 3.18 (dd, J=11.0, 4.2 Hz, 1H), 3.13-2.99 (m, 2H), 2.25 (td, J=10.9, 5.5 Hz, 2H), 2.10-1.99 (m, 1H), 1.99-1.90 (m, 1H), 1.82-1.53 (m, 2H), 1.42 (dd, J=6.9, 2.8 Hz, 8H), 0.85 (d, J=6.6 Hz, 3H) ppm.

Example 19

N-(4-((3S,5R)-3-Amino-5-methylpiperidin-1-yl)pyridin-3-yl)-3-(2,6-difluorophenyl)furo[3,2-b]pyridine-5-carboxamide

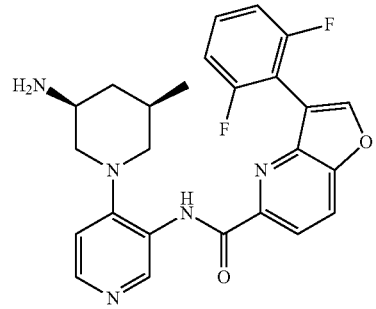 [SMILES: C[C@@H]1C[C@H](N)CN(c2ccncc2NC(=O)c2ccc3occ(-c4c(F)cccc4F)c3n2)C1]

The title compound was synthesized by a procedure analogous to that of Example 18, using 2,6-difluorophenylboronic acid. LCMS calc. for $C_{25}H_{24}F_2N_5O_2$ $(M+H)^+$ m/z=464.2. found: 464.2. $^1H$ NMR (500 MHz, DMSO-$d_6$) δ 10.15 (s, 1H), 9.46 (s, 1H), 8.81 (s, 1H), 8.44 (d, J=8.6 Hz, 1H), 8.33 (d, J=8.6 Hz, 1H), 8.23 (d, J=5.3 Hz, 1H), 7.68 (ddd, J=15.0, 8.4, 6.6 Hz, 1H), 7.34 (t, J=7.9 Hz, 2H), 7.07 (d, J=5.3 Hz, 1H), 3.03 (d, J=7.0 Hz, 1H), 2.92 (d, J=11.3 Hz, 1H), 2.43 (dt, J=10.7, 6.6 Hz, 2H), 2.13 (t, J=10.6 Hz, 1H), 1.98 (t, J=11.3 Hz, 1H), 1.41 (d, J=12.2 Hz, 2H), 1.29 (dq, J=13.8, 6.7 Hz, 1H), 0.60 (d, J=6.7 Hz, 3H), 0.58-0.50 (m, 1H) ppm.

Example 20

N-(4-((3S,5R)-3-Amino-5-methylpiperidin-1-yl)pyridin-3-yl)-3-ethylfuro[3,2-b]pyridine-5-carboxamide

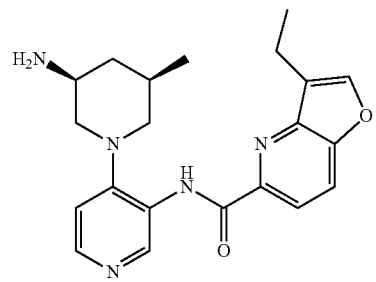 [SMILES: CCc1coc2ccc(C(=O)Nc3cnccc3N3C[C@H](C)C[C@H](N)C3)nc12]

The title compound was synthesized by a procedure analogous to that of Example 18, using 4,4,5,5-tetramethyl-2-vinyl-1,3,2-dioxaborolane. LCMS calc. for $C_{21}H_{26}N_5O_2$ $(M+H)^+$ m/z=380.2. found: 380.2.

$^1H$ NMR (500 MHz, DMSO-$d_6$) δ 10.47 (s, 1H), 9.49 (s, 1H), 8.31 (t, J=1.1 Hz, 1H), 8.27 (d, J=5.2 Hz, 1H), 8.25-8.18 (m, 2H), 7.17 (d, J=5.2 Hz, 1H), 3.22-3.15 (m, 1H), 3.15-3.00 (m, 2H), 2.80 (qd, J=7.5, 1.0 Hz, 2H), 2.27 (td, J=10.9, 8.6 Hz, 2H), 2.12-2.01 (m, 1H), 1.97 (d, J=12.7 Hz, 1H), 1.36 (t, J=7.5 Hz, 3H), 0.86 (d, J=6.6 Hz, 3H) ppm.

Example 21

N-(4-((3S,5R)-3-Amino-5-methylpiperidin-1-yl)pyridin-3-yl)-3-(2-fluorophenyl)furo[3,2-b]pyridine-5-carboxamide

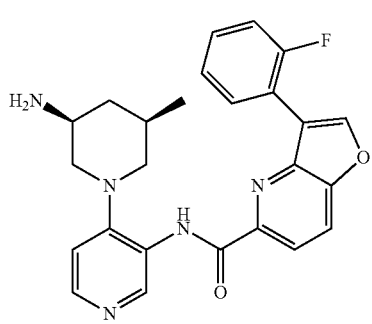 [SMILES: C[C@@H]1C[C@H](N)CN(c2ccncc2NC(=O)c2ccc3occ(-c4ccccc4F)c3n2)C1]

The title compound was synthesized by a procedure analogous to that of Example 18, using 2-fluorophenylboronic acid. LCMS calc. for $C_{25}H_{25}FN_5O_2$ (M+H)+ m/z=446.2. found: 446.2. $^1$H NMR (500 MHz, DMSO-d$_6$) δ 10.10 (s, 1H), 9.32 (s, 1H), 8.80 (d, J=1.6 Hz, 1H), 8.41 (d, J=8.6 Hz, 1H), 8.32 (d, J=8.6 Hz, 1H), 8.24 (d, J=5.3 Hz, 1H), 8.19-8.11 (m, 1H), 7.62-7.49 (m, 1H), 7.47-7.31 (m, 2H), 7.07 (d, J=5.3 Hz, 1H), 3.13 (d, J=7.3 Hz, 1H), 3.03 (d, J=11.3 Hz, 1H), 2.60 (dq, J=10.5, 5.3, 4.0 Hz, 1H), 2.14 (t, J=10.7 Hz, 1H), 2.07 (t, J=11.3 Hz, 1H), 1.62-1.45 (m, 1H), 1.41 (J=12.5 Hz, 2H), 0.59 (d, J=6.6 Hz, 3H) ppm.

Example 22

N-(4-((3S,5R)-3-Amino-5-methylpiperidin-1-yl)pyridin-3-yl)-3-(2,6-difluoro-3-methoxyphenyl)furo[3,2-b]pyridine-5-carboxamide

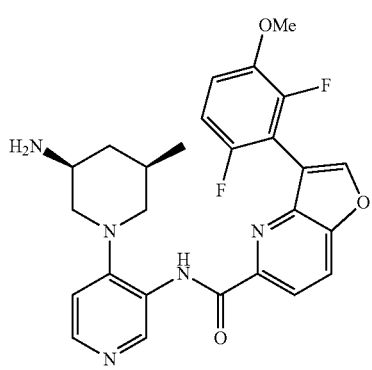 [SMILES: COc1ccc(F)c(-c2coc3ccc(C(=O)Nc4cnccc4N4C[C@H](C)C[C@H](N)C4)nc23)c1F]

The title compound was synthesized by a procedure analogous to that of Example 18, using 2,6-difluoro-3-methoxyphenylboronic acid. LCMS calc. for $C_{26}H_{26}F_2N_5O_3$ (M+H)+ m/z=494.2. found: 494.2. $^1$H NMR (500 MHz, DMSO-d$_6$) δ 10.11 (s, 1H), 9.45 (s, 1H), 8.80 (s, 1H), 8.44 (d, J=8.7 Hz, 1H), 8.32 (d, J=8.6 Hz, 1H), 8.24 (d, J=5.3 Hz, 1H), 7.41 (td, J=9.4, 5.1 Hz, 1H), 7.27 (td, J=9.1, 1.8 Hz, 1H), 7.07 (d, J=5.3 Hz, 1H), 3.93 (s, 3H), 3.09 (d, J=6.9 Hz, 1H), 2.96 (d, J=10.4 Hz, 1H), 2.20 (t, J=10.6 Hz, 1H), 1.97 (t, J=11.4 Hz, 1H), 1.43 (d, J=12.4 Hz, 1H), 1.27 (d, J=42.5 Hz, 1H), 0.59 (d, J=6.7 Hz, 3H) ppm.

Example 23

N-(4-((3S,5R)-3-Amino-5-methylpiperidin-1-yl)pyridin-3-yl)-3-(6-methoxypyridin-3-yl)furo[3,2-b]pyridine-5-carboxamide

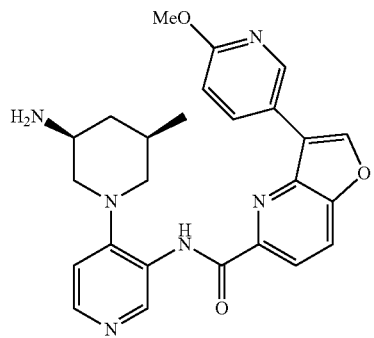 [SMILES: COc1ccc(-c2coc3ccc(C(=O)Nc4cnccc4N4C[C@H](C)C[C@H](N)C4)nc23)cn1]

The title compound was synthesized by a procedure analogous to that of Example 18, using 2-methoxy-5-(4,4,5,5-tetramethyl-1,3,2-dioxaborolan-2-yl)pyridine. LCMS calc. for $C_{25}H_{22}N_6O_3$ (M+H)+ m/z=459.2. found: 459.1.

Example 24

N-(4-((3S,5R)-3-Amino-5-methylpiperidin-1-yl)pyridin-3-yl)-3-(1-methylpiperidin-4-yl)furo[3,2-b]pyridine-5-carboxamide

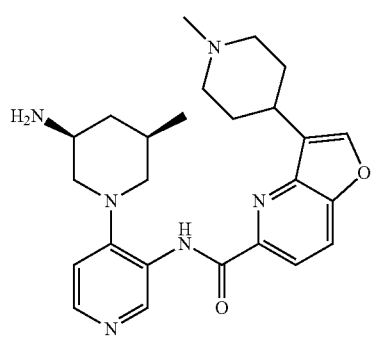 [SMILES: C[C@@H]1C[C@H](N)CN(c2ccncc2NC(=O)c2ccc3occ(C4CCN(C)CC4)c3n2)C1]

The title compound was synthesized by a procedure analogous to that of Example 18, using 1-methyl-4-(4,4,5,5-tetramethyl-1,3,2-dioxaborolan-2-yl)-1,2,3,6-tetrahydropyridine hydrochloride. LCMS calc. for $C_{25}H_{33}N_6O_2$ (M+H)+ m/z=449.3. found: 449.2.

Example 25

N-(4-((3S,5R)-3-Amino-5-methylpiperidin-1-yl)pyridin-3-yl)-3-(tetrahydro-2H-pyran-4-yl)furo[3,2-b]pyridine-5-carboxamide

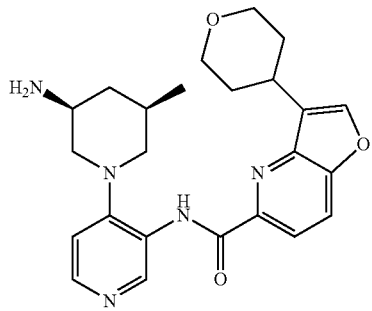 [SMILES: C[C@@H]1C[C@H](N)CN(c2ccncc2NC(=O)c2ccc3occ(C4CCOCC4)c3n2)C1]

The title compound was synthesized by a procedure analogous to that of Example 18, using 2-(3,6-dihydro-2H-pyran-4-yl)-4,4,5,5-tetramethyl-1,3,2-dioxaborolane. LCMS calc. for $C_{24}H_{30}N_5O_3$ (M+H)$^+$ m/z=436.2. found: 436.2.

Example 26

N-(4-((3S,5R)-3-Amino-5-methylpiperidin-1-yl)pyridin-3-yl)-3-(5-cyanopyridin-3-yl)furo[3,2-b]pyridine-5-carboxamide

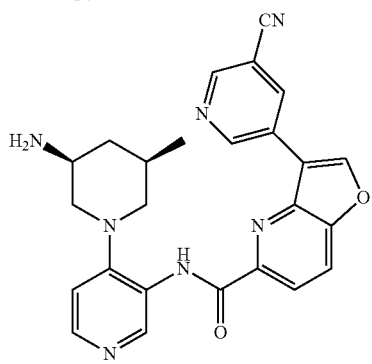 [SMILES: C[C@@H]1C[C@H](N)CN(c2ccncc2NC(=O)c2ccc3occ(-c4cncc(C#N)c4)c3n2)C1]

The title compound was synthesized by a procedure analogous to that of Example 18, using 5-(4,4,5,5-tetramethyl-1,3,2-dioxaborolan-2-yl)nicotinonitrile. LCMS calc. for $C_{25}H_{24}N_7O_2$ (M+H)$^+$ m/z=454.2. found: 454.1.

Example 27

N-(4-((3S,5R)-3-Amino-5-methylpiperidin-1-yl)pyridin-3-yl)-3-(2,6-difluoropyridin-4-yl)furo[3,2-b]pyridine-5-carboxamide

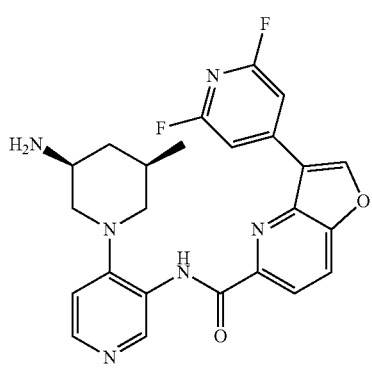 [SMILES: C[C@@H]1C[C@H](N)CN(c2ccncc2NC(=O)c2ccc3occ(-c4cc(F)nc(F)c4)c3n2)C1]

The title compound was synthesized by a procedure analogous to that of Example 18, using 2,6-difluoropyridin-4-ylboronic acid. LCMS calc. for $C_{24}H_{23}F_2N_6O_2$ (M+H)$^+$ m/z=465.2. found: 465.2.

Example 28

N-(4-((3S,5R)-3-Amino-5-methylpiperidin-1-yl)pyridin-3-yl)-3-(isoxazol-4-yl)furo[3,2-b]pyridine-5-carboxamide

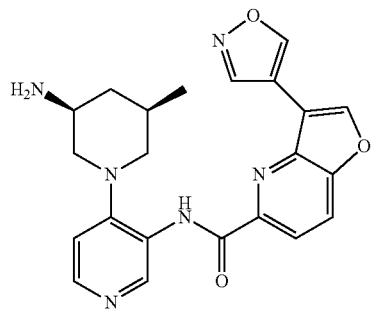 [SMILES: C[C@@H]1C[C@H](N)CN(c2ccncc2NC(=O)c2ccc3occ(-c4cnoc4)c3n2)C1]

The title compound was synthesized by a procedure analogous to that of Example 18, using 4-(4,4,5,5-tetramethyl-1,3,2-dioxaborolan-2-yl)isoxazole. LCMS calc. for $C_{22}H_{23}N_6O_3$ (M+H)$^+$ m/z=419.2. found: 419.1.

Example 29

N-(4-((3S,5R)-3-Amino-5-methylpiperidin-1-yl)pyridin-3-yl)-3-(1-methyl-1H-pyrazol-4-yl)furo[3,2-b]pyridine-5-carboxamide

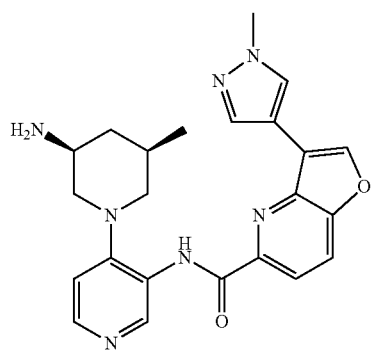 [SMILES: C[C@@H]1C[C@H](N)CN(c2ccncc2NC(=O)c2ccc3occ(-c4cnn(C)c4)c3n2)C1]

The title compound was synthesized by a procedure analogous to that of Example 18, using 1-methyl-4-(4,4,5,5-tetramethyl-1,3,2-dioxaborolan-2-yl)-1H-pyrazole. LCMS calc. for $C_{23}H_{26}N_7O_2$ (M+H)$^+$ m/z=432.2. found: 432.2.

Example 30

N-(4-((3S,5R)-3-Amino-5-methylpiperidin-1-yl)pyridin-3-yl)-3-(pyrimidin-5-yl)furo[3,2-b]pyridine-5-carboxamide

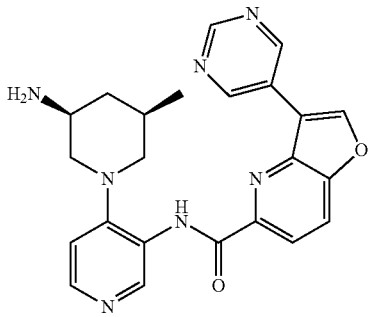 [SMILES: C[C@@H]1C[C@H](N)CN(c2ccncc2NC(=O)c2ccc3occ(-c4cncnc4)c3n2)C1]

The title compound was synthesized by a procedure analogous to that of Example 18, using pyrimidin-5-ylboronic acid. LCMS calc. for $C_{23}H_{24}N_7O_2$ $(M+H)^+$ m/z=430.2. found: 430.1.

Example 31

N-(4-((3S,5R)-3-Amino-5-methylpiperidin-1-yl)pyridin-3-yl)-3-(tetrahydrofuran-3-yl)furo[3,2-b]pyridine-5-carboxamide (diastereomeric mixture)

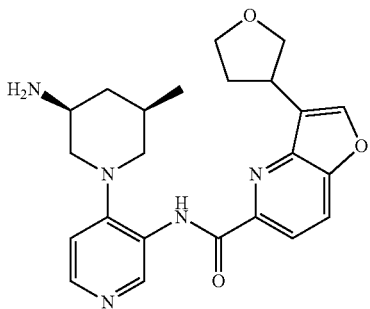 [SMILES: C[C@@H]1C[C@H](N)CN(c2ccncc2NC(=O)c2ccc3occ(C4CCOC4)c3n2)C1]

The title compound was synthesized by a procedure analogous to that of Example 18, using 2-(4,5-dihydrofuran-3-yl)-4,4,5,5-tetramethyl-1,3,2-dioxaborolane. LCMS calc. for $C_{23}H_{25}N_5O_3$ $(M+H)^+$ m/z=422.2. found: 422.2.

Example 32

N-(4-((3S,5R)-3-Amino-5-methylpiperidin-1-yl)pyridin-3-yl)-3-(5-methoxypyridin-3-yl)furo[3,2-b]pyridine-5-carboxamide

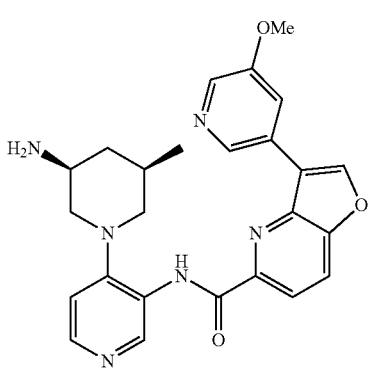 [SMILES: COc1cncc(-c2coc3ccc(C(=O)Nc4cnccc4N4C[C@H](C)C[C@H](N)C4)nc23)c1]

The title compound was synthesized by a procedure analogous to that of Example 18, using 3-methoxy-5-(4,4,5,5-tetramethyl-1,3,2-dioxaborolan-2-yl)pyridine. LCMS calc. for $C_{25}H_{27}N_6O_3$ $(M+H)^+$ m/z=459.2. found: 459.2.

Example 33

N-(4-((3S,5R)-3-Amino-5-methylpiperidin-1-yl)pyridin-3-yl)-3-(3,4-dihydro-2H-pyran-5-yl)furo[3,2-b]pyridine-5-carboxamide

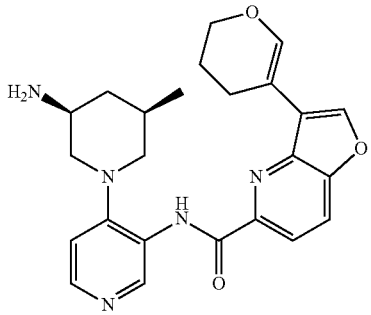 [SMILES: C[C@@H]1C[C@H](N)CN(c2ccncc2NC(=O)c2ccc3occ(C4=COCCC4)c3n2)C1]

The title compound was synthesized by a procedure analogous to that of Example 18, using 2-(3,4-dihydro-2H-pyran-5-yl)-4,4,5,5-tetramethyl-1,3,2-dioxaborolane. LCMS calc. for $C_{24}H_{28}N_5O_3$ $(M+H)^+$ m/z=434.2. found: 434.2.

Example 34

N-(4-((3R,4R,5S)-3-Amino-4-hydroxy-5-methylpiperidin-1-yl)pyridin-3-yl)-3-cyclopropylfuro[3,2-b]pyridine-5-carboxamide

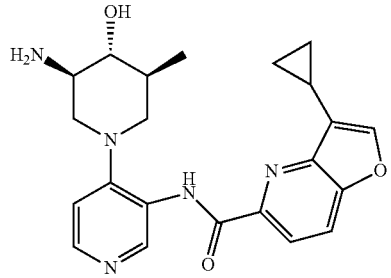 [SMILES: C[C@H]1CN(c2ccncc2NC(=O)c2ccc3occ(C4CC4)c3n2)C[C@@H](N)[C@@H]1O]

Step 1. tert-Butyl (3R,4R,5S)-4-(tert-butyldimethylsilyloxy)-1-(3-(3-cyclopropylfuro[3,2-b]pyridine-5-carboxamido)pyridin-4-yl)-5-methylpiperidin-3-ylcarbamate

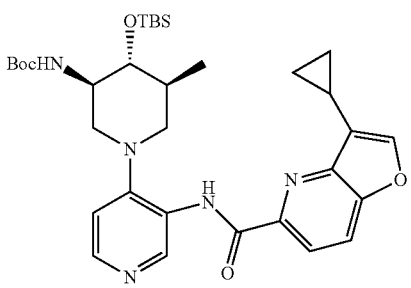 [SMILES: C[C@H]1CN(c2ccncc2NC(=O)c2ccc3occ(C4CC4)c3n2)C[C@@H](NC(=O)OC(C)(C)C)[C@@H]1O[Si](C)(C)C(C)(C)C]

To a vial was added tert-butyl ((3R,4R,5S)-1-(3-{[(3-bromofuro[3,2-b]pyridin-5-yl)carbonyl]amino}pyridin-4-yl)-4-{[tert-butyl(dimethyl)silyl]oxy}-5-methylpiperidin-3-yl)carbamate (30 mg, 0.151 mmol), potassium cyclopropyltrifluoroborate (13 mg, 0.091 mmol), Cs$_2$CO$_3$ (44.4 mg, 0.136 mmol), Pd(OAc)$_2$ (1.5 mg, 0.0068 mmol) and di-1-adamantyl(butyl)phosphine (4.9 mg, 0.014 mmol). The vial was sealed and evacuated and filled with N$_2$ three times. Toluene (1.0 mL) and water (100 μL) were then added and the reaction mixture was stirred at 100° C. overnight. The reaction mixture was then diluted with EtOAc and the obtained solution was washed with brine, dried over Na$_2$SO$_4$ and the solvent evaporated. Crude product was purified by chromatography on silica gel using Biotage Isolera™ apparatus to give the sub-title compound (22 mg, 77%). LCMS calc. for C$_{33}$H$_{48}$N$_5$O$_5$Si (M+H)$^+$ m/z=622.3. found: 622.3.

Step 2. N-(4-((3R,4R,5S)-3-Amino-4-hydroxy-5-methylpiperidin-1-yl)pyridin-3-yl)-3-cyclopropyl-furo[3,2-b]pyridine-5-carboxamide tert-Butyl (3R,4R,5S)-4-(tert-butyldimethylsilyloxy)-1-(3-(3-cyclopropylfuro[3,2-b]pyridine-5-carboxamido)pyridin-4-yl)-5-methylpiperidin-3-ylcarbamate (22 mg, 0.035 mmol) was dissolved in DCM (2.0 mL) and TFA (2 mL, 14 mmol), followed by addition of 4.0 M HCl in dioxane (1 mL, 4 mmol). The reaction mixture was stirred at 50° C. for 3 h and was then neutralized by addition of NH$_3$ solution and purified by RP-HPLC (water XBridge™ C18 column, 30 mm×100 mm, 5 μm particle size, eluting with a gradient of MeCN/water containing 0.1% NH$_4$OH, at flow rate of 60 mL/min). LCMS calc. for C$_{22}$H$_{26}$N$_5$O$_3$ (M+H)$^+$ m/z=408.2. found: 408.1. $^1$H NMR (500 MHz, DMSO-d$_6$) δ 10.48 (s, 1H), 9.49 (s, 1H), 8.27 (d, J=5.2 Hz, 1H), 8.24-8.19 (m, 3H), 7.18 (d, J=5.3 Hz, 1H), 4.95 (d, J=4.1 Hz, 1H), 3.24-3.15 (m, 1H), 3.15-3.07 (m, 1H), 2.97 (td, J=10.4, 4.5 Hz, 1H), 2.77 (td, J=9.2, 4.2 Hz, 1H), 2.18-2.06 (m, 1H), 2.05-1.92 (m, 1H), 1.12-1.04 (m, 3H), 0.89 (d, J=6.6 Hz, 3H), 0.86-0.78 (m, 2H) ppm.

Example 35

N-(4-((3S,5R)-3-Amino-5-methylpiperidin-1-yl)pyridin-3-yl)-3-cyclopropylfuro[3,2-b]pyridine-5-carboxamide

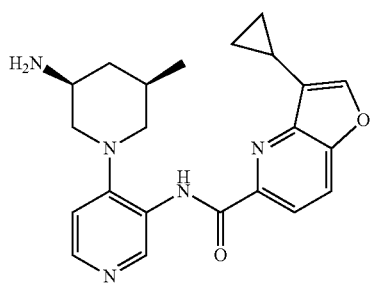 [SMILES: C[C@@H]1C[C@H](N)CN(c2ccncc2NC(=O)c2ccc3occ(C4CC4)c3n2)C1]

The title compound was synthesized by a procedure analogous to that of Example 34, using tert-butyl (3S,5R)-1-(3-(3-bromofuro[3,2-b]pyridine-5-carboxamido)pyridin-4-yl)-5-methylpiperidin-3-ylcarbamate. LCMS calc. for C$_{22}$H$_{26}$N$_5$O$_2$ (M+H)$^+$ m/z=392.2. found: 392.2. $^1$H NMR (500 MHz, DMSO-d$_6$) δ 10.42 (s, 1H), 9.46 (s, 1H), 8.27 (d, J=5.3 Hz, 1H), 8.25 (d, J=0.8 Hz, 1H), 8.21 (d, J=1.2 Hz, 2H), 7.17 (d, J=5.3 Hz, 1H), 3.19 (dd, J=11.0, 4.2 Hz, 1H), 3.13-3.05 (m, 2H), 2.29-2.20 (m, 2H), 2.12-1.99 (m, 2H), 1.90 (d, J=12.7 Hz, 1H), 1.04-0.85 (m, 5H), 0.83 (d, J=6.6 Hz, 3H) ppm.

Example 36

(S)-N-(4-(3-Aminopiperidin-1-yl)pyridin-3-yl)-3-isopropylfuro[3,2-b]pyridine-5-carboxamide

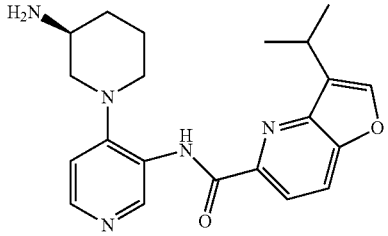 [SMILES: CC(C)c1coc2ccc(C(=O)Nc3cnccc3N3CCC[C@H](N)C3)nc12]

Step 1. (S)-tert-Butyl 1-(3-(3-bromofuro[3,2-b]pyridine-5-carboxamido)pyridin-4-yl)piperidin-3-ylcarbamate

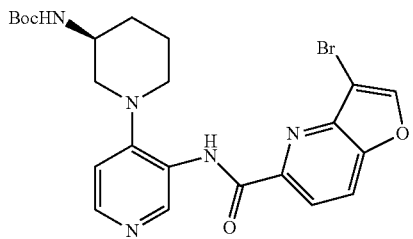 [SMILES: CC(C)(C)OC(=O)N[C@H]1CCCN(c2ccncc2NC(=O)c2ccc3occ(Br)c3n2)C1]

(S)-tert-Butyl 1-(3-aminopyridin-4-yl)piperidin-3-ylcarbamate (132 mg, 0.45 mmol) and 3-bromofuro[3,2-b]pyridine-5-carboxylic acid (132 mg, 0.545 mmol) were dissolved in DMF (7.8 mL), then DIPEA (240 μL, 1.4 mmol) and HATU (430 mg, 1.1 mmol) were added and reaction mixture was stirred at room temperature for 2 h. After full conversion was achieved, the reaction mixture was quenched with a saturated solution of NaHCO$_3$ and the product was extracted with EtOAc. The organic phase was washed with brine and dried over Na$_2$SO$_4$. After the solvent was evaporated, the product was purified by chromatography on silica gel using Biotage Isolera™ apparatus to give the sub-title compound (188 mg, 81%). LCMS calc. for C$_{23}$H$_{27}$BrN$_5$O$_4$ (M+H)$^+$ m/z=516.1 and 518.1. found: 516.0 and 518.0.

Step 2. (S)-tert-Butyl 1-(3-(3-(prop-1-en-2-yl)furo[3,2-b]pyridine-5-carboxamido)pyridin-4-yl)piperidin-3-ylcarbamate

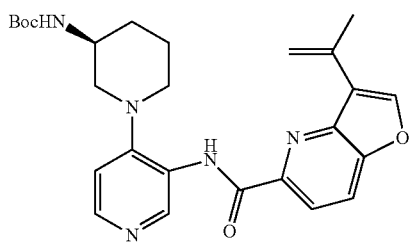 [SMILES: C=C(C)c1coc2ccc(C(=O)Nc3cnccc3N3CCC[C@H](NC(=O)OC(C)(C)C)C3)nc12]

(S)-tert-Butyl 1-(3-(3-bromofuro[3,2-b]pyridine-5-carboxamido)pyridin-4-yl)piperidin-3-ylcarbamate (78 mg, 0.151 mmol), dicyclohexyl(2',4',6'-triisopropylbiphenyl-2-yl)phosphine-(2'-aminobiphenyl-2-yl)(chloro)palladium (1:1) (12 mg, 0.015 mmol), $K_3PO_4$ (100 mg, 0.4 mmol) and a magnetic stirring bar were placed in a vial with a septum. The vial was then evacuated and backfilled with $N_2$ three times, followed by addition of 1,4-dioxane (1.1 mL) and degassed water (0.4 mL). Finally, 2-isopropenyl-4,4,5,5-tetramethyl-1,3,2-dioxaborolane (51 mg, 0.30 mmol) was added and reaction mixture was stirred at 55° C. for 1 h. The reaction mixture was then diluted with EtOAc, and the obtained solution was washed with brine, dried over $Na_2SO_4$, and the solvent evaporated. The crude product was purified by chromatography on silica gel using Biotage Isolera™ apparatus to give the sub-title compound (56 mg, 78%). LCMS calc. for $C_{26}H_{32}N_5O_4$ $(M+H)^+$ m/z=478.3. found: 478.2.

Step 3. (S)-tert-Butyl 1-(3-(3-isopropylfuro[3,2-b]pyridine-5-carboxamido)pyridin-4-yl)piperidin-3-ylcarbamate

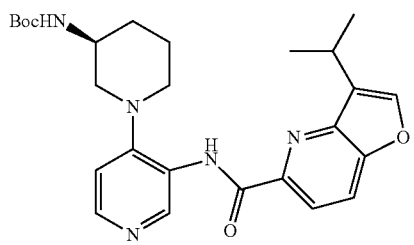 [SMILES: CC(C)c1coc2ccc(C(=O)Nc3cnccc3N3CCC[C@H](NC(=O)OC(C)(C)C)C3)nc12]

(S)-tert-Butyl 1-(3-(3-(prop-1-en-2-yl)furo[3,2-b]pyridine-5-carboxamido)pyridin-4-yl)piperidin-3-ylcarbamate (56 mg, 0.12 mmol) was dissolved in MeOH (2.0 mL) and 5 wt % of Pd on carbon (13 mg, 0.0060 mmol) was added. The vial was closed with a septum and was connected to a balloon with $H_2$ and the reaction mixture was stirred at room temperature overnight. The reaction mixture was filtered through diatomaceous earth and the solvent was evaporated to give pure product which was used in the next step without further purification (55 mg, 99%). LCMS calc. for $C_{26}H_{34}N_5O_4$ $(M+H)^+$ m/z=480.3. found: 480.2.

Step 4. (S)-N-(4-(3-Aminopiperidin-1-yl)pyridin-3-yl)-3-isopropylfuro[3,2-b]pyridine-5-carboxamide (S)-tert-Butyl 1-(3-(3-isopropylfuro[3,2-b]pyridine-5-carboxamido)pyridin-4-yl)piperidin-3-ylcarbamate (22 mg, 0.046 mmol) was dissolved in DCM (2.0 mL) and TFA (2 mL, 14 mmol) and the reaction mixture was stirred at 40° C. for 1 h. The mixture was then neutralized by addition of $NH_3$ solution and purified by RP-HPLC (water XBridge™ C18 column, 30 mm×100 mm, 5 μm particle size, eluting with a gradient of MeCN/water containing 0.1% $NH_4OH$, at flow rate of 60 mL/min) LCMS calc. for $C_{21}H_{26}N_5O_2$ $(M+H)^+$ m/z=380.2. found: 380.2. $^1$H NMR (500 MHz, DMSO-$d_6$) δ 10.43 (s, 1H), 9.47 (s, 1H), 8.28 (d, J=1.1 Hz, 1H), 8.27 (d, J=5.3 Hz, 1H), 8.25-8.20 (m, 2H), 7.17 (d, J=5.3 Hz, 1H), 3.21-3.12 (m, 1H), 3.10-2.95 (m, 2H), 2.71-2.57 (m, 1H), 2.37 (dd, J=10.9, 9.7 Hz, 1H), 1.96-1.88 (m, 1H), 1.85-1.74 (m, 3H), 1.43 (dd, J=6.9, 2.8 Hz, 6H), 1.22-1.06 (m, 1H) ppm.

Example 37

(S)-N-(4-(3-Aminopiperidin-1-yl)pyridin-3-yl)-3-(2,6-difluorophenyl)furo[3,2-b]pyridine-5-carboxamide

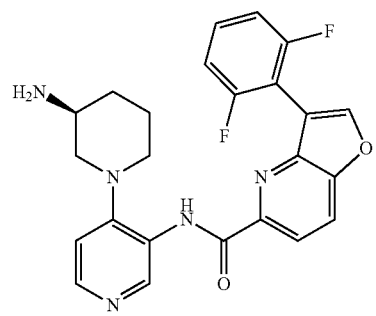 [SMILES: N[C@H]1CCCN(c2ccncc2NC(=O)c2ccc3occ(-c4c(F)cccc4F)c3n2)C1]

The title compound was synthesized by a procedure analogous to that of Example 36, using 2,6-difluorophenylboronic acid. LCMS calc. for $C_{24}H_{22}F_2N_5O_2$ $(M+H)^+$ m/z=450.2. found: 450.1. $^1$H NMR (500 MHz, DMSO-$d_6$) δ 9.46 (s, 1H), 8.81 (s, 1H), 8.44 (d, J=8.6 Hz, 1H), 8.32 (d, J=8.6 Hz, 1H), 8.24 (d, J=5.3 Hz, 1H), 7.73-7.59 (m, 1H), 7.39-7.31 (m, 2H), 7.09 (d, J=5.3 Hz, 2H), 3.02 (d, J=7.1 Hz, 1H), 2.94 (d, J=11.5 Hz, 1H), 2.45-2.31 (m, 3H), 2.27-2.16 (m, 1H), 1.51-1.37 (m, 2H), 1.15 (q, J=12.8 Hz, 1H), 0.96-0.79 (m, 1H) ppm.

Example 38

N-(4-((3R,4R,5S)-3-Amino-4-hydroxy-5-methylpiperidin-1-yl)pyridin-3-yl)-2-propylthieno[3,2-b]pyridine-5-carboxamide

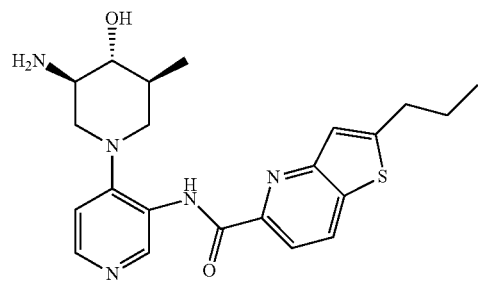 [SMILES: CCCc1cc2nc(C(=O)Nc3cnccc3N3C[C@@H](N)[C@H](O)[C@@H](C)C3)ccc2s1]

Step 1. Methyl 5-fluoro-6-pent-1-yn-1-ylpyridine-2-carboxylate

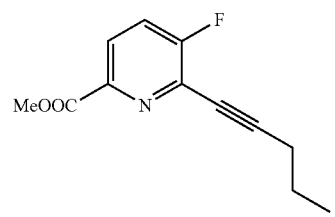 [SMILES: CCCC#Cc1nc(C(=O)OC)ccc1F]

Methyl 6-bromo-5-fluoropyridine-2-carboxylate (Frontier Scientific 300 mg, 1.28 mmol), CuI (36.6 mg, 0.192 mmol), dichloro[bis(triphenylphosphonio)]palladate (90 mg, 0.13 mmol), and a magnetic stirring bar were placed in a vial. The vial was then evacuated and backfilled with N₂ three times, followed by addition of DMF (1.70 mL) and TEA (450 μL, 3.2 mmol). The resulting reaction mixture was stirred for 5 min., followed by addition of 1-pentyne (144 μL, 1.46 mmol). The resulting reaction mixture was then stirred at 60° C. for 3 h. After this time, the reaction mixture was quenched with water and the product was extracted with EtOAc. The organic fraction was washed with brine, dried over Na₂SO₄, and the solvent was evaporated under reduced pressure. Crude product was purified by chromatography on silica gel using Biotage Isolera™ apparatus to give the sub-title product (284 mg, 82%). LCMS calc. for C₁₂H₁₃FNO₂ (M+H)⁺ m/z=222.1. found 222.1.

Step 2. 2-Propylthieno[3,2-b]pyridine-5-carboxylic acid

Methyl 5-fluoro-6-pent-1-yn-1-ylpyridine-2-carboxylate (315 mg, 1.42 mmol) was dissolved in DMF (1.89 mL), Na₂S (440 mg, 5.7 mmol) was added, and the reaction mixture was stirred at 60° C. for 3 h. After this time, the mixture was cooled to room temperature and 1 M NaOH (1 mL) was added and the reaction mixture was stirred at room temperature for 30 min. The mixture was then acidified to pH 3 with 1 M HCl. The reaction mixture was diluted with water and the product extracted with EtOAc. The organic phase was washed with brine and the solvent was evaporated under reduced pressure. The obtained product was dried under reduced pressure and was used in the next step without further purification (280 mg, 89%). LCMS calc. for C₁₁H₁₂NO₂S (M+H)⁺ m/z=222.1. found 222.0.

Step 3. tert-Butyl [(3R,4R,5S)-4-{[tert-butyl(dimethyl)silyl]oxy}-5-methyl-1-(3-{[(2-propylthieno[3,2-b]pyridin-5-yl)carbonyl]amino}pyridin-4-yl)piperidin-3-yl]carbamate

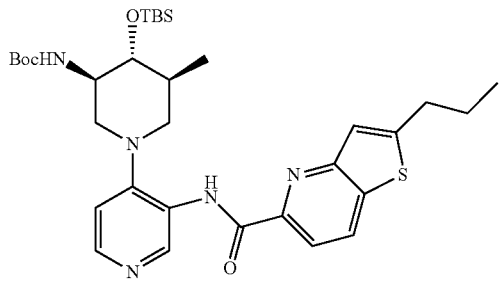 [SMILES: CCCc1cc2nc(C(=O)Nc3cnccc3N3C[C@H](C)[C@@H](O[Si](C)(C)C(C)(C)C)[C@H](NC(=O)OC(C)(C)C)C3)ccc2s1]

tert-Butyl ((3R,4R,5S)-1-(3-aminopyridin-4-yl)-4-{[tert-butyl(dimethyl)silyl]oxy}-5-methylpiperidin-3-yl)carbamate (20 mg, 0.046 mmol) and 2-propylthieno[3,2-b]pyridine-5-carboxylic acid (12 mg, 0.056 mmol) were dissolved in DMF (1 mL). Then DIPEA (24 μL, 0.14 mmol) and HATU (44 mg, 0.12 mmol) were added and reaction mixture was stirred at room temperature for 2 h. After full conversion was achieved, the reaction mixture was quenched with a saturated solution of NaHCO₃ and the product extracted with EtOAc. The organic phase was washed with brine and dried over Na₂SO₄. After the solvent was evaporated, the product was purified by chromatography on silica gel using Biotage Isolera™ apparatus to give the sub-title compound (25 mg, 84%). LCMS calc. for C₃₃H₅₀N₅O₄SSi (M+H)⁺ m/z=640.3. found 640.3.

Step 4. N-(4-((3R,4R,5S)-3-Amino-4-hydroxy-5-methylpiperidin-1-yl)pyridin-3-yl)-2-propylthieno[3,2-b]pyridine-5-carboxamide tert-Butyl [(3R,4R,5S)-4-{[tert-butyl(dimethyl)silyl]oxy}-5-methyl-1-(3-{[(2-propylthieno[3,2-b]pyridin-5-yl)carbonyl]amino}pyridin-4-yl)piperidin-3-yl]carbamate (25 mg, 0.039 mmol) was dissolved in DCM (2.0 mL) and TFA (2 mL, 14 mmol), followed by addition of 4.0 M HCl in dioxane (1 mL, 4 mmol). The reaction mixture was then stirred at 50° C. for 3 h. The mixture was then neutralized by addition of NH₃ solution and purified by RP-HPLC (water XBridge™ C18 column, 30 mm×100 mm, 5 nm particle size, eluting with a gradient of MeCN/water containing 0.1% NH₄OH, at flow rate of 60 mL/min) LCMS calc. for C₂₂H₂₈N₅O₂S (M+H)⁺ m/z=426.2. found 426.2.

Example 39

N-(4-((3R,4R,5S)-3-Amino-4-hydroxy-5-methylpiperidin-1-yl)pyridin-3-yl)-2-isopropylthieno[3,2-b]pyridine-5-carboxamide

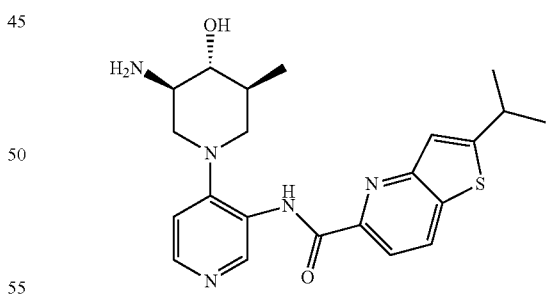

The title compound was synthesized by a procedure analogous to that of Example 38, using 3-methylbut-1-yne. LCMS calc. for C₂₂H₂₈N₅O₂S (M+H)⁺ m/z=426.2. found 426.2. ¹H NMR (500 MHz, DMSO-d₆) δ 10.51 (s, 1H), 9.43 (s, 1H), 8.65 (d, J=8.3 Hz, 1H), 8.26 (br, 1H), 8.09 (d, J=8.3 Hz, 1H), 7.42 (s, 1H), 7.13 (d, J=5.2 Hz, 1H), 4.87 (d, J=5.6 Hz, 1H), 3.43-3.31 (m, 1H), 3.24 (d, J=10.9 Hz, 1H), 3.18 (d, J=11.7 Hz, 1H), 3.10-2.92 (m, 1H), 2.82-2.72 (m, 1H), 2.54 (t, J=10.9 Hz, 1H), 2.15-2.03 (m, 1H), 1.40 (d, J=6.9 Hz, 6H), 0.91 (d, J=6.6 Hz, 3H) ppm.

Example 40

N-(4-((3R,4R,5S)-3-Amino-4-hydroxy-5-methylpiperidin-1-yl)pyridin-3-yl)-2-(2,6-difluorophenyl)thieno[3,2-b]pyridine-5-carboxamide

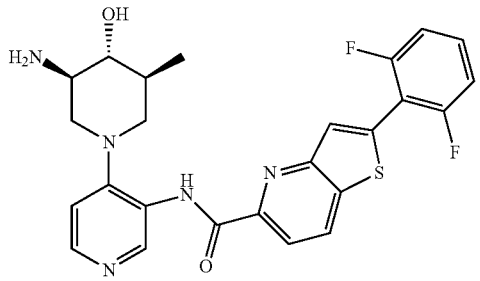 [SMILES: C[C@H]1CN(c2ccncc2NC(=O)c2ccc3sc(-c4c(F)cccc4F)cc3n2)C[C@@H](N)[C@@H]1O]

The title compound was synthesized by a procedure analogous to that of Example 38, using 2-ethynyl-1,3-difluorobenzene. LCMS calc. for $C_{25}H_{24}F_2N_5O_2S$ $(M+H)^+$ m/z=496.2. found 496.2.

Example 41

N-(4-((3R,4R,5S)-3-Amino-4-hydroxy-5-methylpiperidin-1-yl)pyridin-3-yl)-2-(2-fluorophenyl)thieno[3,2-b]pyridine-5-carboxamide

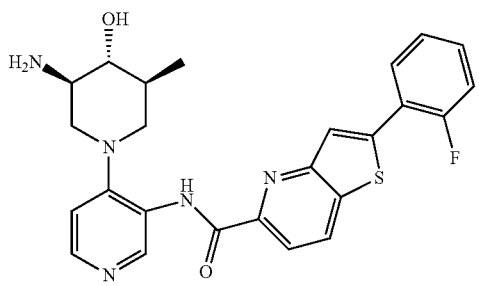 [SMILES: C[C@H]1CN(c2ccncc2NC(=O)c2ccc3sc(-c4ccccc4F)cc3n2)C[C@@H](N)[C@@H]1O]

The title compound was synthesized by a procedure analogous to that of Example 38, using 1-ethynyl-2-fluorobenzene. LCMS calc. for $C_{25}H_{25}FN_5O_2S$ $(M+H)^+$ m/z=478.2. found 478.1.

Example 42

N-(4-((3R,4R,5S)-3-Amino-4-hydroxy-5-methylpiperidin-1-yl)pyridin-3-yl)-2-benzylthieno[3,2-b]pyridine-5-carboxamide

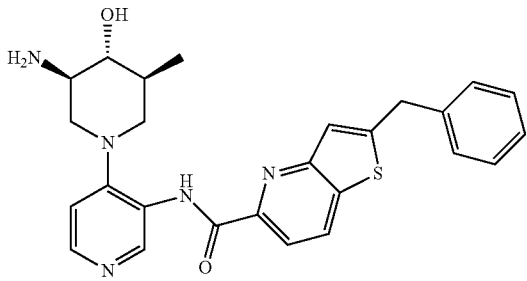 [SMILES: C[C@H]1CN(c2ccncc2NC(=O)c2ccc3sc(Cc4ccccc4)cc3n2)C[C@@H](N)[C@@H]1O]

The title compound was synthesized by a procedure analogous to that of Example 38, using prop-2-ynylbenzene. LCMS calc. for $C_{26}H_{28}N_5O_2S$ $(M+H)^+$ m/z=474.2. found 474.2.

Example 43

N-(4-((3R,4R,5S)-3-Amino-4-hydroxy-5-methylpiperidin-1-yl)pyridin-3-yl)-2-(6-methoxypyridin-3-yl)thieno[3,2-b]pyridine-5-carboxamide

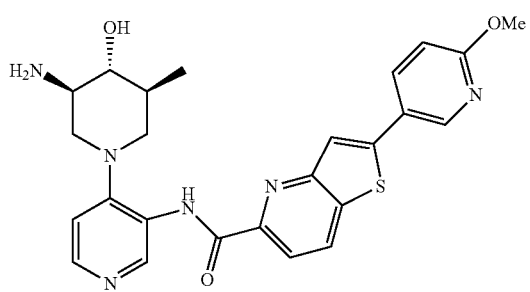 [SMILES: COc1ccc(-c2cc3nc(C(=O)Nc4cnccc4N4C[C@@H](N)[C@H](O)[C@@H](C)C4)ccc3s2)cn1]

The title compound was synthesized by a procedure analogous to that of Example 38, using 5-ethynyl-2-methoxypyridine. LCMS calc. for $C_{25}H_{27}N_6O_3S$ $(M+H)^+$ m/z=491.2. found 491.1.

Example 44

N-(4-((3R,4R,5S)-3-Amino-4-hydroxy-5-methylpiperidin-1-yl)pyridin-3-yl)-2-(6-morpholinopyridin-3-yl)thieno[3,2-b]pyridine-5-carboxamide

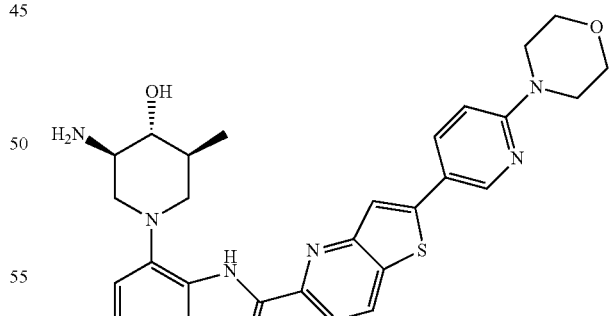

The title compound was synthesized by a procedure analogous to that of Example 38, using 4-(5-ethynylpyridin-2-yl)morpholine. LCMS calc. for $C_{28}H_{32}N_7O_3S$ $(M+H)^+$ m/z=546.2. found 546.4.

Example 45

N-(4-((3R,4R,5S)-3-Amino-4-hydroxy-5-methylpiperidin-1-yl)pyridin-3-yl)-2-(2,6-difluoro-4-methoxyphenyl)thieno[3,2-b]pyridine-5-carboxamide

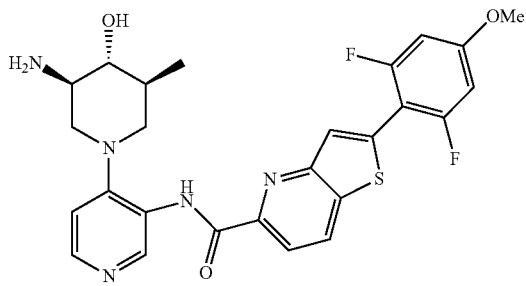 [SMILES: COc1cc(F)c(-c2cc3nc(C(=O)Nc4cnccc4N4C[C@@H](N)[C@H](O)[C@@H](C)C4)ccc3s2)c(F)c1]

The title compound was synthesized by a procedure analogous to that of Example 38, using 2-ethynyl-1,3-difluoro-5-methoxybenzene. LCMS calc. for $C_{26}H_{26}F_2N_5O_3S$ (M+H)+ m/z=526.2. found 526.1.

Example 46

N-(4-((3R,4R,5S)-3-Amino-4-hydroxy-5-methylpiperidin-1-yl)pyridin-3-yl)-2-phenylthieno[3,2-b]pyridine-5-carboxamide

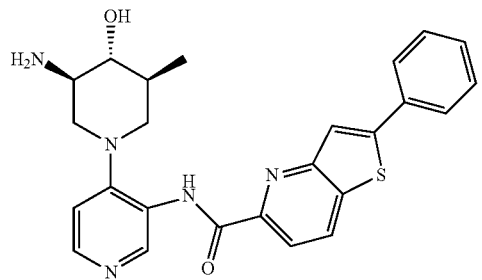 [SMILES: C[C@H]1CN(c2ccncc2NC(=O)c2ccc3sc(-c4ccccc4)cc3n2)C[C@@H](N)[C@@H]1O]

The title compound was synthesized by a procedure analogous to that of Example 38, using ethynylbenzene. LCMS calc. for $C_{25}H_{26}N_5O_2S$ (M+H)+ m/z=460.2. found 460.2.

Example 47

N-(4-((3R,4R,5S)-3-Amino-4-hydroxy-5-methylpiperidin-1-yl)pyridin-3-yl)-2-cyclopropylthieno[3,2-b]pyridine-5-carboxamide

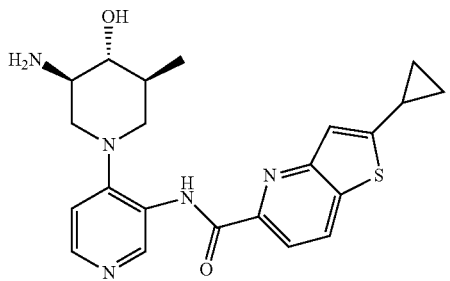 [SMILES: C[C@H]1CN(c2ccncc2NC(=O)c2ccc3sc(C4CC4)cc3n2)C[C@@H](N)[C@@H]1O]

The title compound was synthesized by a procedure analogous to that of Example 38, using ethynylcyclopropane. LCMS calc. for $C_{22}H_{26}N_5O_2S$ (M+H)+ m/z=424.2. found 424.2.

$^1$H NMR (500 MHz, DMSO-d$_6$) δ 10.50 (s, 1H), 9.42 (s, 1H), 8.60 (d, J=8.3 Hz, 1H), 8.24 (s, 1H), 8.06 (d, J=8.3 Hz, 1H), 7.35 (s, 1H), 7.13 (d, J=5.3 Hz, 1H), 4.88 (s, 1H), 3.23 (d, J=11.6 Hz, 1H), 3.17 (d, J=10.7 Hz, 1H), 2.81-2.70 (m, OH), 2.57-2.50 (m, 1H), 2.44-2.35 (m, 1H), 2.10-2.00 (m, 1H), 1.25-1.20 (m, 3H), 0.95-0.88 (m, 5H) ppm.

Example 48

N-(4-((3R,4R,5S)-3-Amino-4-hydroxy-5-methylpiperidin-1-yl)pyridin-3-yl)-2-(1-methyl-1H-pyrazol-4-yl)thieno[3,2-b]pyridine-5-carboxamide

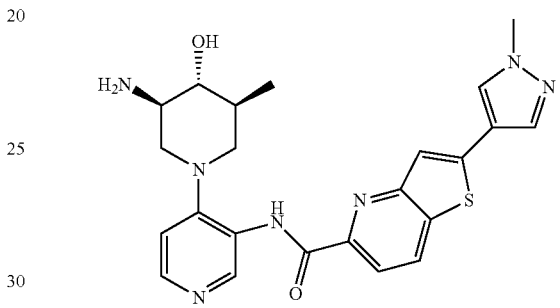

The title compound was synthesized by a procedure analogous to that of Example 38, using 4-ethynyl-1-methyl-1H-pyrazole. LCMS calc. for $C_{23}H_{26}N_7O_2S$ (M+H)+ m/z=464.2. found 464.1.

$^1$H NMR (500 MHz, DMSO-d$_6$) δ 10.51 (s, 1H), 9.39 (s, 1H), 8.66 (dd, J=8.3, 0.6 Hz, 1H), 8.33 (s, 1H), 8.25 (d, J=5.3 Hz, 1H), 8.08 (d, J=8.3 Hz, 1H), 7.98 (d, J=0.7 Hz, 1H), 7.70-7.67 (m, 2H), 7.14 (d, J=5.3 Hz, 1H), 6.49 (s, 1H), 4.88 (d, J=6.3 Hz, 1H), 3.92 (s, 3H), 3.23-3.15 (m, 1H), 3.11-3.00 (m, 1H), 2.82-2.73 (m, 1H), 2.58-2.50 (m, 2H), 2.12-2.02 (m, 1H), 0.92 (d, J=6.6 Hz, 3H) ppm.

Example 49

N-(4-((3R,4R,5S)-3-Amino-4-hydroxy-5-methylpiperidin-1-yl)pyridin-3-yl)-2-methylthieno[3,2-b]pyridine-5-carboxamide

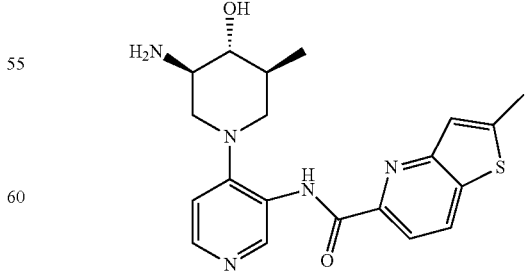

The title compound was synthesized by a procedure analogous to that of Example 38, using prop-1-yne. LCMS calc. for $C_{20}H_{24}N_5O_2S$ (M+H)+ m/z=398.2. found 398.1.

Example 50

N-(4-((3S,5R)-3-Amino-5-methylpiperidin-1-yl)pyridin-3-yl)-2-propylthieno[3,2-b]pyridine-5-carboxamide

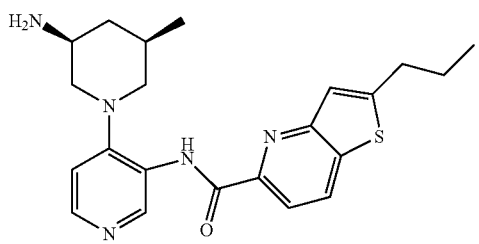 [SMILES: CCCc1cc2nc(C(=O)Nc3cnccc3N3C[C@H](C)C[C@H](N)C3)ccc2s1]

Step 1. tert-Butyl (3S,5R)-5-methyl-1-(3-(2-propylthieno[3,2-b]pyridine-5-carboxamido)pyridin-4-yl)piperidin-3-ylcarbamate

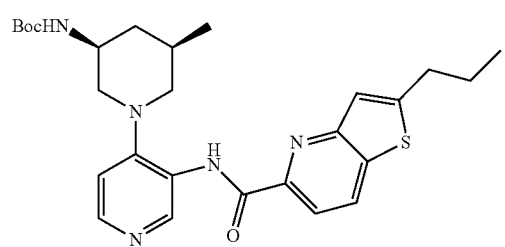 [SMILES: CCCc1cc2nc(C(=O)Nc3cnccc3N3C[C@H](C)C[C@H](NC(=O)OC(C)(C)C)C3)ccc2s1]

tert-Butyl (3S,5R)-1-(3-aminopyridin-4-yl)-5-methylpiperidin-3-ylcarbamate (14 mg, 0.046 mmol) and 2-propylthieno[3,2-b]pyridine-5-carboxylic acid (12 mg, 0.056 mmol) were dissolved in DMF (1 mL). Then DIPEA (24 µL, 0.14 mmol) and HATU (44 mg, 0.12 mmol) were added and the reaction mixture was stirred at room temperature for 2 h. After full conversion was achieved, the reaction mixture was quenched with a saturated solution of NaHCO$_3$ and product was extracted with EtOAc. The organic phase was washed with brine and dried over Na$_2$SO$_4$. After the solvent was evaporated, the product was purified by chromatography on silica gel using Biotage Isolera™ apparatus to give the sub-title compound (21 mg, 89%). LCMS calc. for C$_{22}$H$_{36}$N$_5$O$_3$S (M+H)$^+$ m/z=510.3. found 510.2.

Step 2. N-(4-((3S,5R)-3-Amino-5-methylpiperidin-1-yl)pyridin-3-yl)-2-propylthieno[3,2-b]pyridine-5-carboxamide tert-Butyl (3S,5R)-5-methyl-1-(3-(2-propylthieno[3,2-b]pyridine-5-carboxamido)pyridin-4-yl)piperidin-3-ylcarbamate (21 mg, 0.039 mmol) was dissolved in DCM (2.0 mL) and TFA (2 mL, 14 mmol) and the reaction mixture was stirred at 40° C. for 1 h. The mixture was then neutralized by addition of NH$_3$ solution and purified by RP-HPLC (water XBridge™ C18 column, 30 mm×100 mm, 5 µm particle size, eluting with a gradient of MeCN/water containing 0.1% NH$_4$OH, at flow rate of 60 mL/min). LCMS calc. for C$_{22}$H$_{28}$N$_5$OS (M+H)$^+$ m/z=410.2. found 410.2. $^1$H NMR (500 MHz, DMSO-d$_6$) δ 10.42 (s, 1H), 9.44 (s, 1H), 8.68-8.57 (m, 1H), 8.25 (d, J=5.2 Hz, 1H), 8.08 (d, J=8.3 Hz, 1H), 7.35 (s, 1H), 7.13 (d, J=5.3 Hz, 1H), 3.39-3.22 (m, 3H), 3.18-3.07 (m, 1H), 3.01 (t, J=7.5 Hz, 2H), 2.26 (dt, J=17.1, 11.0 Hz, 2H), 2.16-2.08 (m, 1H), 2.05 (d, J=12.5 Hz, 1H), 1.76 (h, J=7.4 Hz, 2H), 0.99 (t, J=7.3 Hz, 3H), 0.85 (d, J=6.6 Hz, 3H) ppm.

Example 51

N-(4-((3S,5R)-3-Amino-5-methylpiperidin-1-yl)pyridin-3-yl)-2-isopropylthieno[3,2-b]pyridine-5-carboxamide

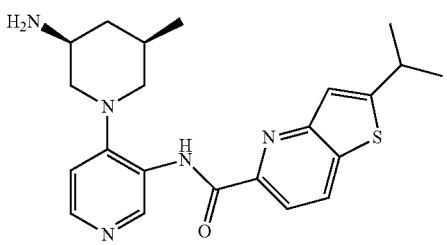

The title compound was synthesized by a procedure analogous to that of Example 50, using 3-methylbut-1-yne. LCMS calc. for C$_{22}$H$_{28}$N$_5$OS (M+H)$^+$ m/z=410.2. found 410.2. $^1$H NMR (500 MHz, DMSO-d$_6$) δ 10.42 (s, 1H), 9.42 (s, 1H), 8.68-8.57 (m, 1H), 8.25 (d, J=5.3 Hz, 1H), 8.09 (d, J=8.3 Hz, 1H), 7.34 (s, 1H), 7.13 (d, J=5.3 Hz, 1H), 3.41 (hept, J=7.2 Hz, 1H), 3.26-3.22 (m, 1H), 3.17 (d, J=11.4 Hz, 1H), 3.14-3.07 (m, 1H), 2.28 (dt, J=21.4, 11.0 Hz, 2H), 2.19-2.08 (m, 1H), 2.04 (d, J=14.2 Hz, 1H), 1.40 (d, J=6.8 Hz, 6H), 0.86 (d, J=6.6 Hz, 3H) ppm.

Example 52

N-(4-((3S,5R)-3-Amino-5-methylpiperidin-1-yl)pyridin-3-yl)-2-(2,6-difluorophenyl)thieno[3,2-b]pyridine-5-carboxamide

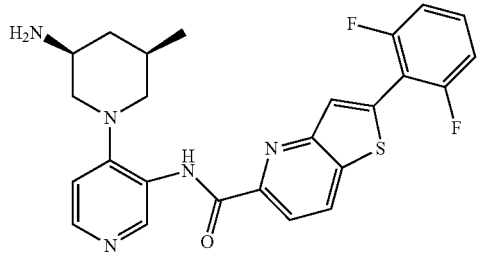 [SMILES: C[C@@H]1C[C@H](N)CN(c2ccncc2NC(=O)c2ccc3sc(-c4c(F)cccc4F)cc3n2)C1]

The title compound was synthesized by a procedure analogous to that of Example 50, using 2-ethynyl-1,3-difluorobenzene. LCMS calc. for C$_{25}$H$_{24}$F$_2$N$_5$OS (M+H)$^+$ m/z=480.2. found 480.2.

Example 53

N-(4-((3S,5R)-3-Amino-5-methylpiperidin-1-yl)pyridin-3-yl)-2-(2-fluorophenyl)thieno[3,2-b]pyridine-5-carboxamide

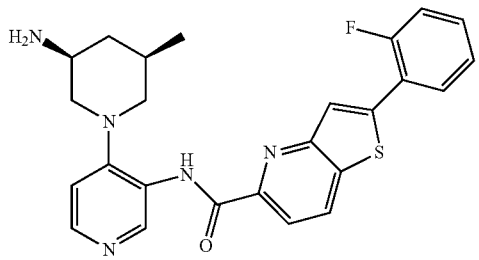 [SMILES: C[C@@H]1C[C@H](N)CN(c2ccncc2NC(=O)c2ccc3sc(-c4ccccc4F)cc3n2)C1]

The title compound was synthesized by a procedure analogous to that of Example 50, using 1-ethynyl-2-fluorobenzene. LCMS calc. for $C_{25}H_{25}FN_5OS$ $(M+H)^+$ m/z=462.2. found 462.2.

Example 54

N-(4-((3S,5R)-3-Amino-5-methylpiperidin-1-yl)pyridin-3-yl)-2-benzylthieno[3,2-b]pyridine-5-carboxamide

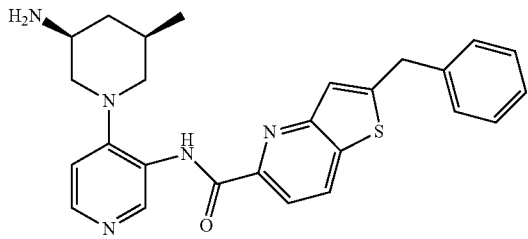 [SMILES: C[C@@H]1C[C@H](N)CN(c2ccncc2NC(=O)c2ccc3sc(Cc4ccccc4)cc3n2)C1]

The title compound was synthesized by a procedure analogous to that of Example 50, using prop-2-ynylbenzene. LCMS calc. for $C_{26}H_{28}N_5OS$ $(M+H)^+$ m/z=458.2. found 458.2.

Example 55

N-(4-((3S,5R)-3-Amino-5-methylpiperidin-1-yl)pyridin-3-yl)-2-(6-methoxypyridin-3-yl)thieno[3,2-b]pyridine-5-carboxamide

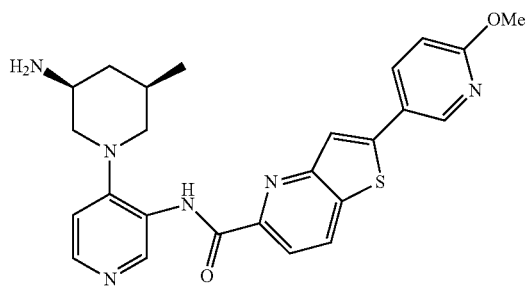 [SMILES: COc1ccc(-c2cc3nc(C(=O)Nc4cnccc4N4C[C@H](C)C[C@H](N)C4)ccc3s2)cn1]

The title compound was synthesized by a procedure analogous to that of Example 50, using 5-ethynyl-2-methoxypyridine. LCMS calc. for $C_{25}H_{27}N_6O_2S$ $(M+H)^+$ m/z=475.2. found 475.2.

Example 56

N-(4-((3S,5R)-3-Amino-5-methylpiperidin-1-yl)pyridin-3-yl)-2-(6-morpholinopyridin-3-yl)thieno[3,2-b]pyridine-5-carboxamide

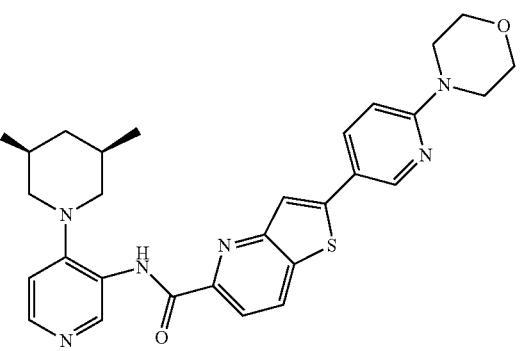

The title compound was synthesized by a procedure analogous to that of Example 50, using 4-(5-ethynylpyridin-2-yl)morpholine. LCMS calc. for $C_{28}H_{32}N_7O_2S$ $(M+H)^+$ m/z=530.2. found 530.2.

Example 57

N-(4-((3S,5R)-3-Amino-5-methylpiperidin-1-yl)pyridin-3-yl)-2-(2,6-difluoro-4-methoxyphenyl)thieno[3,2-b]pyridine-5-carboxamide

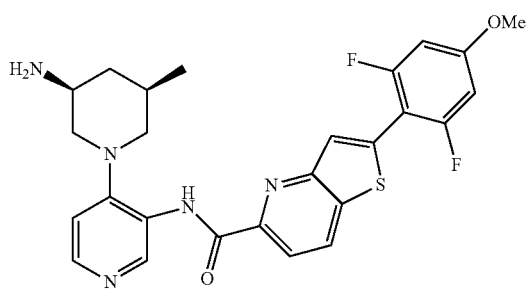 [SMILES: COc1cc(F)c(-c2cc3nc(C(=O)Nc4cnccc4N4C[C@H](C)C[C@H](N)C4)ccc3s2)c(F)c1]

The title compound was synthesized by a procedure analogous to that of Example 50, using 2-ethynyl-1,3-difluoro-5-methoxybenzene. LCMS calc. for $C_{26}H_{26}F_2N_5O_2S$ $(M+H)^+$ m/z=510.2. found 510.2.

Example 58

N-(4-((3S,5R)-3-Amino-5-methylpiperidin-1-yl)pyridin-3-yl)-2-phenylthieno[3,2-b]pyridine-5-carboxamide

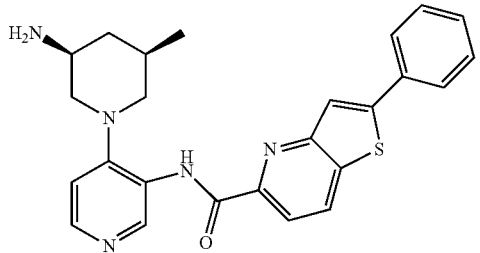 [SMILES: C[C@@H]1C[C@H](N)CN(c2ccncc2NC(=O)c2ccc3sc(-c4ccccc4)cc3n2)C1]

The title compound was synthesized by a procedure analogous to that of Example 50, using ethynylbenzene. LCMS calc. for $C_{25}H_{26}N_5OS$ (M+H)$^+$ m/z=444.2. found 444.2.

Example 59

N-(4-((3S,5R)-3-Amino-5-methylpiperidin-1-yl)pyridin-3-yl)-2-cyclopropylthieno[3,2-b]pyridine-5-carboxamide

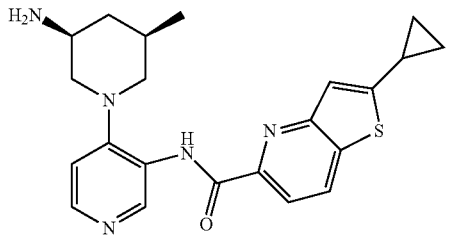

The title compound was synthesized by a procedure analogous to that of Example 50, using ethynylcyclopropane. LCMS calc. for $C_{22}H_{26}N_5OS$ (M+H)$^+$ m/z=408.2. found 408.2.

$^1$H NMR (500 MHz, DMSO-d$_6$) δ 10.40 (s, 1H), 9.42 (s, 1H), 8.59 (dd, J=8.3, 0.6 Hz, 1H), 8.25 (d, J=5.3 Hz, 1H), 8.06 (d, J=8.3 Hz, 1H), 7.32 (s, 1H), 7.13 (d, J=5.3 Hz, 1H), 3.19-3.05 (m, 1H), 2.48-2.40 (m, 1H), 2.33-2.20 (m, 2H), 2.15-2.01 (m, 2H), 1.25-1.18 (m, 3H), 0.92 (ddd, J=6.6, 4.2, 1.4 Hz, 2H), 0.86 (d, J=6.5 Hz, 3H) ppm.

Example 60

N-(4-((3S,5R)-3-Amino-5-methylpiperidin-1-yl)pyridin-3-yl)-2-(1-methyl-1H-pyrazol-4-yl)thieno[3,2-b]pyridine-5-carboxamide

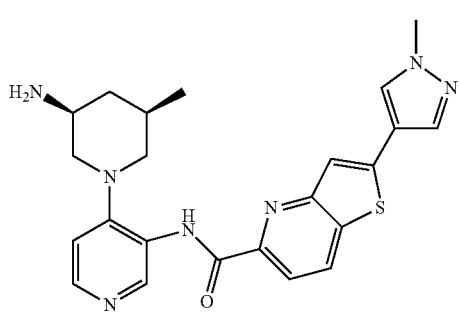 [SMILES: C[C@@H]1C[C@H](N)CN(c2ccncc2NC(=O)c2ccc3sc(-c4cnn(C)c4)cc3n2)C1]

The title compound was synthesized by a procedure analogous to that of Example 50, using 4-ethynyl-1-methyl-1H-pyrazole. LCMS calc. for $C_{23}H_{26}N_7OS$ (M+H)$^+$ m/z=448.2. found 448.2.

$^1$H NMR (500 MHz, DMSO-d$_6$) δ 10.37 (s, 1H), 9.41 (s, 1H), 8.66 (dd, J=8.3, 0.5 Hz, 1H), 8.40 (s, 1H), 8.26 (d, J=5.3 Hz, 1H), 8.08 (d, J=8.3 Hz, 1H), 8.05 (d, J=0.8 Hz, 1H), 7.64-7.56 (m, 1H), 7.14 (d, J=5.3 Hz, 1H), 6.49 (s, 1H), 3.92 (s, 3H), 3.24-3.03 (m, 2H), 2.34-2.22 (m, 3H), 2.17-2.04 (m, 2H), 0.87 (d, J=6.4 Hz, 3H) ppm.

Example 61

N-(4-((3S,5R)-3-Amino-5-methylpiperidin-1-yl)pyridin-3-yl)-2-methylthieno[3,2-b]pyridine-5-carboxamide

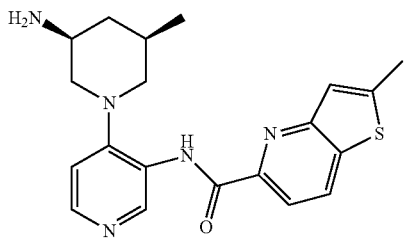 [SMILES: Cc1cc2nc(C(=O)Nc3cnccc3N3C[C@H](C)C[C@H](N)C3)ccc2s1]

The title compound was synthesized by a procedure analogous to that of Example 50, using prop-1-yne. LCMS calc. for $C_{20}H_{24}N_5OS$ (M+H)$^+$ m/z=382.2. found 382.1.

Example 62

N-(4-((3S,5R)-3-Amino-5-methylpiperidin-1-yl)pyridin-3-yl)-3-isopropylthieno[3,2-b]pyridine-5-carboxamide

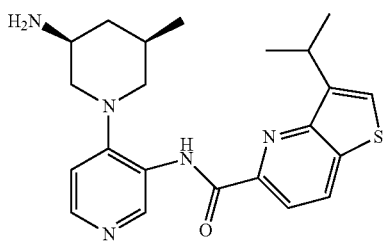 [SMILES: CC(C)c1csc2ccc(C(=O)Nc3cnccc3N3C[C@H](C)C[C@H](N)C3)nc12]

Step 1. (3-Amino-2-thienyl) methanol

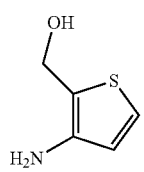

Solution of methyl 3-aminothiophene-2-carboxylate (Aldrich, 5.0 g, 32 mmol) in THF (15 mL) was added to 2.0 M solution of LiAlH$_4$ in THF (32.6 mL, 65.2 mmol) at 0° C.

After completion of the addition, the reaction mixture was warmed to room temperature, and then stirred for 1 h. The mixture was carefully quenched with saturated aq. Na$_2$SO$_4$ (40 mL) and the resulting solid was removed by filtration. The filtrate was concentrated under reduced pressure to provide roughly 50 mL of an aqueous mixture. The product was extracted with EtOAc, and the combined organic layers were dried and concentrated under reduced pressure to provide the sub-title product as a yellow solid (3.71 g, 90%) which was used in the next step without purification. LCMS calc. for C$_5$H$_8$NOS (M+H)$^+$ m/z=130.0. found 130.0.

Step 2. 3-Aminothiophene-2-carbaldehyde

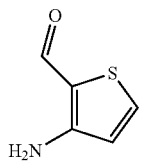

(3-Amino-2-thienyl)methanol (3.71 g, 28.7 mmol) was dissolved in DCM (30 mL) and EtOAc (10 mL) and MnO$_2$ (25.0 g, 287 mmol) was added. The reaction mixture was stirred at room temperature overnight. The MnO$_2$ was then filtered off and the solvent was evaporated under reduced pressure. The obtained product (2.5 g, 68%) was used in the next step without further purification. LCMS calc. for C$_5$H$_6$NOS (M+H)$^+$ m/z=128.0. found 128.0.

Step 3. Thieno[3,2-b]pyridine-5-carboxylic acid

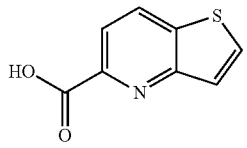 [SMILES: O=C(O)c1ccc2sccc2n1]

3-Aminothiophene-2-carbaldehyde (2.2 g, 17 mmol) was dissolved in EtOH (27.7 mL) and methyl 2-oxopropanoate (2.097 g, 18.49 mmol) was added. A solution of KOH (2.1 g, 38 mmol) in water (20.8 mL) was added and the reaction mixture was stirred at 70° C. for 3 h. After this time, the mixture was cooled to room temperature, neutralized with 1 M HCl to pH 3 and all solvents were evaporated to dryness. Then MeCN was added and solvent was evaporated again. The obtained product was used in the next step without further purification. LCMS calc. for C$_8$H$_6$NO$_2$S (M+H)$^+$ m/z=180.0. found 180.0.

Step 4. Methyl thieno[3,2-b]pyridine-5-carboxylate

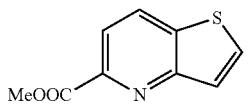

MeOH (40 mL) was added to crude thieno[3,2-b]pyridine-5-carboxylic acid (3.1 g, 17 mmol) from the previous step. Conc. H$_2$SO$_4$ (2.8 mL, 52 mmol) was then carefully added and the reaction mixture was stirred at reflux overnight. After this time, the solvent was evaporated and the product dissolved in EtOAc. The obtained solution was neutralized with a saturated solution of NaHCO$_3$ and the product was extracted with EtOAc (2×). The organic phase was dried over Na$_2$SO$_4$ and the solvent evaporated under reduced pressure. Crude product was purified by chromatography on silica gel using Biotage Isolera™ apparatus to give the sub-title compound (2.03 g, 61% over two steps). LCMS calc. for C$_9$H$_8$NO$_2$S (M+H)$^+$ m/z=194.0. found 194.0.

Step 5. Methyl 3-bromothieno[3,2-b]pyridine-5-carboxylate

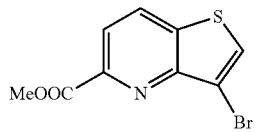

Methyl thieno[3,2-b]pyridine-5-carboxylate (820 mg, 4.24 mmol) was dissolved in DCM (20 mL) and AcOH (8.0 mL). Br$_2$ (1.0 mL, 19 mmol) was carefully added and the reaction mixture was heated to 40° C., followed by addition of N-bromosuccinimide (3.8 g, 21 mmol) portion-wise until complete conversion of starting material was observed by LCMS. When the reaction was complete, water and a saturated solution of Na$_2$S$_2$O$_3$ were added, and the product was extracted with DCM, washed with brine, dried over Na$_2$SO$_4$, and the solvent evaporated. The product was purified by chromatography on silica gel using Biotage Isolera™ apparatus to give the sub-title product (1.15 g, 74%). LCMS calc. for C$_9$H$_7$BrNO$_2$S (M+H)$^+$ m/z=271.9 and 273.9. found 271.9 and 273.9.

Step 6. 3-Bromothieno[3,2-b]pyridine-5-carboxylic acid

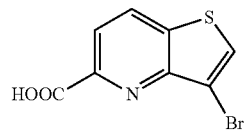 [SMILES: O=C(O)c1ccc2scc(Br)c2n1]

Methyl 3-bromothieno[3,2-b]pyridine-5-carboxylate (850 mg, 3.1 mmol) was dissolved in THF (30 mL), followed by addition of water (10 mL) and MeOH (20 mL). After subsequent addition of LiOH (500 mg, 4 mmol), the reaction mixture was stirred at 60° C. for 4 h. The mixture was cooled to room temperature and the pH was adjusted to 5 by addition of 1 M HCl. The product was then extracted with EtOAc and the organic phase was washed with brine, and dried over Na$_2$SO$_4$, and the solvent was evaporated. The obtained solid product was used in the next step without further purification (768 mg, 95%). LCMS calc. for C$_8$H$_5$BrNO$_2$S (M+H)$^+$ m/z=257.9 and 259.9. found 257.9 and 259.9.

143

Step 7. tert-Butyl [(3S,5R)-1-(3-{[(3-bromothieno[3,2-b]pyridin-5-yl)carbonyl]amino}pyridin-4-yl)-5-methylpiperidin-3-yl]carbamate

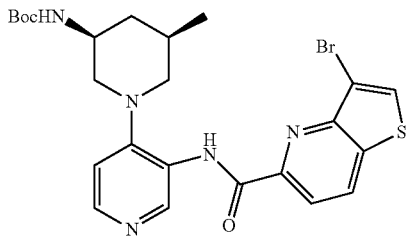 [SMILES: C[C@@H]1C[C@H](NC(=O)OC(C)(C)C)CN(c2ccncc2NC(=O)c2ccc3scc(Br)c3n2)C1]

tert-Butyl [(3S,5R)-1-(3-aminopyridin-4-yl)-5-methylpiperidin-3-yl]carbamate (280 mg, 0.92 mmol) and 3-bromothieno[3,2-b]pyridine-5-carboxylic acid (284 mg, 1.10 mmol) were dissolved in DMF (16 mL), followed by addition of DIPEA (480 µL, 2.7 mmol) and HATU (870 mg, 2.3 mmol), and the reaction mixture was stirred at room temperature for 2 h. After full conversion was achieved, the reaction mixture was quenched with a saturated solution of NaHCO$_3$ and the product extracted with EtOAc. The organic phase was washed with brine and dried over Na$_2$SO$_4$. After the solvent was evaporated, the product was purified by chromatography on silica gel using Biotage Isolera™ apparatus to give the sub-title compound (421 mg, 84%). LCMS calc. for C$_{24}$H$_{29}$BrN$_5$O$_3$S (M+H)$^+$ m/z=546.1 and 548.1. found 546.1 and 548.1.

Step 8. tert-Butyl (3S,5R)-5-methyl-1-(3-(3-(prop-1-en-2-yl)thieno[3,2-b]pyridine-5-carboxamido)pyridin-4-yl)piperidin-3-ylcarbamate

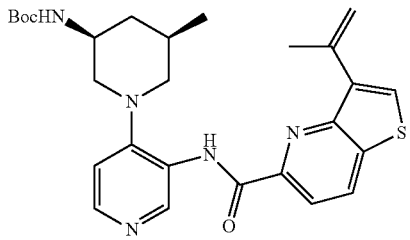 [SMILES: C=C(C)c1csc2ccc(C(=O)Nc3cnccc3N3C[C@H](C)C[C@H](NC(=O)OC(C)(C)C)C3)nc12]

tert-Butyl [(3S,5R)-1-(3-{[(3-bromothieno[3,2-b]pyridin-5-yl)carbonyl]amino}pyridin-4-yl)-5-methylpiperidin-3-yl]carbamate (16.5 mg, 0.0303 mmol), dicyclohexyl(2',4',6'-triisopropylbiphenyl-2-yl)phosphine-(2'-aminobiphenyl-2-yl)(chloro)palladium (1:1) (2.4 mg, 0.0030 mmol), K$_3$PO$_4$ (20 mg, 0.09 mmol), and a magnetic stirring bar were placed in a vial with a septum. The vial was then evacuated and backfilled with N$_2$ three times, followed by addition of 1,4-dioxane (1.0 mL) and degassed water (0.25 mL). Finally, 2-isopropenyl-4,4,5,5-tetramethyl-1,3,2-dioxaborolane (10 mg, 0.060 mmol) was added and the reaction mixture was stirred at 55° C. for 1 h. The reaction mixture was then diluted with EtOAc and the obtained solution was washed with brine, dried over Na$_2$SO$_4$, and the solvent evaporated. Crude product was purified by chromatography on silica gel using Biotage Isolera™ apparatus to give the sub-title compound (13.3 mg, 86%). LCMS calc. for C$_{27}$H$_{34}$N$_5$O$_3$S (M+H)$^+$ m/z=508.2. found 508.2.

144

Step 9. tert-Butyl [(3S,5R)-1-(3-{[(3-isopropylthieno[3,2-b]pyridin-5-yl)carbonyl]amino}pyridin-4-yl)-5-methylpiperidin-3-yl]carbamate

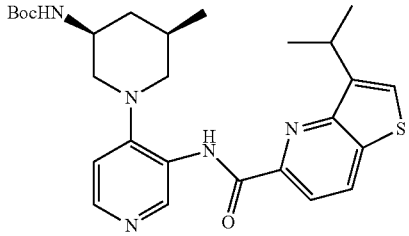 [SMILES: CC(C)c1csc2ccc(C(=O)Nc3cnccc3N3C[C@H](C)C[C@H](NC(=O)OC(C)(C)C)C3)nc12]

tert-Butyl [(3S,5R)-1-(3-{[(3-isopropenylthieno[3,2-b]pyridin-5-yl)carbonyl]amino}pyridin-4-yl)-5-methylpiperidin-3-yl]carbamate (13 mg, 0.03 mmol) was dissolved in MeOH (1.0 mL) and 5 wt % of Pd on carbon (2.3 mg) was added. The vial was closed with a septum and was connected to a balloon with H$_2$ and the reaction mixture was stirred at room temperature overnight. The resulting mixture was then filtered through diatomaceous earth and the solvent was evaporated to give pure product which was used in the next step without further purification (13 mg, 99%). LCMS calc. for C$_{27}$H$_{36}$N$_5$O$_3$S (M+H)$^+$ m/z=510.3. found 510.2.

Step 10. N-(4-((3S,5R)-3-Amino-5-methylpiperidin-1-yl)pyridin-3-yl)-3-isopropylthieno[3,2-b]pyridine-5-carboxamide tert-Butyl [(3S,5R)-1-(3-{[(3-isopropylthieno[3,2-b]pyridin-5-yl)carbonyl]amino}pyridin-4-yl)-5-methylpiperidin-3-yl]carbamate (13 mg, 0.026 mmol) was dissolved in DCM (1.0 mL). TFA (1.1 mL, 14 mmol) was added and the reaction mixture was stirred at 40° C. for 1 h. The mixture was then neutralized by addition of NH$_3$ solution and purified by RP-HPLC (water XBridge™ C18 column, 30 mm×100 mm, 5 µm particle size, eluting with a gradient of MeCN/water containing 0.1% NH$_4$OH, at flow rate of 60 mL/min) LCMS calc. for C$_{22}$H$_{28}$N$_5$OS (M+H)$^+$ m/z=410.2. found 410.2.

$^1$H NMR (500 MHz, DMSO-d$_6$) δ 10.43 (s, 1H), 9.46 (s, 1H), 8.73 (d, J=8.3 Hz, 1H), 8.28 (d, J=5.3 Hz, 1H), 8.20 (d, J=8.4 Hz, 1H), 8.02 (s, 1H), 7.20 (d, J=5.3 Hz, 1H), 3.72 (h, J=7.4, 6.9 Hz, 1H), 3.19 (dd, J=11.0, 4.1 Hz, 1H), 3.10 (d, J=11.2 Hz, 1H), 3.05-2.98 (m, 1H), 2.26 (t, J=10.8 Hz, 2H), 2.06-1.86 (m, 1H), 1.38 (t, J=7.1 Hz, 6H), 0.85 (d, J=6.5 Hz, 3H) ppm.

Example 63

N-(4-((3S,5R)-3-Amino-5-methylpiperidin-1-yl)pyridin-3-yl)-3-(1-methyl-1H-pyrazol-4-yl)thieno[3,2-b]pyridine-5-carboxamide

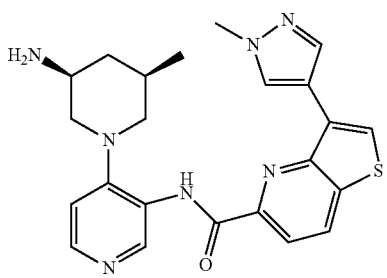 [SMILES: C[C@@H]1C[C@H](N)CN(c2ccncc2NC(=O)c2ccc3scc(-c4cnn(C)c4)c3n2)C1]

The title compound was synthesized by a procedure analogous to that of Example 62, using 1-methyl-4-(4,4,5,5-tetramethyl-1,3,2-dioxaborolan-2-yl)-1H-pyrazole. LCMS calc. for $C_{23}H_{26}N_7OS$ (M+H)$^+$ m/z=448.2. found 448.2.

Example 64

N-(4-((3S,5R)-3-Amino-5-methylpiperidin-1-yl)pyridin-3-yl)-3-(2,6-difluoro-3-methoxyphenyl)thieno[3,2-b]pyridine-5-carboxamide

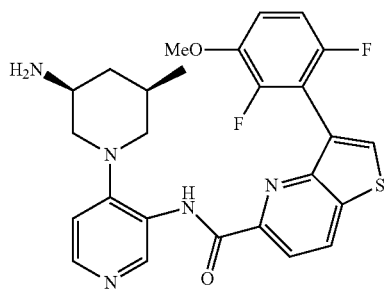 [SMILES: COc1ccc(F)c(-c2csc3ccc(C(=O)Nc4cnccc4N4C[C@H](C)C[C@H](N)C4)nc23)c1F]

The title compound was synthesized by a procedure analogous to that of Example 62, using 2,6-difluoro-3-methoxyphenylboronic acid. LCMS calc. for $C_{26}H_{26}F_2N_5O_2S$ (M+H)$^+$ m/z=510.2. found 510.2.

Example 65

N-(4-((3S,5R)-3-Amino-5-methylpiperidin-1-yl)pyridin-3-yl)-3-cyclopropylthieno[3,2-b]pyridine-5-carboxamide

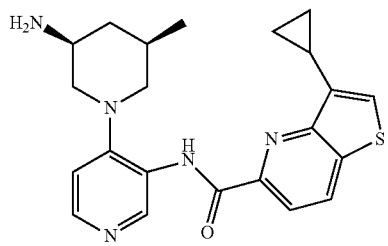 [SMILES: C[C@@H]1C[C@H](N)CN(c2ccncc2NC(=O)c2ccc3scc(C4CC4)c3n2)C1]

Step 1. tert-Butyl [(3S,5R)-1-(3-{[(3-cyclopropylthieno[3,2-b]pyridin-5-yl)carbonyl]amino}pyridin-4-yl)-5-methylpiperidin-3-yl]carbamate

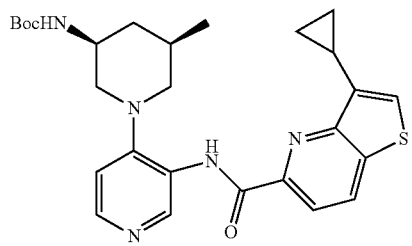 [SMILES: C[C@@H]1C[C@H](NC(=O)OC(C)(C)C)CN(c2ccncc2NC(=O)c2ccc3scc(C4CC4)c3n2)C1]

To a vial was added tert-butyl [(3S,5R)-1-(3-{[(3-bromothieno[3,2-b]pyridin-5-yl)carbonyl]amino}pyridin-4-yl)-5-methylpiperidin-3-yl]carbamate (25 mg, 0.045 mmol), potassium cyclopropyltrifluoroborate (13 mg, 0.091 mmol), $Cs_2CO_3$ (44.4 mg, 0.136 mmol), Pd(OAc)$_2$ (1.5 mg, 0.0068 mmol) and di-1-adamantyl(butyl)phosphine (4.9 mg, 0.014 mmol). The vial was sealed, evacuated, and filled with $N_2$ three times. Toluene (1.0 mL) and water (100 µL) were added and reaction mixture was stirred at 100° C. overnight. The reaction mixture was then diluted with EtOAc. The obtained solution was washed with brine, dried over $Na_2SO_4$, and the solvent evaporated. Crude product was purified by chromatography on silica gel using Biotage Isolera™ apparatus to give the sub-title compound (17 mg, 74%). LCMS calc. for $C_{27}H_{34}N_5O_3S$ (M+H)$^+$ m/z=508.2. found 508.2.

Step 2. N-(4-((3S,5R)-3-Amino-5-methylpiperidin-1-yl)pyridin-3-yl)-3-cyclopropylthieno[3,2-b]pyridine-5-carboxamide

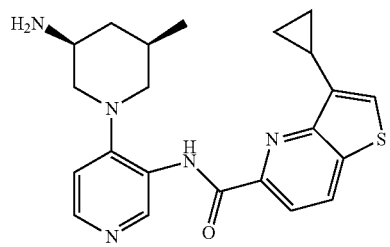 [SMILES: C[C@@H]1C[C@H](N)CN(c2ccncc2NC(=O)c2ccc3scc(C4CC4)c3n2)C1]

N-(4-((3S,5R)-3-Amino-5-methylpiperidin-1-yl)pyridin-3-yl)-3-cyclopropylthieno[3,2-b]pyridine-5-carboxamide (17 mg, 0.026 mmol) was dissolved in DCM (1.0 mL). TFA (1.1 mL, 14 mmol) was added and the reaction mixture was stirred at 40° C. for 1 h. The mixture was then neutralized by addition of $NH_3$ solution and purified by RP-HPLC (water, XBridge™ C18 column, 30 mm×100 mm, 5 µm particle size, eluting with a gradient of MeCN/water containing 0.1% $NH_4OH$, at flow rate of 60 mL/min). LCMS calc. for $C_{22}H_{26}N_5OS$ (M+H)$^+$ m/z=408.2. found 408.1.

Example 66

N-{4-[(3S)-3-Aminopiperidin-1-yl]pyridin-3-yl}-3-ethylthieno[3,2-b]pyridine-5-carboxamide

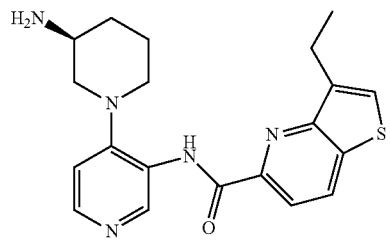 [SMILES: CCc1csc2ccc(C(=O)Nc3cnccc3N3CCC[C@H](N)C3)nc12]

Step 1. (S)-tert-Butyl 1-(3-(3-bromothieno[3,2-b]pyridine-5-carboxamido)pyridin-4-yl)piperidin-3-ylcarbamate

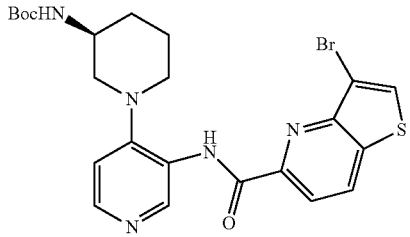

tert-Butyl [(3S)-1-(3-aminopyridin-4-yl)piperidin-3-yl]carbamate (170 mg, 0.59 mmol) and 3-bromothieno[3,2-b]pyridine-5-carboxylic acid (184 mg, 0.713 mmol) were dissolved in DMF (10 mL). Then DIPEA (310 μL, 1.8 mmol) and HATU (560 mg, 1.5 mmol) were added and reaction mixture was stirred at room temperature for 2 h. After full conversion was achieved, the reaction mixture was quenched with a saturated solution of NaHCO$_3$ and the product extracted with EtOAc. The organic phase was washed with brine and dried over Na$_2$SO$_4$. After the solvent was evaporated, the product was purified by chromatography on silica gel using Biotage Isolera™ apparatus to give the sub-title compound (250 mg, 78%). LCMS calc. for C$_{23}$H$_{27}$BrN$_5$O$_3$S (M+H)$^+$ m/z=532.1 and 534.1. found 532.1 and 534.0.

Step 2. (S)-tert-Butyl 1-(3-(3-vinylthieno[3,2-b]pyridine-5-carboxamido)pyridin-4-yl)piperidin-3-ylcarbamate

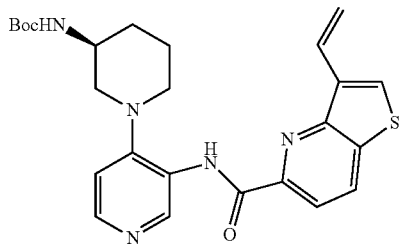 [SMILES: C=Cc1csc2ccc(C(=O)Nc3cnccc3N3CCC[C@H](NC(=O)OC(C)(C)C)C3)nc12]

tert-Butyl [(3S)-1-(3-{[(3-bromothieno[3,2-b]pyridin-5-yl)carbonyl]amino}pyridin-4-yl)piperidin-3-yl]carbamate (16.1 mg, 0.0303 mmol)dicyclohexyl(2',4',6'-triisopropylbiphenyl-2-yl)phosphine-(2'-aminobiphenyl-2-yl)(chloro)palladium (1:1) (2.4 mg, 0.0030 mmol), K$_3$PO$_4$ (20 mg, 0.09 mmol), and a magnetic stirring bar were placed in a vial with a septum. The vial was then evacuated and backfilled with N$_2$ three times, followed by addition of 1,4-dioxane (1.0 mL) and degassed water (0.25 mL). Finally, 4,4,5,5-tetramethyl-2-vinyl-1,3,2-dioxaborolane (9.3 mg, 0.060 mmol) was added and the reaction mixture was stirred at 55° C. for 1 h. The reaction mixture was then diluted with EtOAc. The obtained solution was washed with brine, dried over Na$_2$SO$_4$, and the solvent evaporated. Crude product was purified by chromatography on silica gel using Biotage Isolera™ apparatus to give the sub-title compound (12 mg, 83%). LCMS calc. for C$_{25}$H$_{30}$N$_5$O$_3$S (M+H)$^+$ m/z=480.2. found 480.2.

Step 3. tert-Butyl [(3S)-1-(3-{[(3-ethylthieno[3,2-b]pyridin-5-yl)carbonyl]amino}pyridin-4-yl)piperidin-3-yl]carbamate

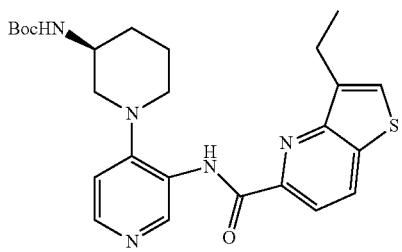 [SMILES: CCc1csc2ccc(C(=O)Nc3cnccc3N3CCC[C@H](NC(=O)OC(C)(C)C)C3)nc12]

tert-Butyl [(3S)-1-(3-{[(3-vinylthieno[3,2-b]pyridin-5-yl)carbonyl]amino}pyridin-4-yl)piperidin-3-yl]carbamate (10 mg, 0.03 mmol) was dissolved in MeOH (1.0 mL) and 5 wt % of Pd on carbon (2.3 mg, 0.0011 mmol) was added. The vial was closed with a septum and was connected to a balloon with H$_2$ and the reaction mixture was stirred at room temperature overnight. LCMS showed complete conversion. The reaction mixture was filtered through diatomaceous earth and the solvent was evaporated to give pure product which was used in the next step without further purification (10 mg, 99%). LCMS calc. for C$_{25}$H$_{32}$N$_5$O$_3$S (M+H)$^+$ m/z=482.2. found 482.2.

Step 4. N-{4-(3S)-3-Aminopiperidin-1-yl)pyridin-3-yl}-3-ethylthieno[3,2-b]pyridine-5-carboxamide tert-Butyl [(3S)-1-(3-{[(3-ethylthieno[3,2-b]pyridin-5-yl)carbonyl]amino}pyridin-4-yl)piperidin-3-yl]carbamate (22 mg, 0.046 mmol) was dissolved in DCM (1.0 mL). TFA (1.1 mL, 14 mmol) was added and the reaction mixture was stirred at 40° C. for 1 h. The mixture was then neutralized by addition of NH$_3$ solution and purified by RP-HPLC (water XBridge™ C18 column, 30 mm×100 mm, 5 μm particle size, eluting with a gradient of MeCN/water containing 0.1% NH$_4$OH, at flow rate of 60 mL/min) LCMS calc. for C$_{20}$H$_{24}$N$_5$OS (M+H)$^+$ m/z=382.2. found 382.2.

Example 67

(S)-N-(4-(3-Aminopiperidin-1-yl)pyridin-3-yl)-3-cyclopropylthieno[3,2-b]pyridine-5-carboxamide

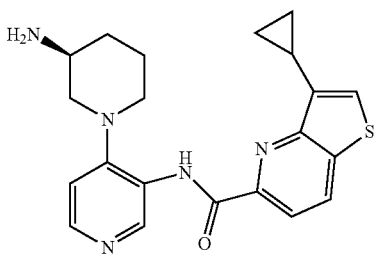 [SMILES: N[C@H]1CCCN(c2ccncc2NC(=O)c2ccc3scc(C4CC4)c3n2)C1]

Step 1. (S)-tert-Butyl 1-(3-(3-cyclopropylthieno[3,2-b]pyridine-5-carboxamido)pyridin-4-yl)piperidin-3-ylcarbamate

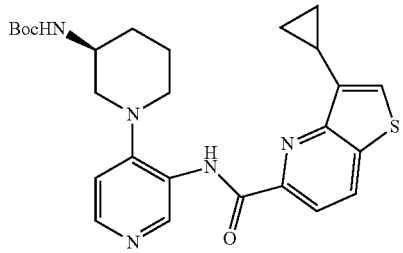 [SMILES: CC(C)(C)OC(=O)N[C@H]1CCCN(c2ccncc2NC(=O)c2ccc3scc(C4CC4)c3n2)C1]

To a vial was added (S)-tert-butyl 1-(3-(3-bromothieno[3,2-b]pyridine-5-carboxamido)pyridin-4-yl)piperidin-3-ylcarbamate (24 mg, 0.045 mmol), potassium cyclopropyltrifluoroborate (13 mg, 0.091 mmol), $Cs_2CO_3$ (44.4 mg, 0.136 mmol), $Pd(OAc)_2$ (1.5 mg, 0.0068 mmol) and di-1-adamantyl(butyl)phosphine (4.9 mg, 0.014 mmol). The vial was sealed and evacuated and filled with $N_2$ three times. Toluene (1.0 mL) and water (100 µL) were added and reaction mixture was stirred at 100° C. overnight. The reaction mixture was then diluted with EtOAc. The obtained solution was washed with brine, dried over $Na_2SO_4$, and the solvent evaporated. Crude product was purified by chromatography on silica gel using Biotage Isolera™ apparatus to give the sub-title compound (15 mg, 68%). LCMS calc. for $C_{26}H_{32}N_5O_3S$ $(M+H)^+$ m/z=494.2. found 494.2.

Step 2. (S)-N-(4-(3-Aminopiperidin-1-yl)pyridin-3-yl)-3-cyclopropylthieno[3,2-b]pyridine-5-carboxamide (S)-tert-Butyl 1-(3-(3-cyclopropylthieno[3,2-b]pyridine-5-carboxamido)pyridin-4-yl)piperidin-3-ylcarbamate (15 mg, 0.026 mmol) was dissolved in DCM (1.0 mL). TFA (1.1 mL, 14 mmol) was added and the reaction mixture was stirred at 40° C. for 1 h. The mixture was then neutralized by addition of $NH_3$ solution and purified by RP-HPLC (water XBridge™ C18 column, 30 mm×100 mm, 5 nm particle size, eluting with a gradient of MeCN/water containing 0.1% $NH_4OH$, at flow rate of 60 mL/min) LCMS calc. for $C_{21}H_{24}N_5OS$ $(M+H)^+$ m/z=394.2. found 394.1.

Example 68

N-{4-[(1R,3S,5S)-3-Amino-5-methylcyclohexyl]pyridin-3-yl}-3-isopropylfuro[3,2-b]pyridine-5-carboxamide

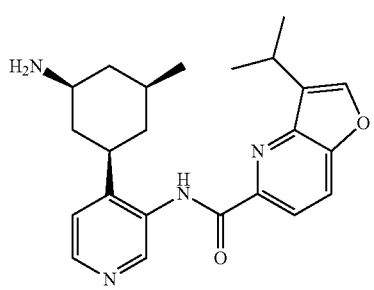 [SMILES: CC(C)c1coc2ccc(C(=O)Nc3cnccc3[C@@H]3C[C@H](C)C[C@H](N)C3)nc12]

Step 1. tert-Butyl [(1S,3R,5S)-3-(3-{[(3-bromofuro[3,2-b]pyridin-5-yl)carbonyl]amino}pyridin-4-yl)-5-methylcyclohexyl]carbamate

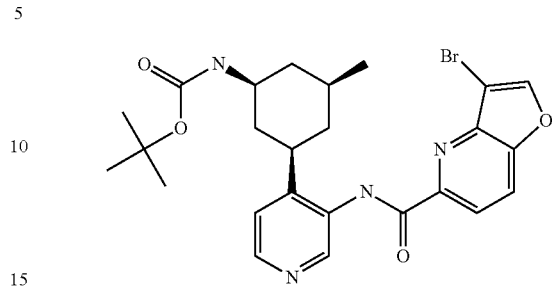

To a solution of 3-bromofuro[3,2-b]pyridine-5-carboxylic acid (16.0 mg, 0.0661 mmol) and tert-butyl [(1S,3R,5S)-3-(3-aminopyridin-4-yl)-5-methylcyclohexyl]carbamate (20.2 mg, 0.0661 mmol) (peak 2 from last step) in DMF (0.5 mL) was added HATU (36.6 mg, 0.0962 mmol) and DIPEA (39 µL, 0.22 mmol) and the reaction mixture was stirred at room temperature overnight. The reaction mixture was then diluted with water, and the aqueous layer was extracted with DCM. The combined organic layers were dried over $Na_2SO_4$, filtered, and concentrated. The residue was purified by flash chromatography (0-100% EtOAc/hexanes) to give the sub-title product. LCMS calc. for $C_{25}H_{30}BrN_4O_4$ $(M+H)^+$: m/z=529.1, 531.1. Found: 529.1, 531.1.

Step 2. tert-Butyl [(1S,3R,5S)-3-(3-{[(3-isopropylfuro[3,2-b]pyridin-5-yl)carbonyl]amino}pyridin-4-yl)-5-methylcyclohexyl]carbamate

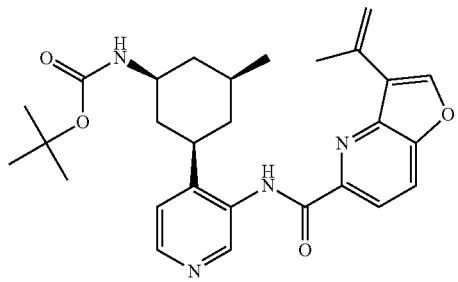 [SMILES: C=C(C)c1coc2ccc(C(=O)Nc3cnccc3[C@@H]3C[C@H](C)C[C@H](NC(=O)OC(C)(C)C)C3)nc12]

A mature of tert-butyl [(1S,3R,5S)-3-(3-{[(3-bromofuro[3,2-b]pyridin-5-yl)carbonyl]amino}pyridin-4-yl)-5-methylcyclohexyl]carbamate (22.0 mg, 0.0416 mmol), 2-isopropenyl-4,4,5,5-tetramethyl-1,3,2-dioxaborolane (11.2 µL, 0.0665 mmol), dicyclohexyl(2',4',6'-triisopropylbiphenyl-2-yl)phosphine-(2'-aminobiphenyl-2-yl)(chloro)palladium (1:1) (2.9 mg, 0.0037 mmol) and $K_3PO_4.H_2O$ (21.1 mg, 0.0915 mmol) in 1,4-dioxane (0.45 mL) and water (0.15 mL) was stirred at 80° C. for 1.5 h. The mixture was diluted with MeOH and purified by preparative LCMS (XBridge™ C18 column, eluting with a gradient of MeCN/water containing 0.05% TFA, at flow rate of 60 mL/min) to give the sub-title product (5.2 mg, 25%). LCMS calc. for $C_{24}H_{35}N_4O_4$ $(M+H)^+$: m/z=491.3. Found: 491.4.

Step 3. N-{4-[(1R,3S,5S)-3-Amino-5-methylcyclohexyl]pyridin-3-yl}-3-isopropylfuro[3,2-b]pyridine-5-carboxamide To a solution of tert-butyl [(1S,3R,5S)-3-(3-{[(3-isopropylfuro[3,2-b]pyridin-5-yl)carbonyl]amino}pyridin-4-yl)-5- methylcyclohexyl]carbamate (5.2 mg, 0.0106 mmol) in MeOH (1 mL) was added 10% Pd on carbon (4 mg). The resulting suspension was stirred under a $H_2$ balloon for 1 h. The reaction mixture was then filtered through a pad of diatomaceous earth and washed with MeOH. The filtrate was concentrated and the residue was treated with 1:1 TFA/DCM (1 mL) for 1 h. The volatiles were removed under reduced pressure and the residue was dissolved in MeOH and purified by preparative LCMS (XBridge™ C18 column, eluting with a gradient of MeCN/water containing 0.1% $NH_4OH$, at flow rate of 60 mL/min) to give the title product (1.6 mg, 31%) as a white solid. LCMS calc. for $C_{23}H_{29}N_4O_2$ $(M+H)^+$: m/z=393.2. Found: 393.1.

N-{4-[(1S,3R,5R)-3-Amino-5-methylcyclohexyl]pyridin-3-yl}-3-isopropylfuro[3,2-b]pyridine-5-carboxamide is prepared by an analogous method starting from 4-tert-butyl [(1R,3S,5R)-3-(3-aminopyridin-4-yl)-5-methylcyclohexyl] carbamate.

Example 69

N-{4-[(3R,4R,5S)-3-Amino-4-hydroxy-5-methylpiperidin-1-yl]pyridin-3-yl}-2-cyclopropylfuro[2,3-b]pyridine-6-carboxamide

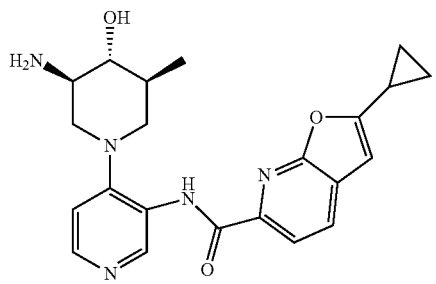 [SMILES: C[C@H]1CN(c2ccncc2NC(=O)c2ccc3cc(C4CC4)oc3n2)C[C@@H](N)[C@@H]1O]

Step 1. Methyl 2-cyclopropylfuro[2,3-b]pyridine-6-carboxylate

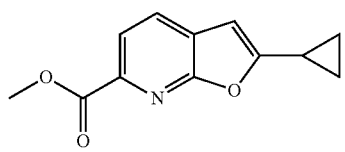 [SMILES: COC(=O)c1ccc2cc(C3CC3)oc2n1]

Methyl 5-bromo-6-hydroxypyridine-2-carboxylate (Ark Pharm, 773 mg, 3.33 mmol), copper(I) iodide (44 mg, 0.23 mmol) and dichloro[bis(triphenylphosphonio)]palladate (140 mg, 0.20 mmol) were placed in a vial. The vial was then evacuated and backfilled with nitrogen three times. After this 1,4-dioxane (14 mL) and triethylamine (696 μL, 5.00 mmol) were added. The reaction mixture was stirred for 5 min, then ethynylcyclopropane (338 μL, 4.00 mmol) was added and the resulting reaction mixture was stirred at 60° C. for 3 h. After this time the reaction was quenched with water and product extracted with EtOAc. The combined organic extracts were washed with brine, dried with $Na_2SO_4$ and solvent was evaporated under reduced pressure. The crude product was purified by chromatography on silica gel using Biotage Isolera™ apparatus to give the sub-title compound (560 mg, 77%). LCMS calc. for $C_{12}H_{12}NO_3$ $(M+H)^+$ m/z=218.1. found: 218.1.

Step 2.
2-Cyclopropylfuro[2,3-b]pyridine-6-carboxylic acid

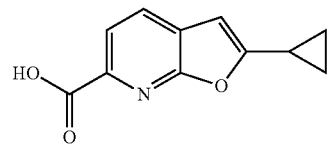 [SMILES: O=C(O)c1ccc2cc(C3CC3)oc2n1]

To a mixture of methyl 2-cyclopropylfuro[2,3-b]pyridine-6-carboxylate (558 mg, 2.57 mmol) in THF (30 mL) was added MeOH (20 mL) and 1.0 M solution of aq. NaOH (10 mL, 10 mmol). The reaction mixture was stirred at room temperature for 30 min. After this time pH was adjusted to 5 by addition of the 1M solution of HCl. Product was then extracted with EtOAc and organic phase was washed with brine and dried with $Na_2SO_4$. Solvent was evaporated under reduced pressure. The crude solid product was used in the next step without further purification (460 mg, 88%). LCMS calc. for $C_{11}H_{10}NO_3$ $(M+H)^+$ m/z=204.1. found: 204.1.

Step 3. tert-Butyl [(3R,4R,5S)-4-{[tert-butyl(dimethyl)silyl]oxy}-1-(3-{[(2-cyclopropylfuro[2,3-b]pyridin-6-yl)carbonyl]amino}pyridin-4-yl)-5-methylpiperidin-3-yl]carbamate

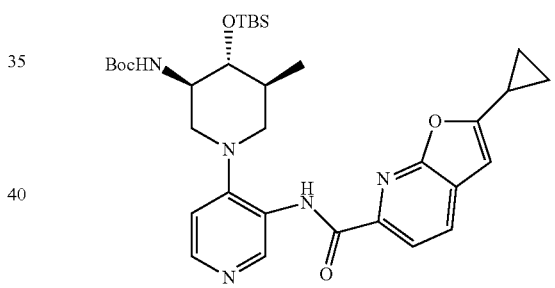

tert-Butyl ((3R,4R,5S)-1-(3-aminopyridin-4-yl)-4-{[tert-butyl(dimethyl)silyl]oxy}-5-methylpiperidin-3-yl)carbamate (Intermediate 2; 900.0 mg, 2.061 mmol) and 2-cyclopropylfuro[2,3-b]pyridine-6-carboxylic acid (460 mg, 2.3 mmol) were dissolved in DMF (36 mL), then DIPEA (540 μL, 3.1 mmol) and HATU (862 mg, 2.27 mmol) were added and the resulting reaction mixture was stirred at 40° C. for 2 h. After full conversion of the starting material was observed by LCMS, water was added and the resulting precipitate was collected by filtration. The precipitate was then redissolved in EtOAc. The solution obtained was washed with brine and dried with $Na_2SO_4$. Evaporation of the solvent gave the sub-title compound which was used in the next step without further purification (1.25 g, 98%). LCMS calc. for $C_{33}H_{48}N_5O_5Si$ $(M+H)^+$ m/z=622.3. found: 622.3.

Step 4. N-{4-[(3R,4R,5S)-3-Amino-4-hydroxy-5-methylpiperidin-1-yl]pyridin-3-yl}-2-cyclopropylfuro[2,3-b]pyridine-6-carboxamide To a mixture of tert-butyl [(3R,4R,5S)-4-{[tert-butyl(dimethyl)silyl]oxy}-1-(3-{[(2-cyclopropylfuro[2,3-b]pyridin- 6-yl)carbonyl]amino}pyridin-4-yl)-5-methylpiperidin-3-yl] carbamate (1.28 g, 2.06 mmol) in MeOH (10 mL) was added 4.0 M solution of HCl in dioxane (20 mL, 80 mmol). The reaction mixture was stirred at room temperature overnight. Then it was neutralized by addition of the ammonia solution and purified by RP-HPLC (Waters XBridge™ C18 column, 30 mm×100 mm, 5 μm particle size, eluting with a gradient of MeCN/water containing 0.1% NH$_4$OH, at flow rate of 60 mL/min) to give the title compound. LCMS calc. for C$_{22}$H$_{26}$N$_5$O$_3$ (M+H)$^+$ m/z=408.2. found: 408.2. $^1$H NMR (500 MHz, DMSO-d$_6$) δ 10.09 (s, 1H), 9.23 (s, 1H), 8.23 (d, J=5.3 Hz, 1H), 8.17 (d, J=7.9 Hz, 1H), 8.09 (d, J=7.9 Hz, 1H), 7.10 (d, J=5.4 Hz, 1H), 6.83 (s, 1H), 4.86 (d, J=5.1 Hz, 1H), 3.27-3.16 (m, 2H), 2.88 (td, J=10.5, 4.6 Hz, 1H), 2.74 (td, J=9.4 and 4.9 Hz, 1H), 2.52 (t, J=11.3 Hz, 1H), 2.45 (t, J=11.7 Hz, 1H), 2.30-2.19 (m, 1H), 2.03-1.88 (m, 1H), 1.65-1.51 (m, 2H), 1.13 (dd, J=8.4 and 3.5 Hz, 2H), 1.04 (dd, J=7.7 and 4.6 Hz, 2H), 0.88 (d, J=6.6 Hz, 3H) ppm.

Example 70

N-{4-[(3S,5R)-3-Amino-5-methylpiperidin-1-yl]pyridin-3-yl}-2-cyclopropylfuro[2,3-b]pyridine-6-carboxamide

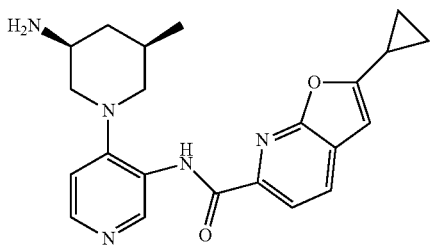 [SMILES: C[C@@H]1C[C@H](N)CN(c2ccncc2NC(=O)c2ccc3cc(C4CC4)oc3n2)C1]

Step 1. tert-Butyl [(3S,5R)-1-(3-{[(2-cyclopropyl-furo[2,3-b]pyridin-6-yl)carbonyl]amino}pyridin-4-yl)-5-methylpiperidin-3-yl]carbamate

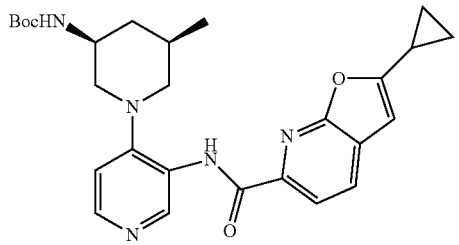 [SMILES: C[C@@H]1C[C@H](NC(=O)OC(C)(C)C)CN(c2ccncc2NC(=O)c2ccc3cc(C4CC4)oc3n2)C1]

tert-Butyl [(3S,5R)-1-(3-aminopyridin-4-yl)-5-methylpiperidin-3-yl]carbamate (Intermediate 1; 250 mg, 0.82 mmol) and 2-cyclopropylfuro[2,3-b]pyridine-6-carboxylic acid (180 mg, 0.886 mmol) were dissolved in DMF (14 mL), and then DIPEA (430 μL, 2.5 mmol) and HATU (780 mg, 2.0 mmol) were added and the resulting reaction mixture was stirred at 40° C. for 2 h. After full conversion of the starting material was observed by LCMS, water was added and the obtained precipitate was collected by filtration. The precipitate was then redissolved in EtOAc. The resulting solution was washed with brine and dried with Na$_2$SO$_4$. Evaporation of the solvent gave the sub-title compound which was used in the next step without further purification (372 mg, 93%). LCMS calc. for C$_{22}$H$_{34}$N$_5$O$_4$ (M+H)$^+$ m/z=492.3. found: 492.2.

Step 2. N-{4-[(3S,5R)-3-Amino-5-methylpiperidin-1-yl]pyridin-3-yl}-2-cyclopropylfuro[2,3-b]pyridine-6-carboxamide To a mixture of tert-butyl [(3S,5R)-1-(3-{[(2-cyclopropylfuro[2,3-b]pyridin-6-yl)carbonyl]amino}pyridin-4-yl)-5-methylpiperidin-3-yl]carbamate (372 mg, 0.76 mmol) in MeOH (5 mL) was added 4.0 M solution of HCl in dioxane (10 mL, 40 mmol). The reaction mixture was stirred at room temperature overnight. Then it was neutralized by addition of the ammonia solution and purified by RP-HPLC (Waters XBridge™ C18 column, 30 mm×100 mm, 5 μm particle size, eluting with a gradient of MeCN/water containing 0.1% NH$_4$OH, at flow rate of 60 mL/min) to give the title compound. LCMS calc. for C$_{22}$H$_{26}$N$_5$O$_2$ (M+H)$^+$ m/z=392.2. found: 392.2.

Example 71 and 72

N-(4-((3R,4R,5S)-3-Amino-4-hydroxy-5-methylpiperidin-1-yl)pyridin-3-yl)-2-((1R,2R)-2-phenylcyclopropyl)furo[2,3-b]pyridine-6-carboxamide and N-(4-((3R,4R,5S)-3-Amino-4-hydroxy-5-methylpiperidin-1-yl)pyridin-3-yl)-2-((1S,2S)-2-phenylcyclopropyl)furo[2,3-b]pyridine-6-carboxamide

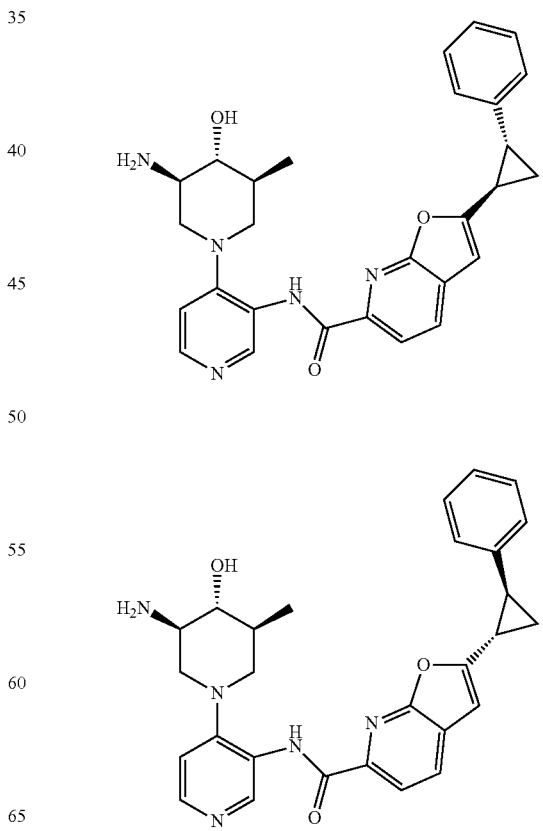

Step 1. trans-(2-Phenylcyclopropyl)methanol

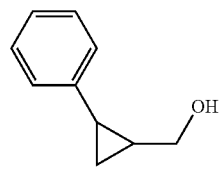 [SMILES: OCC1CC1c1ccccc1]

To a solution of trans-2-phenyl-1-cyclopropanecarboxylic acid (J&W Pharmlab, 1.06 g, 6.54 mmol) and triethylamine (0.956 mL, 6.86 mmol) in THF (20 mL) was slowly added isobutyl chloroformate (0.89 mL, 6.86 mmol). The reaction mixture was stirred at room temperature for 1 h. Then the formed solids were filtered off and to the resulting clear solution was slowly added solution of sodium tetrahydroborate (490 mg, 13 mmol) in water (4 mL). The reaction mixture was stirred at room temperature for 30 min. Then the reaction was quenched with water and the solution was extracted with EtOAc. The combined organic fractions were washed with brine and dried over $Na_2SO_4$. After evaporation of solvent under reduced pressure, the sub-title compound obtained was used in the next step without further purification (960 mg, 99%).

Step 2. trans-2-Phenylcyclopropanecarbaldehyde

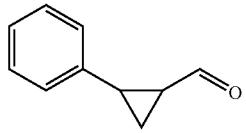 [SMILES: O=CC1CC1c1ccccc1]

To a stirred solution of trans-(2-phenylcyclopropyl)methanol (960 mg, 6.47 mmol) in methylene chloride (45 mL) at 0° C. were added pyridine (625 µL, 7.8 mmol) and Dess-Martin periodinane (2.88 g, 6.8 mmol). The reaction mixture was stirred at room temperature for 3 h. Then saturated solutions of $NaHCO_3$ in water (40 mL) and $Na_2S_2O_3$ in water (20 mL) were added and the resulting reaction mixture was stirred for 30 min. Then the solution was was extracted with DCM. The combined organic fractions were washed with brine, dried with $Na_2SO_4$ and solvent was evaporated under reduced pressure. The crude product was purified by chromatography on silica gel using Biotage Isolera™ apparatus to give the sub-title compound (870 mg, 92%). LCMS calc. for $C_{10}H_{11}O$ $(M+H)^+$ m/z=147.1. found: 147.2.

Step 3. trans-(2-Ethynylcyclopropyl)benzene

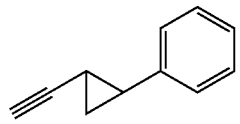

trans-2-Phenylcyclopropanecarbaldehyde (870 mg, 6.0 mmol) was dissolved in MeOH (35 mL) and potassium carbonate (1.03 g, 7.44 mmol) was added, followed by dimethyl (1-diazo-2-oxopropyl)phosphonate (1.10 g, 6.0 mmol) slowly. The reaction mixture was stirred overnight at room temperature. After this time reaction was diluted with water and product was extracted with EtOAc. Combined organic fractions were washed with brine, dried with $Na_2SO_4$ and solvent was evaporated under reduced pressure. The crude product was purified by chromatography on silica gel using Biotage Isolera™ apparatus to give the sub-title compound (690 mg, 81%).

Step 4. Methyl 2-((1R,2R)-2-phenylcyclopropyl)furo[2,3-b]pyridine-6-carboxylate and methyl 2-((1S,2S)-2-phenylcyclopropyl)furo[2,3-b]pyridine-6-carboxylate

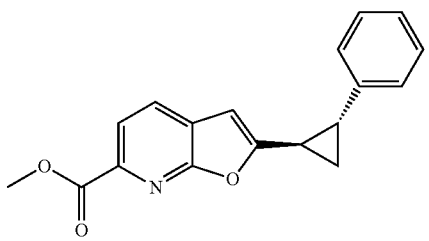

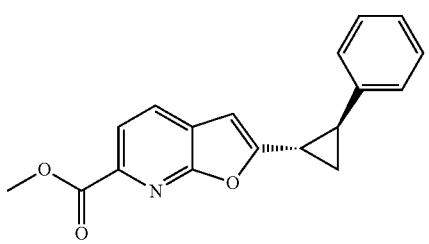

Methyl 5-bromo-6-hydroxypyridine-2-carboxylate (Ark Pharm, 254 mg, 1.1 mmol), copper(I) iodide (14 mg, 0.077 mmol) and dichloro[bis(triphenylphosphonio)]palladate (46 mg, 0.066 mmol) were placed in a vial. The vial was then evacuated and backfilled with nitrogen three times. After this, 1,4-dioxane (6 mL) and triethylamine (229 µL, 1.64 mmol) were added. The reaction mixture was stirred for 5 min. Then trans-(2-ethynylcyclopropyl)benzene (187 mg, 1.31 mmol) was added and the reaction mixture was stirred at 60° C. for 3 h. After this time the reaction was quenched with water and product was extracted with EtOAc. The combined organic extracts were washed with brine, dried with $Na_2SO_4$ and solvent was evaporated under reduced pressure. The crude product was purified by chromatography on silica gel using Biotage Isolera™ apparatus to give the sub-title compound as a mixture of both enantiomers (320 mg, 99%). LCMS calc. for $C_{18}H_{16}NO_3$ $(M+H)^+$ m/z=294.1. found: 294.1. Two enantiomers were separated on chiral HPLC (Chiralcel AD-H column, 20 mm×250 mm, 5 µm particle size, eluting with a mobile phase containing 45% ethanol in hexane, at flow rate of 10 mL/min) First peak retention time 12.73 min; second peak retention time 27.00 min.

Step 5. 2-((1R,2R)-2-Phenylcyclopropyl)furo[2,3-b]pyridine-6-carboxylic acid and 2-((1S,2S)-2-Phenylcyclopropyl)furo[2,3-b]pyridine-6-carboxylic acid

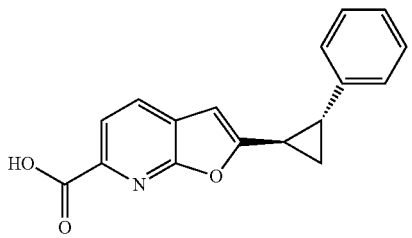

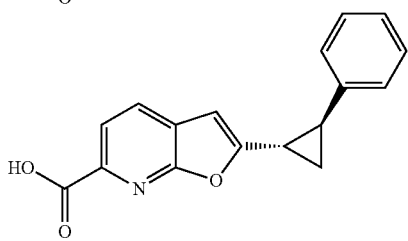

Each of enantiomers of methyl trans-2-(2-phenylcyclopropyl)furo[2,3-b]pyridine-6-carboxylate obtained in previous step was separately used in this reaction.

Methyl 2-(2-phenylcyclopropyl)furo[2,3-b]pyridine-6-carboxylate (122 mg, 0.416 mmol) was dissolved in THF (4 mL). Then MeOH (3 mL) and 1.0 M aq. NaOH (2 mL, 10 mmol) were added and the reaction mixture was stirred at room temperature for 30 min. After this time pH was adjusted to 5 by addition of 1 M aq. HCl. The solution was then extracted with EtOAc and the organic extract was washed with brine and dried with $Na_2SO_4$. Solvent was evaporated under reduced pressure. The solid product obtained was used in the next step without further purification (110 mg, 95%). LCMS calc. for $C_{17}H_{14}NO_3$ $(M+H)^+$ m/z=280.1. found: 280.1.

Step 6. tert-Butyl (3R,4R,5S)-4-(tert-Butyldimethylsilyloxy)-5-methyl-1-(3-(2-((1R,2R)-2-phenylcyclopropyl)furo[2,3-b]pyridine-6-carboxamido)pyridin-4-yl)piperidin-3-ylcarbamate and tert-Butyl (3R,4R,5S)-4-(tert-butyldimethylsilyloxy)-5-methyl-1-(3-(2-((1S,2S)-2-phenylcyclopropyl)furo[2,3-b]pyridine-6-carboxamido)pyridin-4-yl)piperidin-3-ylcarbamate

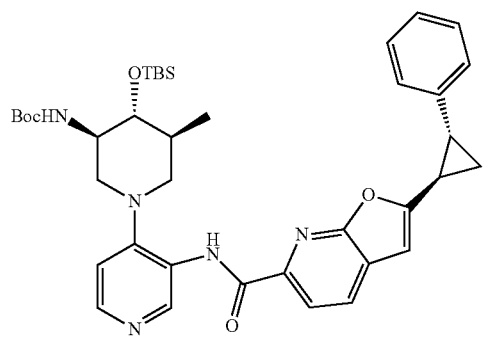

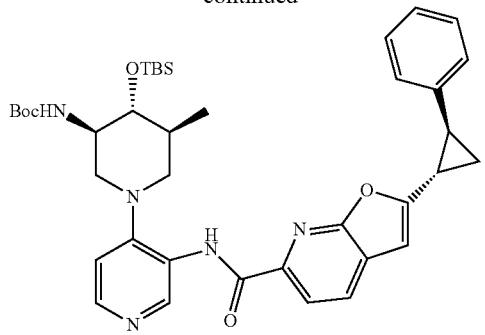

Each of enantiomers of 2-(2-phenylcyclopropyl)furo[2,3-b]pyridine-6-carboxylic acid obtained in previous step was separately used in this reaction.

tert-Butyl ((3R,4R,5S)-1-(3-aminopyridin-4-yl)-4-{[tert-butyl(dimethyl)silyl]oxy}-5-methylpiperidin-3-yl)carbamate (Intermediate 2; 20 mg, 0.046 mmol) and 2-(2-phenylcyclopropyl)furo[2,3-b]pyridine-6-carboxylic acid (13.8 mg, 0.0495 mmol) were dissolved in DMF (2 mL). Then DIPEA (24 µL, 0.14 mmol) and HATU (44 mg, 0.11 mmol) were added and the reaction mixture was stirred at 40° C. for 2 h. After full conversion was achieved, the reaction mixture was quenched with saturated aq. $NaHCO_3$ and the product was extracted with EtOAc. The combined organic fractions were washed with brine and dried with $Na_2SO_4$. After solvent was evaporated, the crude product was used in the next step without further purification. LCMS calc. for $C_{39}H_{52}N_5O_5Si$ $(M+H)^+$ m/z=698.4. found: 698.4.

Step 7. N-(4-((3R,4R,5S)-3-Amino-4-hydroxy-5-methylpiperidin-1-yl)pyridin-3-yl)-2-((1R,2R)-2-phenylcyclopropyl)furo[2,3-b]pyridine-6-carboxamide and N-(4-((3R,4R,5S)-3-Amino-4-hydroxy-5-methylpiperidin-1-yl)pyridin-3-yl)-2-((1S,2S)-2-phenylcyclopropyl)furo[2,3-b]pyridine-6-carboxamide Each of isomers of tert-butyl {4-{[tert-butyl(dimethyl)silyl]oxy}-5-methyl-1-[3-({[2-(2-phenylcyclopropyl)furo[2,3-b]pyridin-6-yl]carbonyl}amino)pyridin-4-yl]piperidin-3-yl}carbamate obtained in previous step was separately used in this reaction. Using the diastereoisomer derived from the first peak in Step 4 gave Example 71. Using the diastereoisomer derived from the second peak in Step 4 gave Example 72.

To a mixture of tert-butyl {(3R,4R,5S)-4-{[tert-butyl(dimethyl)silyl]oxy}-5-methyl-1-[3-({[2-(2-phenylcyclopropyl)furo[2,3-b]pyridin-6-yl]carbonyl}amino)pyridin-4-yl]piperidin-3-yl}carbamate (32 mg, 0.047 mmol) in MeOH (2 mL) was added 4.0 M solution of HCl in dioxane (1 mL, 4 mmol). The reaction mixture was stirred at room temperature overnight. Then it was neutralized by the addition of the ammonia solution and purified by RP-HPLC (Waters XBridge™ C18 column, 30 mm×100 mm, 5 µm particle size, eluting with a gradient of MeCN/water containing 0.1% $NH_4OH$, at flow rate of 60 mL/min) to give the sub-title compound. LCMS calc. for $C_{28}H_{30}N_5O_3$ $(M+H)^+$ m/z=484.2. found: 484.2. $^1H$ NMR (400 MHz, DMSO-$d_6$, for diastereomer from 1st peak of step 4, Example 71) δ 10.15 (s, 1H), 9.25 (s, 1H), 8.28-8.23 (m, 1H), 8.22 (s, 1H), 8.13 (d, J=7.9 Hz, 1H), 7.36-7.30 (m, 2H), 7.30-7.19 (m, 3H), 7.12 (d, J=5.4 Hz, 1H), 6.95 (s, 1H), 4.90 (d, J=5.2 Hz, 1H), 3.25 (d, J=15.2 Hz, 2H), 2.99-2.87 (m, 1H), 2.82-2.74 (m, 1H), 2.68-2.55 (m, 2H), 2.06-1.91 (m, 1H), 1.85-1.76 (m, 1H), 1.69 (dt, J=8.8 and 5.6 Hz, 2H), 1.66-1.54 (m, 2H), 0.91 (d, J=6.5 Hz, 3H) ppm.

Example 73 and 74

N-{4-[(3R,4R,5S)-3-Amino-4-hydroxy-5-methylpiperidin-1-yl]pyridin-3-yl}-2-(cis-2-methylcyclopropyl)furo[2,3-b]pyridine-6-carboxamide (Example 73) and N-{4-[(3R,4R,5S)-3-Amino-4-hydroxy-5-methylpiperidin-1-yl]pyridin-3-yl}-2-(trans-2-methylcyclopropyl)furo[2,3-b]pyridine-6-carboxamide (Example 74)

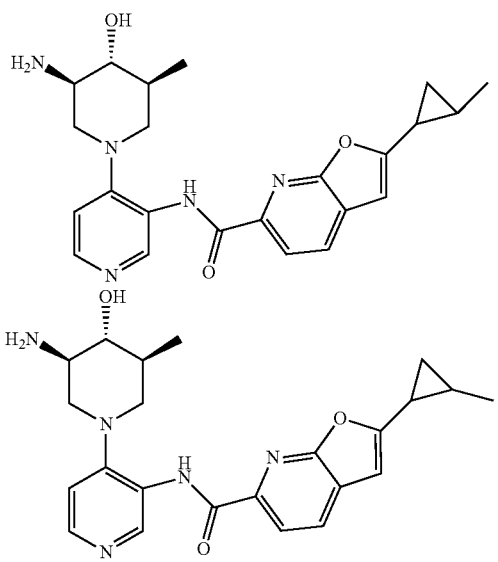

Step 1. 1-Ethynyl-2-methylcyclopropane

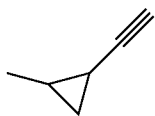

2-Methylcyclopropanecarbaldehyde (from Enamine [contains 25% cis and 75% trans isomer], 180 mg, 2.1 mmol) was dissolved in MeOH (12 mL) and potassium carbonate (370 mg, 2.67 mmol) was added. Then dimethyl (1-diazo-2-oxopropyl)phosphonate (410 mg, 2.1 mmol) was slowly added and the reaction mixture was stirred overnight at room temperature The resulting solids were then filtered-off and a solution of 1-ethynyl-2-methylcyclopropane in MeOH was used in the next step without any further work-up or purification.

Step 2. Methyl 2-(2-methylcyclopropyl)furo[2,3-b]pyridine-6-carboxylate

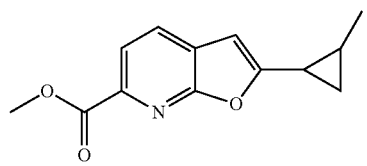

Methyl 5-bromo-6-hydroxypyridine-2-carboxylate (Ark Pharm, 169 mg, 0.7 mmol), copper(I) iodide (9.7 mg, 0.051 mmol) and dichloro[bis(triphenylphosphonio)]palladate (31 mg, 0.044 mmol) were placed in a vial. The vial was then evacuated and backfilled with nitrogen three times. After this 1,4-dioxane (4 mL) and triethylamine (152 µL, 1.09 mmol) were added. The resulting reaction mixture was stirred for 5 min. Then the solution of 1-ethynyl-2-methylcyclopropane in MeOH from the previous step was degassed and added to the reaction mixture. Then the reaction was stirred at 60° C. for 3 h. After this time the reaction was quenched with water and the product was extracted with EtOAc. The combined organic fractions were washed with brine, dried with Na$_2$SO$_4$ and then the solvent was evaporated under reduced pressure. The crude product was purified by chromatography on silica gel using Biotage Isolera™ apparatus to give the sub-title compound (129 mg, 77%). LCMS calc. for C$_{13}$H$_{14}$NO$_3$ (M+H)$^+$ m/z=232.1. found: 232.2.

Step 3. 2-(2-Methylcyclopropyl)furo[2,3-b]pyridine-6-carboxylic acid

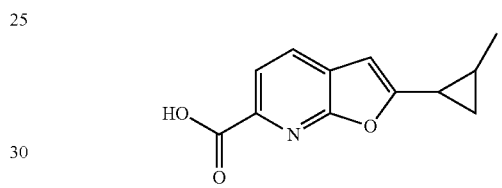

To a mixture of methyl 2-(2-methylcyclopropyl)furo[2,3-b]pyridine-6-carboxylate (129 mg, 0.558 mmol) in THF (6 mL) was added MeOH (6 mL) and 1.0M aq. NaOH (2.2 mL, 10 mmol). The reaction mixture was stirred at room temperature for 30 min. After this time pH was adjusted to 5 by addition of the 1M solution of HCl. The solution was then extracted with EtOAc and the organic phase was washed with brine and dried with Na$_2$SO$_4$. The solvent was evaporated under reduced pressure. The solid product obtained was used in the next step without further purification (115 mg, 95%). LCMS calc. for C$_{12}$H$_{12}$NO$_3$ (M+H)$^+$ m/z=218.1. found: 218.1.

Step 4. tert-Butyl {(3R,4R,5S)-4-{[tert-Butyl(dimethyl)silyl]oxy}-5-methyl-1-[3-({[2-(2-methylcyclopropyl)furo[2,3-b]pyridin-6-yl]carbonyl}amino)pyridin-4-yl]piperidin-3-yl}carbamate

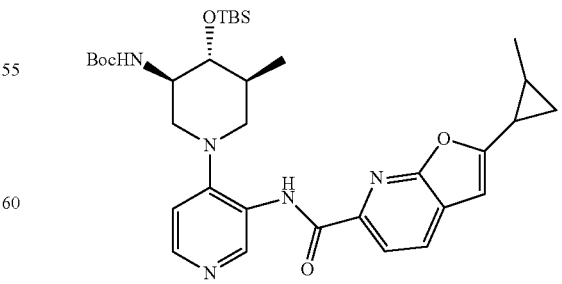

To a mixture of tert-butyl ((3R,4R,5S)-1-(3-aminopyridin-4-yl)-4-{[tert-butyl(dimethyl)silyl]oxy}-5-methylpiperidin-3-yl)carbamate (Intermediate 2; 20 mg, 0.046 mmol)

and 2-(2-methylcyclopropyl)furo[2,3-b]pyridine-6-carboxylic acid (10.7 mg, 0.0495 mmol) in DMF (2 mL) was added DIPEA (24 µL, 0.14 mmol) and HATU (44 mg, 0.11 mmol). The reaction was stirred at 40° C. for 2 h. After full conversion of the starting materials was achieved as determined by LCMS, the reaction mixture was quenched with saturated solution of NaHCO$_3$ and product was extracted with EtOAc. The combined organic extracts were washed with brine and dried with Na$_2$SO$_4$. After solvent was evaporated, the crude product was used in the next step without further purification. LCMS calc. for C$_{34}$H$_{50}$N$_5$O$_5$Si (M+H)$^+$ m/z=636.4. found: 636.3.

Step 5. N-{4-[(3R,4R,5S)-3-Amino-4-hydroxy-5-methylpiperidin-1-yl]pyridin-3-yl}-2-(cis-2-methylcyclopropyl)furo[2,3-b]pyridine-6-carboxamide and N-{4-[(3R,4R,5S)-3-Amino-4-hydroxy-5-methylpiperidin-1-yl]pyridin-3-yl}-2-(trans-2-methylcyclopropyl)furo[2,3-b]pyridine-6-carboxamide To a mixture of tert-butyl {(3R,4R,5S)-4-{[tert-butyl(dimethyl)silyl]oxy}-5-methyl-1-[3-({[2-(2-methylcyclopropyl)furo[2,3-b]pyridin-6-yl]carbonyl}amino)pyridin-4-yl]piperidin-3-yl}carbamate (30 mg, 0.047 mmol) in MeOH (2 mL) was added 4.0 M solution of HCl in dioxane (1 mL, 4 mmol). The reaction mixture was stirred at room temperature overnight. Then it was neutralized by addition of ammonia solution and the products were purified and separated by RP-HPLC (Waters XBridge™ C18 column, 30 mm×100 mm, 5 µm particle size, eluting with a gradient of MeCN/water containing 0.1% NH$_4$OH, at flow rate of 60 mL/min) One of the compounds contains a mixture of 2 diastereomers with trans geometry at cyclopropyl ring (Example 74, RP-HPLC retention time 8.95 min), another compound contains a mixture of 2 diastereomers with cis geometry at cyclopropyl ring (Example 73, RP-HPLC retention time 8.22 min) LCMS calc. for C$_{23}$H$_{28}$N$_5$O$_3$ (M+H)$^+$ m/z=422.2. found: 422.3. $^1$H NMR (400 MHz, DMSO-d$_6$, for trans isomer) δ 10.10 (s, 1H), 9.24 (s, 1H), 8.24 (d, J=5.4 Hz, 1H), 8.17 (d, J=7.9 Hz, 1H), 8.10 (d, J=7.9 Hz, 1H), 7.11 (d, J=5.4 Hz, 1H), 6.81 (s, 1H), 4.89 (d, J=5.0 Hz, 1H), 3.24 (d, J=15.2 Hz, 2H), 2.95-2.83 (m, 1H), 2.84-2.72 (m, 1H), 2.48-2.39 (m, 2H), 2.05-1.89 (m, 1H), 1.60 (br, 2H), 1.53-1.38 (m, 1H), 1.31-1.23 (m, 1H), 1.21 (d, J=6.0 Hz, 3H), 1.03-0.93 (m, 1H), 0.90 (d, J=6.5 Hz, 3H) ppm.

N-{4-[(3R,4R,5S)-3-Amino-4-hydroxy-5-methylpiperidin-1-yl]pyridin-3-yl}-2-(cis-2-methylcyclopropyl)furo[2,3-b]pyridine-6-carboxamide includes N-{4-[(3R,4R,5S)-3-amino-4-hydroxy-5-methylpiperidin-1-yl]pyridin-3-yl}-2-((1R,2S)-2-methylcyclopropyl)furo[2,3-b]pyridine-6-carboxamide and N-{4-[(3R,4R,5S)-3-amino-4-hydroxy-5-methylpiperidin-1-yl]pyridin-3-yl}-2-((1S,2R)-2-methylcyclopropyl)furo[2,3-b]pyridine-6-carboxamide.

N-{4-[(3R,4R,5S)-3-Amino-4-hydroxy-5-methylpiperidin-1-yl]pyridin-3-yl}-2-(trans-2-methylcyclopropyl)furo[2,3-b]pyridine-6-carboxamide includes N-{4-[(3R,4R,5S)-3-amino-4-hydroxy-5-methylpiperidin-1-yl]pyridin-3-yl}-2-((1R,2R)-2-methylcyclopropyl)furo[2,3-b]pyridine-6-carboxamide and N-{4-[(3R,4R,5S)-3-amino-4-hydroxy-5-methylpiperidin-1-yl]pyridin-3-yl}-2-((1S,2S)-2-methylcyclopropyl)furo[2,3-b]pyridine-6-carboxamide.

Example 75 and 76

N-{4-[(3S,5R)-3-Amino-5-methylpiperidin-1-yl]pyridin-3-yl}-2-(cis-2-methylcyclopropyl)furo[2,3-b]pyridine-6-carboxamide (Example 75) and N-{4-[(3S,5R)-3-Amino-5-methylpiperidin-1-yl]pyridin-3-yl}-2-(trans-2-methylcyclopropyl)furo[2,3-b]pyridine-6-carboxamide (Example 76)

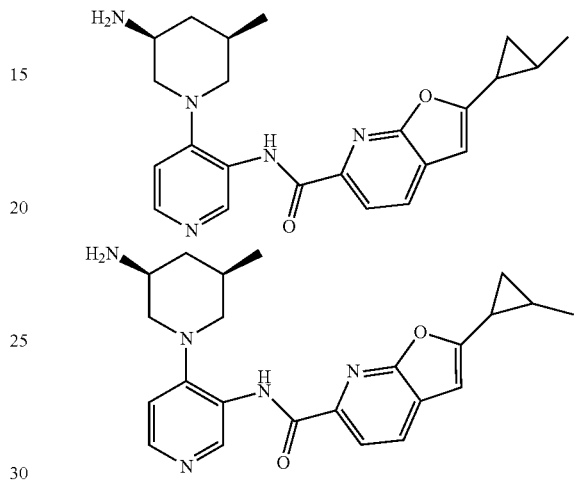

Step 1. tert-Butyl {(3S,5R)-5-methyl-1-[3-({[2-(2-methylcyclopropyl)furo[2,3-b]pyridin-6-yl]carbonyl}amino)pyridin-4-yl]piperidin-3-yl}carbamate

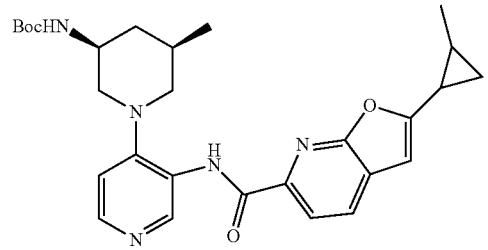 [SMILES: CC1CC1c1cc2ccc(C(=O)Nc3cnccc3N3C[C@H](C)C[C@H](NC(=O)OC(C)(C)C)C3)nc2o1]

To a mixture of tert-butyl [(3S,5R)-1-(3-aminopyridin-4-yl)-5-methylpiperidin-3-yl]carbamate (Intermediate 1; 14 mg, 0.046 mmol) and 2-(2-methylcyclopropyl)furo[2,3-b]pyridine-6-carboxylic acid (10.7 mg, 0.0495 mmol) in DMF (2 mL) was added DIPEA (24 µL, 0.14 mmol) and HATU (44 mg, 0.11 mmol). The reaction was stirred at 40° C. for 2 h. After full conversion of the starting material was achieved as determined by LCMS, the reaction mixture was quenched with saturated solution of NaHCO$_3$ and product extracted with EtOAc. The combined organic fractions were washed with brine and dried with Na$_2$SO$_4$. After solvent was evaporated, the crude product was used in the next step without further purification. LCMS calc. for C$_{28}$H$_{36}$N$_5$O$_4$ (M+H)$^+$ m/z=506.3. found: 506.2.

Step 2. N-{4-[(3S,5R)-3-amino-5-methylpiperidin-1-yl]pyridin-3-yl}-2-(cis-2-methylcyclopropyl)furo[2,3-b]pyridine-6-carboxamide and N-{4-[(3S,5R)-3-amino-5-methylpiperidin-1-yl]pyridin-3-yl}-2-(trans-2-methylcyclopropyl)furo[2,3-b]pyridine-6-carboxamide tert-Butyl {(3S,5R)-5-methyl-1-[3-({[2-(2-methylcyclopropyl)furo[2,3-b]pyridin-6-yl]carbonyl}amino)pyridin-4-yl]piperidin-3-yl}carbamate (23 mg, 0.046 mmol) was dissolved in MeOH (2 mL). Then 4.0 M solution of HCl in dioxane (1 mL, 4 mmol) was added. The reaction mixture was stirred at room temperature overnight. Then it was neutralized by addition of the ammonia solution and two compounds were purified and separated by RP-HPLC (Waters XBridge™ C18 column, 30 mm×100 mm, 5 µm particle size, eluting with a gradient of MeCN/water containing 0.1% NH₄OH, at flow rate of 60 mL/min) One of the compounds contains a mixture of 2 diastereomers with trans geometry at cyclopropyl ring (Example 76, RP-HPLC retention time 6.99 min), another compound contains a mixture of 2 diastereomers with cis geometry at cyclopropyl ring (Example 75, RP-HPLC retention time 6.49 min) LCMS calc. for $C_{23}H_{28}N_5O_2$ (M+H)⁺ m/z=406.2. found: 406.3. ¹H NMR (400 MHz, DMSO-d₆, for trans isomer) δ 10.11 (s, 1H), 9.30 (d, J=1.7 Hz, 1H), 8.25 (d, J=5.3 Hz, 1H), 8.17 (d, J=7.9 Hz, 1H), 8.10 (d, J=7.9 Hz, 1H), 7.12 (d, J=5.4 Hz, 1H), 6.80 (s, 1H), 3.30-3.16 (m, 2H), 3.10-2.97 (m, 1H), 2.38-2.19 (m, 3H), 2.11 (s, 1H), 2.04-1.93 (m, 2H), 1.49-1.34 (m, 1H), 1.28-1.14 (m, 4H), 1.02-0.95 (m, 1H), 0.90-0.82 (m, 4H) ppm.

N-{4-[(3S,5R)-3-Amino-5-methylpiperidin-1-yl]pyridin-3-yl}-2-(cis-2-methylcyclopropyl)furo[2,3-b]pyridine-6-carboxamide includes N-{4-[(3S,5R)-3-Amino-5-methylpiperidin-1-yl]pyridin-3-yl}-2-((1R,2S)-2-methylcyclopropyl)furo[2,3-b]pyridine-6-carboxamide and N-{4-[(3S,5R)-3-Amino-5-methylpiperidin-1-yl]pyridin-3-yl}-2-((1S,2R)-2-methylcyclopropyl)furo[2,3-b]pyridine-6-carboxamide.

N-{4-[(3S,5R)-3-Amino-5-methylpiperidin-1-yl]pyridin-3-yl}-2-(trans-2-methylcyclopropyl)furo[2,3-b]pyridine-6-carboxamide includes N-{4-[(3S,5R)-3-Amino-5-methylpiperidin-1-yl]pyridin-3-yl}-2-((1R,2R)-2-methylcyclopropyl)furo[2,3-b]pyridine-6-carboxamide and N-{4-[(3S,5R)-3-Amino-5-methylpiperidin-1-yl]pyridin-3-yl}-2-((1S,2S)-2-methylcyclopropyl)furo[2,3-b]pyridine-6-carboxamide and Example 77

N-{4-[(3R,4R,5S)-3-Amino-4-hydroxy-5-methylpiperidin-1-yl]pyridin-3-yl}-1-cyclobutyl-1H-pyrrolo[2,3-b]pyridine-6-carboxamide

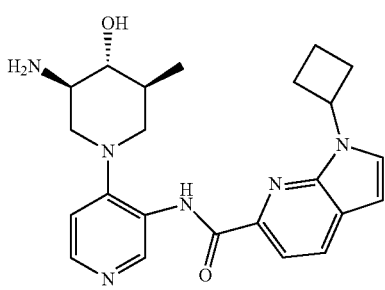 [SMILES: C[C@H]1CN(c2ccncc2NC(=O)c2ccc3ccn(C4CCC4)c3n2)C[C@@H](N)[C@@H]1O]

Step 1. Methyl 6-chloro-5-[(trimethylsilyl)ethynyl]pyridine-2-carboxylate

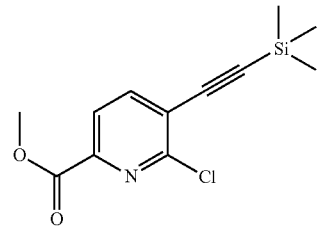 [SMILES: COC(=O)c1ccc(C#C[Si](C)(C)C)c(Cl)n1]

Methyl 5-bromo-6-chloropyridine-2-carboxylate (Ark Pharm, 360 mg, 1.4 mmol), copper(I) iodide (19 mg, 0.10 mmol) and dichloro[bis(triphenylphosphonio)]palladate (60 mg, 0.086 mmol) were placed in a vial. The vial was then evacuated and backfilled with nitrogen three times. After this 1,4-dioxane (6.2 mL) and triethylamine (300 µL, 2.16 mmol) were added. The reaction was stirred for 5 min. Then (trimethylsilyl)acetylene (244 µL, 1.72 mmol) was added and the resulting reaction mixture was stirred at 60° C. for 3 h. After this time the reaction was quenched with water and product was extracted with EtOAc. The combined organic fractions were washed with brine, dried with Na₂SO₄ and solvent was evaporated under reduced pressure. The crude product was purified by chromatography on silica gel using Biotage Isolera™ apparatus to give the sub-title compound (370 mg, 97%). LCMS calc. for $C_{12}H_{15}ClNO_2Si$ (M+H)⁺ m/z=268.1. found: 268.0.

Step 2. Methyl 1-cyclobutyl-2-(trimethylsilyl)-1H-pyrrolo[2,3-b]pyridine-6-carboxylate

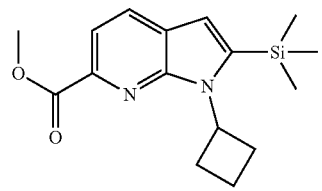 [SMILES: COC(=O)c1ccc2cc([Si](C)(C)C)n(C3CCC3)c2n1]

Methyl 6-chloro-5-[(trimethylsilyl)ethynyl]pyridine-2-carboxylate (156 mg, 0.582 mmol), cesium carbonate (660 mg, 2.0 mmol) and chloro(2-dicyclohexylphosphino-2',6'-diisopropoxy-1,1'-biphenyl)[2-(2'-amino-1,1'-biphenyl)]palladium (24 mg, 0.03 mmol) were placed in a vial. The vial was then evacuated and backfilled with nitrogen three times. After this, 1,4-dioxane (3 mL) and cyclobutanamine (99 µL, 1.2 mmol) were added. The reaction mixture was stirred at 110° C. overnight. After this time the reaction was quenched with water and product extracted with EtOAc. The combined organic fractions were washed with brine, dried with Na₂SO₄ and solvent was evaporated under reduced pressure. The crude product was purified by chromatography on silica gel using Biotage Isolera™ apparatus to give the sub-title compound (30 mg, 17%). LCMS calc. for $C_{16}H_{23}N_2O_2Si$ (M+H)⁺ m/z=303.2. found: 303.1.

Step 3. 1-Cyclobutyl-1H-pyrrolo[2,3-b]pyridine-6-carboxylic acid

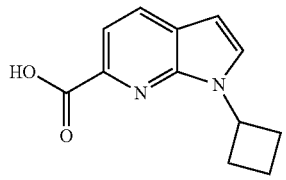 [SMILES: O=C(O)c1ccc2ccn(C3CCC3)c2n1]

To a mixture of methyl 1-cyclobutyl-2-(trimethylsilyl)-1H-pyrrolo[2,3-b]pyridine-6-carboxylate (30 mg, 0.1 mmol) in THF (1 mL) was added MeOH (0.7 mL) and 1.0 M aq. NaOH (0.40 mL, 0.40 mmol). The reaction mixture was stirred at room temperature for 30 min. After this time pH was adjusted to 5 by addition of the 1 M aq. HCl. The product was then extracted with EtOAc and organic phase was washed with brine and dried with $Na_2SO_4$. Solvent was evaporated under reduced pressure. The solid product obtained was used in the next step without further purification (21 mg, 98%). LCMS calc. for $C_{12}H_{13}N_2O_2$ $(M+H)^+$ m/z=217.1. found: 217.1.

Step 4. tert-Butyl [(3R,4R,5S)-4-{[tert-butyl(dimethyl)silyl]oxy}-1-(3-{[(1-cyclobutyl-1H-pyrrolo[2,3-b]pyridin-6-yl)carbonyl]amino}pyridin-4-yl)-5-methylpiperidin-3-yl]carbamate

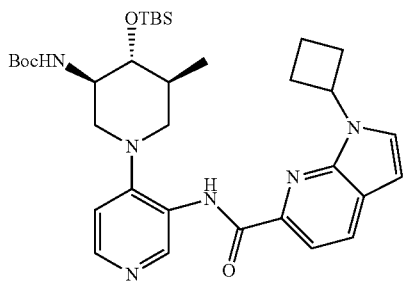 [SMILES: C[C@H]1CN(c2ccncc2NC(=O)c2ccc3ccn(C4CCC4)c3n2)C[C@@H](NC(=O)OC(C)(C)C)[C@@H]1O[Si](C)(C)C(C)(C)C]

tert-Butyl ((3R,4R,5S)-1-(3-aminopyridin-4-yl)-4-{[tert-butyl(dimethyl)silyl]oxy}-5-methylpiperidin-3-yl)carbamate (Intermediate 2; 20 mg, 0.046 mmol) and 1-cyclobutyl-1H-pyrrolo[2,3-b]pyridine-6-carboxylic acid (10.7 mg, 0.0495 mmol) were dissolved in DMF (2 mL). Then DIPEA (24 µL, 0.14 mmol) and HATU (44 mg, 0.11 mmol) were added and the reaction was stirred at 40° C. for 2 h. After full conversion of the starting materials was achieved as determined by LCMS, the reaction mixture was quenched with saturated solution of $NaHCO_3$ and the product was extracted with EtOAc. The combined organic fractions were washed with brine and dried with $Na_2SO_4$. After solvent was evaporated, the crude product was used in the next step without further purification. LCMS calc. for $C_{34}H_{51}N_6O_4Si$ $(M+H)^+$ m/z=635.4. found: 635.4.

Step 5. N-{4-[(3R,4R,5S)-3-Amino-4-hydroxy-5-methylpiperidin-1-yl]pyridin-3-yl}-1-cyclobutyl-1H-pyrrolo[2,3-b]pyridine-6-carboxamide To a mixture of tert-butyl [(3R,4R,5S)-4-{[tert-butyl(dimethyl)silyl]oxy}-1-(3-{[(1-cyclobutyl-1H-pyrrolo[2,3-b]pyridin-6-yl)carbonyl]amino}pyridin-4-yl)-5-methylpiperidin-3-yl]carbamate (30 mg, 0.047 mmol) in MeOH (2 mL) was added 4.0 M solution of HCl in dioxane (1 mL, 4 mmol). The reaction mixture was stirred at room temperature overnight. Then it was neutralized by addition of ammonia solution and purified by RP-HPLC (Waters XBridge™ C18 column, 30 mm×100 mm, 5 µm particle size, eluting with a gradient of MeCN/water containing 0.1% $NH_4OH$, at flow rate of 60 mL/min) to give the title compound. LCMS calc. for $C_{23}H_{29}N_6O_2$ $(M+H)^+$ m/z=421.2. found: 421.2.

Example 78

N-{4-[(3S,5R)-3-Amino-5-methylpiperidin-1-yl]pyridin-3-yl}-1-cyclobutyl-1H-pyrrolo[2,3-b]pyridine-6-carboxamide

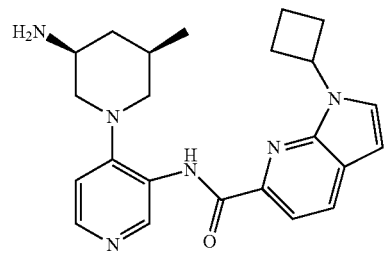 [SMILES: C[C@@H]1C[C@H](N)CN(c2ccncc2NC(=O)c2ccc3ccn(C4CCC4)c3n2)C1]

Step 1. tert-Butyl [(3S,5R)-1-(3-{[(1-cyclobutyl-1H-pyrrolo[2,3-b]pyridin-6-yl)carbonyl]amino}pyridin-4-yl)-5-methylpiperidin-3-yl]carbamate

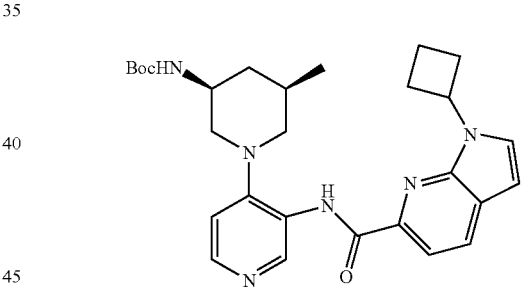

tert-Butyl [(3S,5R)-1-(3-aminopyridin-4-yl)-5-methylpiperidin-3-yl]carbamate (Intermediate 1; 14 mg, 0.046 mmol) and 1-cyclobutyl-1H-pyrrolo[2,3-b]pyridine-6-carboxylic acid (10.7 mg, 0.0495 mmol) were dissolved in DMF (2 mL). Then DIPEA (24 µL, 0.14 mmol) and HATU (44 mg, 0.11 mmol) were added and the reaction mixture was stirred at 40° C. for 2 h. After full conversion was achieved, the reaction mixture was quenched with saturated aq. $NaHCO_3$ and product was extracted with EtOAc. The combined organic fractions were washed with brine and dried with $Na_2SO_4$. After solvent was evaporated, the crude product was used in the next step without further purification. LCMS calc. for $C_{28}H_{37}N_6O_3$ $(M+H)^+$ m/z=505.3. found: 505.3.

Step 2. N-{4-[(3S,5R)-3-Amino-5-methylpiperidin-1-yl]pyridin-3-yl}-1-cyclobutyl-1H-pyrrolo[2,3-b]pyridine-6-carboxamide To a mixture of tert-butyl [(3S,5R)-1-(3-{[(1-cyclobutyl-1H-pyrrolo[2,3-b]pyridin-6-yl)carbonyl]amino}pyridin-4- yl)-5-methylpiperidin-3-yl]carbamate (160 mg, 0.31 mmol) in MeOH (2 mL) was added 4.0 M solution of HCl in dioxane (1 mL, 4 mmol). The reaction mixture was stirred at room temperature overnight. Then it was neutralized by addition of the ammonia solution and purified by RP-HPLC (Waters XBridge™ C18 column, 30 mm×100 mm, 5 µm particle size, eluting with a gradient of MeCN/water containing 0.1% NH$_4$OH, at flow rate of 60 mL/min) to give the title compound. LCMS calc. for $C_{23}H_{29}N_6O$ (M+H)$^+$ m/z=405.2. found: 405.2.

Example 79

N-{4-[(3R,4R,5S)-3-Amino-4-hydroxy-5-methylpiperidin-1-yl]pyridin-3-yl}-2-cyclopropyl[1,3]thiazolo[4,5-b]pyridine-5-carboxamide

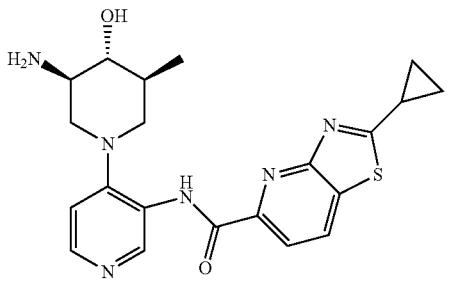

Step 1. Methyl 5-bromo-6-[(cyclopropylcarbonyl)amino]pyridine-2-carboxylate

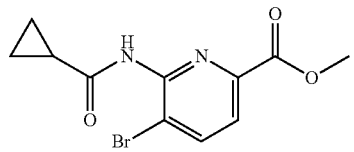 [SMILES: COC(=O)c1ccc(Br)c(NC(=O)C2CC2)n1]

Methyl 6-amino-5-bromopyridine-2-carboxylate (J&W Pharmlab, 300 mg, 1.3 mmol) was dissolved in pyridine (4.6 mL) and the solution was cooled to 0° C. Then cyclopropanecarbonyl chloride (124 µL, 1.36 mmol) was slowly added and the resulting reaction mixture was stirred at room temperature for 1 h. Then the reaction was quenched with water and product extracted with EtOAc. The combined organic fractions were washed with 1 M HCl, then with brine and dried with Na$_2$SO$_4$. After solvent was evaporated, the crude product was used in the next step without further purification. LCMS calc. for $C_{11}H_{12}BrN_2O_3$ (M+H)$^+$ m/z=299.0. found: 299.

Step 2. Methyl 5-bromo-6-[(cyclopropylcarbonothioyl)amino]pyridine-2-carboxylate

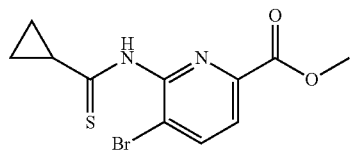 [SMILES: COC(=O)c1ccc(Br)c(NC(=S)C2CC2)n1]

Methyl 5-bromo-6-[(cyclopropylcarbonyl)amino]pyridine-2-carboxylate from the previous step was dissolved in THF (10 mL) and 2,4-bis(4-methoxyphenyl)-2,4-dithioxo-1,3,2,4-dithiadiphosphetane (Lawesson's reagent, 580 mg, 1.4 mmol) was added. The reaction mixture was stirred at 65° C. for 4 h. Then, the solvent was evaporated and the crude product was purified by chromatography on silica gel using Biotage Isolera™ apparatus to give the sub-title compound (410 mg, 99% over 2 steps). LCMS calc. for $C_{11}H_{12}BrN_2O_2S$ (M+H)$^+$ m/z=315.0. found: 315.0.

Step 3. Methyl 2-cyclopropyl[1,3]thiazolo[4,5-b]pyridine-5-carboxylate

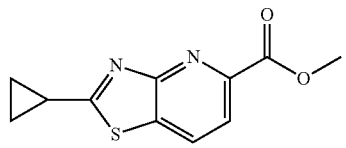 [SMILES: COC(=O)c1ccc2sc(C3CC3)nc2n1]

Methyl 5-bromo-6-[(cyclopropylcarbonothioyl)amino]pyridine-2-carboxylate (410 mg, 1.3 mmol) was dissolved in dimethyl sulfoxide (10 mL) and 60% sodium hydride in mineral oil (67 mg, 1.7 mmol) was added. The reaction mixture was stirred at 60° C. for 1 h. After cooling to room temperature water was added and pH was adjusted to 4 by addition of 1 M HCl solution. The solution was extracted with EtOAc. The combined organic fractions were washed with brine and dried with Na$_2$SO$_4$. After solvent was evaporated, the crude product was purified by chromatography on silica gel using Biotage Isolera™ apparatus to give the sub-title compound (134 mg, 44%). LCMS calc. for $C_{11}H_{11}N_2O_2S$ (M+H)$^+$ m/z=235.1. found: 235.1.

Step 4. 2-Cyclopropyl[1,3]thiazolo[4,5-b]pyridine-5-carboxylic acid

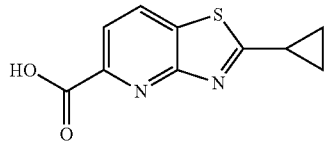 [SMILES: O=C(O)c1ccc2sc(C3CC3)nc2n1]

To a mixture of methyl 2-cyclopropyl[1,3]thiazolo[4,5-b]pyridine-5-carboxylate (134 mg, 0.572 mmol) in THF (6 mL) was added MeOH (4 mL) and 1.0 M aq. NaOH (2.3 mL, 2.3 mmol). The reaction mixture was stirred at room temperature for 30 min. After this time, the pH was adjusted to 5 by addition of the 1M solution of HCl. The solution was then extracted with EtOAc and organic phase was washed with brine and dried with Na$_2$SO$_4$. The solvent was evaporated under reduced pressure. The resulting solid product was used in the next step without further purification (21 mg, 98%). LCMS calc. for $C_{10}H_9N_2O_2S$ (M+H)$^+$ m/z=221.0. found: 221.0.

Step 5. tert-Butyl [(3R,4R,5S)-4-{[tert-butyl(dimethyl)silyl]oxy}-1-(3-{[(2-cyclopropyl[1,3]thiazolo[4,5-b]pyridin-5-yl)carbonyl]amino}pyridin-4-yl)-5-methylpiperidin-3-yl]carbamate

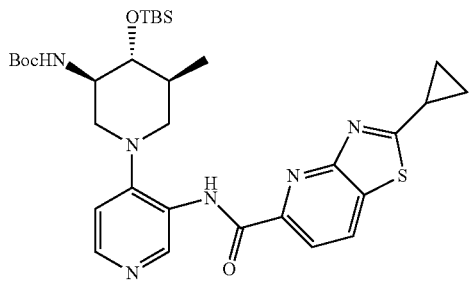 [SMILES: C[C@H]1CN(c2ccncc2NC(=O)c2ccc3sc(C4CC4)nc3n2)C[C@@H](NC(=O)OC(C)(C)C)[C@@H]1O[Si](C)(C)C(C)(C)C]

tert-Butyl ((3R,4R,5S)-1-(3-aminopyridin-4-yl)-4-{[tert-butyl(dimethyl)silyl]oxy}-5-methylpiperidin-3-yl)carbamate (Intermediate 2; 20 mg, 0.046 mmol) and 2-cyclopropyl[1,3]thiazolo[4,5-b]pyridine-5-carboxylic acid (10.9 mg, 0.0495 mmol) were dissolved in DMF (2 mL). Then DIPEA (24 µL, 0.14 mmol) and HATU (44 mg, 0.11 mmol) were added and the reaction was stirred at 40° C. for 2 h. After full conversion of the starting material was achieved as determined by LCMS, the reaction mixture was quenched with saturated aq. NaHCO$_3$ and the solution was extracted with EtOAc. The combined organic fractions were washed with brine and dried with Na$_2$SO$_4$. After solvent was evaporated, the crude product was used in the next step without further purification. LCMS calc. for $C_{32}H_{42}N_6O_4SSi$ (M+H)$^+$ m/z=639.3. found: 639.3.

Step 6. N-{4-[(3R,4R,5S)-3-Amino-4-hydroxy-5-methylpiperidin-1-yl]pyridin-3-yl}-2-cyclopropyl[1,3]thiazolo[4,5-b]pyridine-5-carboxamide To a mixture of tert-butyl [(3R,4R,5S)-4-{[tert-butyl(dimethyl)silyl]oxy}-1-(3-{[(2-cyclopropyl[1,3]thiazolo[4,5-b]pyridin-5-yl)carbonyl]amino}pyridin-4-yl)-5-methylpiperidin-3-yl]carbamate (20 mg, 0.03 mmol) in MeOH (2 mL) was added 4.0 M solution of HCl in dioxane (1 mL, 4 mmol). The reaction mixture was stirred at room temperature overnight. Then it was neutralized by addition of the ammonia solution and purified by RP-HPLC (Waters XBridge™ C18 column, 30 mm×100 mm, 5 µm particle size, eluting with a gradient of MeCN/water containing 0.1% NH$_4$OH, at flow rate of 60 mL/min) to give the title compound. LCMS calc. for $C_{21}H_{25}N_6O_2S$ (M+H)$^+$ m/z=425.2. found: 425.2.

Example 80

N-(4-((3S,5R)-3-Amino-5-methylpiperidin-1-yl)pyridin-3-yl)-2-cyclopropylthiazolo[4,5-b]pyridine-5-carboxamide

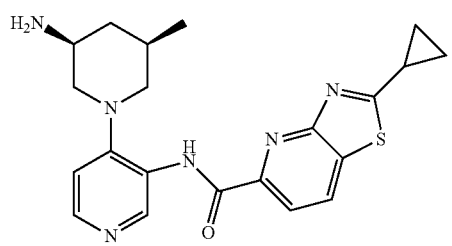 [SMILES: C[C@@H]1C[C@H](N)CN(c2ccncc2NC(=O)c2ccc3sc(C4CC4)nc3n2)C1]

Step 1. tert-Butyl [(3S,5R)-1-(3-{[(2-cyclopropyl[1,3]thiazolo[4,5-b]pyridin-5-yl)carbonyl]amino}pyridin-4-yl)-5-methylpiperidin-3-yl]carbamate

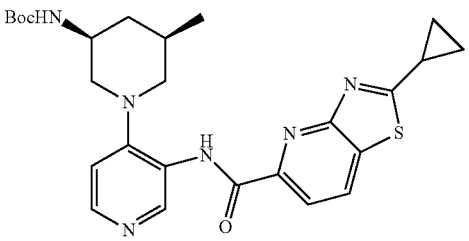 [SMILES: C[C@@H]1C[C@H](NC(=O)OC(C)(C)C)CN(c2ccncc2NC(=O)c2ccc3sc(C4CC4)nc3n2)C1]

ter t-Butyl [(3S,5R)-1-(3-aminopyridin-4-yl)-5-methylpiperidin-3-yl]carbamate (Intermediate 1; 14 mg, 0.046 mmol) and 2-cyclopropyl[1,3]thiazolo[4,5-b]pyridine-5-carboxylic acid (10.9 mg, 0.0495 mmol) were dissolved in DMF (2 mL). Then DIPEA (24 µL, 0.14 mmol) and HATU (44 mg, 0.11 mmol) were added and the reaction was stirred at 40° C. for 2 h. After full conversion of the starting materials was achieved as determined by LCMS, the reaction mixture was quenched with saturated solution of NaHCO$_3$ and product extracted with EtOAc. The combined organic fractions were washed with brine and dried with Na$_2$SO$_4$. After solvent was evaporated, the crude product was used in the next step without further purification. LCMS calc. for $C_{26}H_{33}N_6O_3S$ (M+H)$^+$ m/z=509.2. found: 509.3.

Step 2. N-(4-((3S,5R)-3-Amino-5-methylpiperidin-1-yl)pyridin-3-yl)-2-cyclopropylthiazolo[4,5-b]pyridine-5-carboxamide To a mixture of tert-butyl [(3S,5R)-1-(3-{[(2-cyclopropyl[1,3]thiazolo[4,5-b]pyridin-5-yl)carbonyl]amino}pyridin-4-yl)-5-methylpiperidin-3-yl]carbamate (23 mg, 0.046 mmol) in MeOH (2 mL) was added 4.0 M solution of HCl in dioxane (1 mL, 4 mmol). The reaction mixture was stirred at room temperature overnight. Then it was neutralized by addition of the ammonia solution and purified by RP-HPLC (Waters XBridge™ C18 column, 30 mm×100 mm, 5 µm particle size, eluting with a gradient of MeCN/water containing 0.1% NH$_4$OH, at flow rate of 60 mL/min) to give the title compound. LCMS calc. for $C_{24}H_{25}N_6OS$ (M+H)$^+$ m/z=409.2. found: 409.1.

Example 81

N-{4-[(1R,3S,5S)-3-Amino-5-methylcyclohexyl]pyridin-3-yl}-3-[2,6-difluoro-4-(hydroxymethyl)phenyl]pyrazolo[1,5-a]pyrimidine-5-carboxamide

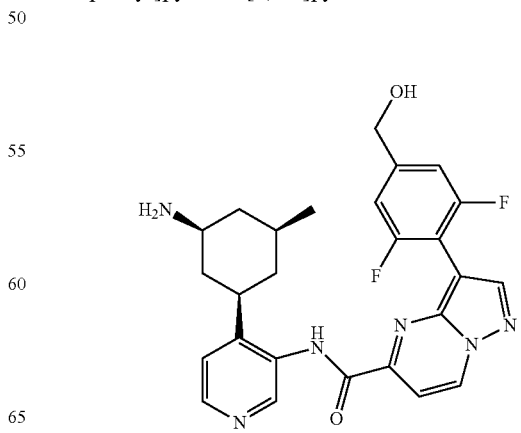

Step 1. Ethyl 7-hydroxypyrazolo[1,5-a]pyrimidine-5-carboxylate

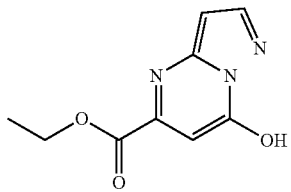

A solution of 1H-pyrazol-3-amine (7.52 g, 90.5 mmol) and ethyl 2-oxosuccinate (17.0 g, 90.5 mmol) in AcOH (72 mL) was heated at 110° C. for 1 h. The solvent was removed under reduced pressure. The resulting residue was diluted with EtOAc and left on bench overnight. A precipitate formed that was filtered and dried under reduced pressure to give the sub-title compound as a yellow solid (2.4 g, 13%). LCMS calc. for $C_9H_{10}N_3O_3$ (M+H)$^+$: m/z=208.1. Found: 208.0.

Step 2. Ethyl 7-chloropyrazolo[1,5-a]pyrimidine-5-carboxylate

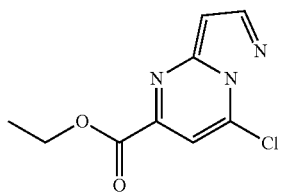

A suspension of ethyl 7-hydroxypyrazolo[1,5-a]pyrimidine-5-carboxylate (621 mg, 3.00 mmol), phosphoryl chloride (5.0 mL, 53.6 mmol) and N,N-dimethylaniline (260 μL, 2.1 mmol) was heated at 110° C. for 5 h. Phosphoryl chloride was removed under reduced pressure. The residue was diluted with EtOAc and saturated aq. NaHCO$_3$. The organic layer was separated and washed with brine, dried over Na$_2$SO$_4$, filtered and concentrated under reduced pressure. The residue was purified with flash chromatography (0-40% EtOAc in hexanes) to give the sub-title compound (402 mg, 59%). LCMS calc. for $C_9H_9ClN_3O_2$ (M+H)$^+$: m/z=226.0. Found: 226.0.

Step 3. Ethyl pyrazolo[1,5-a]pyrimidine-5-carboxylate

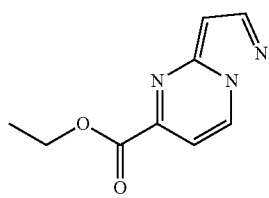

To a flask containing ethyl 7-chloropyrazolo[1,5-a]pyrimidine-5-carboxylate (442 mg, 1.96 mmol) in ethanol (5 mL) was added 10% palladium on carbon (200 mg) and sodium acetate (0.19 g, 2.35 mmol). The reaction mixture was stirred under H$_2$ atmosphere for 1 h. The reaction was filtered through a pad of diatomaceous earth (eluted with MeOH). The filtrate was concentrated under reduced pressure. The residue was dissolved in DCM and 1 equivalent of 2,3-dichloro-5,6-dicyano-1,4-benzoquinone was added and the resulting mixture was stirred for 1 h. The reaction was diluted with water. The organic layer was concentrated under reduced pressure and purified by flash chromatography (0-40% EtOAc in hexanes) to give the sub-title compound (178 mg, 47%). LCMS calc. for $C_9H_{10}N_3O_2$ (M+H)$^+$: m/z=192.1. Found: 192.1. $^1$H NMR (300 MHz, CDCl$_3$) δ 8.78 (m, 1H), 8.22 (m, 1H), 7.57 (m, 1H), 6.94 (m, 1H), 4.51 (m, 2H), 1.45 (m, 3H) ppm.

Step 4. Ethyl 3-bromopyrazolo[1,5-a]pyrimidine-5-carboxylate

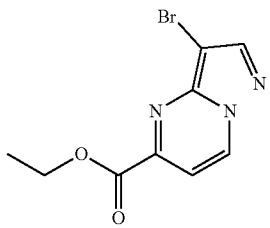

A mixture of ethyl pyrazolo[1,5-a]pyrimidine-5-carboxylate (178 mg, 0.931 mmol) in dichloromethane (6.0 mL) was added N-bromosuccinimide (0.182 g, 1.02 mmol). The reaction was stirred at room temperature for 1 h. The reaction mixture was diluted with dichloromethane and water. The organic solution was dried over Na$_2$SO$_4$, filtered and concentrated. The residue was purified with flash chromatography to give the sub-title compound (237 mg, 94%). LCMS calc. for $C_9H_9BrN_3O_2$ (M+H)$^+$: m/z=270.0. Found: 270.0. $^1$H NMR (400 MHz, CDCl$_3$) δ 8.76 (d, J=7.2 Hz, 1H), 8.22 (s, 1H), 7.59 (d, J=7.3 Hz, 1H), 4.50 (q, J=7.1 Hz, 2H), 1.46 (t, J=7.1 Hz, 3H) ppm.

Step 5. 3-Bromopyrazolo[1,5-a]pyrimidine-5-carboxylic acid

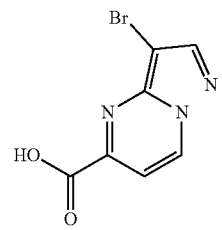 [SMILES: N=C/C(Br)=C1/N=C(C(=O)O)C=CN1]

A mixture of ethyl 3-bromopyrazolo[1,5-a]pyrimidine-5-carboxylate (237 mg, 0.878 mmol), THF (5.3 mL) and aq. 1.0 M NaOH (5.3 mL, 5.3 mmol) was stirred at room temperature overnight. The pH of the solution was adjusted to 7 with 1 M solution of HCl. Layers were separated and the aqueous layer was extracted with EtOAc (2×). The combined organic layers were dried over Na$_2$SO$_4$, filtered and concentrated to give the sub-title compound (160 mg, 75%). LCMS calc. for C₇H₅BrN₃O₂ (M+H)⁺: m/z=242.0. Found: 242.0.

Step 6. tert-Butyl [(1S,3R,5S)-3-(3-{[(3-bromopyrazolo[1,5-a]pyrimidin-5-yl)carbonyl]amino}pyridin-4-yl)-5-methylcyclohexyl]carbamate

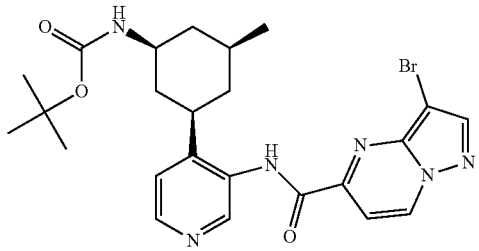 [SMILES: C[C@@H]1C[C@H](NC(=O)OC(C)(C)C)C[C@H](c2ccncc2NC(=O)c2ccn3ncc(Br)c3n2)C1]

To a solution of tert-butyl [(1S,3R,5S)-3-(3-aminopyridin-4-yl)-5-methylcyclohexyl]carbamate (Intermediate 3; 160 mg, 0.54 mmol), 3-bromopyrazolo[1,5-a]pyrimidine-5-carboxylic acid (144 mg, 0.595 mmol), HATU (329 mg, 0.865 mmol) in DMF (4.3 mL, 56 mmol) was added DIPEA (190 µL, 1.1 mmol). The reaction mixture was stirred at room temperature for 2 h, and then diluted with saturated aq. NaHCO₃ and extracted with EtOAc. The organic phase was dried over Na₂SO₄, filtered and concentrated under reduced pressure. The residue was purified by with flash chromatography to give the sub-title compound (260 mg, 91%). LCMS calc. for C₂₄H₃₀BrN₆O₃ (M+H)⁺: m/z=529.2. Found: 529.1.

Step 7. [3,5-Difluoro-4-(4,4,5,5-tetramethyl-1,3,2-dioxaborolan-2-yl)phenyl]methanol

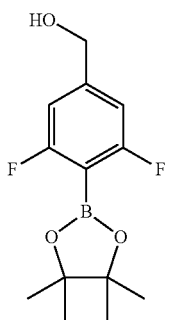 [SMILES: CC1(C)OB(c2c(F)cc(CO)cc2F)OC1(C)C]

3,5-Difluoro-4-(4,4,5,5-tetramethyl-1,3,2-dioxaborolan-2-yl)benzaldehyde (Aldrich; 2.68 g, 10.0 mmol) was dissolved in MeOH (70 mL). The solution was cooled to 0° C., then sodium tetrahydroborate (397 mg, 10.5 mmol) was slowly added and the resulting reaction mixture was stirred for 1 h. Then the reaction mixture was diluted with EtOAc, washed with brine, dried over Na₂SO₄, filtered and concentrated under reduced pressure to give the sub-title compound (1.5 g, 56%). The crude product was used in the next step without further purification.

Step 8. N-{4-[(1R,3S,5S)-3-Amino-5-methylcyclohexyl]pyridin-3-yl}-3-[2,6-difluoro-4-(hydroxymethyl)phenyl]pyrazolo[1,5-a]pyrimidine-5-carboxamide A mixture of tert-butyl [(1S,3R,5S)-3-(3-{[(3-bromopyrazolo[1,5-a]pyrimidin-5-yl)carbonyl]amino}pyridin-4-yl)-5-methylcyclohexyl]carbamate (25.0 mg, 0.0472 mmol), [3,5-difluoro-4-(4,4,5,5-tetramethyl-1,3,2-dioxaborolan-2-yl)phenyl]methanol (20.4 mg, 0.0756 mmol), dicyclohexyl (2',4',6'-triisopropylbiphenyl-2-yl)phosphine-(2'-aminobiphenyl-2-yl)(chloro)palladium (1:1) (3.3 mg, 0.0042 mmol) and tripotassium phosphate hydrate (23.9 mg, 0.104 mmol) in 1,4-dioxane (0.51 mL)/water (0.17 mL) was stirred at 80° C. under a N₂ atmosphere for 1.5 h. The reaction mixture was diluted with DCM and washed with water. The organic layer was concentrated under reduced pressure. The residue was purified by preparative HPLC (XBridge™ C18 column, eluting with a gradient of MeCN/water containing 0.05% TFA, at a flow rate of 60 mL/min) to afford a Boc protected intermediate. The compound was treated with 1:1 DCM/TFA (2 mL) for 2 h. The volatile solvents were removed under reduced pressure and the resulting residue was dissolved in MeOH and purified by preparative LCMS (XBridge™ C18 column, eluting with a gradient of MeCN/water containing 0.1% ammonium hydroxide, at flow rate of 60 mL/min) to give the title compound as a white solid (4.3 mg, 18%). LCMS calc. for C₂₆H₂₂F₂N₆O₂ (M+H)⁺: m/z=493.2. Found: 493.1.

Example 82

N-{4-[(1R,3S,5S)-3-Amino-5-methylcyclohexyl]pyridin-3-yl}-3-isopropylpyrazolo[1,5-a]pyrimidine-5-carboxamide

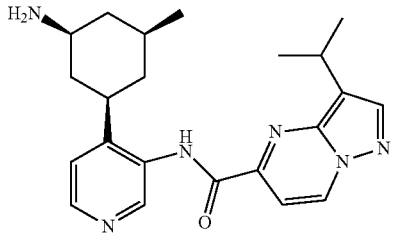 [SMILES: CC(C)c1cnn2ccc(C(=O)Nc3cnccc3[C@@H]3C[C@H](C)C[C@H](N)C3)nc12]

Step 1. tert-Butyl [(1S,3R,5S)-3-(3-{[(3-isopropenylpyrazolo[1,5-a]pyrimidin-5-yl)carbonyl]amino}pyridin-4-yl)-5-methylcyclohexyl]carbamate

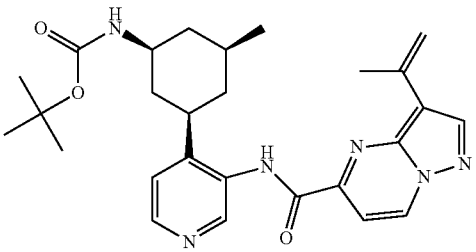 [SMILES: C=C(C)c1cnn2ccc(C(=O)Nc3cnccc3[C@@H]3C[C@H](C)C[C@H](NC(=O)OC(C)(C)C)C3)nc12]

A mixture of tert-butyl [(1S,3R,5S)-3-(3-{[(3-bromopyrazolo[1,5-a]pyrimidin-5-yl)carbonyl]amino}pyridin-4-yl)-5-methylcyclohexyl]carbamate (32.0 mg, 0.0604 mmol), 2-isopropenyl-4,4,5,5-tetramethyl-1,3,2-dioxaborolane (16.2 µL, 0.0967 mmol), dicyclohexyl(2',4',6'-triisopropylbiphenyl-2-yl)phosphine-(2'-aminobiphenyl-2-yl)(chloro) palladium (1:1) (4.2 mg, 0.0053 mmol) and tripotassium phosphate hydrate (30.6 mg, 0.133 mmol) in 1,4-dioxane (0.65 mL) and water (0.22 mL) was stirred at 80° C. under a N₂ atmosphere for 1.5 h. The reaction mixture was diluted with MeOH and purified by preparative HPLC (XBridge™ C18 column, eluting with a gradient of MeCN/water containing 0.05% TFA, at a flow rate of 60 mL/min) to afford the sub-title compound (6.3 mg, 21%). LCMS calc. for C₂₇H₃₅N₆O₃ (M+H)⁺: m/z=491.3. Found: 491.4.

Step 2. N-{4-[(1R,3S,5S)-3-Amino-5-methylcyclohexyl]pyridin-3-yl}-3-isopropylpyrazolo[1,5-a]pyrimidine-5-carboxamide tert-Butyl [(1S,3R,5S)-3-(3-{[(3-isopropenylpyrazolo[1,5-a]pyrimidin-5-yl)carbonyl]amino}pyridin-4-yl)-5-methylcyclohexyl]carbamate (6.3 mg) was hydrogenated under a H₂ balloon using 10% Pd on carbon (10 mg) for 1 h. After filtration, the filtrate was concentrated under reduced pressure. The resulting residue was treated with 1:1 DCM/TFA (2 mL) for 2 h. The volatile solvents were removed under reduced pressure and the resulting residue was dissolved in MeOH and purified with prep-LCMS (XBridge™ C18 column, eluting with a gradient of MeCN/water containing 0.1% NH₄OH, at a flow rate of 60 mL/min) to give the title compound as a white solid (2.2 mg, 60%). LCMS calc. for $C_{22}H_{29}N_6O$ (M+H)⁺: m/z=393.2. Found: 393.2.

Example 83

N-{4-[(1R,3S,5S)-3-Amino-5-methylcyclohexyl]pyridin-3-yl}-3-(2,6-difluorophenyl)pyrazolo[1,5-a]pyrimidine-5-carboxamide

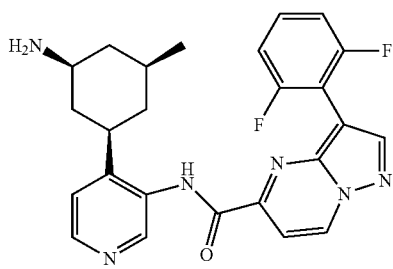 [SMILES: C[C@@H]1C[C@H](N)C[C@H](c2ccncc2NC(=O)c2ccn3ncc(-c4c(F)cccc4F)c3n2)C1]

This compound was prepared according to a procedure analogous to that described in Example 81, Step 8, using tert-butyl [(1S,3R,5S)-3-(3-{[(3-bromopyrazolo[1,5-a]pyrimidin-5-yl)carbonyl]amino}pyridin-4-yl)-5-methylcyclohexyl]carbamate (from Example 81, step 6) and 2-(2,6-difluorophenyl)-4,4,5,5-tetramethyl-1,3,2-dioxaborolane instead of [3,5-difluoro-4-(4,4,5,5-tetramethyl-1,3,2-dioxaborolan-2-yl)phenyl]methanol as a starting material. LCMS calc. for $C_{25}H_{25}F_2N_6O$ (M+H)⁺: m/z=463.2. Found: 463.1.

Example 84

N-{4-[(1R,3S,5S)-3-Amino-5-methylcyclohexyl]pyridin-3-yl}-3-(2,6-difluoro-4-methoxyphenyl)pyrazolo[1,5-a]pyrimidine-5-carboxamide

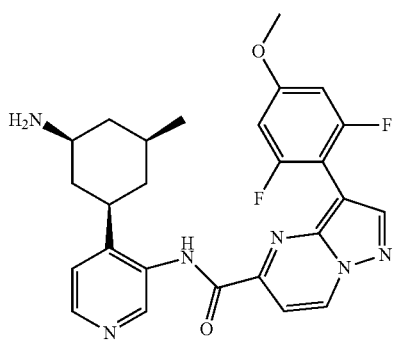 [SMILES: COc1cc(F)c(-c2cnn3ccc(C(=O)Nc4cnccc4[C@@H]4C[C@H](C)C[C@H](N)C4)nc23)c(F)c1]

This compound was prepared according to the procedure described in Example 81, Step 8, using tert-butyl [(1S,3R,5S)-3-(3-{[(3-bromopyrazolo[1,5-a]pyrimidin-5-yl)carbonyl]amino}pyridin-4-yl)-5-methylcyclohexyl]carbamate (from Example 81, step 6) and (2,6-difluoro-4-methoxyphenyl)boronic acid instead of [3,5-difluoro-4-(4,4,5,5-tetramethyl-1,3,2-dioxaborolan-2-yl)phenyl]methanol as starting material. LCMS calc. for $C_{26}H_{27}F_2N_6O_2$ (M+H)⁺: m/z=493.2. Found: 493.1.

Example 85

N-(4-((3R,4R,5S)-3-amino-4-hydroxy-5-methylpiperidin-1-yl)pyridin-3-yl)-2-ethylthieno[3,2-b]pyridine-5-carboxamide

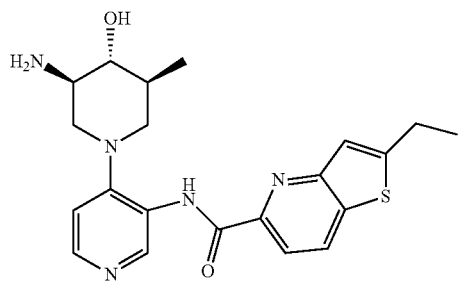 [SMILES: CCc1cc2nc(C(=O)Nc3cnccc3N3C[C@@H](N)[C@H](O)[C@@H](C)C3)ccc2s1]

Step 1. Methyl 6-but-1-yn-1-yl-5-fluoropyridine-2-carboxylate

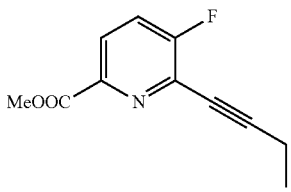

Methyl 6-bromo-5-fluoropyridine-2-carboxylate (Frontier Scientific 1.0 g, 4.3 mmol), copper iodide (57 mg, 0.30 mmol), dichloro[bis(triphenylphosphine)]palladate (180 mg, 0.26 mmol) and a magnet bar were placed in a flask and the flask was closed with the septum. The flask was then evacuated and backfilled with nitrogen three times. Then 1,4-dioxane (18 mL) and triethylamine (0.893 mL, 6.41 mmol) were added. The reaction was stirred at r.t. for 5 min. Then a balloon containing 1-butyne was connected to the reaction flask and the reaction was stirred at 60° C. for 3 hours. After this time the reaction was quenched with water and the product was extracted with ethyl acetate. Organic fractions were washed with brine, dried over sodium sulfate and solvent was evaporated under reduced pressure. Crude product was purified by Biotage Isolera to give the desired compound (890 mg, 99%). LCMS calculated for $C_{11}H_{11}FNO_2$ (M+H)⁺ m/z=208.1. found 208.1.

Step 2. 2-ethylthieno[3,2-b]pyridine-5-carboxylic acid

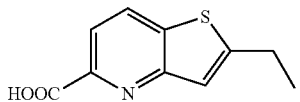

Sodium sulfide (1.1 g, 14 mmol) was added to a solution of methyl 6-but-1-yn-1-yl-5-fluoropyridine-2-carboxylate (890 mg, 4.3 mmol) in N,N-dimethylformamide (10 mL). The reaction mixture was stirred at 60° C. for 3 h. After this time it was cooled to r.t. and 1 M solution of NaOH (5 mL) was added. The reaction was stirred at r.t. for 30 min, then it was acidified to pH=3 with 1 M solution of HCl. After addition of water, the product was extracted with ethyl acetate. The organic phase was washed with brine, dried over sodium sulfate and solvent was evaporated under reduced pressure. The resulting product was dried under vacuum and was used in the next step without further purification (880 mg, 99%). LCMS calculated for $C_{10}H_{10}NO_2S$ (M+H)$^+$ m/z=208.0. found 208.1.

Step 3. tert-Butyl [(3R,4R,5S)-4-{[tert-butyl(dimethyl)silyl]oxy}-5-methyl-1-(3-{[(2-ethyl thieno[3,2-b]pyridin-5-yl)carbonyl]amino}pyridin-4-yl)piperidin-3-yl]carbamate

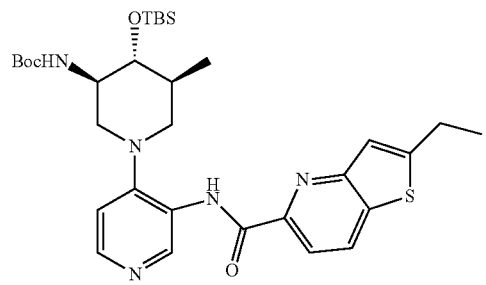 [SMILES: CCc1cc2nc(C(=O)Nc3cnccc3N3C[C@H](C)[C@@H](O[Si](C)(C)C(C)(C)C)[C@H](NC(=O)OC(C)(C)C)C3)ccc2s1]

To a solution of tert-butyl ((3R,4R,5S)-1-(3-aminopyridin-4-yl)-4-{[tert-butyl(dimethyl)silyl]oxy}-5-methylpiperidin-3-yl)carbamate (600 mg, 1.37 mmol) and 2-ethylthieno[3,2-b]pyridine-5-carboxylic acid (308 mg, 1.48 mmol) in N,N-dimethylformamide (24 mL) were added N,N-diisopropylethylamine (480 µL, 2.7 mmol) and N,N,N',N'-tetramethyl-O-(7-azabenzotriazol-1-yl)uronium hexafluorophosphate (780 mg, 2.1 mmol). After the reaction mixture was stirred at r.t. for 2 hours, it was quenched with saturated solution of NaHCO$_3$ and the product was extracted with ethyl acetate. Organic phase was washed with brine and dried over sodium sulfate. After the solvent was evaporated, crude product was purified by Biotage Isolera to give the desired compound (448 mg, 52%). LCMS calculated for $C_{32}H_{48}N_5O_4SSi$ (M+H)$^+$ m/z=626.3. found 626.3.

Step 4. N-(4-((3R,4R,5S)-3-amino-4-hydroxy-5-methylpiperidin-1-yl)pyridin-3-yl)-2-ethylthieno[3,2-b]pyridine-5-carboxamide tert-Butyl [(3R,4R,5S)-4-{[tert-butyl(dimethyl)silyl]oxy}-5-methyl-1-(3-{[(2-ethylthieno[3,2-b]pyridin-5-yl)carbonyl]amino}pyridin-4-yl)piperidin-3-yl]carbamate (448 mg, 0.716 mmol) was dissolved in methylene chloride (10.0 mL) and trifluoroacetic acid (10 mL, 70 mmol). Then 4.0 M solution of HCl in dioxane (10 mL, 40 mmol) was added. The reaction mixture was stirred at 50° C. for 3 hours. Then it was neutralized by addition of the ammonia solution and purified by RP-HPLC (water XBridge C18 column, 30 mm×100 mm, 5 µm particle size, eluting with a gradient of acetonitrile/water containing 0.1% NH$_4$OH, at flow rate of 60 mL/min) LCMS calculated for $C_{21}H_{26}N_5O_2S$ (M+H)$^+$ m/z=412.2. found 412.1.

$^1$H NMR (500 MHz, DMSO-d$_6$) δ 10.51 (s, 1H), 9.42 (s, 1H), 8.64 (d, J=8.3 Hz, 1H), 8.24 (d, J=5.3 Hz, 1H), 8.08 (d, J=8.3 Hz, 1H), 7.41 (s, 1H), 7.13 (d, J=5.3 Hz, 1H), 4.87 (d, J=5.8 Hz, 1H), 3.23 (dd, J=10.6, 3.4 Hz, 1H), 3.17 (dd, J=11.7, 3.5 Hz, 1H), 3.09-2.97 (m, 4H), 2.80-2.71 (m, 1H), 2.57-2.44 (m, 2H), 2.12-1.97 (m, 1H), 1.73-1.53 (m, 1H), 1.37 (t, J=7.5 Hz, 3H), 0.91 (d, J=6.6 Hz, 3H) ppm.

Example A

Pim Enzyme Assays

Pim-1 and Pim-3 kinase assays—20 µL reactions were run in white 384 well polystyrene plates dotted with 0.8 µL compound/DMSO in the assay buffer (50 mM Tris, pH 7.5, 0.01% Tween-20, 5 mM MgCl$_2$, 0.01% BSA, 5 mM DTT), containing 0.05 µM Biotin-labeled BAD peptide substrate (AnaSpec 62269), 1 mM ATP, and 2.5 µM (Pim-1, Invitrogen PV3503) or 1.25 µM (Pim-3, Millipore 14-738) enzyme for 1 h at 25° C. Reactions were stopped by addition of 10 µL STOP Buffer (150 mM Tris, pH=7.5, 150 mM NaCl, 75 mM EDTA, 0.01% Tween-20, 0.3% BSA) supplemented with Phospho-Bad (Ser112) Antibody (Cell Signaling 9291) diluted 666-fold, and Streptavidin donor beads (PerkinElmer 6760002) along with Protein-A acceptor beads (PerkinElmer 6760137) at 15 µg/mL each. Supplementation of the STOP buffer with beads and stopping the reactions were done under reduced light. Prior to the stopping reactions STOP buffer with beads was preincubated for 1 h in the dark at room temperature. After stopping the reactions, plates were incubated for 1 h in the dark at room temperature before reading on a PHERAstar FS plate reader (BMG Labtech) under reduced light.

Pim-2 kinase assay—20 µL reactions were run in white 384 well polystyrene plates dotted with 0.8 µL compound/DMSO in the assay buffer (50 mM Tris, pH 7.5, 0.01% Tween-20, 5 mM MgCl$_2$, 0.01% BSA, 5 mM DTT), containing 0.05 µM Fluorescein-labeled CREBtide peptide substrate (Invitrogen PV3508), 1 mM ATP, and 1 nM enzyme (Invitrogen PV3649) for 2 h at 25° C. Reactions were stopped by addition of 10 µL TR-FRET Dilution Buffer (Invitrogen PV3574) with 30 mM EDTA and 1.5 nM LanthaScreen Tb-CREB pSer133 antibody (Invitrogen PV3566). After 30 min. incubation at room temperature, plates were read on a PHERAstar FS plate reader (BMG Labtech).

Compounds of the invention having an IC$_{50}$ of 2 µM or less when tested for PIM kinase activity under the assay conditions disclosed above are considered active.

Although the above in vitro assays are conducted at 1 mM ATP compounds can also be evaluated for potency and in vitro activity against PIM targets utilizing K$_m$ conditions, where the concentration of ATP is set to the K$_m$ value and the assay is more sensitive to PIM inhibition activity.

Example B

Pim Cellular Assays

One or more compounds of the invention were tested for inhibitory activity of PIM according to at least one of the following cellular assays. Compounds of the invention having an $IC_{50}$ of 10 μM or less when tested for PIM kinase activity under the cellular assay conditions disclosed below would be and were considered active.

Pim Cell Proliferation Assays

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the anti-proliferation activity of test compounds, both cell lines are plated with the culture medium ($2\times10^3$ cells/well/in 200 μL) into 96-well polystyrene ultralow binding (Costar) in the presence or absence of a concentration range of test compounds. After 4 days, [$^3$H]-thymidine, 1 μCi/10 μL/well (PerkinElmer, Boston, Mass.) in culture medium is then added to the cell culture for an additional 16 h before the incorporated radioactivity is separated by filtration with a Packard Micro plate Harvester with water through a 0.3% PEI pre wetted GF/B filter plates (Packard Bioscience/PerkinElmer, Boston, Mass.). The plate is measured by liquid scintillation counting with a TopCount (PerkinElmer). $IC_{50}$ determination is performed by fitting the curve of percent inhibition versus the log of the inhibitor concentration using the GraphPad Prism 5.0 software.

Pim Cell Proliferation Assay

MOLM-16 cells are purchased from DSMZ (Germany) and maintained in the culture medium recommended, RPMI, 20% FBS. To measure the anti-proliferation activity of test compounds, the cells are plated with the RPMI, 10% FBS ($1\times10^4$ cells/well/in 200 μL) into 96-well polystyrene ultralow binding plates (Costar) in the presence or absence of a concentration range of test compounds. After 4 days, [$^3$H]-thymidine, 1 μCi/10 μL/well (PerkinElmer, Boston, Mass.) in RPMI, 10% FBS is then added to the cell culture for an additional 16 h before the incorporated radioactivity is separated by filtration with a Packard Micro plate Harvester with water through a 0.3% PEI pre wetted GF/B filter plates (Packard Bioscience/PerkinElmer, Boston, Mass.). The plate is measured by liquid scintillation counting with a TopCount (PerkinElmer). $IC_{50}$ determination is performed by fitting the curve of percent inhibition versus the log of the inhibitor concentration using the GraphPad Prism 5.0 software.

Pim pBAD Signaling Assay

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the pBAD inhibitory activity of the compounds, both cell lines are plated with the culture medium ($1\times10^6$/well/100 μL for KG1A and $4\times10^5$ cells/well/in 100 μL for KMS12BM) into 96-well V bottom polypropylene plates (Matrix, Thermo Fisher, USA) and incubated 30 min. at 37° C. to normalize cell signaling from handling. Test compounds are added at an appropriate concentration range and further incubated for 2.5 h for KMS.12.BM cells and 4 h for KG1-A cells. Plates are centrifuged at 2000 RPM for 10 min. and supernatants aspirated. 100 μL lysis buffer with protease inhibitors (Cell Signaling Technologies, Danver, Mass., Sigma, St Louis Mo., EMD, USA) is added to the pellets, mixed well and set on ice for 30 min. Lysates are frozen overnight at −80° C. To measure the pBAD activity, a Cell Signaling ELISA kit (Cell Signaling Path Scan phosphor pBAD ELISA) is utilized. 50 μL of the lysate is tested per the ELISA protocol and the data analysis is performed by software on a SpectrMax5 plate reader (Molecular Devices, Sunnyvale, Calif.). $IC_{50}$ determination is performed by fitting the curve of percent inhibition versus the log of the inhibitor concentration using the GraphPad Prism 5.0 software.

Data obtained for the Example compounds, obtained using the methods described in Example A, are provided in Table 1.

TABLE 1

Pim Enzyme Assay Data

| Example | Pim1 $IC_{50}$ (nM)[a] | Pim2 $IC_{50}$ (nM)[b] | Pim3 $IC_{50}$ (nM)[a] |
|---|---|---|---|
| 1 | * | ++ | * |
| 2 | ** | ++ | * |
| 3 | * | >2000 | * |
| 4 | * | >2000 | ** |
| 5 | * | +++ | * |
| 6 | ** | ++ | * |
| 7 | * | >2000 | * |
| 8 | * | >2000 | ** |
| 9 | * | +++ | * |
| 10 | * | + | * |
| 11 | * | + | * |
| 12 | * | ++ | * |
| 13 | * | ++ | * |
| 14 | * | +++ | ** |
| 15 | * | + | * |
| 16 | ** | >2000 | >40 |
| 17 | * | ++ | * |
| 18 | * | + | * |
| 19 | * | + | * |
| 20 | * | + | * |
| 21 | * | + | * |
| 22 | * | + | * |
| 23 | * | +++ | ** |
| 24 | * | >2000 | >40 |
| 25 | * | ++ | * |
| 26 | * | >2000 | ** |
| 27 | ** | >2000 | >40 |
| 28 | * | >2000 | ** |
| 29 | * | +++ | ** |
| 30 | ** | >2000 | >40 |
| 31 | * | ++ | * |
| 32 | * | +++ | * |
| 33 | * | + | * |
| 34 | * | + | * |
| 35 | * | + | * |
| 36 | * | + | * |
| 37 | * | + | * |
| 38 | * | ++ | * |
| 39 | * | + | * |
| 40 | * | ++ | * |
| 41 | * | ++ | * |
| 42 | * | ++ | * |
| 43 | * | ++ | * |
| 44 | * | ++ | * |
| 45 | * | ++ | * |
| 46 | * | ++ | * |
| 47 | * | + | * |
| 48 | * | + | * |
| 49 | * | ++ | * |
| 50 | * | + | * |
| 51 | * | + | * |
| 52 | * | ++ | * |
| 53 | * | ++ | * |
| 54 | * | ++ | * |
| 55 | * | ++ | * |
| 56 | * | ++ | * |
| 57 | * | ++ | * |

TABLE 1-continued

Pim Enzyme Assay Data

| Example | Pim1 IC$_{50}$ (nM)$^a$ | Pim2 IC$_{50}$ (nM)$^b$ | Pim3 IC$_{50}$ (nM)$^a$ |
|---|---|---|---|
| 58 | * | ++ | * |
| 59 | * | + | * |
| 60 | * | + | * |
| 61 | * | ++ | * |
| 62 | * | + | * |
| 63 | * | >2000 | >40 |
| 64 | * | ++ | ** |
| 65 | * | + | * |
| 66 | * | ++ | * |
| 67 | * | ++ | * |
| 68 | * | + | * |
| 69 | * | + | * |
| 70 | * | + | * |
| 71 | * | + | * |
| 72 | * | +++ | * |
| 73 | * | + | * |
| 74 | * | + | * |
| 75 | * | + | * |
| 76 | * | + | * |
| 77 | * | +++ | * |
| 78 | * | ++ | * |
| 79 | * | ++ | * |
| 80 | * | ++ | * |
| 81 | * | + | * |
| 82 | * | +++ | ** |
| 83 | * | ++ | * |
| 84 | * | + | * |
| 85 | * | + | * |

$^a$IC$_{50}$ ≤ 10 nM: *; 10 nM < IC$_{50}$ ≤ 50 nM: ; 50 nM < IC$_{50}$ ≤ 500 nM: *; 500 nM < IC$_{50}$ ≤ 2000 nM: ****.
$^b$IC$_{50}$ ≤ 100 nM: +; 100 nM < IC$_{50}$ ≤ 1000 nM: ++; 1000 nM < IC$_{50}$ ≤ 10000 nM: +++.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:
1. A compound of any one of the following Formulae (XVI), (XX), and (XXIV):

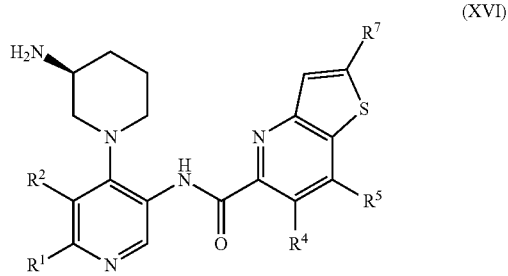

(XVI)

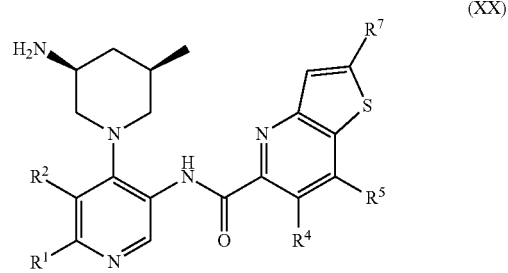

(XX)

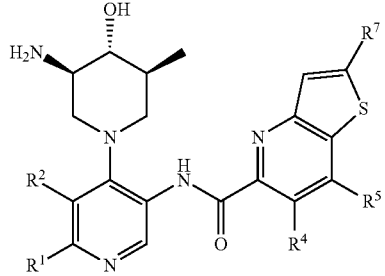

(XXIV)

or a pharmaceutically acceptable salt thereof, wherein:
R$^1$ is H;
R$^2$ is H, halogen, C$_{1-6}$ alkyl, C$_{2-6}$ alkenyl, C$_{2-6}$ alkynyl, C$_{1-6}$ haloalkyl, CN, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{e2}$)NR$^{c2}$R$^{d2}$, NR$^{c2}$C(=NR$^{e2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$ or S(O)$_2$NR$^{c2}$R$^{d2}$;
R$^4$ is H or halogen;
R$^5$ is H or halogen;
each R$^7$ is independently, at each occurrence, C$_{1-6}$ alkyl, C$_{2-6}$ alkenyl, C$_{2-6}$ alkynyl, C$_{1-6}$ haloalkyl, Cy$^6$, -L$^6$-Cy$^6$, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$ or S(O)$_2$NR$^{c3}$R$^{d3}$,
wherein said C$_{1-6}$ alkyl, C$_{2-6}$ alkenyl, or C$_{2-6}$ alkynyl forming R$^7$ are each independently unsubstituted or substituted with 1, 2 or 3 substituents independently selected from halogen, C$_{1-6}$ alkyl, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$ and S(O)$_2$NR$^{c3}$R$^{d3}$;
Cy$^6$ is unsubstituted or substituted C$_{6-10}$ aryl, unsubstituted or substituted 5-10 membered heteroaryl, unsubstituted or substituted C$_{3-6}$ cycloalkyl, or unsubstituted or substituted 4-12 membered heterocycloalkyl,
wherein the substituted C$_{6-10}$ aryl, 5-10 membered heteroaryl, C$_{3-6}$ cycloalkyl or 4-12 membered heterocycloalkyl forming Cy$^6$ is substituted with 1, 2, 3, 4 or 5 substituents each independently selected from halogen, R$^{Cy6}$, C$_{2-6}$ alkenyl, C$_{2-6}$ alkynyl, C$_{1-6}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$ and S(O)$_2$NR$^{c3}$R$^{d3}$, wherein each R$^{Cy6}$ is C$_{1-6}$ alkyl, each of which is independently unsubstituted or substituted by 1, 2 or 3 substituents independently selected from halogen, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$ NR$^{c3}$S(O)$_2$R$^{b3}$ and S(O)$_2$NR$^{c3}$R$^{d3}$; or
alternatively, the substituted C$_{6-10}$aryl, 5-10 membered heteroaryl, C$_{3-6}$ cycloalkyl or 4-12 membered heterocycloalkyl forming Cy$^6$ is substituted with unsubstituted C$_{6-10}$ aryl or C$_{6-10}$ aryl substituted by 1, 2, 3, 4 or 5 substituents independently selected from halogen, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$ NR$^{c3}$S(O)$_2$R$^{b3}$ and S(O)$_2$NR$^{c3}$R$^{d3}$;

L$^6$ is unsubstituted C$_{1-6}$ alkylene or C$_{1-6}$ alkylene substituted with 1, 2 or 3 substituents independently selected from F, Cl, CN, OH, O(C$_{1-6}$ alkyl), NH$_2$, NH(C$_{1-6}$alkyl) and N(C$_{1-6}$ alkyl)$_2$;

R$^{a2}$, R$^{b2}$, R$^{c2}$ and R$^{d2}$ are each independently selected from H, C$_{1-6}$ alkyl, C$_{2-6}$alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$alkyl forming R$^{a2}$, R$^{b2}$, R$^{c2}$ and R$^{d2}$ are each optionally substituted with 1, 2, 3, 4 or 5 substituents independently selected from C$_{1-6}$ alkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$ and S(O)$_2$NR$^{c5}$R$^{d5}$;

or R$^{c2}$ and R$^{d2}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$, C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$S(O)R$^{b5}$, S(O)NR$^{c5}$R$^{d5}$, S(O)$_2$R$^{b5}$, NR$^{c5}$S(O)$_2$R$^{b5}$ and S(O)$_2$NR$^{c5}$R$^{d5}$;

R$^{a3}$, R$^{b3}$, R$^{c3}$ and R$^{d3}$ are each independently selected from H, C$_{1-6}$ alkyl, C$_{2-6}$alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{2-6}$ alkenyl, C$_{2-6}$ alkynyl, C$_{6-10}$ aryl-C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$alkyl forming R$^{a3}$, R$^{b3}$, R$^{c3}$ and R$^{d3}$ are each optionally substituted with 1, 2, 3, 4 or 5 substituents independently selected from C$_{1-6}$ alkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$) NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$ and S(O)$_2$NR$^{c6}$R$^{d6}$;

or R$^{c3}$ and R$^{d3}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a6}$, SR$^{a6}$, C(O)R$^{b6}$, C(O) NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$ NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$) NR$^{c6}$R$^{d6}$, S(O)R$^{b6}$, S(O)NR$^{c6}$R$^{d6}$, S(O)$_2$R$^{b6}$, NR$^{c6}$S (O)$_2$R$^{b6}$ and S(O)$_2$NR$^{c6}$R$^{d6}$;

R$^{a5}$, R$^{b5}$, R$^{c5}$ and R$^{d5}$ are each independently selected from H, C$_{1-6}$ alkyl, C$_{1-6}$haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-3}$ alkyl, 5-6 membered heteroaryl-C$_{1-3}$ alkyl, C$_{3-7}$cycloalkyl-C$_{1-3}$ alkyl and 4-7 membered heterocycloalkyl-C$_{1-3}$ alkyl, wherein said C$_{1-6}$alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-3}$ alkyl, 5-6 membered heteroaryl-C$_{1-3}$ alkyl, C$_{3-7}$ cycloalkyl-C$_{1-3}$ alkyl and 4-7 membered heterocycloalkyl-C$_{1-3}$ alkyl forming R$^{a5}$, R$^{b5}$, R$^{c5}$ and R$^{d5}$ are each optionally substituted with 1, 2 or 3 substituents independently selected from OH, CN, amino, NH(C$_{1-6}$ alkyl), N(C$_{1-6}$ alkyl)$_2$, halo, C$_{1-6}$alkyl, C$_{1-6}$ alkoxy, C$_{1-6}$ haloalkyl and C$_{1-6}$ haloalkoxy;

or R$^{c5}$ and R$^{d5}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy;

R$^{a6}$, R$^{b6}$, R$^{c6}$ and R$^{d6}$ are each independently selected from H, C$_{1-6}$ alkyl, C$_{1-6}$haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-3}$ alkyl, 5-6 membered heteroaryl-C$_{1-3}$ alkyl, C$_{3-7}$cycloalkyl-C$_{1-3}$ alkyl and 4-7 membered heterocycloalkyl-C$_{1-3}$ alkyl, wherein said C$_{1-6}$alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-3}$ alkyl, 5-6 membered heteroaryl-C$_{1-3}$ alkyl, C$_{3-7}$ cycloalkyl-C$_{1-3}$ alkyl and 4-7 membered heterocycloalkyl-C$_{1-3}$ alkyl forming R$^{a6}$, R$^{b6}$, R$^{c6}$ and R$^{d6}$ are each optionally substituted with 1, 2 or 3 substituents independently selected from OH, CN, amino, NH(C$_{1-6}$ alkyl), N(C$_{1-6}$ alkyl)$_2$, halo, C$_{1-6}$alkyl, C$_{1-6}$ alkoxy, C$_{1-6}$ haloalkyl and C$_{1-6}$ haloalkoxy;

or R$^{c6}$ and R$^{d6}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH(C$_{1-6}$ alkyl), N(C$_{1-6}$ alkyl)$_2$, halo, C$_{1-6}$alkyl, C$_{1-6}$ alkoxy, C$_{1-6}$ haloalkyl and C$_{1-6}$ haloalkoxy; and R$^{e2}$, R$^{e3}$, R$^{e5}$ and R$^{e6}$ are each, independently, H, CN or NO$_2$.

2. The compound of claim 1, or a pharmaceutically acceptable salt thereof, wherein
Cy$^6$ is unsubstituted or substituted C$_{6-10}$ aryl, unsubstituted or substituted 5-10 membered heteroaryl, unsubstituted or substituted C$_{3-6}$ cycloalkyl, or unsubstituted or substituted 4-12 membered heterocycloalkyl,
wherein the substituted C$_{6-10}$ aryl, 5-10 membered heteroaryl, C$_{3-6}$ cycloalkyl or 4-12 membered heterocycloalkyl forming $Cy^6$ is substituted with 1, 2, 3, 4 or 5 substituents each independently selected from halogen, $R^{Cy6}$, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$.

3. The compound of claim 1, or a pharmaceutically acceptable salt thereof, wherein $R^1$ is H and $R^2$ is H.

4. The compound of claim 1, or a pharmaceutically acceptable salt thereof, wherein $R^4$ is H.

5. The compound of claim 1, or a pharmaceutically acceptable salt thereof, wherein $R^4$ is halogen.

6. The compound of claim 1, or a pharmaceutically acceptable salt thereof, wherein $R^5$ is H.

7. The compound of claim 1, or a pharmaceutically acceptable salt thereof, wherein $R^5$ is halogen.

8. The compound of claim 1, or a pharmaceutically acceptable salt thereof, wherein $R^1$, $R^2$, $R^4$ and $R^5$ are each H.

9. The compound of claim 1, or a pharmaceutically acceptable salt thereof, wherein:
   each $R^7$ is independently, $C_{1-6}$ alkyl, $Cy^6$, or -L-$Cy^6$;
   $Cy^6$ is unsubstituted or substituted $C_{6-10}$ aryl, unsubstituted or substituted 5-10 membered heteroaryl, unsubstituted or substituted $C_{3-6}$ cycloalkyl, or unsubstituted or substituted 4-12 membered heterocycloalkyl,
   wherein the substituted $C_{6-10}$ aryl, 5-10 membered heteroaryl, $C_{3-6}$ cycloalkyl or 4-12 membered heterocycloalkyl forming $Cy^6$ is substituted with 1, 2 or 3 substituents each independently selected from halogen, $R^{Cy6}$, CN, $OR^{a3}$, and $NR^{c3}R^{d3}$,
   alternatively, the substituted $C_{6-10}$ aryl, 5-10 membered heteroaryl, $C_{3-6}$ cycloalkyl or 4-12 membered heterocycloalkyl forming $Cy^6$ is substituted with unsubstituted $C_{6-10}$ aryl;
   wherein each $R^{Cy6}$ is $C_{1-6}$ alkyl, each of which is independently unsubstituted or substituted by 1, 2 or 3 substituents independently selected from halogen, CN, and $OR^{a3}$; and
   wherein $R^{c3}$ and $R^{d3}$ attached to the same N atom, together with the N atom to which they are both attached, form a 6-membered heterocycloalkyl group or 5-membered heteroaryl group, each optionally substituted with 1 or 2 substituents independently selected from $C_{1-6}$ alkyl, halo, CN, and $OR^{a6}$.

10. The compound of claim 1, or a pharmaceutically acceptable salt thereof, wherein:
    each $R^7$ is independently, $C_{1-6}$ alkyl, $Cy^6$, or -L-$Cy^6$;
    $Cy^6$ is unsubstituted or substituted $C_{6-10}$ aryl, unsubstituted or substituted 5-10 membered heteroaryl, unsubstituted or substituted $C_{3-6}$ cycloalkyl, or unsubstituted or substituted 4-12 membered heterocycloalkyl,
    wherein the substituted $C_{6-10}$ aryl, 5-10 membered heteroaryl, $C_{3-6}$ cycloalkyl or 4-12 membered heterocycloalkyl forming $Cy^6$ is substituted with 1, 2 or 3 substituents each independently selected from halogen, $R^{Cy6}$, CN, $OR^{a3}$, and $NR^{c3}R^{d3}$,
    alternatively, the substituted $C_{6-10}$ aryl, 5-10 membered heteroaryl, $C_{3-6}$ cycloalkyl or 4-12 membered heterocycloalkyl forming $Cy^6$ is substituted with unsubstituted $C_{6-10}$ aryl;
    wherein each $R^{Cy6}$ is $C_{1-6}$ alkyl, each of which is independently unsubstituted or substituted by 1, 2 or 3 substituents independently selected from halogen, CN, and $OR^{a3}$; and
    wherein $R^{c3}$ and $R^{d3}$ attached to the same N atom, together with the N atom to which they are both attached, form a 6-membered heterocycloalkyl group optionally substituted with 1 or 2 substituents independently selected from $C_{1-6}$ alkyl, halo, CN, and $OR^{a6}$.

11. The compound of claim 1, or a pharmaceutically acceptable salt thereof, wherein $R^7$ is $C_{1-6}$ alkyl.

12. The compound of claim 1, or a pharmaceutically acceptable salt thereof, wherein $R^7$ is methyl, ethyl, propyl, or isopropyl.

13. The compound of claim 1, or a pharmaceutically acceptable salt thereof, wherein $R^7$ is $Cy^6$ or -L-$Cy^6$.

14. The compound of claim 13, or a pharmaceutically acceptable salt thereof, wherein $R^7$ is $Cy^6$.

15. The compound of claim 13, or a pharmaceutically acceptable salt thereof, wherein $R^7$ is -L-$Cy^6$.

16. The compound of claim 1, or a pharmaceutically acceptable salt thereof, wherein each $Cy^6$ unsubstituted or substituted $C_{6-10}$ aryl.

17. The compound of claim 16, or a pharmaceutically acceptable salt thereof, wherein each $Cy^6$ is unsubstituted or substituted phenyl.

18. The compound of claim 17, or a pharmaceutically acceptable salt thereof, wherein each $Cy^6$ is phenyl substituted with 1, 2 or 3 substituents.

19. The compound of claim 18, or a pharmaceutically acceptable salt thereof, wherein each $Cy^6$ is phenyl substituted with 1, 2 or 3 substituents each independently selected from halogen and $OR^{a3}$.

20. The compound of claim 19, or a pharmaceutically acceptable salt thereof, wherein each $Cy^6$ is 2-fluorophenyl, 2,6-difluorophenyl, 2,6-difluoro-3-methoxyphenyl, or 2,6-difluoro-4-methoxyphenyl.

21. The compound of claim 1, or a pharmaceutically acceptable salt thereof, wherein each $Cy^6$ is unsubstituted or substituted 5-10 membered heteroaryl.

22. The compound of claim 21, or a pharmaceutically acceptable salt thereof, wherein each $Cy^6$ is unsubstituted or substituted 5-10 membered heteroaryl, the ring atoms of which consist of carbon atoms and 1 or 2 heteroatoms independently selected from O and N.

23. The compound of claim 21, or a pharmaceutically acceptable salt thereof, wherein each $Cy^6$ is unsubstituted or substituted 5-10 membered heteroaryl, the ring atoms of which consist of carbon atoms and 1 or 2 nitrogen atoms.

24. The compound of claim 21, or a pharmaceutically acceptable salt thereof, wherein each $Cy^6$ is unsubstituted or substituted 5-10 membered heteroaryl, the ring atoms of which consist of carbon atoms, 1 oxygen atom and 1 nitrogen atom.

25. The compound of claim 21, or a pharmaceutically acceptable salt thereof, wherein each $Cy^6$ is unsubstituted or substituted pyridinyl, isoxazolyl, pyrazolyl or pyrimidinyl.

26. The compound of claim 21, or a pharmaceutically acceptable salt thereof, wherein each $Cy^6$ is unsubstituted or substituted pyridin-3-yl, pyridin-4-yl, isoxazol-4-yl, 1H-pyrazol-4-yl, or pyrimidin-5-yl.

27. The compound of claim 26, or a pharmaceutically acceptable salt thereof, wherein each $Cy^6$ is pyridin-3-yl, pyridin-4-yl, isoxazol-4-yl, 1H-pyrazol-4-yl, or pyrimidin-5-yl, each of which is unsubstituted or substituted with one or two substituents selected from halogen, $C_{1-6}$ alkyl, CN, $OR^{a3}$, and $NR^{c3}R^{d3}$.

28. The compound of claim 27, or a pharmaceutically acceptable salt thereof, wherein each $Cy^6$ is 6-morpholinopyridin-3-yl, 6-methoxypyridin-3-yl, 5-methoxypyridin-3-yl, 5-cyanopyridin-3-yl, 2,6-difluoropyridin-4-yl, isoxazol-4-yl, 1-methyl-1H-pyrazol-4-yl, or pyrimidin-5-yl.

29. The compound of claim 1, or a pharmaceutically acceptable salt thereof, wherein each $Cy^6$ is unsubstituted or substituted $C_{3-6}$ cycloalkyl.

30. The compound of claim 29, or a pharmaceutically acceptable salt thereof, wherein each $Cy^6$ is unsubstituted cyclopropyl.

31. The compound of claim 29, or a pharmaceutically acceptable salt thereof, wherein each $Cy^6$ is cyclopropyl substituted by phenyl.

32. The compound of claim 1, or a pharmaceutically acceptable salt thereof, wherein each $Cy^6$ is unsubstituted or substituted 4-12 membered heterocycloalkyl.

33. The compound of claim 32, or a pharmaceutically acceptable salt thereof, wherein each $Cy^6$ is 4-12 membered heterocycloalkyl which is unsubstituted or substituted with one or two $C_{1-6}$ alkyl groups.

34. The compound of claim 32, or a pharmaceutically acceptable salt thereof, wherein each $Cy^6$ is 4-tetrahydropyranyl, 3-tetrahydrofuryl, 3,4-dihydro-2H-pyran-5-yl, or 1-methylpiperidin-4-yl.

35. The compound of claim 1, or a pharmaceutically acceptable salt thereof, wherein each $L^6$ is unsubstituted $C_{1-6}$ alkylene or $C_{1-6}$ alkylene substituted with 1, 2, or 3 substituents independently selected from F, Cl, CN, OH, and $O(C_{1-6}$ alkyl).

36. The compound of claim 35, or a pharmaceutically acceptable salt thereof, wherein each $L^6$ is unsubstituted $C_{1-6}$ alkylene.

37. The compound of claim 36, or a pharmaceutically acceptable salt thereof, wherein each $L^6$ is $CH_2$.

38. The compound of claim 1, or a pharmaceutically acceptable salt thereof, wherein each $R^7$ is methyl, ethyl, propyl, isopropyl, cyclopropyl, phenyl, 2-fluorophenyl, 2,6-difluorophenyl, 2,6-difluoro-3-methoxyphenyl, 2,6-difluoro-4-methoxyphenyl, benzyl, 2-fluorobenzyl, 2,6-difluorobenzyl, 2,6-difluoro-3-methoxybenzyl, 2,6-difluoro-4-methoxybenzyl, pyridin-3-yl, pyridin-4-yl, isoxazol-4-yl, 1H-pyrazol-4-yl, pyrimidin-5-yl, 6-morpholinopyridin-3-yl, 6-methoxypyridin-3-yl, 5-methoxypyridin-3-yl, 5-cyanopyridin-3-yl, 2,6-difluoropyridin-4-yl, isoxazol-4-yl, 1-methyl-1H-pyrazol-4-yl, pyrimidin-5-yl, 4-tetrahydropyranyl, 3-tetrahydrofuryl, 3,4-dihydro-2H-pyran-5-yl, or 1-methylpiperidin-4-yl.

39. The compound of claim 1, or a pharmaceutically acceptable salt thereof, wherein $R^{a2}$, $R^{b2}$, $R^{c2}$, $R^{d2}$, $R^{a3}$, $R^{b3}$, $R^{c3}$, $R^{d3}$, $R^{a5}$, $R^{b5}$, $R^{c5}$, $R^{d5}$, $R^{a6}$, $R^{b6}$, $R^{c6}$ and $R^{d6}$ are each independently selected from H and $C_{1-6}$ alkyl.

40. The compound of claim 1, or a pharmaceutically acceptable salt thereof, wherein $R^{e2}$, $R^{e3}$, $R^{e5}$ and $R^{e6}$ are each independently selected from H and $C_{1-6}$ alkyl.

41. The compound of claim 1 selected from the following compounds, or a pharmaceutically acceptable salt thereof:

N-(4-((3R,4R,5S)-3-amino-4-hydroxy-5-methylpiperidin-1-yl)pyridin-3-yl)-2-propylthieno[3,2-b]pyridine-5-carboxamide;

N-(4-((3R,4R,5S)-3-amino-4-hydroxy-5-methylpiperidin-1-yl)pyridin-3-yl)-2-isopropylthieno[3,2-b]pyridine-5-carboxamide;

N-(4-((3R,4R,5S)-3-amino-4-hydroxy-5-methylpiperidin-1-yl)pyridin-3-yl)-2-(2,6-difluorophenyl)thieno[3,2-b]pyridine-5-carboxamide;

N-(4-((3R,4R,5S)-3-amino-4-hydroxy-5-methylpiperidin-1-yl)pyridin-3-yl)-2-(2-fluorophenyl)thieno[3,2-b]pyridine-5-carboxamide;

N-(4-((3R,4R,5S)-3-amino-4-hydroxy-5-methylpiperidin-1-yl)pyridin-3-yl)-2-benzylthieno[3,2-b]pyridine-5-carboxamide;

N-(4-((3R,4R,5S)-3-amino-4-hydroxy-5-methylpiperidin-1-yl)pyridin-3-yl)-2-(6-methoxypyridin-3-yl)thieno[3,2-b]pyridine-5-carboxamide;

N-(4-((3R,4R,5S)-3-amino-4-hydroxy-5-methylpiperidin-1-yl)pyridin-3-yl)-2-(6-morpholinopyridin-3-yl)thieno[3,2-b]pyridine-5-carboxamide;

N-(4-((3R,4R,5S)-3-amino-4-hydroxy-5-methylpiperidin-1-yl)pyridin-3-yl)-2-(2,6-difluoro-4-methoxyphenyl)thieno[3,2-b]pyridine-5-carboxamide;

N-(4-((3R,4R,5S)-3-amino-4-hydroxy-5-methylpiperidin-1-yl)pyridin-3-yl)-2-phenylthieno[3,2-b]pyridine-5-carboxamide;

N-(4-((3R,4R,5S)-3-amino-4-hydroxy-5-methylpiperidin-1-yl)pyridin-3-yl)-2-cyclopropylthieno[3,2-b]pyridine-5-carboxamide;

N-(4-((3R,4R,5S)-3-amino-4-hydroxy-5-methylpiperidin-1-yl)pyridin-3-yl)-2-(1-methyl-1H-pyrazol-4-yl)thieno[3,2-b]pyridine-5-carboxamide;

N-(4-((3R,4R,5S)-3-amino-4-hydroxy-5-methylpiperidin-1-yl)pyridin-3-yl)-2-methylthieno[3,2-b]pyridine-5-carboxamide;

N-(4-((3S,5R)-3-amino-5-methylpiperidin-1-yl)pyridin-3-yl)-2-propylthieno[3,2-b]pyridine-5-carboxamide;

N-(4-((3S,5R)-3-amino-5-methylpiperidin-1-yl)pyridin-3-yl)-2-isopropylthieno[3,2-b]pyridine-5-carboxamide;

N-(4-((3S,5R)-3-amino-5-methylpiperidin-1-yl)pyridin-3-yl)-2-(2,6-difluorophenyl)thieno[3,2-b]pyridine-5-carboxamide;

N-(4-((3S,5R)-3-amino-5-methylpiperidin-1-yl)pyridin-3-yl)-2-(2-fluorophenyl)thieno[3,2-b]pyridine-5-carboxamide;

N-(4-((3S,5R)-3-amino-5-methylpiperidin-1-yl)pyridin-3-yl)-2-benzylthieno[3,2-b]pyridine-5-carboxamide;

N-(4-((3S,5R)-3-amino-5-methylpiperidin-1-yl)pyridin-3-yl)-2-(6-methoxypyridin-3-yl)thieno[3,2-b]pyridine-5-carboxamide;

N-(4-((3S,5R)-3-amino-5-methylpiperidin-1-yl)pyridin-3-yl)-2-(6-morpholinopyridin-3-yl)thieno[3,2-b]pyridine-5-carboxamide;

N-(4-((3S,5R)-3-amino-5-methylpiperidin-1-yl)pyridin-3-yl)-2-(2,6-difluoro-4-methoxyphenyl)thieno[3,2-b]pyridine-5-carboxamide;

N-(4-((3S,5R)-3-amino-5-methylpiperidin-1-yl)pyridin-3-yl)-2-phenylthieno[3,2-b]pyridine-5-carboxamide;

N-(4-((3S,5R)-3-amino-5-methylpiperidin-1-yl)pyridin-3-yl)-2-cyclopropylthieno[3,2-b]pyridine-5-carboxamide;

N-(4-((3S,5R)-3-amino-5-methylpiperidin-1-yl)pyridin-3-yl)-2-(1-methyl-1H-pyrazol-4-yl)thieno[3,2-b]pyridine-5-carboxamide; and N-(4-((3S,5R)-3-amino-5-methylpiperidin-1-yl)pyridin-3-yl)-2-methylthieno[3,2-b]pyridine-5-carboxamide.

42. The compound of claim 1 which is N-(4-((3R,4R,5S)-3-amino-4-hydroxy-5-methylpiperidin-1-yl)pyridin-3-yl)-2-ethylthieno[3,2-b]pyridine-5-carboxamide, or a pharmaceutically acceptable salt thereof.

43. A composition comprising a compound of claim 1, or a pharmaceutically acceptable salt thereof, and at least one pharmaceutically acceptable carrier.

* * * * *

UNITED STATES PATENT AND TRADEMARK OFFICE
CERTIFICATE OF CORRECTION

PATENT NO. : 9,822,124 B2
APPLICATION NO. : 14/798137
DATED : November 21, 2017
INVENTOR(S) : Oleg Vechorkin, Yun-Long Li and Wenyu Zhu It is certified that error appears in the above-identified patent and that said Letters Patent is hereby corrected as shown below:

In the Claims

Column 182, Lines 33, Claim 1, delete "alkenyl," and insert -- alkenyl --;

Column 182, Line 42, Claim 1, delete "S(O)$_2$R$^{b3}$and" and insert -- S(O)$_2$R$^{b3}$,NR$^{c3}$S(O)$_2$R$^{b3}$ and --;

Column 182, Lines 56-57, Claim 1, delete "S(O)$_2$NR$^{c3}$R$^{d3}$,wherein" and insert -- S(O)$_2$NR$^{c3}$R$^{d3}$, wherein --;

Column 182, Line 64, Claim 1, after "S(O)$_2$R$^{b3}$" insert -- , --;

Column 182, Line 66, Claim 1, delete "C$_{6-10}$aryl," and insert -- C$_{6-10}$ aryl, --;

Column 183, Line 8, Claim 1, after "S(O)$_2$R$^{b3}$" insert -- , --;

Column 183, Line 11, Claim 1, delete "NH(C$_{1-6}$alkyl)" and insert -- NH(C$_{1-6}$ alkyl) --;

Column 183, Line 13, Claim 1, delete "R$^{c2}$and" and insert -- R$^{c2}$ and --;

Column 183, Line 14, Claim 1, delete "C$_{2-6}$alkenyl," and insert -- C$_{2-6}$ alkenyl, --;

Column 183, Line 16, Claim 1, delete "4-10membered" and insert -- 4-10 membered --;

Column 183, Line 24, Claim 1, delete "-C$_{1-3}$alkyl" and insert -- -C$_{1-3}$ alkyl --;

Column 183, Line 40, Claim 1, delete "NR$^{c5}$,C(O)NR$^{c5}$R$^{d5}$," and insert -- NR$^{c5}$C(O)NR$^{c5}$R$^{d5}$, --;

Column 183, Lines 41-42, Claim 1, delete "NR$^{c5}$C(=NR$^{e5}$)NR$^{c5}$R$^{d5}$S(O)R$^{b5}$," and insert -- NR$^{c5}$C(=NR$^{e5}$)NR$^{c5}$R$^{d5}$, S(O)R$^{b5}$, --;

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,822,124 B2

Column 183, Line 45, Claim 1, delete "$C_{2-6}$alkenyl," and insert -- $C_{2-6}$ alkenyl, --;

Column 183, Line 51, Claim 1, delete "aryl-$C_{3-7}$" and insert -- aryl, $C_{3-7}$ --;

Column 183, Lines 54-55, Claim 1, delete "-$C_{1-3}$alkyl" and insert -- -$C_{1-3}$ alkyl --;

Column 184, Line 4, Claim 1, after "$R^{b6}$" insert -- , --;

Column 184, Line 9, Claim 1, delete "$C_{1-6}$haloalkyl," and insert -- $C_{1-6}$ haloalkyl, --;

Column 184, Lines 12-13, Claim 1, delete "$C_{3-7}$cycloalkyl-" and insert -- $C_{3-7}$ cycloalkyl- --;

Column 184, Line 14, Claim 1, delete "$C_{1-6}$alkyl," and insert -- $C_{1-6}$ alkyl, --;

Column 184, Line 23, Claim 1, delete "$C_{1-6}$alkyl," and insert -- $C_{1-6}$ alkyl, --;

Column 184, Line 34, Claim 1, delete "$C_{1-6}$haloalkyl," and insert -- $C_{1-6}$ haloalkyl, --;

Column 184, Lines 37-38, Claim 1, delete "$C_{3-7}$cycloalkyl-" and insert -- $C_{3-7}$ cycloalkyl- --;

Column 184, Line 39, Claim 1, delete "$C_{1-6}$alkyl," and insert -- $C_{1-6}$ alkyl, --;

Column 184, Line 48, Claim 1, delete "$C_{1-6}$alkyl," and insert -- $C_{1-6}$ alkyl, --;

Column 184, Line 56, Claim 1, delete "$C_{1-6}$alkyl," and insert -- $C_{1-6}$ alkyl, --;

Column 185, Line 35, Claim 9, delete "$R^{cy6}$," and insert -- $R^{Cy6}$, --;

Column 186, Line 22, Claim 16, after "Cy6," insert -- is --;

Column 188, Lines 1-2, Claim 41, delete "-5- methylpiperidin-" and insert -- -5-methylpiperidin- --;

Column 188, Lines 55, Claim 41, delete "-1H -" and insert -- -1H- --.